US007465571B1

(12) United States Patent
Lam et al.

(10) Patent No.: US 7,465,571 B1
(45) Date of Patent: Dec. 16, 2008

(54) ENDOGLUCANASES

(75) Inventors: David Lam, San Marcos, CA (US); Eric J. Mathur, Carlsbad, CA (US)

(73) Assignee: Verenium Corporation, San Diego, CA (US)

( * ) Notice: Subject to any disclaimer, the term of this patent is extended or adjusted under 35 U.S.C. 154(b) by 0 days.

(21) Appl. No.: 09/914,543

(22) PCT Filed: May 22, 1997

(86) PCT No.: PCT/US97/08793

§ 371 (c)(1),
(2), (4) Date: Jan. 17, 2002

(87) PCT Pub. No.: WO97/44361

PCT Pub. Date: Nov. 27, 1997

Related U.S. Application Data

(63) Continuation-in-part of application No. 08/651,572, filed on May 22, 1996, now Pat. No. 5,789,228.

(51) Int. Cl.
*C12N 9/42* (2006.01)
*C12P 19/34* (2006.01)
*C07K 1/00* (2006.01)
*D06M 16/00* (2006.01)
*C11D 3/00* (2006.01)
*C07H 21/04* (2006.01)
*A23L 1/31* (2006.01)

(52) U.S. Cl. ............... 435/209; 435/69.1; 435/91.1; 435/93; 435/254.11; 435/262.5; 435/263; 435/320.1; 435/325; 435/252.3; 435/254.2; 435/267; 435/277; 435/348; 435/419; 426/56

(58) Field of Classification Search ............... 435/4, 435/6, 69.1, 183, 200, 209, 252.3, 320.1, 435/262, 263, 264, 267, 277, 279; 510/114, 510/392, 515; 536/23.2, 23.7, 24.31
See application file for complete search history.

(56) References Cited

U.S. PATENT DOCUMENTS

| 4,487,833 | A | | 12/1984 | Donahoe |
| 5,393,670 | A | | 2/1995 | Knowles et al. |
| 5,475,101 | A | | 12/1995 | Ward et al. |
| 5,536,655 | A | | 7/1996 | Thomas et al. |
| 5,605,793 | A | | 2/1997 | Stemmer |
| 5,643,791 | A | | 7/1997 | Warren et al. |
| 5,723,328 | A | | 3/1998 | Dalboege et al. |
| 5,789,228 | A | * | 8/1998 | Lam et al. ............... 435/209 |
| 5,817,499 | A | | 10/1998 | Dalboge et al. |
| 5,830,696 | A | | 11/1998 | Short |
| 5,939,250 | A | | 8/1999 | Short |
| 6,074,867 | A | | 6/2000 | Lam et al. |
| 6,368,844 | B1 | * | 4/2002 | Bylina ............... 435/207 |
| 2002/0155550 | A1 | * | 10/2002 | Bylina et al. ............... 435/105 |
| 2003/0078397 | A1 | * | 4/2003 | Short et al. ............... 536/23.1 |

FOREIGN PATENT DOCUMENTS

| DE | 42 04 476 | 8/1992 |
| EP | 0 606 008 | 7/1994 |
| EP | 0 648 843 | 4/1995 |
| EP | 0 687 732 | 12/1995 |
| JP | 02 276578 | 11/1990 |
| JP | 09 173077 | 7/1997 |
| WO | WO 95/02043 | 1/1995 |
| WO | WO 95/20047 | 7/1995 |
| WO | WO 96/02551 | 2/1996 |
| WO | WO 97/20918 | 6/1997 |
| WO | WO 97/25417 | 7/1997 |
| WO | WO 98/24799 | 6/1998 |
| WO | WO 98/33895 | 8/1998 |

OTHER PUBLICATIONS

Dakhova et al., Cloning and expression in *Escherichia coli* of *Thermatoga neapolitana* genes coding for enzymes of carbohydrate substrate degradation. Biochem. Biophys. Res. Commun., 1993, vol. 194: 1359-1364.*
Fetrow et al. (1998). J. Mol. Biol. 282:703-711.
Pons et al. (1997). The J. of Biol. Chemistry 20:13006-13012.
Skolnick and Fetrow (2000). TIBTECH 18:34-39.
Zhang and Wilson, (1997). J. of Biotechnology 57:101-113.
Baba, T., et al., "Identification and Characterization of Clustered Genes for Thermostable Xylan-Degrading Enzymes, Beta-Xylosidase and Xylanase, of *Bacillus stearothermophilus* 21" *Applied and Environmental Microbiology*, U.S. Washington, D.C., vol. 60., No. 7, Jul. 1, 1994 (pp. 2252-2258).
Dean, R.C., "Mechanisms of Wood Digestion in the Shipworm Bankia-Gouldi Enzyme Degradation of Celluloses Hemi Celluloses and Wood Cell Walls", *Databases Accession No. PREV198069003408 XP002159358* (Abstract) and Biological Bulletin (Woods Hole), vol. 155, No. 2, 1978 (pp. 297-316).
Lao et al., "DNA Sequences of Three Beta-1,4 Endoglucanase Genes From Thermomonospora Fusca", XP002094152 *Journal of Bacteriology*, vol. 173, Jun. 1, 1991 (pp. 3397-3407).
Lin, E.S., et al., "Thermomonospora Fusca Beta-1,4-Endoglucanase Precursor (E4) Gene, Complete CDS", Accession L20093, XP002159359 Jul. 8, 1993 (pp. 70-469).
Jung et al., DNA Sequences and Expression in Streptomyces Lividans of an Exoglucanase Gene and an Endoglucanase Gene From Thermomonospora Fusca, Accession P26221 XP002159360 May 1, 1992, pp. 6-864).

(Continued)

*Primary Examiner*—Rebecca E. Prouty
*Assistant Examiner*—Ganapathirama Raghu
(74) *Attorney, Agent, or Firm*—Morrison & Foerster LLP

(57) ABSTRACT

In one aspect, the invention provides a purified thermostable enzyme derived from the archael bacterium AEPII 1a. In one aspect, the enzyme has a molecular weight of about 60.9 kilodaltons and has a cellulase activity. The enzyme can be produced from native or recombinant host cells, and can be used to aid in the digestion of cellulose. The invention also provides polypeptides having endoglucanase activity having homology to SEQ ID NO:2.

50 Claims, 121 Drawing Sheets

OTHER PUBLICATIONS

Milward-Sadler Sarah J. et al., "Novel Cellulose-Binding Domains, NodB Homologues and Conserved Modular Architecture in Xylanases From the Aerobic Soil Bacteria Pseudomonas Fluorescens Subsp. Cellulosa and Cellvibrio Mixtus", *Biochemical Journal* vol. 312, No. 1, 1995 (pp. 39-48).

Clarke, J.H., "P. Fluorescens SSP. Cellulosa Gene for Endo-Beta-1,4-Xylanase", Accession Z48928, XP002159361, Mar. 30, 1995 (pp. 982-1604).

Millward-Sadler S.J. et al., "Endo-Beta-1,4-Xylanase Precursor (EC 3.2.1.8) (Endo-1,4-Beta Xylanase)", Accession No. Q59765 XP002159362 Nov. 1, 1996 (pp. 298-580).

Hall J. et al., "The Non-Catalytic Cellulose-Binding Domain of a Novel Cellulose From Pseudomonoas Fluorescens Subsp. Cellulose is Important for the Efficient Hydrolysis of a Vicel", *Biochemical Journal, G.B., Portland Press*, London, vol. 309, No. part 3, Aug. 1, 1995 (pp. 749-756).

Hall, J., et al., "P. Fluorescens Cele Gen", Accession No. X86798, XP002159363, May 11, 1995 (pp. 1159-1831).

Hall, J., et al., "Endo-1,4-Beta-Glucanase(EC 3.2.1.4) (Cellulase) (Endoglucanase) (Carboxylmethyl Cellulase)", Accession No. Q59665, XP002159364 Nov. 1, 1996 (pp. 6-565).

Waterbury J.B. et al., "A Cellulolytic Nitrogen Fixing Bacterium Cultured From the Gland of Deshayes in Shipworms Bivalvia Teredinidae", Database Accession No. PREV198477059970, XP002159365 (Abstract) and Science (Washington, DC) vol. 221, No. 4618, 1983 (pp. 1401-1403).

Watanabe et al., "Proline Residues Responsible for Thermostability Occur With High Frequency in the Loop Regions of and Extremely Thermostable Oligo-1 6-Glucosidase From Bacillus-Thermoglucosidasius KP 1006", *Journal of Biological Chemistry*, vol. 266, No. 36, 1991 (pp. 24287-24294).

King Michael et al., "Thermostable Alpha-Galactosidase From Thermotoga Neapolitana: Cloning Sequencing and Expression", *FEMS Microbiology Letters*, vol. 163, No. 1, Jun. 1, 1998 (pp. 37-42).

King, M.R. et al., "Alpha-1,6-Galactosidase (EC 3.2.1.22)", Accession No. Q9R7H1, XP002159366 (May 1, 2000) (pp. 68-618).

King M.R. et al., "Thermotoga Neapolitana Alpha-1,6-Galactosidase (ag1A) Gene, Complete CDS", Accession No. AF011400, XP002159367, Jun. 19, 1998 (pp. 1-1716).

Voorhorst W.G. et al., "Pyrococcus Furiosus Beta-Glucosidase (celB) Gene, Complete CDS; ADH-1AM Operon, Complete Sequence; Biotin Ligase Bira Homolog (BIRA) Gene, Complete CDS; and -Posphoglycerate Kinase (PGK) Gene, Partial CDS", Accession No. AFO13169, XP002159371 Jul. 7, 1998 (pp. 1624-729).

Parker, et al., "Thermotoga Neopolitana manB Gene", Accession No. Y17981, XP002159369, Sep. 30, 1999.

Hayden et al., "Sec-Independent Protein Translocase Protein Tate", Accession No. P25895, XP002159370, May 1, 1992 (pp. 5-59).

Voorhorst Wilfried G.B. et al., "Characterization of the Celb Gene Coding for Beta-Glucosidase From the Hyperhtermophilic Archaeon Pyrococcus Furiosus and its Expression and Site-Directed Mutation in *Escherichia coli*", *Journal of Bacteriology*, vol. 177, No. 24, 1994 (pp. 7105-7111).

Voorhorst W.G. et al., "PyrococcusFuriosus Beta Glucosidase (celB) Gene, Complete CDS; ADH-1AM Operon, Complete Sequence; Biotin Ligase Bira Homolog (BIRA) Gene, Complete CDS; and—Posphoglycerate Kinase (PGK) Gene, Partial CDS", Accession No. AFO13169, XP002159371 Jul. 7, 1998 (pp. 1624-1729).

Voorhorst, et al., "Beta-Glucosidase", Accession No. Q51723, XP002159372, Nov. 1, 1996 (pp. 1-478).

Tachibana Yoshihisa et al., "Cloning and Expression of the Alpha-Amylase Gene From the Hyperthermophilic *Archaeon pyrococcus SP. KOD1*, and Characterization of the Enzyme", *Journal of Fermentation and Bioengineering*, vol. 82, No. 3, 1996 (pp. 224-232).

Nelson K.E. et al., "Thermotoga Maritima Section 125 of 136 of the Complete Genome", Accesssion No. AE001813, XP002159373, Jun. 4, 1999.

Wang W., et al., "Nucleotide Sequence of the ce1A Gene Encoding a Cellodesctrinase of Ruminococcus Flavefaciens Formal Drawings-1", Accesssion No. P16169, XP002159374, Apr. 1, 1990 (pp. 17-287).

Nelson K.E., et al., "Thermotoga Maritima Section 134 of 136 of the Complete Genome", Accession No. AE001822, XP002159375, Jun. 4, 1999.

Yoshihisa et al., Alpha-Mannosidase (EC 3.2.1.24) (Alpha-D Mannoside Mannohydrolase), Accession No. P22855, XP-002159376, Aug. 1, 1991 (pp. 9-946).

Nelson K.E. et al., "Thermotoga Maritima Section 6 of 136 of the Complete Genome", Accession No. AE001694, XP-002159377, Jun. 4, 1999 (pp. 4969-8305).

Yernool D.A. et al., "Thermotoga Neopolitana Mannosidase (manA) Xylosidase (xloaA), and Acetyle Xylan Esterase (axeA) Genes, Complete CDS", Accession No. U58632, XP002159378, Jun. 21, 1996.

Breves et al., "T-Brockii CGLF, CGLG, XGLS, and CTLT Genes", Accession No. Z56279, XP002159379, Oct. 13, 1995.

Gilbert H.J., "P-Fluorescens ceID Gene for 1,4-B-D-Glucan Glucohydrolase", Accession No. X65527, XP002159380, May 5, 1992.

Svitil A.L, et al., "Vibrio Harveyi Chitinase A (Chia) Gene, Complete CDS", Accession No. U81496, XP002159381, Jan. 5, 1997.

Ramesh et al., "Cellulytic Activity of 1-13 Luminous Bacteria", *Mircen Journal of Applied Microbiology and Biotechnology*, vol. 4, No. 2, 1988 (pp. 227-230).

Dakhova O.N. et al., "Cloning and Expression in *Escherichia coli* of Thermotoga Neapolitana Genes Cloning for Enzymes of Carbohydrate Substrate Degradation", *Biochemical and Biophysical Research Communications*, vol. 194, No. 3, Aug. 16, 1993, pp. 1359-1364.

Creuzet et al., Biochemie 65:149-156.

Huber, et al., "*Thermotoga martima* sp. Nov. Represents a New Genus of Unique Extremely *Thermophilic eubacteria* growing up to 90° C", *Archives of Microbiology*, 1986 144:324-333.

Coughlan, Michael P., "The Properties of Fungal and Bacterial Cellulases With Comment on Their Production and Application", *Biotechnology and Genetic Engineering Reviews*, vol. 3, Sep. 1985, (pp. 39-109).

Gough et al., Gene 89:53-59.

Bragger et al., Appl Microbiol. Biotechnol. 31:556-561.

Honda et al., Appl. Microbiol. Biotechnol. 29:264-268.

Mladenovska et al., Arch. Microbiol. 163:223-230.

Matthews et al., Analytical Biochemistry 169:1-25 (1988).

Bronnenmeier et al., Purification of *Thermotoga maritima* enzymes for the degradation of cellulosic materials. Applied and Environmentla Microbiology, Apr. 1995, vol. 61, No. 4, pp. 1399-1407.

Bok et al., Cloning and characterization of an endoglucanase and a xylanase from the hyperthermophilic eubacterium, *Thermotoga maritima*. Abstracts of the General Meeting of the American Society for Microbiology, 1992, vol. 92, p. 312.

Liebl et al., Analysis of a *Thermotoga maritima* DNA fragmernt encoding two similar thermostable cellulases. CelA and CelB, and characterization of the recombinant enzymes. Microbiology. May 15, 1996, vol. 142, pp. 2533-2542.

* cited by examiner (SEQ ID NO:1 - nucleotide sequence and SEQ ID NO:2 - amino acid sequence)
AEPIIIa Archeal Endoglucanase Sequence

```
              9          18         27         36         45         54
5'  ATG ATA AAC GTT GCA ACG GGA GAG GAG ACC CCA ATA CAC CTC TTT GGA GTC AAC
    --- --- --- --- --- --- --- --- --- --- --- --- --- --- --- --- --- ---
    Met Ile Asn Val Ala Thr Gly Glu Glu Thr Pro Ile His Leu Phe Gly Val Asn 63         72         81         90         99        108
    TGG TTC GGC TTT GAG ACA CCG AAC TAC GTT GTT CAC GGC CTA TGG AGT AGG AAC
    --- --- --- --- --- --- --- --- --- --- --- --- --- --- --- --- --- ---
    Trp Phe Gly Phe Glu Thr Pro Asn Tyr Val Val His Gly Leu Trp Ser Arg Asn 117        126        135        144        153        162
    TGG GAG GAC ATG CTC CTC CAG ATC AAG AGC CTT GGC TTC AAT GCG ATA AGG CTT
    --- --- --- --- --- --- --- --- --- --- --- --- --- --- --- --- --- ---
    Trp Glu Asp Met Leu Leu Gln Ile Lys Ser Leu Gly Phe Asn Ala Ile Arg Leu 171        180        189        198        207        216
    CCC TTC TGT ACC CAG TCA GTA AAA CCG GGG ACG ATG CCA ACG GCG ATT GAC TAC
    --- --- --- --- --- --- --- --- --- --- --- --- --- --- --- --- --- ---
    Pro Phe Cys Thr Gln Ser Val Lys Pro Gly Thr Met Pro Thr Ala Ile Asp Tyr 225        234        243        252        261        270
    GCC AAG AAC CCA GAC CTC CAG GGT CTT GAC AGC GTC CAG ATA ATG GAG AAA ATA
    --- --- --- --- --- --- --- --- --- --- --- --- --- --- --- --- --- ---
    Ala Lys Asn Pro Asp Leu Gln Gly Leu Asp Ser Val Gln Ile Met Glu Lys Ile 279        288        297        306        315        324
    ATC AAG AAG GCT GGA GAC CTG GGC ATA TTC GTG CTC CTC GAC TAC CAC AGA ATA
    --- --- --- --- --- --- --- --- --- --- --- --- --- --- --- --- --- ---
    Ile Lys Lys Ala Gly Asp Leu Gly Ile Phe Val Leu Leu Asp Tyr His Arg Ile
```

FIG. 1A-1

```
        333         342         351         360         369         378
GGA TGC AAC TTC ATA GAA CCC CTA TGG TAC ACC GAC AGC TTC TCG GAG CAG GAC
--- --- --- --- --- --- --- --- --- --- --- --- --- --- --- --- --- ---
Gly Cys Asn Phe Ile Glu Pro Leu Trp Tyr Thr Asp Ser Phe Ser Glu Gln Asp 387         396         405         414         423         432
TAC ATA AAC ACC TGG GTT GAA GTC GCC CAG AGG TTC GGC AAG TAC TGG AAC GTT
--- --- --- --- --- --- --- --- --- --- --- --- --- --- --- --- --- ---
Tyr Ile Asn Thr Trp Val Glu Val Ala Gln Arg Phe Gly Lys Tyr Trp Asn Val 441         450         459         468         477         486
ATC GGC GCG GAC CTG AAG AAC GAA CCC CAC AGC TCA AGC CCC GCA CCT GCC GCC
--- --- --- --- --- --- --- --- --- --- --- --- --- --- --- --- --- ---
Ile Gly Ala Asp Leu Lys Asn Glu Pro His Ser Ser Ser Pro Ala Pro Ala Ala 495         504         513         522         531         540
TAC ACT GAC GGA AGT GGG GCC ACG TGG GGA ATG GGC AAC AAC GCC ACC GAC TGG
--- --- --- --- --- --- --- --- --- --- --- --- --- --- --- --- --- ---
Tyr Thr Asp Gly Ser Gly Ala Thr Trp Gly Met Gly Asn Asn Ala Thr Asp Trp 549         558         567         576         585         594
AAC CTG GCG GCT GAG AGG ATA GGA AGG GCA ATT CTG GAG GTT GCC CCA CAA TGG
--- --- --- --- --- --- --- --- --- --- --- --- --- --- --- --- --- ---
Asn Leu Ala Ala Glu Arg Ile Gly Arg Ala Ile Leu Glu Val Ala Pro Gln Trp 603         612         621         630         639         648
GTT ATA TTT GTT GAG GGA ACC CAG TTC ACC ACC CCC GAG ATA GAC GGT AGG TAC
--- --- --- --- --- --- --- --- --- --- --- --- --- --- --- --- --- ---
Val Ile Phe Val Glu Gly Thr Gln Phe Thr Thr Pro Glu Ile Asp Gly Arg Tyr 657         666         675         684         693         702
AAG TGG GGC CAC AAC GCC TGG TGG GGC GGA AAC CTT ATG GGT GTT AGG AAG TAC
--- --- --- --- --- --- --- --- --- --- --- --- --- --- --- --- --- ---
Lys Trp Gly His Asn Ala Trp Trp Gly Gly Asn Leu Met Gly Val Arg Lys Tyr
```

FIG. 1A-2

```
        711         720         729         738         747         756
CCA GTT AAC CTG CCC AGG GAC AAG GTT GTT TAC AGC CCC CAA GTT TAC GGT TCA
--- --- --- --- --- --- --- --- --- --- --- --- --- --- --- --- --- ---
Pro Val Asn Leu Pro Arg Asp Lys Val Val Tyr Ser Pro Gln Val Tyr Gly Ser 765         774         783         792         801         810
GAA GTT TAC GAC CAG CCC TAC TTT GAC CCC GGT GAG GGG TTC CCC GAC AAC CTC
--- --- --- --- --- --- --- --- --- --- --- --- --- --- --- --- --- ---
Glu Val Tyr Asp Gln Pro Tyr Phe Asp Pro Gly Glu Gly Phe Pro Asp Asn Leu 819         828         837         846         855         864
CCC GAA ATA TGG TAC CAC CAC TTC GGC TAC GTA AAG CTT GAT CTC GGT TAC CCT
--- --- --- --- --- --- --- --- --- --- --- --- --- --- --- --- --- ---
Pro Glu Ile Trp Tyr His His Phe Gly Tyr Val Lys Leu Asp Leu Gly Tyr Pro 873         882         891         900         909         918
GTT GTT ATA GGT GAG TTC GGA GGC AAG TAC GGC CAT GGG GGA GAC CCG AGG GAT
--- --- --- --- --- --- --- --- --- --- --- --- --- --- --- --- --- ---
Val Val Ile Gly Glu Phe Gly Gly Lys Tyr Gly His Gly Gly Asp Pro Arg Asp 927         936         945         954         963         972
GTC ACT TGG CAG AAC AAG ATA ATA GAC TGG ATG ATC CAG AAC AAA TTC TGT GAC
--- --- --- --- --- --- --- --- --- --- --- --- --- --- --- --- --- ---
Val Thr Trp Gln Asn Lys Ile Ile Asp Trp Met Ile Gln Asn Lys Phe Cys Asp 981         990         999        1008        1017        1026
TTC TTC TAC TGG AGC TGG AAC CCA AAC AGC GGT GAC ACC GGT GGA ATT CTG AAG
--- --- --- --- --- --- --- --- --- --- --- --- --- --- --- --- --- ---
Phe Phe Tyr Trp Ser Trp Asn Pro Asn Ser Gly Asp Thr Gly Gly Ile Leu Lys 1035        1044        1053        1062        1071        1080
GAT GAC TGG ACG ACA ATA TGG GAG GAC AAG TAC AAC AAC CTG AAG AGG CTC ATG
--- --- --- --- --- --- --- --- --- --- --- --- --- --- --- --- --- ---
Asp Asp Trp Thr Thr Ile Trp Glu Asp Lys Tyr Asn Asn Leu Lys Arg Leu Met
```

FIG. 1A-3

```
        1089        1098        1107        1116        1125        1134
GAC AGC TGT TCT GGA AAC GCC ACT GCC CCG TCC GTC CCC ACG ACA ACT ACA ACA
--- --- --- --- --- --- --- --- --- --- --- --- --- --- --- --- --- ---
Asp Ser Cys Ser Gly Asn Ala Thr Ala Pro Ser Val Pro Thr Thr Thr Thr Thr 1143        1152        1161        1170        1179        1188
ACA AGC ACA CCG CCA ACG ACC ACA ACG ACT ACA ACA TCC ACT CCA ACG ACC ACT
--- --- --- --- --- --- --- --- --- --- --- --- --- --- --- --- --- ---
Thr Ser Thr Pro Pro Thr Thr Thr Thr Thr Thr Thr Ser Thr Pro Thr Thr Thr 1197        1206        1215        1224        1233        1242
ACC CAG ACC CCG ACC ACC ACT ACT CCA ACT ACG ACA ACC ACC ACG ACC ACA ACT
--- --- --- --- --- --- --- --- --- --- --- --- --- --- --- --- --- ---
Thr Gln Thr Pro Thr Thr Thr Thr Pro Thr Thr Thr Thr Thr Thr Thr Thr Thr 1251        1260        1269        1278        1287        1296
CCT TCA AAT AAC GTC CCA TTT GAA ATT GTG AAC GTT CTC CCG ACT AGC TCC CAG
--- --- --- --- --- --- --- --- --- --- --- --- --- --- --- --- --- ---
Pro Ser Asn Asn Val Pro Phe Glu Ile Val Asn Val Leu Pro Thr Ser Ser Gln 1305        1314        1323        1332        1341        1350
TAC GAG GGA ACC AGC GTG GAG GTT GTA TGT GAT GGA ACC CAG TGT GCC TCC AGC
--- --- --- --- --- --- --- --- --- --- --- --- --- --- --- --- --- ---
Tyr Glu Gly Thr Ser Val Glu Val Val Cys Asp Gly Thr Gln Cys Ala Ser Ser 1359        1368        1377        1386        1395        1404
GTT TGG GGA GCT CCG AAC CTC TGG GGA GTC GTT AAA ATC GGA AAC GCC ACC ATG
--- --- --- --- --- --- --- --- --- --- --- --- --- --- --- --- --- ---
Val Trp Gly Ala Pro Asn Leu Trp Gly Val Val Lys Ile Gly Asn Ala Thr Met 1413        1422        1431        1440        1449        1458
GAC CCC AAC GTT TGG GGC TGG GAG GAC GTT TAC AAG ACT GCA CCC CAG GAC ATT
--- --- --- --- --- --- --- --- --- --- --- --- --- --- --- --- --- ---
Asp Pro Asn Val Trp Gly Trp Glu Asp Val Tyr Lys Thr Ala Pro Gln Asp Ile 1467        1476        1485        1494        1503        1512
```

FIG. 1A-4

```
GGA ACC GGC AGC ACA AAG ATG GAG ATA AGG AAC GGG GTG CTC AAG GTT ACA AAC
--- --- --- --- --- --- --- --- --- --- --- --- --- --- --- --- --- ---
Gly Thr Gly Ser Thr Lys Met Glu Ile Arg Asn Gly Val Leu Lys Val Thr Asn 1521      1530      1539      1548      1557      1566
CTC TGG AAC ATC AAC ATG CAT CCG AAG TAT AAC ACA ATG GCA TAC CCG GAG GTC
--- --- --- --- --- --- --- --- --- --- --- --- --- --- --- --- --- ---
Leu Trp Asn Ile Asn Met His Pro Lys Tyr Asn Thr Met Ala Tyr Pro Glu Val 1575      1584      1593      1602      1611      1620
ATA TAC GGC GCC AAG CCT TGG GGC AAC CAG CCA ATA AAC GCT CCG AAC TTC GTG
--- --- --- --- --- --- --- --- --- --- --- --- --- --- --- --- --- ---
Ile Tyr Gly Ala Lys Pro Trp Gly Asn Gln Pro Ile Asn Ala Pro Asn Phe Val 1629      1638      1647      1656      1665      1674
CTC CCG ATA AAG GTC TCC CAG CTT CCG AGG ATA CTC GTT GAC ACA AAG TAC ACG
--- --- --- --- --- --- --- --- --- --- --- --- --- --- --- --- --- ---
Leu Pro Ile Lys Val Ser Gln Leu Pro Arg Ile Leu Val Asp Thr Lys Tyr Thr
        1683      1692      1701      1710      1719      1728
CTC GAA AAG AGC TTC CCG GGA AAC AAC TTC GCC TTT GAG GCC TGG CTC TTC AAG
--- --- --- --- --- --- --- --- --- --- --- --- --- --- --- --- --- ---
Leu Glu Lys Ser Phe Pro Gly Asn Asn Phe Ala Phe Glu Ala Trp Leu Phe Lys 1737      1746      1755      1764      1773      1782
GAT GCC AAC AAC ATG AGG GCA CCA GGC CAG GGG GAC TAC GAG ATA ATG GTA CAG
--- --- --- --- --- --- --- --- --- --- --- --- --- --- --- --- --- ---
Asp Ala Asn Asn Met Arg Ala Pro Gly Gln Gly Asp Tyr Glu Ile Met Val Gln 1791      1800      1809      1818      1827      1836
CTC TAC ATC GAG GGC GGC TAT CCT GCG GGC TAC GAC AAG GGG CCA GTT CTC ACC
--- --- --- --- --- --- --- --- --- --- --- --- --- --- --- --- --- ---
Leu Tyr Ile Glu Gly Gly Tyr Pro Ala Gly Tyr Asp Lys Gly Pro Val Leu Thr 1845      1854      1863      1872      1881      1890
GTT GAT GTT CCG ATA ATC GTC GAT GGA AGG CTT GTA AAC CAG ACT TTT GAG CTC
```

FIG. 1A-5

```
    ---  ---  ---  ---  ---  ---  ---  ---  ---  ---  ---  ---  ---  ---  ---  ---  ---
    Val  Asp  Val  Pro  Ile  Ile  Val  Asp  Gly  Arg  Leu  Val  Asn  Gln  Thr  Phe  Glu  Leu 1899           1908           1917           1926           1935           1944
    TAC  GAC  GTC  ATA  GCG  GAT  GCC  GGA  TGG  AGG  TTC  TTC  ACC  TTC  AAG  CCA  ACT  AAG
    ---  ---  ---  ---  ---  ---  ---  ---  ---  ---  ---  ---  ---  ---  ---  ---  ---
    Tyr  Asp  Val  Ile  Ala  Asp  Ala  Gly  Trp  Arg  Phe  Phe  Thr  Phe  Lys  Pro  Thr  Lys 1953           1962           1971           1980           1989           1998
    AAC  TAC  AAC  GGC  TCA  GAG  GTT  GTG  TTC  GAC  TAC  ACC  AAA  TTC  ATA  GAA  ATA  GTT
    ---  ---  ---  ---  ---  ---  ---  ---  ---  ---  ---  ---  ---  ---  ---  ---  ---
    Asn  Tyr  Asn  Gly  Ser  Glu  Val  Val  Phe  Asp  Tyr  Thr  Lys  Phe  Ile  Glu  Ile  Val 2007           2016           2025           2034           2043           2052
    GAC  AAC  TAC  CTC  GGC  GGT  GGC  AGC  CTC  ACG  AAC  CAC  TAC  CTG  ATG  TCC  CTG  GAA
    ---  ---  ---  ---  ---  ---  ---  ---  ---  ---  ---  ---  ---  ---  ---  ---  ---
    Asp  Asn  Tyr  Leu  Gly  Gly  Gly  Ser  Leu  Thr  Asn  His  Tyr  Leu  Met  Ser  Leu  Glu 2061           2070           2079           2088           2097           2106
    TTC  GGT  ACC  GAG  ATA  TAC  ACC  AAC  GGG  TGC  ACC  TCA  TTC  CCA  TGC  ACA  GTG  GAC
    ---  ---  ---  ---  ---  ---  ---  ---  ---  ---  ---  ---  ---  ---  ---  ---  ---
    Phe  Gly  Thr  Glu  Ile  Tyr  Thr  Asn  Gly  Cys  Thr  Ser  Phe  Pro  Cys  Thr  Val  Asp
         2115           2124           2133           2142           2151           2160
    GTA  AGG  TGG  ACC  CTT  GAC  AAG  TAC  AGG  TTC  ATC  CTG  GCC  CCA  GGA  ACA  ATG  GCC
    ---  ---  ---  ---  ---  ---  ---  ---  ---  ---  ---  ---  ---  ---  ---  ---  ---
    Val  Arg  Trp  Thr  Leu  Asp  Lys  Tyr  Arg  Phe  Ile  Leu  Ala  Pro  Gly  Thr  Met  Ala 2169           2178           2187           2196           2205           2214
    ACT  GAG  GAG  GCC  ATG  AGA  GTT  CTC  GTC  GGA  GAG  GTC  CAG  CCT  CCC  GCT  TCC  ACA
    ---  ---  ---  ---  ---  ---  ---  ---  ---  ---  ---  ---  ---  ---  ---  ---  ---
    Thr  Glu  Glu  Ala  Met  Arg  Val  Leu  Val  Gly  Glu  Val  Gln  Pro  Pro  Ala  Ser  Thr 2223           2232           2241           2250           2259           2268
    ACA  ACA  TCG  CAG  ACG  ACT  ACT  TCA  ACC  ACA  ACC  CCA  ACG  CCC  ACT  ACC  ACT  ACT
    ---  ---  ---  ---  ---  ---  ---  ---  ---  ---  ---  ---  ---  ---  ---  ---  ---
```

FIG. 1A-6

```
Thr Thr Ser Gln Thr Thr Thr Ser Thr Thr Thr Pro Thr Pro Thr Thr Thr Thr 2277         2286         2295         2304         2313         2322
ACG ACT CAG ACT TCA ACC ACC ACT ACA ACC ACC TCA CCG CCG ACA ACC ACC GCA
--- --- --- --- --- --- --- --- --- --- --- --- --- --- --- --- --- ---
Thr Thr Gln Thr Ser Thr Thr Thr Thr Thr Thr Ser Pro Pro Thr Thr Thr Ala 2331         2340         2349         2358         2367         2376
CCT GCT CAG GAC GTA ATT AAG CTC AGG TAC CCG GAC GAT GGG CAG TGG CCC GAG
--- --- --- --- --- --- --- --- --- --- --- --- --- --- --- --- --- ---
Pro Ala Gln Asp Val Ile Lys Leu Arg Tyr Pro Asp Asp Gly Gln Trp Pro Glu 2385         2394         2403         2412         2421         2430
GCC CCA ATT GAC AGG GAT GGA GAC GGA AAC CCA GAG TTC TAC ATA GAA ATA AAC
--- --- --- --- --- --- --- --- --- --- --- --- --- --- --- --- --- ---
Ala Pro Ile Asp Arg Asp Gly Asp Gly Asn Pro Glu Phe Tyr Ile Glu Ile Asn 2439         2448         2457         2466         2475         2484
CCG TGG AAC ATA CTG AGC GCT GAA AGC TAC GCC GAG ATG ACC TAC AAC TTG AGC
--- --- --- --- --- --- --- --- --- --- --- --- --- --- --- --- --- ---
Pro Trp Asn Ile Leu Ser Ala Glu Ser Tyr Ala Glu Met Thr Tyr Asn Leu Ser 2493         2502         2511         2520         2529
AGC GGG GTT CTC CAC TAC GTC CAG GCC CTG GAT AGT ATA TGA TGA 3'
--- --- --- --- --- --- --- --- --- --- --- --- --- --- ---
Ser Gly Val Leu His Tyr Val Gln Ala Leu Asp Ser Ile *** ***
```

FIG. 1A-7

(SEQ ID NO:3 - nucleotide sequence and SEQ ID NO:4 - amino acid sequence)
OC9a (clone # 27GA1) Glycosidase

```
  1
ATG CCA ACC AAT GTA TTT TTC AAC GCC CAT CAC TCG CCG GTT GGG GCG TTT
Met Pro Thr Asn Val Phe Phe Asn Ala His His Ser Pro Val Gly Ala Phe

GCC AGC TTT ACG CTA GGG TTT CCG GGA AAA AGC GGA GGA CTG GAC TTG GAA
Ala Ser Phe Thr Leu Gly Phe Pro Gly Lys Ser Gly Gly Leu Asp Leu Glu

CTT GCC CGA CCG CCA CGG CAA AAT GTC TTT ATT GGC GTT GAG TCG CCG CAT
Leu Ala Arg Pro Pro Arg Gln Asn Val Phe Ile Gly Val Glu Ser Pro His

GAG CCG GGG CTG TAT CAT ATC CTT CCA TTC GCG GAA ACA GCA GGC GAG GAT
Glu Pro Gly Leu Tyr His Ile Leu Pro Phe Ala Glu Thr Ala Gly Glu Asp

GAA AGC AAA CGA TAT GAC ATT GAA AAT CCT GAT CCG AAT CCG CAA AAA CCA
Glu Ser Lys Arg Tyr Asp Ile Glu Asn Pro Asp Pro Asn Pro Gln Lys Pro

AAC ATC CTG ATT CCA TTT GCG AAA GAG CGG ATC GAA CGC GAA TTT CGC GTT
Asn Ile Leu Ile Pro Phe Ala Lys Glu Arg Ile Glu Arg Glu Phe Arg Val

GCC ACG GAT ACA TGG AAG GCC GGG GAC TTG ACG TTG ACG ATT TAT TCA CCG
Ala Thr Asp Thr Trp Lys Ala Gly Asp Leu Thr Leu Thr Ile Tyr Ser Pro
```

FIG. 1B-1

GTG AAG GCC GTA CCA GAT CCG GAA ACG GCC TCC GAG GAA GAA CTC AAG TTG
Val Lys Ala Val Pro Asp Pro Glu Thr Ala Ser Glu Glu Glu Leu Lys Leu

GCG TTG GTT CCA GCT GTC ATT GTC GAG ATG ACG ATC GAT AAT ACG AAC GGA
Ala Leu Val Pro Ala Val Ile Val Glu Met Thr Ile Asp Asn Thr Asn Gly

ACA AGA ACA CGA CGG GCG TTT TTC GGA TTC GAA GGC ACT GAC CCG TAT ACC
Thr Arg Thr Arg Arg Ala Phe Phe Gly Phe Glu Gly Thr Asp Pro Tyr Thr

TCG ATG CGG GGG ATC GAT GAT ACA TGC CCG CAG CTG CGC GGT GTC GGT CAA
Ser Met Arg Gly Ile Asp Asp Thr Cys Pro Gln Leu Arg Gly Val Gly Gln

GGG CGG ATT TTG GGC ATA GCA TCC AAG GAT GAG GGC GTT CGT TCA GCA CTG
Gly Arg Ile Leu Gly Ile Ala Ser Lys Asp Glu Gly Val Arg Ser Ala Leu

CAT TTT AGC ATG GAG GAT ATC TTA ACG GCG ACT CTC GAA GAA AAC TGG ACG
His Phe Ser Met Glu Asp Ile Leu Thr Ala Thr Leu Glu Glu Asn Trp Thr

TTT GGG CTC GGG AAA GTC GGT GCA TTA ATT GCG GAT GTG CCG GCG GGA GAA
Phe Gly Leu Gly Lys Val Gly Ala Leu Ile Ala Asp Val Pro Ala Gly Glu

AAG AAA ACG TAT CAA TTT GCT GTT TGC TTC TAT CGT GGG GGT TGT GTG ACG
Lys Lys Thr Tyr Gln Phe Ala Val Cys Phe Tyr Arg Gly Gly Cys Val Thr

FIG. 1B-2

```
GCG GGA ATG GAT GCC TCT TAT TTT TAC ACC CGT TTC TTC CAT AAT ATC GAA
Ala Gly Met Asp Ala Ser Tyr Phe Tyr Thr Arg Phe Phe His Asn Ile Glu

GAA GTC GGT CTT TAT GCG TTA GAG CAG GCC GAG GTG TTA AAA GAG CAG GCG
Glu Val Gly Leu Tyr Ala Leu Glu Gln Ala Glu Val Leu Lys Glu Gln Ala

TTC CGT TCG AAT GAA CTC ATT GAA AAA GAA TGG CTC TCC GAT GAT CAA AAG
Phe Arg Ser Asn Glu Leu Ile Glu Lys Glu Trp Leu Ser Asp Asp Gln Lys

TTT ATG ATG GCG CAC GCG ATC CGT AGC TAC TAT GGC AAT ACA CAG CTG CTT
Phe Met Met Ala His Ala Ile Arg Ser Tyr Tyr Gly Asn Thr Gln Leu Leu

GAG CAT GAA GGA AAG CCG ATT TGG GTC GTC AAT GAA GGC GAG TAC CGG ATG
Glu His Glu Gly Lys Pro Ile Trp Val Val Asn Glu Gly Glu Tyr Arg Met

ATG AAT ACG TTT GAT CTC ACC GTC GAC CAG CTC TTT TTT GAA TTG AAA ATG
Met Asn Thr Phe Asp Leu Thr Val Asp Gln Leu Phe Phe Glu Leu Lys Met

AAT CCG TGG ACG GTG AAA AAT GTG CTT GAC TTT TAT GTC GAG CGC TAC AGC
Asn Pro Trp Thr Val Lys Asn Val Leu Asp Phe Tyr Val Glu Arg Tyr Ser

TAT GAG GAT CGT GTC CGT TTC CCA GGA GAT GAG ACG GAA TAC CCC GGC GGC
```

FIG. 1B-3

```
Tyr Glu Asp Arg Val Arg Phe Pro Gly Asp Glu Thr Glu Tyr Pro Gly Gly

ATC AGC TTC ACT CAC GAT ATG GGA GTC GCC AAC ACG TTC TCA CGC CCG CAT
Ile Ser Phe Thr His Asp Met Gly Val Ala Asn Thr Phe Ser Arg Pro His

TAC TCG TCA TAT GAG CTA TAC GGG ATC AGC GGC TGC TTT TCA CAT ATG ACG
Tyr Ser Ser Tyr Glu Leu Tyr Gly Ile Ser Gly Cys Phe Ser His Met Thr

CAC GAA CAG CTC GTC AAC TGG GTG CTT TGC GCA GCG GTA TAC ATC GAA CAA
His Glu Gln Leu Val Asn Trp Val Leu Cys Ala Ala Val Tyr Ile Glu Gln

ACG AAA GAC TGG GCA TGG CGC GAC CGG CGG CTT ACG ATC TTG GAA CAA TGT
Thr Lys Asp Trp Ala Trp Arg Asp Arg Arg Leu Thr Ile Leu Glu Gln Cys

CTC GAA AGC ATG GTG CGC CGC GAT CAT CCG GAT CCA GAA AAG CGG AAC GGC
Leu Glu Ser Met Val Arg Arg Asp His Pro Asp Pro Glu Lys Arg Asn Gly

GTG ATG GGG CTT GAC AGC ACC CGC ACG ATG GGT GGA GCG GAA ATC ACA ACG
Val Met Gly Leu Asp Ser Thr Arg Thr Met Gly Gly Ala Glu Ile Thr Thr

TAT GAT AGT TTG GAT GTT TCT CTT GGC CAG GCG CGC AAC AAT TTA TAT TTG
Tyr Asp Ser Leu Asp Val Ser Leu Gly Gln Ala Arg Asn Asn Leu Tyr Leu
```

FIG. 1B-4

```
GCA GGA AAA TGT TGG GCT GCC TAT GTG GCG CTC GAA AAG TTG TTC CGC GAT
Ala Gly Lys Cys Trp Ala Ala Tyr Val Ala Leu Glu Lys Leu Phe Arg Asp

GTC GGC AAA GAA GAA CTG GCT GCA TTG GCA AGG GAG CAG GCG GAA AAA TGC
Val Gly Lys Glu Glu Leu Ala Ala Leu Ala Arg Glu Gln Ala Glu Lys Cys

GCC GCG ACG ATT GTC AGT CAC GTG ACG GAG GAC GGG TAT ATC CCA GCC GTG
Ala Ala Thr Ile Val Ser His Val Thr Glu Asp Gly Tyr Ile Pro Ala Val

ATG GGA GAA GGA AAT GAC TCG AAA ATC ATT CCG GCT ATT GAG GGG CTT GTG
Met Gly Glu Gly Asn Asp Ser Lys Ile Ile Pro Ala Ile Glu Gly Leu Val

TTT CCT TAC TTT ACG AAC TGC CAT GAG GCG TTA AGA GAA GAC GGA CGT TTT
Phe Pro Tyr Phe Thr Asn Cys His Glu Ala Leu Arg Glu Asp Gly Arg Phe

GGA GAC TAT ATT CGT GCA CTG CGA CAA CAT TTG CAA TAT GTG TTG CGG GAA
Gly Asp Tyr Ile Arg Ala Leu Arg Gln His Leu Gln Tyr Val Leu Arg Glu

GGA ATT TAC CTA TTC CCG GAC GGG GGA TGG AAA ATT TGC CTC GAC AAG CAA
Gly Ile Tyr Leu Phe Pro Asp Gly Gly Trp Lys Ile Cys Leu Asp Lys Gln

CAA CTC GTG GTT GAG CAA AAT TTA CTT ATG CCA GTT TAT TGC CCG CCG CAT
Gln Leu Val Val Glu Gln Asn Leu Leu Met Pro Val Tyr Cys Pro Pro His
```

FIG. 1B-5

```
TTT AGG GTG GGA ATG GGA TGA        1958
Phe Arg Val Gly Met Gly END
```

FIG. 1B-6

(SEQ ID NO:5 - nucleotide sequence and SEQ ID NO:6 - amino acid sequence)
Bankia gouldi mix (Clone # 37GP2) Glycosidase 1
ATG TTG AAA AAA CTG GCT TTA GCA GCC GGG ATC GCA GCA GCA ACA CTG GCT
Met Leu Lys Lys Leu Ala Leu Ala Ala Gly Ile Ala Ala Ala Thr Leu Ala GCA TCC GGT TCC CAT GGG CAG ACG TTC GCG TAC GGC GAA GCT CTG CAA AAA
Ala Ser Gly Ser His Gly Gln Thr Phe Ala Tyr Gly Glu Ala Leu Gln Lys TCC ATC TAT TTT TAT GAG GCT CAA CAG GCC GGC CCA CTC CCG GAA TGG AAC
Ser Ile Tyr Phe Tyr Glu Ala Gln Gln Ala Gly Pro Leu Pro Glu Trp Asn CGC GTT GCC TGG CGT GGC GAC TCA GTT CCT GAT GAC GGT GCC GAC GTC GGA
Arg Val Ala Trp Arg Gly Asp Ser Val Pro Asp Asp Gly Ala Asp Val Gly CTG GAT TTA CGC GGT GGC TGG TTC GAT GCG GGC GAC CAC GTT AAG TTT GGC
Leu Asp Leu Arg Gly Gly Trp Phe Asp Ala Gly Asp His Val Lys Phe Gly TTT CCA ATG GCC GCG TCA GCG ACA CTC GTC GCC TGG GGA GGC GTC GAT TAC
Phe Pro Met Ala Ala Ser Ala Thr Leu Val Ala Trp Gly Gly Val Asp Tyr AAA GAC GCG TAC GAA CAG TCG GGG CAA ATG GAA CAT CTG CGC AAC AAC CTG
Lys Asp Ala Tyr Glu Gln Ser Gly Gln Met Glu His Leu Arg Asn Asn Leu

FIG. 1C-1

```
CGC TTC GTC AAT GAC TAC TTT ATC AGC GCG CAC CCC GCT CCG AAC GTG CTT
Arg Phe Val Asn Asp Tyr Phe Ile Ser Ala His Pro Ala Pro Asn Val Leu

TAC GGG CAG GTT GGC GAT GGC AGT GCA GAC CAT ACC TTC TGG GGT CCC GCT
Tyr Gly Gln Val Gly Asp Gly Ser Ala Asp His Thr Phe Trp Gly Pro Ala

GAG GTT CTG CAC CAC AAG ATC CCC GGC TCG CGC ATT TCT ATG AAG ATT GAC
Glu Val Leu His His Lys Ile Pro Gly Ser Arg Ile Ser Met Lys Ile Asp

GAA AGC TGC CCG GGT ACC GAT CTG GCC GCA GAG ACC GCA GCA GCG ATG GCC
Glu Ser Cys Pro Gly Thr Asp Leu Ala Ala Glu Thr Ala Ala Ala Met Ala

GCG TCT GCG ATG GTT TTT CAG GGT GAG GAC GAT GCT TAC GCA GCA ACC CTG
Ala Ser Ala Met Val Phe Gln Gly Glu Asp Asp Ala Tyr Ala Ala Thr Leu

ATC ACT CAC GCC AAA CAG CTG TGG CAA TTT GCT GAT TCA ACC AAA GGC ACA
Ile Thr His Ala Lys Gln Leu Trp Gln Phe Ala Asp Ser Thr Lys Gly Thr

ACC GGT ACA GAT ACA GCC TAT TCC AAT TGC ATA ACA GGT GCA CAG GGC TTT
Thr Gly Thr Asp Thr Ala Tyr Ser Asn Cys Ile Thr Gly Ala Gln Gly Phe

TAT ACG TCG ACG TAT GGC GTT TAC TAC GAT GAA CTT GCC TGG GGT GCT CTC
Tyr Thr Ser Thr Tyr Gly Val Tyr Tyr Asp Glu Leu Ala Trp Gly Ala Leu
```

FIG. 1C-2

```
TGG TTA TGG CGC GCA ACT GGA GAA GAC TTC TAC CTG GAA CAA GCC AAG CAT
Trp Leu Trp Arg Ala Thr Gly Glu Asp Phe Tyr Leu Glu Gln Ala Lys His

TAC TAC GGT TTG ATG GGC TTT GAA AAC CAG ACG ACA ACT CCG GTA TAT ACC
Tyr Tyr Gly Leu Met Gly Phe Glu Asn Gln Thr Thr Thr Pro Val Tyr Thr

TGG TCG CTT GGC TGG AAC GAT AAA GCG TAT GCC GTT TAT GTA CTT ATG GCC
Trp Ser Leu Gly Trp Asn Asp Lys Ala Tyr Ala Val Tyr Val Leu Met Ala

GCA CTT GTA GGT GAC GAG GTT TAC CAC GCA GAT GCA CAG CGC TAC CTG GAT
Ala Leu Val Gly Asp Glu Val Tyr His Ala Asp Ala Gln Arg Tyr Leu Asp

CAC TGG AGC GTC GGC GAG GGT AAC CGC ACA CCC AAT GGG CTG ATT CTG GTC
His Trp Ser Val Gly Glu Gly Asn Arg Thr Pro Asn Gly Leu Ile Leu Val

GAC TCC TGG GGG GTA AAC CGC TAT GCG GCC AAC GCG GGT TAT CTC GCA CTC
Asp Ser Trp Gly Val Asn Arg Tyr Ala Ala Asn Ala Gly Tyr Leu Ala Leu

TTT TAT GCA GAT GCG ATT GGC AGT GAC CAC CCC CTT TAT GAT CGT TAC CAC
Phe Tyr Ala Asp Ala Ile Gly Ser Asp His Pro Leu Tyr Asp Arg Tyr His

AAT TTT GGT AAG AAG CAG ATC GAT CAT ATC CTG GGC GAC AAC CCT GAC AAC
```

FIG. 1C-3

```
Asn Phe Gly Lys Lys Gln Ile Asp His Ile Leu Gly Asp Asn Pro Asp Asn

CAA AGC TAC GTC GTC GGC TTT GGC GAT AAT TTC CCA ATC AAT GTT CAC CAC
Gln Ser Tyr Val Val Gly Phe Gly Asp Asn Phe Pro Ile Asn Val His His

CGT GGC TCC CAC GGT TCC TGG TCC GAC AGC ATT TCC AAC CCG GTT AAT CAA
Arg Gly Ser His Gly Ser Trp Ser Asp Ser Ile Ser Asn Pro Val Asn Gln

CGC CAT GTG CTA TAC GGC GCA GTT GCC GGT GGT CCG CAG GGC GAT ACA GGC
Arg His Val Leu Tyr Gly Ala Val Ala Gly Gly Pro Gln Gly Asp Thr Gly

TAT GAA GAA GAC CGC AAT GAC TAT GTG CAG AAT GAG GTC GCA ACA GAC TAC
Tyr Glu Glu Asp Arg Asn Asp Tyr Val Gln Asn Glu Val Ala Thr Asp Tyr

AAC TCA GGC TTC ACC AGT GCC GTC GCT GCA CTT TAT GAT CAC TAT GGT GGC
Asn Ser Gly Phe Thr Ser Ala Val Ala Ala Leu Tyr Asp His Tyr Gly Gly

GCG CCC CTG GCG AAC TTC CCG CCT CCC GAA CCA GAG TCG GTG GAG TAT CTG
Ala Pro Leu Ala Asn Phe Pro Pro Pro Glu Pro Glu Ser Val Glu Tyr Leu

GTG GGG GCC AAG ATC AAT TCC TCT GGC AAC CGC TTC GTG GAA ATG AAA GCC
Val Gly Ala Lys Ile Asn Ser Ser Gly Asn Arg Phe Val Glu Met Lys Ala
```

FIG. 1C-4

```
GTT ATT CAA AAC CAC AGC ACA ACA CCC GCC CAA GGT AAA GAC GAC CTT TAC
Val Ile Gln Asn His Ser Thr Thr Pro Ala Gln Gly Lys Asp Asp Leu Tyr

ATG CGC TAT TTC TAT GAT CTG AGC GAA GTA TTT GCC GCA GGC TAC AGT TTG
Met Arg Tyr Phe Tyr Asp Leu Ser Glu Val Phe Ala Ala Gly Tyr Ser Leu

AAT GAT CTA ACG GTG GCG TCC GGA TAC AAC CAA GCC TCG GAT GTG AAT GGC
Asn Asp Leu Thr Val Ala Ser Gly Tyr Asn Gln Ala Ser Asp Val Asn Gly

CTG CAA CAT TGG GAT GGC AAC GTC TAC TAT GTG GAA GCC CAG TTC TAT GAC
Leu Gln His Trp Asp Gly Asn Val Tyr Tyr Val Glu Ala Gln Phe Tyr Asp

GAT GTG GTA TTT CCC GGT GGT CAG TCC GCG CAC CGA CGG GAA GTA CAA TTT
Asp Val Val Phe Pro Gly Gly Gln Ser Ala His Arg Arg Glu Val Gln Phe

CGC GTG TCC CTG CCA ACC ACA TCC AAT CTT GCC GAG TGG GAC AAC ACG AAC
Arg Val Ser Leu Pro Thr Thr Ser Asn Leu Ala Glu Trp Asp Asn Thr Asn

GAC CCC TCG TTT GAT CCA AGT TAT TTA ACG GTC GAT AGT AGT CTG ACT TAC
Asp Pro Ser Phe Asp Pro Ser Tyr Leu Thr Val Asp Ser Ser Leu Thr Tyr

GGT ATC GAC GCG CCG AAA ATT CCA CTC TAC GAC GCC AAC GGC CTG CTC TGG
Gly Ile Asp Ala Pro Lys Ile Pro Leu Tyr Asp Ala Asn Gly Leu Leu Trp
```

FIG. 1C-5

```
GGC GAG GAG CCA CCC CGT GGC GGA ACT TCC TCC AGC TCA TCG TCG AGC AGT
Gly Glu Glu Pro Pro Arg Gly Gly Thr Ser Ser Ser Ser Ser Ser Ser Ser

TCG TCC TCT AGC TCA TCC AGC AGT TCA TCG TCG AGC AGC TCC TCG AGC AGT
Ser Ser Ser Ser Ser Ser Ser Ser Ser Ser Ser Ser Ser Ser Ser Ser Ser

TCG TCC TCG AGT AAT TCG TCC TCT AGC TCG TCC AGC TCT TCG TCG AAT TCT
Ser Ser Ser Ser Asn Ser Ser Ser Ser Ser Ser Ser Ser Ser Ser Asn Ser

TCG TCG TCT AAC AGC AGT TCC TCG TCC AGC TCA AGC TCA TCG AGC AGT TCC
Ser Ser Ser Asn Ser Ser Ser Ser Ser Ser Ser Ser Ser Ser Ser Ser Ser

AGT TCG TCG AGT TCG GGC GGC ACC TGT GCG GAC GTG AAC GTA TAC CCC AAC
Ser Ser Ser Ser Ser Gly Gly Thr Cys Ala Asp Val Asn Val Tyr Pro Asn

TGG ACC GCA CGT GAC TGG GCC GGT GGA GTA CCG AAC CAC GCG GAA GCC GGT
Trp Thr Ala Arg Asp Trp Ala Gly Gly Val Pro Asn His Ala Glu Ala Gly

GAT TTG ATG GTT TAC CAA GGT ACT GTC TAC CAA GCT AAT TGG TAC ACC AAC
Asp Leu Met Val Tyr Gln Gly Thr Val Tyr Gln Ala Asn Trp Tyr Thr Asn

AGT GTG CCT GGC AGT GAT GCA TCC TGG ACC AAC CAA GGG TTA TGT GCC GGC
```

FIG. 1C-6

```
Ser Val Pro Gly Ser Asp Ala Ser Trp Thr Asn Gln Gly Leu Cys Ala Gly

GGC GGA TCC AGC TCC AGC AGC TCA TCA TCC AGC TCA AGC AGC TCT TCG TCC
Gly Gly Ser Ser Ser Ser Ser Ser Ser Ser Ser Ser Ser Ser Ser Ser Ser

AGC AGC AGC TCA AGC TCG TCC AGT GGT GCG TCC GGT TCA TCC TCC AGC TCG
Ser Ser Ser Ser Ser Ser Ser Ser Gly Ala Ser Gly Ser Ser Ser Ser Ser

AGC AGT TCG TCC TCG TCA AGT TCG AGC AGC AGC TCT TCG AGT TCG TCT TCT
Ser Ser Ser Ser Ser Ser Ser Ser Ser Ser Ser Ser Ser Ser Ser Ser Ser

GGT GGC GGC GCC ATG TGT AAC TGG TAT GGC TGG CAA GTA CCT ATT TGT GAA
Gly Gly Gly Ala Met Cys Asn Trp Tyr Gly Trp Gln Val Pro Ile Cys Glu

AAC ACC CCA TCT GGC TGG GGC AAC GAA AAT GGC CAA ACA TGT GTC GGC CCC
Asn Thr Pro Ser Gly Trp Gly Asn Glu Asn Gly Gln Thr Cys Val Gly Pro

GAT ACT TGC CAA GAG GTC GTC AAC TAA         2627
Asp Thr Cys Gln Glu Val Val Asn END
```

FIG. 1C-7

(SEQ ID NO:7 - nucleotide sequence and SEQ ID NO:8 - amino acid sequence)
Banki gouldi mix (Clone # 37GP3) Glycosidase
1

ATG AAG ATG ACC TAC ATG CAT CCG GCT GAA GAT ACT TAC TCG TTT GGT CAA
Met Lys Met Thr Tyr Met His Pro Ala Glu Asp Thr Tyr Ser Phe Gly Gln

GCG GAT CAG TTG GTC AAC TGG GCG AAA GCG AAT GGT ATT GGC GTG CAC GGC
Ala Asp Gln Leu Val Asn Trp Ala Lys Ala Asn Gly Ile Gly Val His Gly

CAC ACT CTG GTT TGG CAC TCC GAA TAC CAG GTA CCC AAT TGG ATG AAA AAT
His Thr Leu Val Trp His Ser Glu Tyr Gln Val Pro Asn Trp Met Lys Asn

TAC TCT GGT GAT GCA ACT GCA TTC CAA ACC ATG CTC AAC ACC CAT GTG AAA
Tyr Ser Gly Asp Ala Thr Ala Phe Gln Thr Met Leu Asn Thr His Val Lys

ACT GTG GCT GAG CAT TTT GCT GGC GAA CTG GAC AGC TGG GAC GTT GTG AAT
Thr Val Ala Glu His Phe Ala Gly Glu Leu Asp Ser Trp Asp Val Val Asn

GAA GTG CTG GAG CCG GGC TCC AAT GGT TGC TGG CGT GAA AAC TCT CTG TTC
Glu Val Leu Glu Pro Gly Ser Asn Gly Cys Trp Arg Glu Asn Ser Leu Phe

TAC CAG AAG CTT GGC AAA GAC TTT GTC GCG AAC GCA TTC CGT GCA GCT CGC
Tyr Gln Lys Leu Gly Lys Asp Phe Val Ala Asn Ala Phe Arg Ala Ala Arg

FIG. 1D-1

```
GAG GGC GAT CCC AAT GCA GAC TTG TAT TAC AAC GAT TAC TCG ACT GAA AAT
Glu Gly Asp Pro Asn Ala Asp Leu Tyr Tyr Asn Asp Tyr Ser Thr Glu Asn

GGT GTA ACT TCC GAT GAG AAG TTC AGT TGT TTG TTG GAA CTA GTC GAT GAG
Gly Val Thr Ser Asp Glu Lys Phe Ser Cys Leu Leu Glu Leu Val Asp Glu

CTT CTG GAA GCG GAC GTG CCG ATT ACA GGT GTT GGT TTC CAA ATG CAC GTG
Leu Leu Glu Ala Asp Val Pro Ile Thr Gly Val Gly Phe Gln Met His Val

CAG GCG ACG TGG CCT AGC AAT GCC AAC ATC GGC AAG GCA TTC AAA GCC ATC
Gln Ala Thr Trp Pro Ser Asn Ala Asn Ile Gly Lys Ala Phe Lys Ala Ile

GCG GAT CGC GGT CTG AAA GTT AAA ATT TCT GAG CTC GAT GTT CCT GTT AAC
Ala Asp Arg Gly Leu Lys Val Lys Ile Ser Glu Leu Asp Val Pro Val Asn

AAC CCT TAC GGA ACC ACT AAT TTC CCG CAA TAC AGC AGT TTT ACC GCG GAA
Asn Pro Tyr Gly Thr Thr Asn Phe Pro Gln Tyr Ser Ser Phe Thr Ala Glu

GCC GCC GAG CTG CAG AAG CAG CGC TAC AAG GGC ATT ATG CAA GCG TAC CTT
Ala Ala Glu Leu Gln Lys Gln Arg Tyr Lys Gly Ile Met Gln Ala Tyr Leu

GAT AAC GTA CCG GCC AAC CTG CGT GGT GGT TTC ACC GTG TGG GGC GTT TGG
Asp Asn Val Pro Ala Asn Leu Arg Gly Gly Phe Thr Val Trp Gly Val Trp
```

FIG. 1D-2

GAT GGC GAT AGC TGG ATC ATG ACG TTC AGC CAG TAC ACC AAC GCT AAC GCC
Asp Gly Asp Ser Trp Ile Met Thr Phe Ser Gln Tyr Thr Asn Ala Asn Ala

AAC GAC TGG CCA CTG TTG TTC ACC GGG CCG TAA        848
Asn Asp Trp Pro Leu Leu Phe Thr Gly Pro END

FIG. 1D-3

(SEQ ID NO:9 - nucleotide sequence and SEQ ID NO:10 - amino acid sequence)
Teredinibacter, pure (Clone # 42GP1) Glycosidase

1

ATG GGA ACA TCT CTT ATG ATC AAA TCT ACA CTG ACA GGT ATG ATT ACT GCT
Met Gly Thr Ser Leu Met Ile Lys Ser Thr Leu Thr Gly Met Ile Thr Ala

GTT GCC GCC GCA GTT TTC ACC ACC TCT GCA GCT TTC GCG GAT GTA CCT CCG
Val Ala Ala Ala Val Phe Thr Thr Ser Ala Ala Phe Ala Asp Val Pro Pro

TTG ACA GTG AGC GGA AAT CAG GTT TTA AGT GGC GGT GAA GCA AAA AGC TTC
Leu Thr Val Ser Gly Asn Gln Val Leu Ser Gly Gly Glu Ala Lys Ser Phe

GCT GGT AAC AGC TTC TTT TGG AGC AAT ACC GGA TGG GGC CAG GAA CGT TTT
Ala Gly Asn Ser Phe Phe Trp Ser Asn Thr Gly Trp Gly Gln Glu Arg Phe

TAC AAC GCA GAA ACT GTG CGT TGG TTG AAA GAC GAC TGG AAC GCA ACC ATT
Tyr Asn Ala Glu Thr Val Arg Trp Leu Lys Asp Asp Trp Asn Ala Thr Ile

GTC CGC GCC GCT ATG GGC GTA GAC TTT GAT GGC AGC TAT ATC CCC GAG CAT
Val Arg Ala Ala Met Gly Val Asp Phe Asp Gly Ser Tyr Ile Pro Glu His

GAA GAC GCC GAC CCC GAG GGT AAC GTC GCT CGC GTA CGT GCA TTG GTG GAT
Glu Asp Ala Asp Pro Glu Gly Asn Val Ala Arg Val Arg Ala Leu Val Asp

FIG. 1E-1

```
GCA GCC ATC GCA GAA GAC ATG TAC GTG ATT ATC GAT TTT CAC ACT CAC CAC
Ala Ala Ile Ala Glu Asp Met Tyr Val Ile Ile Asp Phe His Thr His His

GCA GAA GAT TAC CAA GCC GAA TCT ATC GAG TTC TTC GAA GAA ATG GCC ACA
Ala Glu Asp Tyr Gln Ala Glu Ser Ile Glu Phe Phe Glu Glu Met Ala Thr

CTG TAC GGT GGG TAC GAC AAT GTT ATT TAT GAA ATC TAT AAC GAG CCC CTG
Leu Tyr Gly Gly Tyr Asp Asn Val Ile Tyr Glu Ile Tyr Asn Glu Pro Leu

CAA ATC AGC TGG GAC AAT GTT ATT AAA CCT TAT GCA GAA TCG GTG ATT GGC
Gln Ile Ser Trp Asp Asn Val Ile Lys Pro Tyr Ala Glu Ser Val Ile Gly

GCT ATC CGC GCA ATC GAC CCG GAC AAC CTG ATT ATC GTC GGC ACG CCC ACT
Ala Ile Arg Ala Ile Asp Pro Asp Asn Leu Ile Ile Val Gly Thr Pro Thr

TGG TCA CAG GAC GTG GAC GCC GCT GCG CGC AAT CCA ATC ACC AGC TAC AGC
Trp Ser Gln Asp Val Asp Ala Ala Ala Arg Asn Pro Ile Thr Ser Tyr Ser

AAT ATT GCG TAC ACC CTG CAC TTT TAC GCA GGC ACT CAC GGT TCA TGG TTG
Asn Ile Ala Tyr Thr Leu His Phe Tyr Ala Gly Thr His Gly Ser Trp Leu

CGC GAT AAA GCG CGT AAC GCT ATG AAC AGT GGT ATT GCG CTG TTT GTG ACT
Arg Asp Lys Ala Arg Asn Ala Met Asn Ser Gly Ile Ala Leu Phe Val Thr
```

FIG. 1E-2

```
GAG TGG GGC ACC GTT AAT GCA GAT GGC GAT GGT GCG CCT GCA GTT AAC GAA
Glu Trp Gly Thr Val Asn Ala Asp Gly Asp Gly Ala Pro Ala Val Asn Glu

ACT CAG CAA TGG ATG GAC TTC CTC AAG CAG AAC AAT ATC TCT CAC TTG AAC
Thr Gln Gln Trp Met Asp Phe Leu Lys Gln Asn Asn Ile Ser His Leu Asn

TGG TCC GTG AGT GAT AAA TTG GAA GGT GCG TCT ATC GTA CAA CCT GGC ACG
Trp Ser Val Ser Asp Lys Leu Glu Gly Ala Ser Ile Val Gln Pro Gly Thr

CCC ATT AGC GGC TGG AAC GCT TCT GAC CTT ACG GCC TCC GGC ACA CTG GTT
Pro Ile Ser Gly Trp Asn Ala Ser Asp Leu Thr Ala Ser Gly Thr Leu Val

AAG AAC ATC GTT TCC AAC TGG GGC ACC ACA ATC GGT AAC GGC AGC TCC TCA
Lys Asn Ile Val Ser Asn Trp Gly Thr Thr Ile Gly Asn Gly Ser Ser Ser

AGT TCA TCC AGC TCC TCT TCC AGC TCT TCA AGC AGT TCT TCT TCG AGC AGT
Ser Ser Ser Ser Ser Ser Ser Ser Ser Ser Ser Ser Ser Ser Ser Ser Ser

TCC TCC TCC AGC AGC TCT TCC TCG TCA AGC AGC TCC GGA TCA ACT GGT GGC
Ser Ser Ser Ser Ser Ser Ser Ser Ser Ser Ser Ser Gly Ser Thr Gly Gly

GGC AAC TGT GCT GGA GTG AAT GTG TAC CCG AAC TGG ACC GCG CGT GAC TGG
```

FIG. 1E-3

```
                Gly Asn Cys Ala Gly Val Asn Val Tyr Pro Asn Trp Thr Ala Arg Asp Trp

TCT GGC GGC GCC TAC AAC CAT GCG AAC GCT GGC GAC CAA ATG GTC TAT CAA
Ser Gly Gly Ala Tyr Asn His Ala Asn Ala Gly Asp Gln Met Val Tyr Gln

AAC AGC CTG TAT CGT GCC AAC TGG TAC ACC AAC AGC GTG CCT GGC AGC GAC
Asn Ser Leu Tyr Arg Ala Asn Trp Tyr Thr Asn Ser Val Pro Gly Ser Asp

GCC TCC TGG ACT AGC CTT GGC GCC TGC GGA GGC AAC GGA AGT ACG ACC TCA
Ala Ser Trp Thr Ser Leu Gly Ala Cys Gly Gly Asn Gly Ser Thr Thr Ser

TCC AGC TCA AGC AGC TCC TCG TCA AGC AGC AGC TCT TCT TCC AGC AGC TCC
Ser Ser Ser Ser Ser Ser Ser Ser Ser Ser Ser Ser Ser Ser Ser Ser Ser

TCG TCT ACT GGC GGT GGC TCC AGC TCC TCC AGC AGT TCA TCT TCT TCA TCG
Ser Ser Thr Gly Gly Gly Ser Ser Ser Ser Ser Ser Ser Ser Ser Ser Ser

TCG TCT TCC AGC AGC TCT AGC AGC ACT GGT GGC GGT CAA TGT ACC GAA GTG
Ser Ser Ser Ser Ser Ser Ser Ser Thr Gly Gly Gly Gln Cys Thr Glu Val

TGC AAC TGG TAC GGT CAG GGA ACC TAC CCA CTG TGT AAC AAC ACC AGT GGT
Cys Asn Trp Tyr Gly Gln Gly Thr Tyr Pro Leu Cys Asn Asn Thr Ser Gly
```

FIG. 1E-4

```
TGG GGT TGG GAA AAC AAT CAG AGC TGT ATC GGC CGT CAA ACC TGT GAG TCA
Trp Gly Trp Glu Asn Asn Gln Ser Cys Ile Gly Arg Gln Thr Cys Glu Ser

CAG AAC GGT GGC GCT GGC GGC GTG GTG AGC AAC TGC ACC GGT TCG AGT ACA
Gln Asn Gly Gly Ala Gly Gly Val Val Ser Asn Cys Thr Gly Ser Ser Thr

TCC AGC AGC TCC TCT TCC AGC AGT AGT TCT TCC TCA AGT AGC AGC TCC AGT
Ser Ser Ser Ser Ser Ser Ser Ser Ser Ser Ser Ser Ser Ser Ser Ser Ser

TCA TCC AGC AGC TCT TCA TCT GGC ACT GGT AGC AGT ACA TCT TCC AGC AGC
Ser Ser Ser Ser Ser Ser Ser Gly Thr Gly Ser Ser Thr Ser Ser Ser Ser

AGC TCT TCC AGC AGC TCC AGC TCA AGT ACC GGT TCC TCC GGT ATG CCT GGA
Ser Ser Ser Ser Ser Ser Ser Ser Ser Thr Gly Ser Ser Gly Met Pro Gly

CCA CGC GTG GAC AAC CCC TTC GCC GCT GCG CAG AAG TGG TAC ATA AAC CCA
Pro Arg Val Asp Asn Pro Phe Ala Ala Ala Gln Lys Trp Tyr Ile Asn Pro

ATG TGG TCA GCG AGT GCT GCA AAC GAA CCC GGC GGC TCT GTC ATT GCC AAC
Met Trp Ser Ala Ser Ala Ala Asn Glu Pro Gly Gly Ser Val Ile Ala Asn

GAA CCC TCG TTT GTA TGG ATG GAC CGT ATC GGC GCA ATC GAA GGG CCT GCT
Glu Pro Ser Phe Val Trp Met Asp Arg Ile Gly Ala Ile Glu Gly Pro Ala
```

FIG. 1E-5

```
GAC GGT ATG GGC CTG CGC GAC CAC TTG AAC GAA GCC CTT GCA CAA GGC GCC
Asp Gly Met Gly Leu Arg Asp His Leu Asn Glu Ala Leu Ala Gln Gly Ala

GAC CTG TTC ATG TTT GTT GTG TAC GAC CTG CCA AAC CGT GAC TGT GCT GCA
Asp Leu Phe Met Phe Val Val Tyr Asp Leu Pro Asn Arg Asp Cys Ala Ala

CTC GCC TCC AAC GGT GAA CTG CGC ATC TCC GAA GAT GGC TTC AAC ATC TAC
Leu Ala Ser Asn Gly Glu Leu Arg Ile Ser Glu Asp Gly Phe Asn Ile Tyr

AAG TCC GAC TAC ATC GCA CCT ATC GTT GAA ATC ATC AGC GAC CCT GCA TAC
Lys Ser Asp Tyr Ile Ala Pro Ile Val Glu Ile Ile Ser Asp Pro Ala Tyr

GCA GGT ATC AAA ATC GCT GCG GTT ATC GAG GTG GAC TCA CTG CCT AAC CTG
Ala Gly Ile Lys Ile Ala Ala Val Ile Glu Val Asp Ser Leu Pro Asn Leu

GTT ACC AAT CTG AGC GAA CCT GAC TGT CAG GAA GCA AAT GGT CCT GGC GGC
Val Thr Asn Leu Ser Glu Pro Asp Cys Gln Glu Ala Asn Gly Pro Gly Gly

TAC CGC GAC GGC ATT CGT CAC GCT ATC ACT GAA CTG GGC AAA ATC CCC AAC
Tyr Arg Asp Gly Ile Arg His Ala Ile Thr Glu Leu Gly Lys Ile Pro Asn

GTA TAC TCC TAC GTG GAT ATT GCA CAC TCA GGC TGG CTG GGC TGG AAC GAC
```

FIG. 1E-6

Val Tyr Ser Tyr Val Asp Ile Ala His Ser Gly Trp Leu Gly Trp Asn Asp

AAC TTC GCG CAA GGC GTT AAC CTG ATT TAT GAA GTG GTT GCC AAC CTC GGT
Asn Phe Ala Gln Gly Val Asn Leu Ile Tyr Glu Val Val Ala Asn Leu Gly

TCC GGC ATT AAC CCA ATC GCC GGT TTC GTC AGT AAC TCC GCT AAC TAC ACG
Ser Gly Ile Asn Pro Ile Ala Gly Phe Val Ser Asn Ser Ala Asn Tyr Thr

CCT GTG GAA GAA CCC TTC TTG CCA GAC GCC AAC CTG CAG GTC GGT GGT CAG
Pro Val Glu Glu Pro Phe Leu Pro Asp Ala Asn Leu Gln Val Gly Gly Gln

CCC GTT CGC TCT TCC GAT TTC TAT GAG TGG AAC AGC TAC CTG GCA GAG AAA
Pro Val Arg Ser Ser Asp Phe Tyr Glu Trp Asn Ser Tyr Leu Ala Glu Lys

CCC TTC GTG ACC GAT TGG CGT TCT GCC ATG ATC TCG AAA GGT ATG CCA AGC
Pro Phe Val Thr Asp Trp Arg Ser Ala Met Ile Ser Lys Gly Met Pro Ser

TCC ATC GGT ATG CTG ATC GAT ACC GCA CGT AAC GGC TGG GGT GGC CCT GAG
Ser Ile Gly Met Leu Ile Asp Thr Ala Arg Asn Gly Trp Gly Gly Pro Glu

CGT CCA ACT GCG CAG TCT ACC TCC AAC AAC CTG AAC ACC TTC GTT AAC GAA
Arg Pro Thr Ala Gln Ser Thr Ser Asn Asn Leu Asn Thr Phe Val Asn Glu

FIG. 1E-7

```
TCA CGT ATC GAC CGT CGT GAG CAC CGC GGC AAC TGG TGT AAC CAG CCT GGT
Ser Arg Ile Asp Arg Arg Glu His Arg Gly Asn Trp Cys Asn Gln Pro Gly

GGT GTC GGC TAC CGT CCA ACC GCT GCA CCT TCT CCA GGT ATT GAT GCC TAC
Gly Val Gly Tyr Arg Pro Thr Ala Ala Pro Ser Pro Gly Ile Asp Ala Tyr

GTT TGG GTG AAA CCA CAG GGT GAG TCT GAC GGT GTT TCC GAT CCT AAC TTC
Val Trp Val Lys Pro Gln Gly Glu Ser Asp Gly Val Ser Asp Pro Asn Phe

GAG ATC GAT CCT AAC GAC CCG AAC AAA CAG CAC GAC CCA ATG TGT GAT CCG
Glu Ile Asp Pro Asn Asp Pro Asn Lys Gln His Asp Pro Met Cys Asp Pro

TTC GCC AGC AAC TCG TCC AAC AGT GCA TAC GGC ACC GGC GCT ATG CCA AAT
Phe Ala Ser Asn Ser Ser Asn Ser Ala Tyr Gly Thr Gly Ala Met Pro Asn

GCT CCG CAC GCT GGT CGC TGG TTC CCT GAA GCC TTC CAG TTA CTG CTT GAA
Ala Pro His Ala Gly Arg Trp Phe Pro Glu Ala Phe Gln Leu Leu Leu Glu

AAC GCT TAC CCA CCA ATT AAC TAA      3032
Asn Ala Tyr Pro Pro Ile Asn END
```

FIG. 1E-8

(SEQ ID NO:11 - nucleotide sequence and SEQ ID NO:12 - amino acid sequence)
Microscilla furvescens (Clone # 53GC1)

```
1
ATG AAC AAG AAG TGG TGG AAA GAA GCC GTG GTG TAT CAA GTC TAC CCG CGG
Met Asn Lys Lys Trp Trp Lys Glu Ala Val Val Tyr Gln Val Tyr Pro Arg

AGC TTC AAA GAC AGC AAT GGA GAT GGT GTA GGC GAT CTG CCT GGG GTT ATT
Ser Phe Lys Asp Ser Asn Gly Asp Gly Val Gly Asp Leu Pro Gly Val Ile

GAA AAG CTT GAT TAC ATC AAA AGC CTT GGG GTG GAT GTT ATC TGG CTA TGC
Glu Lys Leu Asp Tyr Ile Lys Ser Leu Gly Val Asp Val Ile Trp Leu Cys

CCG GTG TAC GAT TCC CCC AAT GAT GAC AAT GGT TAC GAT ATT CGT GAC TAC
Pro Val Tyr Asp Ser Pro Asn Asp Asp Asn Gly Tyr Asp Ile Arg Asp Tyr

TAC GAT ATC ATG GCT GAT TTC GGC ACG ATG GCT GAT TTT GAT CAG CTG CTC
Tyr Asp Ile Met Ala Asp Phe Gly Thr Met Ala Asp Phe Asp Gln Leu Leu

GAG GGA ATA CAT CAG CGT GGG ATG AAA CTG CTA ATG GAC CTG GTG GTA AAC
Glu Gly Ile His Gln Arg Gly Met Lys Leu Leu Met Asp Leu Val Val Asn

CAC TGC TCT GAT GAG CAC AAA TGG TTT CAG GAG TCC CGC AAG AGT AAA GAC
His Cys Ser Asp Glu His Lys Trp Phe Gln Glu Ser Arg Lys Ser Lys Asp
```

FIG. 1F-1

```
AAC CCT TAC CGG GAC TAC TTC ATC TGG AAG CCT GGC AAA AAC GGA GGC CCA
Asn Pro Tyr Arg Asp Tyr Phe Ile Trp Lys Pro Gly Lys Asn Gly Gly Pro

CCT AAC AAC TGG CAG TCC TTT TTT AGT GGT AAT GCC TGG GAA TAC GAT GAG
Pro Asn Asn Trp Gln Ser Phe Phe Ser Gly Asn Ala Trp Glu Tyr Asp Glu

GCC ACT GAC GAG TAT TAC CTA CAT CTT TTC ACC AAA AAG CAA CCA GAC CTC
Ala Thr Asp Glu Tyr Tyr Leu His Leu Phe Thr Lys Lys Gln Pro Asp Leu

AAT TGG GAA AAC CCG AAA GTA CGT GAG GAG GTG CAC AAG CTG ATG AAG TAT
Asn Trp Glu Asn Pro Lys Val Arg Glu Glu Val His Lys Leu Met Lys Tyr

TGG CTG GAC AAA GGA GTA GAT GGG TTC CGG ATG GAT GTG ATT TCC GTG ATT
Trp Leu Asp Lys Gly Val Asp Gly Phe Arg Met Asp Val Ile Ser Val Ile

TCA AAA AGA AAC TTC GAA GAT TCA CCT TAC AAG GAC TTC AAC AAG ACC ATC
Ser Lys Arg Asn Phe Glu Asp Ser Pro Tyr Lys Asp Phe Asn Lys Thr Ile

GAT AAC GTC TAC GCC AAT GGC CCG CGT GTG CAG GAG TTT CTC CAG GAA ATG
Asp Asn Val Tyr Ala Asn Gly Pro Arg Val Gln Glu Phe Leu Gln Glu Met

AAC CGT GAA GTA CTG AGT AAG TAC GAT GTG ATG ACA GTA GGT GAG GGT CCA
Asn Arg Glu Val Leu Ser Lys Tyr Asp Val Met Thr Val Gly Glu Gly Pro
```

FIG. 1F-2

```
GGT ATC AAT CTG GAA AGC GGC CTG CAA TAT GTA TCC AGC TCA GCG GAG GCT
Gly Ile Asn Leu Glu Ser Gly Leu Gln Tyr Val Ser Ser Ser Ala Glu Ala

CTT AAT ATG ATT TTT CAT TTT GGG CAC ATG TTT ATG GAT CAT GGA CCC GGA
Leu Asn Met Ile Phe His Phe Gly His Met Phe Met Asp His Gly Pro Gly

GGT AGA TTT GAT CCC AAG CCC ATC GAT TTT CTG GAA TTC AAA AAA GTC TTC
Gly Arg Phe Asp Pro Lys Pro Ile Asp Phe Leu Glu Phe Lys Lys Val Phe

AGG CTG TGG GAT GAG TAC CTT AAA GAA GAG GGC TGG GGT AGC GTC TTT CTA
Arg Leu Trp Asp Glu Tyr Leu Lys Glu Glu Gly Trp Gly Ser Val Phe Leu

GGG AAT CAT GAT TTT CAG CGA ATC GTT TCT CGC TTT GGG GAT GAC GGA GCG
Gly Asn His Asp Phe Gln Arg Ile Val Ser Arg Phe Gly Asp Asp Gly Ala

TAC TGG AAA GAG TCC GCC AAA CTG CTG AGC TTG TTG CTA TTT AGC ATG CGC
Tyr Trp Lys Glu Ser Ala Lys Leu Leu Ser Leu Leu Leu Phe Ser Met Arg

GGC ACG GTC TAC GTT TAC CAG GGT GAT GAA ATA GGT ATG ACC AAT GTG GCT
Gly Thr Val Tyr Val Tyr Gln Gly Asp Glu Ile Gly Met Thr Asn Val Ala

TTT GAC ACC ATA GAA GAA TAT GAC GAT GTG GAG ATC AAA AAT GCT TAC AAG
```

FIG. 1F-3

```
Phe Asp Thr Ile Glu Glu Tyr Asp Asp Val Glu Ile Lys Asn Ala Tyr Lys

GAG TGG AAA GCT GAA GGA AAA GAC CTG GAT CAG TTT TTA AAG AAC GTC CAT
Glu Trp Lys Ala Glu Gly Lys Asp Leu Asp Gln Phe Leu Lys Asn Val His

ATC AAT GGC CGT GAC AAT GCC CGT ACA CCG CTG CAA TGG AAT GAT GCT GAG
Ile Asn Gly Arg Asp Asn Ala Arg Thr Pro Leu Gln Trp Asn Asp Ala Glu

CAG GCT GGT TTT ACC TCA GGC ACT CCA TGG CTC AAA GTC AAC CCT AAC TAT
Gln Ala Gly Phe Thr Ser Gly Thr Pro Trp Leu Lys Val Asn Pro Asn Tyr

ACG GCA ATC AAT GTG GCT AGT CAG GAA GGA GAT GAG AAC TCT ATT CTG GCA
Thr Ala Ile Asn Val Ala Ser Gln Glu Gly Asp Glu Asn Ser Ile Leu Ala

TTT TAT CGC CGG ATG GTG GCG ATG CGA AAG GAG CAC CCG ACA CTT GTT TAT
Phe Tyr Arg Arg Met Val Ala Met Arg Lys Glu His Pro Thr Leu Val Tyr

GGT GAT TTT GCC CCC ATT CAG GAA GAT CAT CCG AGT GTA TTT GCT TTT TGG
Gly Asp Phe Ala Pro Ile Gln Glu Asp His Pro Ser Val Phe Ala Phe Trp

AGA TGG GAT GAA GAG GCT GCA TAT TTA GTC TTA CTC AAT TTT TCT GAG GAG
Arg Trp Asp Glu Glu Ala Ala Tyr Leu Val Leu Leu Asn Phe Ser Glu Glu
```

FIG. 1F-4

```
ACT CAG GAA TTT GGG CTG GAC GAT CGA TTT GAT AGT AGT AAG CTT CGC ATA
Thr Gln Glu Phe Gly Leu Asp Asp Arg Phe Asp Ser Ser Lys Leu Arg Ile

GTA GAG GCC AAT GAC TTT GAC TTT GGT GAG CCA CAA AGT GGA AAA GTG AAA
Val Glu Ala Asn Asp Phe Asp Phe Gly Glu Pro Gln Ser Gly Lys Val Lys

1682
CTA AAA CCG TGG CAG GCG GTG TTG GCG CGT GTT CGG CAT ATT GAA TTG TAA
Leu Lys Pro Trp Gln Ala Val Leu Ala Arg Val Arg His Ile Glu Leu END
```

FIG. 1F-5

(SEQ ID NO:13 - nucleotide sequence and SEQ ID NO:14 - amino acid sequence)
Thermotoga neapolitana (Clone # 56GC2) Glycosidase

```
1
TCT TCT GAA CGA TTC TCC ACT GAG CAG AAA AGA CCA GAT CAT ACT CTT TGT
Ser Ser Glu Arg Phe Ser Thr Glu Gln Lys Arg Pro Asp His Thr Leu Cys

GGA CGG AAA AGA ACA TTC GGC AAA GAA GGT GGT TAT ACC ACC CTT CAA AGA
Gly Arg Lys Arg Thr Phe Gly Lys Glu Gly Gly Tyr Thr Thr Leu Gln Arg

GGA AAC GCT GGT CTT CAA AGT GAA CGG ACT GAA GAG GGG AGA GCA CCT CGT
Gly Asn Ala Gly Leu Gln Ser Glu Arg Thr Glu Glu Gly Arg Ala Pro Arg

ATC CAC CAG TCT GAA CAC GGG AAA AAC CAT CTA TGT GAG GTG ATC TGT GTG
Ile His Gln Ser Glu His Gly Lys Asn His Leu Cys Glu Val Ile Cys Val

GAG ATC TTC AAA AGA CCG TTC AGA GAA GGG AGC TTC GTT CTG AAA GAG AAG
Glu Ile Phe Lys Arg Pro Phe Arg Glu Gly Ser Phe Val Leu Lys Glu Lys

GAC TAC ACC GTT GAG TTC GAG GTG GAG AAG ATC CAT CTT GGA TGG AAG ATT
Asp Tyr Thr Val Glu Phe Glu Val Glu Lys Ile His Leu Gly Trp Lys Ile

TCA GGG AGA GTG AAG GGA AAT CCC GGA AGG CTT GAG ATC TTT CGG ACA AAC
Ser Gly Arg Val Lys Gly Asn Pro Gly Arg Leu Glu Ile Phe Arg Thr Asn
```

FIG. 1G-1

```
GCA CCG AAG AAA CTC CTC GTG AAC AAC TGG CAG TCC TGG GGA CCC TGC AGG
Ala Pro Lys Lys Leu Leu Val Asn Asn Trp Gln Ser Trp Gly Pro Cys Arg

GTG GTG GAT CTT CCA TCC TTC ACC CCA CCC GAG ATA GAT CCA AAC TGG CAG
Val Val Asp Leu Pro Ser Phe Thr Pro Pro Glu Ile Asp Pro Asn Trp Gln

TAC ACG GCC TCT GTG GTA CCG GAT GTG ATC AAA AAC CGT CTT CAG AGT GAC
Tyr Thr Ala Ser Val Val Pro Asp Val Ile Lys Asn Arg Leu Gln Ser Asp

TAC TTC GTG GCA GAG GAA GGG AGA GTA TAC GGT TTT TTG AGT TCG AAG ATC
Tyr Phe Val Ala Glu Glu Gly Arg Val Tyr Gly Phe Leu Ser Ser Lys Ile

GCA CAT CCT TTC TTT GCG GCA GAG AAT GGA GAA CTT GTT GCG TAT CTT GAG
Ala His Pro Phe Phe Ala Ala Glu Asn Gly Glu Leu Val Ala Tyr Leu Glu

TAC TTC GAT GTG AAT TTC GAT GAC TTC GTC CCG ATA GAA CCT TTT GTC GTC
Tyr Phe Asp Val Asn Phe Asp Asp Phe Val Pro Ile Glu Pro Phe Val Val

CTT GAA AAT CCA ATC ACC TCT CTC CTT CTG GAA AAG TAC GCT GAA CTC GTC
Leu Glu Asn Pro Ile Thr Ser Leu Leu Leu Glu Lys Tyr Ala Glu Leu Val

GGG AAG GAA AAC AGC GCG AGG ATT CCA AAA CGT ACA CCG GTT GGA TGG TGC
Gly Lys Glu Asn Ser Ala Arg Ile Pro Lys Arg Thr Pro Val Gly Trp Cys
```

FIG. 1G-2

```
AGC TGG TAC CAC TAT TTC CTC GAT CTC ACC TGG GAG GAG ACT TTG AAG AAT
Ser Trp Tyr His Tyr Phe Leu Asp Leu Thr Trp Glu Glu Thr Leu Lys Asn

CTG GAA CTT GCA GGA GAG TTT CCC TTC GAG GTC TTT CAG ATA GAC GAC GCG
Leu Glu Leu Ala Gly Glu Phe Pro Phe Glu Val Phe Gln Ile Asp Asp Ala

TAT GAA AAA GAC ATC GGA GAC TGG CTC GTC ACG AAG AAA GAC TTC CCA TCT
Tyr Glu Lys Asp Ile Gly Asp Trp Leu Val Thr Lys Lys Asp Phe Pro Ser

GTG GAC GAG ATG GCA AGG ACG ATA CAG GAG AAA GGC TTT GTT CCT GGT ATA
Val Asp Glu Met Ala Arg Thr Ile Gln Glu Lys Gly Phe Val Pro Gly Ile

TGG ACC GCA CCG TTC AGT GTT TCA GAA ACA TCG GAT GTG TTC AAC TCC TAT
Trp Thr Ala Pro Phe Ser Val Ser Glu Thr Ser Asp Val Phe Asn Ser Tyr

CCG GAC TGG GTC GTG AAG GAA AAC GGA ATG CCA AAG ATG GCG TAC AGG AAC
Pro Asp Trp Val Val Lys Glu Asn Gly Met Pro Lys Met Ala Tyr Arg Asn

TGG AAC AGA AAG ATC TAC GCT CTT GAC CTT TCA AAC AAA GAA GTC CTG GAC
Trp Asn Arg Lys Ile Tyr Ala Leu Asp Leu Ser Asn Lys Glu Val Leu Asp

TGG CTC TTC GAC CTC TTC AGC TCT CTC AAG AAG ATG GGC TAC AGA TAC TTC
```

FIG. 1G-3

```
Trp Leu Phe Asp Leu Phe Ser Ser Leu Lys Lys Met Gly Tyr Arg Tyr Phe

AAG ATC GAC TTT CTC TTT GCA GGA GCG ATT CCG GGT GAG AGG AAA GAA AAC
Lys Ile Asp Phe Leu Phe Ala Gly Ala Ile Pro Gly Glu Arg Lys Glu Asn

ATC ACA CCC GTT CAG GCG TTC AGA AAG GGG ATG GAG GTG ATC AGA AAG GCG
Ile Thr Pro Val Gln Ala Phe Arg Lys Gly Met Glu Val Ile Arg Lys Ala

GTT GGA GAC TTG TTC ATA CTC GGA TGT GGC TCT CCC CTT CTT CCT GCG GTG
Val Gly Asp Leu Phe Ile Leu Gly Cys Gly Ser Pro Leu Leu Pro Ala Val

GGC TAC GTT GAC GGC ATG AGG ATA GGG CCG GAC ACC ACA CCC TTC TGG GGT
Gly Tyr Val Asp Gly Met Arg Ile Gly Pro Asp Thr Thr Pro Phe Trp Gly

GAT CAA ATA GAA GAC AAC GGA GCA CCC GCT GCA AGA TGG GCT CTG AGA AAT
Asp Gln Ile Glu Asp Asn Gly Ala Pro Ala Ala Arg Trp Ala Leu Arg Asn

GCC ATC ACA CGT TAC TTC ATG CAC GAC AGA CTC TGG CTG AAC GAT CCG GAC
Ala Ile Thr Arg Tyr Phe Met His Asp Arg Leu Trp Leu Asn Asp Pro Asp

TGC CTC ATC CTG AGA GAG GAA AAA ACA GAA CTG ACC CCA AAA GAG AGA GAG
Cys Leu Ile Leu Arg Glu Glu Lys Thr Glu Leu Thr Pro Lys Glu Arg Glu
```

FIG. 1G-4

```
CTC TAC TCG TAC ACC TGT GGG ATC CTC GAC AAC ATG ATC ATA GAA AGT GAC
Leu Tyr Ser Tyr Thr Cys Gly Ile Leu Asp Asn Met Ile Ile Glu Ser Asp

GAC CTG TCA CTT GTG AAA GAG CAC GGA AGG AAG GTT CTG AGA GAG ACA CTC
Asp Leu Ser Leu Val Lys Glu His Gly Arg Lys Val Leu Arg Glu Thr Leu

GAT CTT CTC GGG GGA AAG CCC CGT GTT CTG AAC ATC ATG ACA GAG GAT CTG
Asp Leu Leu Gly Gly Lys Pro Arg Val Leu Asn Ile Met Thr Glu Asp Leu

AAG TAC GAG ATC GTC TCG TCT GGC ACG ATC TCT GGA AAC ACC AGG CTC GTT
Lys Tyr Glu Ile Val Ser Ser Gly Thr Ile Ser Gly Asn Thr Arg Leu Val

GTC GAT CTC AAA AAC AGA GAG TAC CAT CTG GAA AAA GAG GGA AAG TCC TCT
Val Asp Leu Lys Asn Arg Glu Tyr His Leu Glu Lys Glu Gly Lys Ser Ser

CTG AGA AAG AAG GTT GTC AAA AGA GAA GAC GGA AGA AAC TTC TAC TTC TAC
Leu Arg Lys Lys Val Val Lys Arg Glu Asp Gly Arg Asn Phe Tyr Phe Tyr

GAA GAG GGT GAG AGA GAA TGA    1856
Glu Glu Gly Glu Arg Glu END
```

FIG. 1G-5

(SEQ ID NO:15 - nucleotide sequence and SEQ ID NO:16 - amino acid sequence)
Thermotoga neapolitana (Clone # 56GP1) Glycosidase

1

ATG AGA AAA CTT GTG TTC TCA TTT TTG ATT GTG ACA TTG CCC ATC GTC CTC
Met Arg Lys Leu Val Phe Ser Phe Leu Ile Val Thr Leu Pro Ile Val Leu

TTT GCA AAC AGT GAT TTC GTG AAA GTG GAA AAC GGC AGG TTC ATA CTG AAC
Phe Ala Asn Ser Asp Phe Val Lys Val Glu Asn Gly Arg Phe Ile Leu Asn

GGA GAA GAG TTC AGA TTC GTT GGA AGC AAC AAC TAC TAC ATG CAC TAC AAG
Gly Glu Glu Phe Arg Phe Val Gly Ser Asn Asn Tyr Tyr Met His Tyr Lys

AGC AAT CGA ATG ATA GAC AGT GTC CTT GAA AGT GCA AAA GCC ATG GGG GTG
Ser Asn Arg Met Ile Asp Ser Val Leu Glu Ser Ala Lys Ala Met Gly Val

AAG GTG CTC AGA ATT TGG GGA TTC CTC GAT GGT GAG AGT TAC TGC CGT GAC
Lys Val Leu Arg Ile Trp Gly Phe Leu Asp Gly Glu Ser Tyr Cys Arg Asp

AAG AAC ACC TAC ATG CAC CCC GCA CCG GGA GTA TTT GGA TTG CCA GAG GGT
Lys Asn Thr Tyr Met His Pro Ala Pro Gly Val Phe Gly Leu Pro Glu Gly

ACG AAC GCT CAG GAC GGT TTT GAA AGA CTC GAC TAC ACG GTA GCG AAA GCA
Thr Asn Ala Gln Asp Gly Phe Glu Arg Leu Asp Tyr Thr Val Ala Lys Ala

FIG. 1H-1

AAA GAA CTG GGC ATA AAG CTC ATA ATC GTT CTT GTG AAC AAC TGG GAC GAC
Lys Glu Leu Gly Ile Lys Leu Ile Ile Val Leu Val Asn Asn Trp Asp Asp

TTC GGT GGA ATG AAT CAA TAC GTG AGA TGG TTT GGG GGC ATC CAT CAC GAT
Phe Gly Gly Met Asn Gln Tyr Val Arg Trp Phe Gly Gly Ile His His Asp

GAC TTC TAC AGG AAC GAG AAG ATC AAA GAA GAA TAC AAA AAG TAC GTG TCT
Asp Phe Tyr Arg Asn Glu Lys Ile Lys Glu Glu Tyr Lys Lys Tyr Val Ser

TTC CTC ATA AAC AGG GTG AAC ACC TAC ACG GGT GTT CCT TAC AGG GAA GAG
Phe Leu Ile Asn Arg Val Asn Thr Tyr Thr Gly Val Pro Tyr Arg Glu Glu

CCC ACC ATC ATG GCA TGG GAA CTG GCG AAC GAG CCC AGG TGT GAA ACG GAC
Pro Thr Ile Met Ala Trp Glu Leu Ala Asn Glu Pro Arg Cys Glu Thr Asp

AAG TCT GGT AAC ACA CTC GTT GAA TGG GTA GAG GAG ATG AGT GCT TAC ATA
Lys Ser Gly Asn Thr Leu Val Glu Trp Val Glu Glu Met Ser Ala Tyr Ile

AAG AGT CTG GAT CCA AAC CAC CTG GTT GCC GTG GGA GAC GAG GGA TTC TTC
Lys Ser Leu Asp Pro Asn His Leu Val Ala Val Gly Asp Glu Gly Phe Phe

AAC AAC TAC GAA GGC TTC AGA CCT TAC GGT GGA GAG GCT GAG TGG GCC TAC
Asn Asn Tyr Glu Gly Phe Arg Pro Tyr Gly Gly Glu Ala Glu Trp Ala Tyr

FIG. 1H-2

```
AAC GGA TGG TCC GGT GTT GAC TGG AAG AGA CTT CTG GAG ATA GAG ACG GTG
Asn Gly Trp Ser Gly Val Asp Trp Lys Arg Leu Leu Glu Ile Glu Thr Val

GAT TTT GGT ACG TTC CAT CTC TAC CCC TCC CAC TGG GGT GTG AGC CCT GAA
Asp Phe Gly Thr Phe His Leu Tyr Pro Ser His Trp Gly Val Ser Pro Glu

AAC TAC GCA CAG TGG GGG GCA AAG TGG ATA GAA GAT CAC ATA AAG ATC GCA
Asn Tyr Ala Gln Trp Gly Ala Lys Trp Ile Glu Asp His Ile Lys Ile Ala

AAA GAG GTT GGA AAA CCC GTC GTT CTG GAA GAG TAC GGT ATT CCC AAA AGT
Lys Glu Val Gly Lys Pro Val Val Leu Glu Glu Tyr Gly Ile Pro Lys Ser

GCC CCG GTC AAC AGG GTT GCC ATT TAC AAA TTG TGG AAC GAT CTG GTC TAC
Ala Pro Val Asn Arg Val Ala Ile Tyr Lys Leu Trp Asn Asp Leu Val Tyr

AAC CTC GGT GGA AAC GGT GCC ATG TTC TGG ATG CTC GCA GGA ATC GGT GAA
Asn Leu Gly Gly Asn Gly Ala Met Phe Trp Met Leu Ala Gly Ile Gly Glu

GGA TGG GAC AGA GAC GAA AAG GGT TAC TAC CCC GAT TAC GAC GGC TTC AGA
Gly Trp Asp Arg Asp Glu Lys Gly Tyr Tyr Pro Asp Tyr Asp Gly Phe Arg

ATA GTG AAC GAT GAA AGT GAA GAG GCA AAG TTG ATC AGA GAG TAC GCG AAA
```

FIG. 1H-3

```
                Ile Val Asn Asp Glu Ser Glu Glu Ala Lys Leu Ile Arg Glu Tyr Ala Lys

CTG TTC AGC ACG GGT GAG GAT ACG AGG GAA GAT ACC TGC ATG TTC ATC ACA
Leu Phe Ser Thr Gly Glu Asp Thr Arg Glu Asp Thr Cys Met Phe Ile Thr

CCA AAG GAT GGT CAG GAG ATC AAA AAG ACT GTG AAG GTG AGA GTG GGT GTC
Pro Lys Asp Gly Gln Glu Ile Lys Lys Thr Val Lys Val Arg Val Gly Val

TTC GAC TAC AGC AAC ACG TTC AAA GGA ATT TCC GTC GGG GTT GAA AAT CTG
Phe Asp Tyr Ser Asn Thr Phe Lys Gly Ile Ser Val Gly Val Glu Asn Leu

CTC TTT GAA GAT GAG ATA AAA CAT CTC GGA TAT GGA GTT TAC GGA TTC GAA
Leu Phe Glu Asp Glu Ile Lys His Leu Gly Tyr Gly Val Tyr Gly Phe Glu

TTT GAC ACA ACG CGG ATT TCA GAC GGA GAA CAC GAG ATG TTC CTT GAG GCA
Phe Asp Thr Thr Arg Ile Ser Asp Gly Glu His Glu Met Phe Leu Glu Ala

CAT TTC AGG GGA GAA ACG GTG AAA GAC ACA ATC AGG GTG AAA GTT GTG AAC
His Phe Arg Gly Glu Thr Val Lys Asp Thr Ile Arg Val Lys Val Val Asn

AGA GCG CAG TAT GTA CTC GCA GAA GAA GTG GAT TTT TCC AGA CCC GAA GAA
Arg Ala Gln Tyr Val Leu Ala Glu Glu Val Asp Phe Ser Arg Pro Glu Glu
```

FIG. 1H-4

```
GTC AAG AAC TGG TGG AAC AGC GGA ACA TGG CAG GCT GAG TTC AAA ACA CCC
Val Lys Asn Trp Trp Asn Ser Gly Thr Trp Gln Ala Glu Phe Lys Thr Pro

GAT ATA GAG TGG AAC GGT GAG GTG GGG AAC GGT GCT CTC CAG ATG AAC GTG
Asp Ile Glu Trp Asn Gly Glu Val Gly Asn Gly Ala Leu Gln Met Asn Val

GTG CTT CCC GGA AAG GGT GAC TGG GAA GAG GTG AGG GTG GTC AGG AAA TTC
Val Leu Pro Gly Lys Gly Asp Trp Glu Glu Val Arg Val Val Arg Lys Phe

GAT CAA CTC CCC GTG TGT GAG ATC CTC GAG TAC GAT ATC TAC ATA CCA GAC
Asp Gln Leu Pro Val Cys Glu Ile Leu Glu Tyr Asp Ile Tyr Ile Pro Asp

GTT GAA GGG CTT ACA GGA AGG CTC AGA CCG TAC GCG GTG CTG AAT CCC GGC
Val Glu Gly Leu Thr Gly Arg Leu Arg Pro Tyr Ala Val Leu Asn Pro Gly

TGG GTG AAG ATA GGG CTC GAC ATG AAC AAC ACC TCG ATT GAC AGC GGA GAA
Trp Val Lys Ile Gly Leu Asp Met Asn Asn Thr Ser Ile Asp Ser Gly Glu

CTT GTC AGT TTC GAT GGC AAA AAG TAC AGA AAG TTC CAT GTG AGG ATC GAG
Leu Val Ser Phe Asp Gly Lys Lys Tyr Arg Lys Phe His Val Arg Ile Glu

TTC GAC AAG ACA CCT GGA GTG AAC GAG CTC CAC ATA GGT GTA GTT GGA GAC
Phe Asp Lys Thr Pro Gly Val Asn Glu Leu His Ile Gly Val Val Gly Asp
```

FIG. 1H-5

CAC CTG GAG TAT GAT GGG CCG ATT TTC ATC GAT AAT GTG AGG CTC TAT AAA

His Leu Glu Tyr Asp Gly Pro Ile Phe Ile Asp Asn Val Arg Leu Tyr Lys

AAA TCT TCT TGA      2000
Lys Ser Ser END

FIG. 1H-6

(SEQ ID NO:17 - nucleotide sequence and SEQ ID NO:18 - amino acid sequence)
ARP 2.3 (Alum Rock sulfur spring, Clone # 58GB3) Glycosidase 1
ATG CAT TTT AGC CCA CTA CAA TTG ATC CTC GTC TTA GTC ATT GTC ATT CTG
Met His Phe Ser Pro Leu Gln Leu Ile Leu Val Leu Val Ile Val Ile Leu CTG TTT GGC ACC AAA AAA TTA CGC AAT ATG GGC GGC GAT TTA GGC GAA GCC
Leu Phe Gly Thr Lys Lys Leu Arg Asn Met Gly Gly Asp Leu Gly Glu Ala TTC AAG AAT TTC AGA AAA GCA GTC AAA GAC GGC GAT GAT GCT GAA ACA CAA
Phe Lys Asn Phe Arg Lys Ala Val Lys Asp Gly Asp Asp Ala Glu Thr Gln AAA GAT GTT GCT GTG CAA AAA GTT GAC CAA CAG CCA CCA GCA CAG CCC ATC
Lys Asp Val Ala Val Gln Lys Val Asp Gln Gln Pro Pro Ala Gln Pro Ile 254
CCA CAA GGT CGA GTC ATT GAT TCG GAA GCC AAG GAA AAG GAT AAG GTC TAA
Pro Gln Gly Arg Val Ile Asp Ser Glu Ala Lys Glu Lys Asp Lys Val END

FIG. 1I

(SEQ ID NO:19 - nucleotide sequence and SEQ ID NO:20 - amino acid sequence)
AEPII 1a (Clone # 63GA3) Glycosidase 1
ATG GAA GGA CTT CGA GGA GGT GTG AGG ATG AAG TTC CCA TCT AAC TTT CTT
Met Glu Gly Leu Arg Gly Gly Val Arg Met Lys Phe Pro Ser Asn Phe Leu TTT GGC TAC TCC TGG TCG GGC TTC CAG TTT GAA ATG GGT TTA CCT GGG AGT
Phe Gly Tyr Ser Trp Ser Gly Phe Gln Phe Glu Met Gly Leu Pro Gly Ser GAA GTT GAG AGC GAC TGG TGG GCA TGG GTC CAC GAT AAG GAG AAC ATC TTC
Glu Val Glu Ser Asp Trp Trp Ala Trp Val His Asp Lys Glu Asn Ile Phe TCG GGC CTA GTT AGC GGT GAC CTA CCA GAG AAC GGG CCT GCT TAC TGG CAC
Ser Gly Leu Val Ser Gly Asp Leu Pro Glu Asn Gly Pro Ala Tyr Trp His CTC TAC AAG AAA GAC CAC GAC ATA GCT GAA AGC CTT GGC ATG GAC GCG ATA
Leu Tyr Lys Lys Asp His Asp Ile Ala Glu Ser Leu Gly Met Asp Ala Ile AGA GGC GGA ATC GAG TGG GCG AGG ATC TTC CCA AAA CCC ACC TTT GAC GTG
Arg Gly Gly Ile Glu Trp Ala Arg Ile Phe Pro Lys Pro Thr Phe Asp Val AAG GTT GAC GTG GAA AAG GAC GAA AAC GGG AAC ATA ATC TCC ATT GAC GTC
Lys Val Asp Val Glu Lys Asp Glu Asn Gly Asn Ile Ile Ser Ile Asp Val

FIG. 1J-1

CCG GAG AGC GCG ATA GAG GAG CTA GAA AAG CTT GCC AAC ATG GAT GCC CTC
Pro Glu Ser Ala Ile Glu Glu Leu Glu Lys Leu Ala Asn Met Asp Ala Leu

AAC CAC TAC CGC GAA ATC TAC TCG GAC TGG AAG GAG AGG GGC AAG ACC TTC
Asn His Tyr Arg Glu Ile Tyr Ser Asp Trp Lys Glu Arg Gly Lys Thr Phe

ATA TTG AAC CTC TAT CAC TGG CCC CTT CCC CTC TGG CTC CAC GAC CCG ATA
Ile Leu Asn Leu Tyr His Trp Pro Leu Pro Leu Trp Leu His Asp Pro Ile

GGC GTT AGA AAG CTC GGC CCT GAT AGA GCT CCC TCG GGC TGG CTG GAC GAG
Gly Val Arg Lys Leu Gly Pro Asp Arg Ala Pro Ser Gly Trp Leu Asp Glu

AGG AGC GTG GTG GAG TTC ACC AAG TTC GCT GCA TTC ATC GCC TAC CAC TTG
Arg Ser Val Val Glu Phe Thr Lys Phe Ala Ala Phe Ile Ala Tyr His Leu

GAT GAC CTC GTT GAC ATG TGG AGC ACG ATG AAC GAG CCG AAT GTG GTT TAC
Asp Asp Leu Val Asp Met Trp Ser Thr Met Asn Glu Pro Asn Val Val Tyr

GAG CAG GGT TAC ACG AGG CCT CAG TCG GGC TTT CCA CCG GGT TAT CTC AGC
Glu Gln Gly Tyr Thr Arg Pro Gln Ser Gly Phe Pro Pro Gly Tyr Leu Ser

CAC GAG GCC GCT GGA AAG GCG AAG CTC AAC CTC ATG CAG GCT CAC GCT AGA
His Glu Ala Ala Gly Lys Ala Lys Leu Asn Leu Met Gln Ala His Ala Arg

FIG. 1J-2

```
GCT TAC GAT GCG ATA AAA GAG CAC TCG GAC AAG CCC GTG GGG TTG ATA TAC
Ala Tyr Asp Ala Ile Lys Glu His Ser Asp Lys Pro Val Gly Leu Ile Tyr

TCC TTT GTC TGG CAC GAT GCC CTA AAC GAG GAA GCG GAG GAG ATT GTG AAG
Ser Phe Val Trp His Asp Ala Leu Asn Glu Glu Ala Glu Glu Ile Val Lys

GAG ATA AGG AGG AGA CAC TAC GAC TTC GTA ACC GGC CTT CAC TCC GGC TCA
Glu Ile Arg Arg Arg His Tyr Asp Phe Val Thr Gly Leu His Ser Gly Ser

TCG GAG TTC GGG GAG AGG GAG GAC TTC AAG GGG AAG ATC GAC TGG ATA GGC
Ser Glu Phe Gly Glu Arg Glu Asp Phe Lys Gly Lys Ile Asp Trp Ile Gly

GTG AAC TAC TAC ACT AGG GTT GCT TAC GAG ATG AGG AAC GGC CGC TTT ATG
Val Asn Tyr Tyr Thr Arg Val Ala Tyr Glu Met Arg Asn Gly Arg Phe Met

GCC CTA CCC GGG TAC GGC TAC ATG TGC GAG AGG AGT GGT TAC GCA AAA TCC
Ala Leu Pro Gly Tyr Gly Tyr Met Cys Glu Arg Ser Gly Tyr Ala Lys Ser

GGA AGG CCC GCG AGC GAT TTT GGC TGG GAG ACC TAT CCT GAG GGC CTC GAA
Gly Arg Pro Ala Ser Asp Phe Gly Trp Glu Thr Tyr Pro Glu Gly Leu Glu

AAC GTC CTG ATG GAT CTG AAG GAG CTC TAC GGC CTG CCA ATG ATG GTG ACG
```

FIG. 1J-3

```
Asn Val Leu Met Asp Leu Lys Glu Leu Tyr Gly Leu Pro Met Met Val Thr

GAG AAC GGG ATG GCG GAT ATG GCA GAC AGG CAC CGC TCT TAC TAC CTC GTG
Glu Asn Gly Met Ala Asp Met Ala Asp Arg His Arg Ser Tyr Tyr Leu Val

AGC CAC CTC GCG GCT ATC CAC AGG GCG ATG GAG AAG GGT GCC GAC GTT AGG
Ser His Leu Ala Ala Ile His Arg Ala Met Glu Lys Gly Ala Asp Val Arg

GGG TAC CTC CAC TGG TCT CTG ACC GAC AAC TAC GAG TGG GCG CAG GGC TTC
Gly Tyr Leu His Trp Ser Leu Thr Asp Asn Tyr Glu Trp Ala Gln Gly Phe

AGA ATG CGC TTT GGG CTG GTG ATG GTG GAC TTC GAG ACT AAG AAG CGC TAC
Arg Met Arg Phe Gly Leu Val Met Val Asp Phe Glu Thr Lys Lys Arg Tyr

ATA AGG CCG AGC GCA CTC GTC TTC AGG GAG ATA GCC ACG CAG AAG GAA ATA
Ile Arg Pro Ser Ala Leu Val Phe Arg Glu Ile Ala Thr Gln Lys Glu Ile

1478
CCC GAA GAG CTC TCC CAC CTA GCG AAC CTC GAA CTG GTA ACG AAG AAG TAA
Pro Glu Glu Leu Ser His Leu Ala Asn Leu Glu Leu Val Thr Lys Lys END
```

FIG. 1J-4

(SEQ ID NO:21 - nucleotide sequence and SEQ ID NO:22 - amino acid sequence)
AEPII 1a (Clone # 63GA4) Glycosidase

```
1
ATG AAG TTC CCA TCT AAC TTT CTT TTT GGC TAC TCC TGG TCG GGC TTC CAG
Met Lys Phe Pro Ser Asn Phe Leu Phe Gly Tyr Ser Trp Ser Gly Phe Gln

TTT GAA ATG GGT TTA CCT GGG AGT GAA GTT GAG AGC GAC TGG TGG GCA TGG
Phe Glu Met Gly Leu Pro Gly Ser Glu Val Glu Ser Asp Trp Trp Ala Trp

GTC CAC GAT AAG GAG AAC ATC TTC TCG GGC CTA GTT AGC GGT GAC CTA CCA
Val His Asp Lys Glu Asn Ile Phe Ser Gly Leu Val Ser Gly Asp Leu Pro

GAG AAC GGG CCT GCT TAC TGG CAC CTC TAC AAG AAA GAC CAC GAC ATA GCT
Glu Asn Gly Pro Ala Tyr Trp His Leu Tyr Lys Lys Asp His Asp Ile Ala

GAA AGC CTT GGC ATG GAC GCG ATA AGA GGC GGA ATC GAG TGG GCG AGG ATC
Glu Ser Leu Gly Met Asp Ala Ile Arg Gly Gly Ile Glu Trp Ala Arg Ile

TTC CCA AAA CCC ACC TTT GAC GTG AAG GTT GAC GTG GAA AAG GAC GAA AAC
Phe Pro Lys Pro Thr Phe Asp Val Lys Val Asp Val Glu Lys Asp Glu Asn

GGG AAC ATA ATC TCC ATT GAC GTC CCG GAG AGC GCG ATA GAG GAG CTA GAA
Gly Asn Ile Ile Ser Ile Asp Val Pro Glu Ser Ala Ile Glu Glu Leu Glu
```

FIG. 1K-1

```
AAG CTT GCC AAC ATG GAT GCC CTC AAC CAC TAC CGC GAA ATC TAC TCG GAC
Lys Leu Ala Asn Met Asp Ala Leu Asn His Tyr Arg Glu Ile Tyr Ser Asp

TGG AAG GAG AGG GGC AAG ACC TTC ATA TTG AAC CTC TAT CAC TGG CCC CTT
Trp Lys Glu Arg Gly Lys Thr Phe Ile Leu Asn Leu Tyr His Trp Pro Leu

CCC CTC TGG CTC CAC GAC CCG ATA GGC GTT AGA AAG CTC GGC CCT GAT AGA
Pro Leu Trp Leu His Asp Pro Ile Gly Val Arg Lys Leu Gly Pro Asp Arg

GCT CCC TCG GGC TGG CTG GAC GAG AGG AGC GTG GTG GAG TTC ACC AAG TTC
Ala Pro Ser Gly Trp Leu Asp Glu Arg Ser Val Val Glu Phe Thr Lys Phe

GCT GCA TTC ATC GCC TAC CAC TTG GAT GAC CTC GTT GAC ATG TGG AGC ACG
Ala Ala Phe Ile Ala Tyr His Leu Asp Asp Leu Val Asp Met Trp Ser Thr

ATG AAC GAG CCG AAT GTG GTT TAC GAG CAG GGT TAC ACG AGG CCT CAG TCG
Met Asn Glu Pro Asn Val Val Tyr Glu Gln Gly Tyr Thr Arg Pro Gln Ser

GGC TTT CCA CCG GGT TAT CTC AGC CAC GAG GCC GCT GGA AAG GCG AAG CTC
Gly Phe Pro Pro Gly Tyr Leu Ser His Glu Ala Ala Gly Lys Ala Lys Leu

AAC CTC ATG CAG GCT CAC GCT AGA GCT TAC GAT GCG ATA AAA GAG CAC TCG
Asn Leu Met Gln Ala His Ala Arg Ala Tyr Asp Ala Ile Lys Glu His Ser
```

FIG. 1K-2

```
GAC AAG CCA GTT GGA GTT ATC TAC GCA TAT AAG TGG ATT GAT GCG GAG GAT
Asp Lys Pro Val Gly Val Ile Tyr Ala Tyr Lys Trp Ile Asp Ala Glu Asp

GAA GCT GCA GAG GAA TCC GTT CTG GAA CTC CGC AGG AGG GAT TAC GAC TTC
Glu Ala Ala Glu Glu Ser Val Leu Glu Leu Arg Arg Arg Asp Tyr Asp Phe

GTT GAT GGT CTC TAC TCA GGC AAG TCC CTG ACT GCA GGT GAG AGG GAG GAC
Val Asp Gly Leu Tyr Ser Gly Lys Ser Leu Thr Ala Gly Glu Arg Glu Asp

TTC AAA GGC AGG GTC GAC TGG GTT GGC GTC AAC TAC TAC TCC CGC CTG CTC
Phe Lys Gly Arg Val Asp Trp Val Gly Val Asn Tyr Tyr Ser Arg Leu Leu

TTT GGA AAG GCC GGA GAT TCA GTG AGA TTA CTT CAG GGC TAC GGT TTT GTC
Phe Gly Lys Ala Gly Asp Ser Val Arg Leu Leu Glu Gly Tyr Gly Phe Val

TCC CCG AGG GGT GGC TAC GCC AAA TCG GGA AGG CCT GCG AGC GAT TTT GGC
Ser Pro Arg Gly Gly Tyr Ala Lys Ser Gly Arg Pro Ala Ser Asp Phe Gly

TGG GAG ATT TAT CCT GAG GGC CTC GAA AAG CTC CTG GTT GAG CTG AGT GGC
Trp Glu Ile Tyr Pro Glu Gly Leu Glu Lys Leu Leu Val Glu Leu Ser Gly

AGG TAC GAG CTT CCG CTC TTC ATA ACG GAG AAT GGT ATG GCT GAT GCT GTC
```

FIG. 1K-3

```
Arg Tyr Glu Leu Pro Leu Phe Ile Thr Glu Asn Gly Met Ala Asp Ala Val

GAT AGG TAC AGG CCT TAC TAC CTC GTG AGC CAC CTC GCG GCT ATC CAC AGG
Asp Arg Tyr Arg Pro Tyr Tyr Leu Val Ser His Leu Ala Ala Ile His Arg

GCG ATG GAG AAG GGT GCC GAC ATT AGG GGG TAC CTC CAC TGG TCT CTG ACC
Ala Met Glu Lys Gly Ala Asp Ile Arg Gly Tyr Leu His Trp Ser Leu Thr

GAC AAC TAC GAG TGG GCG CAG GGC TTC AGA ATG CGC TTT GGG CTG GTG ATG
Asp Asn Tyr Glu Trp Ala Gln Gly Phe Arg Met Arg Phe Gly Leu Val Met

GTG GAC TTC GAG ACT AAG AAG CGC TAC TTG AGG CCG AGC GCA CTC GTC TTC
Val Asp Phe Glu Thr Lys Lys Arg Tyr Leu Arg Pro Ser Ala Leu Val Phe

AGG GAA ATA GCC ACG CGG AAG GAA ATA CCC GAA GAG CTT GAA CAC CTT GCC
Arg Glu Ile Ala Thr Arg Lys Glu Ile Pro Glu Glu Leu Glu His Leu Ala

GAT GTG GAT GCA ATC ATT GCT CGG TGA      1454
Asp Val Asp Ala Ile Ile Ala Arg END
```

FIG. 1K-4

(SEQ ID NO:23 - nucleotide sequence and SEQ ID NO:24 - amino acid sequence)
AEPII 1a (Clone #63GA9) Glycosidase
1
ATG CTA CCA GAA GAG TTC CTA TGG GGC GTT GGG CAG TCA GGC TTT CAG TTC Met Leu Pro Glu Glu Phe Leu Trp Gly Val Gly Gln Ser Gly Phe Gln Phe

GAA ATG GGC GAC AAG CTC AGG AGG CAC ATC GAT CCA AAT ACC GAC TGG TGG

Glu Met Gly Asp Lys Leu Arg Arg His Ile Asp Pro Asn Thr Asp Trp Trp

AAG TGG GTT CGC GAT CCT TTC AAC ATA AAA AAG GAG CTT GTG AGT GGG GAC

Lys Trp Val Arg Asp Pro Phe Asn Ile Lys Lys Glu Leu Val Ser Gly Asp

CTT CCC GAG GAC GGC ATC AAC AAC TAC GAA CTT TTT GAA AAC GAT CAC AAG

Leu Pro Glu Asp Gly Ile Asn Asn Tyr Glu Leu Phe Glu Asn Asp His Lys

CTC GCT AAA GGC CTT GGA CTC AAC GCA TAC AGG ATT GGA ATA GAG TGG AGC

Leu Ala Lys Gly Leu Gly Leu Asn Ala Tyr Arg Ile Gly Ile Glu Trp Ser

AGA ATC TTT CCC TGG CCG ACG TGG ACG GTC GAT ACC GAG GTC GAG TTC GAC

Arg Ile Phe Pro Trp Pro Thr Trp Thr Val Asp Thr Glu Val Glu Phe Asp

ACT TAC GGT TTA GTA AAG GAC GTT AAG ATA GAC AAG TCC ACC CTT GCT GAA

Thr Tyr Gly Leu Val Lys Asp Val Lys Ile Asp Lys Ser Thr Leu Ala Glu

FIG. 1L-1

```
CTC GAC AGG CTG GCC AAC AAG GAG GAG GTA ATG TAC TAC AGG CGC GTT ATT
Leu Asp Arg Leu Ala Asn Lys Glu Glu Val Met Tyr Tyr Arg Arg Val Ile

CAG CAT TTG AGG GAG CTC GGC TTC AAG GTC TTC GTT AAC CTC AAC CAC TTC
Gln His Leu Arg Glu Leu Gly Phe Lys Val Phe Val Asn Leu Asn His Phe

ACG CTT CCA ATA TGG CTC CAC GAC CCG ATA GTG GCA AGG GAG AAG GCC CTC
Thr Leu Pro Ile Trp Leu His Asp Pro Ile Val Ala Arg Glu Lys Ala Leu

ACA AAC GAC AGA ATC GGC TGG GTC TCC CAG AGG ACA GTT GTT GAG TTT GCC
Thr Asn Asp Arg Ile Gly Trp Val Ser Gln Arg Thr Val Val Glu Phe Ala

AAG TAT GCT GCT TAC ATC GCC CAT GCG CTC GGA GAC CTC GTG GAC ACA TGG
Lys Tyr Ala Ala Tyr Ile Ala His Ala Leu Gly Asp Leu Val Asp Thr Trp

AGC ACC TTC AAC GAA CCT ATG GTA GTT GTG GAG CTC GGC TAC CTC GCC CCC
Ser Thr Phe Asn Glu Pro Met Val Val Val Glu Leu Gly Tyr Leu Ala Pro

TAC TCA GGA TTT CCC CCG GGA GTC ATG AAC CCC GAG GCC GCG AAG CTG GCG
Tyr Ser Gly Phe Pro Pro Gly Val Met Asn Pro Glu Ala Ala Lys Leu Ala

ATC CTC AAC ATG ATA AAC GCC CAC GCC TTG GCA TAT AAG ATG ATA AAG AGG
Ile Leu Asn Met Ile Asn Ala His Ala Leu Ala Tyr Lys Met Ile Lys Arg
```

FIG. 1L-2

```
TTC GAC ACC AAG AAG GCC GAT GAG GAT AGC AAG TCC CCT GCG GAC GTT GGC
Phe Asp Thr Lys Lys Ala Asp Glu Asp Ser Lys Ser Pro Ala Asp Val Gly

ATA ATC TAC AAC AAC ATC GGT GTT GCC TAC CCT AAA GAC CCT AAC GAT CCC
Ile Ile Tyr Asn Asn Ile Gly Val Ala Tyr Pro Lys Asp Pro Asn Asp Pro

AAG GAC GTT AAA GCA GCC GAA AAC GAC AAC TAC TTC CAC AGC GGA CTG TTC
Lys Asp Val Lys Ala Ala Glu Asn Asp Asn Tyr Phe His Ser Gly Leu Phe

TTT GAT GCC ATC CAC AAG GGT AAG CTC AAC ATA GAG TTC GAC GGC GAA AAC
Phe Asp Ala Ile His Lys Gly Lys Leu Asn Ile Glu Phe Asp Gly Glu Asn

TTT GTA AAA GTT AGA CAC CTA AAA GGC AAT GAC TGG ATA GGC CTC AAC TAC
Phe Val Lys Val Arg His Leu Lys Gly Asn Asp Trp Ile Gly Leu Asn Tyr

TAC ACC CGC GAG GTT GTT AGA TAT TCG GAG CCC AAG TTC CCA AGT ATA CCC
Tyr Thr Arg Glu Val Val Arg Tyr Ser Glu Pro Lys Phe Pro Ser Ile Pro

CTC ATA TCC TTC AAG GGC GTT CCC AAC TAC GGC TAC TCC TGC AGG CCC GGC
Leu Ile Ser Phe Lys Gly Val Pro Asn Tyr Gly Tyr Ser Cys Arg Pro Gly

ACG ACC TCC GCC GAT GGC ATG CCC GTC AGC GAT ATC GGC TGG GAA GTC TAT
```

FIG. 1L-3

```
                Thr Thr Ser Ala Asp Gly Met Pro Val Ser Asp Ile Gly Trp Glu Val Tyr

CCC CAG GGA ATC TAC GAC TCG ATA GTC GAG GCC ACC AAG TAC AGT GTT CCT
Pro Gln Gly Ile Tyr Asp Ser Ile Val Glu Ala Thr Lys Tyr Ser Val Pro

GTT TAC GTC ACC GAG AAC GGT GTT GCG GAT TCC GCG GAC ACG CTG AGG CCA
Val Tyr Val Thr Glu Asn Gly Val Ala Asp Ser Ala Asp Thr Leu Arg Pro

TAC TAC ATA GTC AGC CAC GTC TCA AAG ATA GAG GAA GCC ATT GAG AAT GGA
Tyr Tyr Ile Val Ser His Val Ser Lys Ile Glu Glu Ala Ile Glu Asn Gly

TAC CCC GTA AAA GGC TAC ATG TAC TGG GCG CTT ACG GAT AAC TAC GAG TGG
Tyr Pro Val Lys Gly Tyr Met Tyr Trp Ala Leu Thr Asp Asn Tyr Glu Trp

GCC CTC GGC TTC AGC ATG AGG TTT GGT CTC TAC AAG GTC GAC CTC ATC TCC
Ala Leu Gly Phe Ser Met Arg Phe Gly Leu Tyr Lys Val Asp Leu Ile Ser

AAG GAG AGG ATC CCG AGG GAG AGA AGC GTT GAG ATA TAT CGC AGG ATA GTG
Lys Glu Arg Ile Pro Arg Glu Arg Ser Val Glu Ile Tyr Arg Arg Ile Val

CAG TCC AAC GGT GTT CCT AAG GAT ATC AAA GAG GAG TTC CTG AAG GGT GAG
Gln Ser Asn Gly Val Pro Lys Asp Ile Lys Glu Glu Phe Leu Lys Gly Glu
```

FIG. 1L-4

```
GAG AAA TGA      1538
Glu Lys END
```

FIG. 1L-5

(SEQ ID NO:25 - nucleotide sequence and SEQ ID NO:26 - amino acid sequence)
AEPII 1a (Clone # 63GB1) Glycosidase
1

ATG CTA CCA GAA GAG TTC CTA TGG GGC GTT GGG CAG TCA GGC TTT CAG TTC
Met Leu Pro Glu Glu Phe Leu Trp Gly Val Gly Gln Ser Gly Phe Gln Phe

GAA ATG GGC GAC AAG CTC AGG AGG CAC ATC GAT CCA AAT ACC GAC TGG TGG
Glu Met Gly Asp Lys Leu Arg Arg His Ile Asp Pro Asn Thr Asp Trp Trp

AAG TGG GTT CGC GAT CCT TTC AAC ATA AAA AAG GAG CTT GTG AGT GGG GAC
Lys Trp Val Arg Asp Pro Phe Asn Ile Lys Lys Glu Leu Val Ser Gly Asp

CTT CCC GAG GAC GGC ATC AAC AAC TAC GAA CTT TTT GAA AAC GAT CAC AAG
Leu Pro Glu Asp Gly Ile Asn Asn Tyr Glu Leu Phe Glu Asn Asp His Lys

CTC GCT AAA GGC CTT GGA CTC AAC GCA TAC GGG ATT GGA ATA GAG TGG AGC
Leu Ala Lys Gly Leu Gly Leu Asn Ala Tyr Gly Ile Gly Ile Glu Trp Ser

AGA ATC TTT CCC TGG CCG ACG TGG ACG GTC GAT ACC GAG GTC GAG TTC GAC
Arg Ile Phe Pro Trp Pro Thr Trp Thr Val Asp Thr Glu Val Glu Phe Asp

ACT TAC GGT TTA GTA AAG GAC GTT AAG ATA GAC AAG TCC ACC CTT GCT GAA
Thr Tyr Gly Leu Val Lys Asp Val Lys Ile Asp Lys Ser Thr Leu Ala Glu

FIG. 1M-1

```
CTC GAC AGG CTG GCC AAC AAG GAG GAG GTA ATG TAC TAC AGG CGC GTT ATT
Leu Asp Arg Leu Ala Asn Lys Glu Glu Val Met Tyr Tyr Arg Arg Val Ile

CAG CAT TTG AGG GAG CTC GGC TTC AAG GTC TTC GTT AAC CTC AAC CAC TTC
Gln His Leu Arg Glu Leu Gly Phe Lys Val Phe Val Asn Leu Asn His Phe

ACG CTT CCA ATA TGG CTC CAC GAC CCG ATA GTG GCA AGG GAG AAG GCC CTC
Thr Leu Pro Ile Trp Leu His Asp Pro Ile Val Ala Arg Glu Lys Ala Leu

ACA AAC GAC AGA ATC GGC TGG GTC TCC CAG AGG ACA GTT GTT GAG TTT GCC
Thr Asn Asp Arg Ile Gly Trp Val Ser Gln Arg Thr Val Val Glu Phe Ala

AAG TAT GCT GCT TAC ATC GCC CAT GCG CTC GGA GAC CTC GTG GAC ACA TGG
Lys Tyr Ala Ala Tyr Ile Ala His Ala Leu Gly Asp Leu Val Asp Thr Trp

AGC ACC TTC AAC GAA CCT ATG GTA GTT GTG GAG CTC GGA TAC CTC GCC CCC
Ser Thr Phe Asn Glu Pro Met Val Val Val Glu Leu Gly Tyr Leu Ala Pro

TAC TCA GGA TTT CCC CCG GGA GTC ATG AAC CCC GAG GCC GCG AAG CTG GCG
Tyr Ser Gly Phe Pro Pro Gly Val Met Asn Pro Glu Ala Ala Lys Leu Ala

ATC CTC AAC ATG ATA AAC GCC CAC GCC TTG GCA TAT AAG ATG ATA AAG AGG
Ile Leu Asn Met Ile Asn Ala His Ala Leu Ala Tyr Lys Met Ile Lys Arg
```

FIG. 1M-2

```
TTC GAC ACC AAG AAG GCC GAT GAG GAT AGC AAG TCC CCT GCG GAC GTT GGC
Phe Asp Thr Lys Lys Ala Asp Glu Asp Ser Lys Ser Pro Ala Asp Val Gly

ATA ATC TAC AAC AAC ATC GGT GTT GCC TAC CCT AAA GAC CCT AAC GAT CCC
Ile Ile Tyr Asn Asn Ile Gly Val Ala Tyr Pro Lys Asp Pro Asn Asp Pro

AAG GAC GTT AAA GCA GCC GAA AAC GAC AAC TAC TTC CAC AGC GGA CTG TTC
Lys Asp Val Lys Ala Ala Glu Asn Asp Asn Tyr Phe His Ser Gly Leu Phe

TTT GAT GCC ATC CAC AAG GGT AAG CTC AAC ATA GAG TTC GAC GGC GAA AAC
Phe Asp Ala Ile His Lys Gly Lys Leu Asn Ile Glu Phe Asp Gly Glu Asn

TTT GTA AAA GTT AGA CAC CTA AAA GGC AAT GAC TGG ATA GGC CTC AAC TAC
Phe Val Lys Val Arg His Leu Lys Gly Asn Asp Trp Ile Gly Leu Asn Tyr

TAC ACC CGC GAG GTT GTT AGA TAT TCG GAG CCC AAG TTC CCA AGT ATA CCC
Tyr Thr Arg Glu Val Val Arg Tyr Ser Glu Pro Lys Phe Pro Ser Ile Pro

CTC ATA TCC TTC AAG GGC GTT CCC AAC TAC GGC TAC TCC TGC AGG CCC GGC
Leu Ile Ser Phe Lys Gly Val Pro Asn Tyr Gly Tyr Ser Cys Arg Pro Gly

ACG ACC TCC GCC GAT GGC ATG CCC GTC AGC GAT ATC GGC TGG GAA GTC TAT
```

FIG. 1M-3

Thr Thr Ser Ala Asp Gly Met Pro Val Ser Asp Ile Gly Trp Glu Val Tyr

CCC CAG GGA ATC TAC GAC TCG ATA GTC GAG GCC ACC AAG TAC AGT GTT CCT
Pro Gln Gly Ile Tyr Asp Ser Ile Val Glu Ala Thr Lys Tyr Ser Val Pro

GTT TAC GTC ACC GAG AAC GGT GTT GCG GAT TCC GCG GAC ACG CTG AGG CCA
Val Tyr Val Thr Glu Asn Gly Val Ala Asp Ser Ala Asp Thr Leu Arg Pro

TAC TAC ATA GTC AGC CAC GTC TCA AAG ATA GAG GAA GCC ATT GAG AAT GGA
Tyr Tyr Ile Val Ser His Val Ser Lys Ile Glu Glu Ala Ile Glu Asn Gly

TAC CCC GTA AAA GGC TAC ATG TAC TGG GCG CTT ACG GAT AAC TAC GAG TGG
Tyr Pro Val Lys Gly Tyr Met Tyr Trp Ala Leu Thr Asp Asn Tyr Glu Trp

GCC CTC GGC TTC AGC ATG AGG TTT GGT CTC TAC AAG GTC GAC CTC ATC TCC
Ala Leu Gly Phe Ser Met Arg Phe Gly Leu Tyr Lys Val Asp Leu Ile Ser

AAG GAG AGG ATC CCG AGG GAG AGA AGC GTT GAG ATA TAT CGC AGG ATA GTG
Lys Glu Arg Ile Pro Arg Glu Arg Ser Val Glu Ile Tyr Arg Arg Ile Val

CAG TCC AAC GGT GTT CCT AAG GAT ATC AAA GAG GAG TTC CTG AAG GGT GAG
Gln Ser Asn Gly Val Pro Lys Asp Ile Lys Glu Glu Phe Leu Lys Gly Glu

FIG. 1M-4

GAG AAA TGA    1538
Glu Lys END

FIG. 1M-5

(SEQ ID NO:27 - nucleotide sequence and SEQ ID NO:28 - amino acid sequence)
AEPII 1a (Clone # 63GP1) Glycosidase

```
1
ATG CGT CCA TTC TTG TTA ATT TCT ATT TTG GAC TTT CGA GTT GCT GAC TAC
Met Arg Pro Phe Leu Leu Ile Ser Ile Leu Asp Phe Arg Val Ala Asp Tyr

CTC CAA CGT AAC ATA AAG ACA CAA AAC CAA TAT TGG GCA TTG TGC GTA GTA
Leu Gln Arg Asn Ile Lys Thr Gln Asn Gln Tyr Trp Ala Leu Cys Val Val

ATG TTC TCC AAT GTT CTT AGA TGG CAA AAC TTA AAT ATT TCA CCA GCG GTG
Met Phe Ser Asn Val Leu Arg Trp Gln Asn Leu Asn Ile Ser Pro Ala Val

ATA CAT AGA GAC ACC GCT GAA CAC AGA GGT GAT TCC ATG AAG AAG TTT GTC
Ile His Arg Asp Thr Ala Glu His Arg Gly Asp Ser Met Lys Lys Phe Val

GCC CTG TTC ATA ACC ATG TTT TTC GTA GTG AGC ATG GCA GTC GTT GCA CAG
Ala Leu Phe Ile Thr Met Phe Phe Val Val Ser Met Ala Val Val Ala Gln

CCA GCT AGC GCC GCA AAG TAT TCC GAG CTC GAA GAA GGC GGC GTT ATA ATG
Pro Ala Ser Ala Ala Lys Tyr Ser Glu Leu Glu Glu Gly Gly Val Ile Met

CAG GCC TTC TAC TGG GAC GTC CCA GGT GGA GGA ATC TGG TGG GAC ACC ATC
Gln Ala Phe Tyr Trp Asp Val Pro Gly Gly Gly Ile Trp Trp Asp Thr Ile
```

FIG. 1N-1

```
AGG AGC AAG ATA CCG GAG TGG TAC GAG GCG GGA ATA TCC GCC ATT TGG ATT
Arg Ser Lys Ile Pro Glu Trp Tyr Glu Ala Gly Ile Ser Ala Ile Trp Ile

CCG CCA GCC AGC AAG GGG ATG AGC GGC GGT TAC TCG ATG GGC TAC GAT CCC
Pro Pro Ala Ser Lys Gly Met Ser Gly Gly Tyr Ser Met Gly Tyr Asp Pro

TAC GAT TTC TTT GAC CTC GGC GAG TAC AAC CAG AAG GGA ACC ATC GAA ACG
Tyr Asp Phe Phe Asp Leu Gly Glu Tyr Asn Gln Lys Gly Thr Ile Glu Thr

CGC TTT GGC TCT AAA CAG GAG CTC ATC AAT ATG ATA AAC ACG GCC CAT GCC
Arg Phe Gly Ser Lys Gln Glu Leu Ile Asn Met Ile Asn Thr Ala His Ala

TAC GGC ATA AAG GTC ATA GCG GAC ATC GTC ATA AAC CAC CGC GCA GGC GGA
Tyr Gly Ile Lys Val Ile Ala Asp Ile Val Ile Asn His Arg Ala Gly Gly

GAC CTC GAG TGG AAC CCG TTC GTT GGG GAC TAC ACC TGG ACG GAC TTC TCA
Asp Leu Glu Trp Asn Pro Phe Val Gly Asp Tyr Thr Trp Thr Asp Phe Ser

AAG GTG GCC TCG GGC AAA TAT ACT GCC AAC TAC CTC GAC TTC CAC CCC AAC
Lys Val Ala Ser Gly Lys Tyr Thr Ala Asn Tyr Leu Asp Phe His Pro Asn

GAG GTC AAG TGC TGT GAC GAG GGC ACA TTT GGA GGC TTC CCA GAC ATA GCC
Glu Val Lys Cys Cys Asp Glu Gly Thr Phe Gly Gly Phe Pro Asp Ile Ala
```

FIG. 1N-2

```
CAC GAG AAG AGC TGG GAC CAG CAC TGG CTC TGG GCG AGC GAT GAG AGC TAC
His Glu Lys Ser Trp Asp Gln His Trp Leu Trp Ala Ser Asp Glu Ser Tyr

GCC GCC TAC CTA AGG AGC ATC GGC GTT GAT GCC TGG CGC TTT GAC TAC GTG
Ala Ala Tyr Leu Arg Ser Ile Gly Val Asp Ala Trp Arg Phe Asp Tyr Val

AAG GGC TAC GGA GCG TGG GTC GTC AAG GAC TGG CTC AAC TGG TGG GGC GGC
Lys Gly Tyr Gly Ala Trp Val Val Lys Asp Trp Leu Asn Trp Trp Gly Gly

TGG GCC GTT GGC GAG TAC TGG GAC ACC AAC GTT GAT GCA CTC CTC AAC TGG
Trp Ala Val Gly Glu Tyr Trp Asp Thr Asn Val Asp Ala Leu Leu Asn Trp

GCC TAC TCG AGC GGC GCC AAG GTC TTC GAC TTC CCG CTC TAC TAC AAG ATG
Ala Tyr Ser Ser Gly Ala Lys Val Phe Asp Phe Pro Leu Tyr Tyr Lys Met

GAT GAG GCC TTT GAC AAC AAA AAC ATT CCA GCG CTC GTC TCT GCC CTT CAG
Asp Glu Ala Phe Asp Asn Lys Asn Ile Pro Ala Leu Val Ser Ala Leu Gln

AAC GGC CAG ACT GTT GTC TCC CGC GAC CCG TTC AAG GCC GTA ACC TTT GTA
Asn Gly Gln Thr Val Val Ser Arg Asp Pro Phe Lys Ala Val Thr Phe Val

GCA AAC CAC GAC ACC GAT ATA ATC TGG AAC AAG TAC CTT GCT TAT GCT TTC
```

FIG. 1N-3

```
Ala Asn His Asp Thr Asp Ile Ile Trp Asn Lys Tyr Leu Ala Tyr Ala Phe

ATC CTC ACC TAC GAA GGC CAG CCC GTC ATA TTT TAC CGC GAC TAC GAG GAG
Ile Leu Thr Tyr Glu Gly Gln Pro Val Ile Phe Tyr Arg Asp Tyr Glu Glu

TGG CTC AAC AAG GAC AGG TTG AAC AAC CTC ATA TGG ATA CAC GAC CAC CTC
Trp Leu Asn Lys Asp Arg Leu Asn Asn Leu Ile Trp Ile His Asp His Leu

GCA GGT GGA AGC ACG AGC ATA GTT TAC TAC GAC AGC GAC GAG ATG ATT TTC
Ala Gly Gly Ser Thr Ser Ile Val Tyr Tyr Asp Ser Asp Glu Met Ile Phe

GTG AGG AAC GGC TAT GGA AGC AAG CCT GGC CTT ATA ACT TAC ATC AAC CTC
Val Arg Asn Gly Tyr Gly Ser Lys Pro Gly Leu Ile Thr Tyr Ile Asn Leu

GGC TCG AGC AAG GTT GGA AGG TGG GTT TAT GTG CCG AAG TTC GCG GGC GCG
Gly Ser Ser Lys Val Gly Arg Trp Val Tyr Val Pro Lys Phe Ala Gly Ala

TGC ATC CAC GAG TAT ACT GGT AAC CTC GGA GGC TGG GTA GAC AAG TAC GTC
Cys Ile His Glu Tyr Thr Gly Asn Leu Gly Gly Trp Val Asp Lys Tyr Val

TAC TCA AGC GGC TGG GTC TAT TTC GAA GCT CCA GCT TAC GAC CCT GCC AAC
Tyr Ser Ser Gly Trp Val Tyr Phe Glu Ala Pro Ala Tyr Asp Pro Ala Asn
```

FIG. 1N-4

```
GGG CAG TAT GGC TAC TCC GTG TGG AGC TAT TGC GGT GTT GGG TGA    1574
Gly Gln Tyr Gly Tyr Ser Val Trp Ser Tyr Cys Gly Val Gly END
```

FIG. 1N-5

(SEQ ID NO:29 - nucleotide sequence and SEQ ID NO:30 - amino acid sequence)
AEPII 1a (Clone # 63GP2) Glycosidase

```
1
ATG ATA AAC GTT GCA ACG GGA GAG GAG ACC CCA ATA CAC CTC TTT GGA GTC
Met Ile Asn Val Ala Thr Gly Glu Glu Thr Pro Ile His Leu Phe Gly Val

AAC TGG TTC GGC TTT GAG ACA CCG AAC TAC GTT GTT CAC GGC CTA TGG AGT
Asn Trp Phe Gly Phe Glu Thr Pro Asn Tyr Val Val His Gly Leu Trp Ser

AGG AAC TGG GAG GAC ATG CTC CTC CAG ATC AAG AGC CTT GGC TTC AAT GCG
Arg Asn Trp Glu Asp Met Leu Leu Gln Ile Lys Ser Leu Gly Phe Asn Ala

ATA AGG CTT CCC TTC TGT ACC CAG TCA GTA AAA CCG GGG ACG ATG CCA ACG
Ile Arg Leu Pro Phe Cys Thr Gln Ser Val Lys Pro Gly Thr Met Pro Thr

GCG ATT GAC TAC GCC AAG AAC CCA GAC CTC CAG GGT CTT GAC AGC GTC CAG
Ala Ile Asp Tyr Ala Lys Asn Pro Asp Leu Gln Gly Leu Asp Ser Val Gln

ATA ATG GAG AAA ATA ATC AAG AAG GCT GGA GAC CTG GGC ATA TTC GTG CTC
Ile Met Glu Lys Ile Ile Lys Lys Ala Gly Asp Leu Gly Ile Phe Val Leu

CTC GAC TAC CAC AGA ATA GGA TGC AAC TTC ATA GAA CCC CTA TGG TAC ACC
Leu Asp Tyr His Arg Ile Gly Cys Asn Phe Ile Glu Pro Leu Trp Tyr Thr
```

FIG. 10-1

```
GAC AGC TTC TCG GAG CAG GAC TAC ATA AAC ACC TGG GTT GAA GTC GCC CAG
Asp Ser Phe Ser Glu Gln Asp Tyr Ile Asn Thr Trp Val Glu Val Ala Gln

AGG TTC GGC AAG TAC TGG AAC GTT ATC GGC GCG GAC CTG AAG AAC GAA CCC
Arg Phe Gly Lys Tyr Trp Asn Val Ile Gly Ala Asp Leu Lys Asn Glu Pro

CAC AGC TCA AGC CCC GCA CCT GCC GCC TAC ACT GAC GGA AGT GGG GCC ACG
His Ser Ser Ser Pro Ala Pro Ala Ala Tyr Thr Asp Gly Ser Gly Ala Thr

TGG GGA ATG GGC AAC AAC GCC ACC GAC TGG AAC CTG GCG GCT GAG AGG ATA
Trp Gly Met Gly Asn Asn Ala Thr Asp Trp Asn Leu Ala Ala Glu Arg Ile

GGA AGG GCA ATT CTC GAG GTT GCC CCA CAA TGG GTT ATA TTT GTT GAG GGA
Gly Arg Ala Ile Leu Glu Val Ala Pro Gln Trp Val Ile Phe Val Glu Gly

ACC CAG TTC ACC ACC CCC GAG ATA GAC GGT AGG TAC AAG TGG GGC CAC AAC
Thr Gln Phe Thr Thr Pro Glu Ile Asp Gly Arg Tyr Lys Trp Gly His Asn

GCC TGG TGG GGC GGA AAC CTT ATG GGT GTT AGG AAG TAC CCA GTT AAC CTG
Ala Trp Trp Gly Gly Asn Leu Met Gly Val Arg Lys Tyr Pro Val Asn Leu

CCC AGG GAC AAG CTT GTT TAC AGC CCC CAA GTT TAC GGT CCA GAC GTT TAC
Pro Arg Asp Lys Leu Val Tyr Ser Pro Gln Val Tyr Gly Pro Asp Val Tyr
```

FIG. 10-2

```
GAC CAG CCC TAC TTT GAC CCC GGT GAG GGG TTC CCC GAC AAC CTC CCC GAA
Asp Gln Pro Tyr Phe Asp Pro Gly Glu Gly Phe Pro Asp Asn Leu Pro Glu

ATA TGG TAC CAC CAC TTC GGC TAC GTA AAG CTT GAT CTC GGT TAC CCT GTT
Ile Trp Tyr His His Phe Gly Tyr Val Lys Leu Asp Leu Gly Tyr Pro Val

GTT ATA GGT GAG TTC GGA GGC AAG TAC GGC CAT GGG GGA GAC CCG AGG GAT
Val Ile Gly Glu Phe Gly Gly Lys Tyr Gly His Gly Gly Asp Pro Arg Asp

GTC ACT TGG CAG AAC AAG ATA ATA GAC TGG ATG ATC CAG AAC AAA TTC TGT
Val Thr Trp Gln Asn Lys Ile Ile Asp Trp Met Ile Gln Asn Lys Phe Cys

GAC TTC TTC TAC TGG AGC TGG AAC CCA AAC AGC GGT GAC ACC GGT GGA ATT
Asp Phe Phe Tyr Trp Ser Trp Asn Pro Asn Ser Gly Asp Thr Gly Gly Ile

CTG AAG GAT GAC TGG ACG ACA ATA TGG GAG GAC AAG TAC AAC AAC CTG AAG
Leu Lys Asp Asp Trp Thr Thr Ile Trp Glu Asp Lys Tyr Asn Asn Leu Lys

AGG CTC ATG GAC AGC TGT TCT GGA AAC GCC ACT GCC CCG TCC GTC CCC ACG
Arg Leu Met Asp Ser Cys Ser Gly Asn Ala Thr Ala Pro Ser Val Pro Thr

ACA ACT ACA ACA ACA AGC ACA CCG CCA ACG ACC ACA ACG ACT ACA ACA TCC
```

FIG. 10-3

```
Thr Thr Thr Thr Thr Ser Thr Pro Pro Thr Thr Thr Thr Thr Thr Ser

ACT CCA ACG ACC ACT ACC CAG ACC CCG ACC ACC ACT ACT CCA ACT ACG ACA
Thr Pro Thr Thr Thr Thr Gln Thr Pro Thr Thr Thr Thr Pro Thr Thr Thr

ACC ACC ACG ACC ACA ACT CCT TCA AAT AAC GTC CCA TTT GAA ATT GTG AAC
Thr Thr Thr Thr Thr Thr Pro Ser Asn Asn Val Pro Phe Glu Ile Val Asn

GTT CTC CCG ACT AGC TCC CAG TAC GAG GGA ACC AGC GTG GAG GTT GTA TGT
Val Leu Pro Thr Ser Ser Gln Tyr Glu Gly Thr Ser Val Glu Val Val Cys

GAT GGA ACC CAG TGT GCC TCC AGC GTT TGG GGA GCT CCG AAC CTC TGG GGA
Asp Gly Thr Gln Cys Ala Ser Ser Val Trp Gly Ala Pro Asn Leu Trp Gly

GTC GTT AAA ATC GGA AAC GCC ACC ATG GAC CCC AAC GTT TGG GGC TGG GAG
Val Val Lys Ile Gly Asn Ala Thr Met Asp Pro Asn Val Trp Gly Trp Glu

GAC GTT TAC AAG ACT GCA CCC CAG GAC ATT GGA ACC GGC AGC ACA AAG ATG
Asp Val Tyr Lys Thr Ala Pro Gln Asp Ile Gly Thr Gly Ser Thr Lys Met

GAG ATA AGG AAC GGG GTG CTC AAG GTT ACA AAC CTC TGG AAC ATC AAC ATG
Glu Ile Arg Asn Gly Val Leu Lys Val Thr Asn Leu Trp Asn Ile Asn Met
```

FIG. 10-4

(SEQ ID NO:31 - nucleotide sequence and SEQ ID NO:32 - amino acid sequence)
AEPII 1a (Clone # 63GP4) Glycosidase
1
GCT GGA GTG GGT GAG CAA CGG GAT AAC CTA CCA GAT ATT CCC CGA CAG GTT
Ala Gly Val Gly Glu Gln Arg Asp Asn Leu Pro Asp Ile Pro Arg Gln Val CAA CAA CGG AAA CAG GAG CAA CGA TGC CCT AGC TTT GGA CCA CGA CGA GCT
Gln Gln Arg Lys Gln Glu Gln Arg Cys Pro Ser Phe Gly Pro Arg Arg Ala AAT TCT GAA CCA GGT CAA TCC AGG CAA ACC AAT CCT CTC CAA CTG GAG CGA
Asn Ser Glu Pro Gly Gln Ser Arg Gln Thr Asn Pro Leu Gln Leu Glu Arg CCC TAT AAC GCC CCT CCA CTG CTG CCA CCA GTA CTT CGG CGG CGA CAT AAA
Pro Tyr Asn Ala Pro Pro Leu Leu Pro Pro Val Leu Arg Arg Arg His Lys GGG AAT AAC GGA GAA GCT CGA CTA CCT TCA GAG CCT AGG TGT TAC TAT AAT
Gly Asn Asn Gly Glu Ala Arg Leu Pro Ser Glu Pro Arg Cys Tyr Tyr Asn CTA CCT CAA CCC GAT TTT CCT CTC GGG AAG CGC CCA CGG CTA CGA CAC CTA
Leu Pro Gln Pro Asp Phe Pro Leu Gly Lys Arg Pro Arg Leu Arg His Leu CGA CTA CTA CCG GCT TGA CCC CAA GTT CGG GAC CGA GGA GGA GCT GAG AGA
Arg Leu Leu Pro Ala End Pro Gln Val Arg Asp Arg Gly Gly Ala Glu Arg

FIG. 1P-1

```
CAT CCG AAG TAT AAC ACA ATG GCA TAC CCG GAG GTC ATA TAC GGC GCC AAG
His Pro Lys Tyr Asn Thr Met Ala Tyr Pro Glu Val Ile Tyr Gly Ala Lys

CCT TGG GGC AAC CAG CCA ATA AAC GCT CCG AAC TTC GTG CTC CCG ATA AAG
Pro Trp Gly Asn Gln Pro Ile Asn Ala Pro Asn Phe Val Leu Pro Ile Lys

GTC TCC CAG CTT CCG AGG ATA CTC GTT GAC ACA AAG TAC ACG CTC GAA AAG
Val Ser Gln Leu Pro Arg Ile Leu Val Asp Thr Lys Tyr Thr Leu Glu Lys

AGC TTC CCG GGA AAC AAC TTC GCC TTT GAG GCC TGG CTC TTC AAG GAT GCC
Ser Phe Pro Gly Asn Asn Phe Ala Phe Glu Ala Trp Leu Phe Lys Asp Ala

AAC AAC ATG AGG GCA CCA GGC CAG GGG GAC TAC GAG AGG AAT TCC GCC GAT
Asn Asn Met Arg Ala Pro Gly Gln Gly Asp Tyr Glu Arg Asn Ser Ala Asp

ACT GAC GGG CTC CAG GAG TCG TCG CCA CCA ATC CCC ATA TGG AAA CCG TCG
Thr Asp Gly Leu Gln Glu Ser Ser Pro Pro Ile Pro Ile Trp Lys Pro Ser

1886
ATA AGC TTG CGG CCG CCA CCG CGG TGG AGC TCC AGC TTT TGT TCC CTT TAA
Ile Ser Leu Arg Pro Pro Pro Arg Trp Ser Ser Ser Phe Cys Ser Leu END
```

FIG. 1P-2

```
GTT CCT CGA TGA GGC ACA CAG GCG GGG AAT GAG GGT AAT TTT CGA TTT TGT
Val Pro Arg End Gly Thr Gln Ala Gly Asn Glu Gly Asn Phe Arg Phe Cys

GCC CAA CCA CTG CGG CAT AGG GAA TCC AGC CTT CCT AGA AGT TTG GAA GAA
Ala Gln Pro Leu Arg His Arg Glu Ser Ser Leu Pro Arg Ser Leu Glu Glu

GGG CAA CGA AAG CCC ATA CTG GGA CTG GTT CTT CGT CAA GAA GTG GCC GTT
Gly Gln Arg Lys Pro Ile Leu Gly Leu Val Leu Arg Gln Glu Val Ala Val

CAA GCT CGG CGA TGG GAA CGC CTA CGT CGG CTG GTG GGG CTT TGG GAG CCT
Gln Ala Arg Arg Trp Glu Arg Leu Arg Arg Leu Val Gly Leu Trp Glu Pro

TCC AAA GCT CAA CAC TGC CAA CCC GGA GGT CAG GGA ATA CCT GAT AGG AGC
Ser Lys Ala Gln His Cys Gln Pro Gly Gly Gln Gly Ile Pro Asp Arg Ser

GGC CCT CCA CTG GAT AGA GTT CGG CTT TGA CGG CAT CAG GGT TGA TGT GCC
Gly Pro Pro Leu Asp Arg Val Arg Leu End Arg His Gln Gly End Cys Ala

GAA CGA AGT CCT CGA CCC GGG AAC GTT CTT CCC GGA GCT GAG AAA GGC AGT
Glu Arg Ser Pro Arg Pro Gly Asn Val Leu Pro Gly Ala Glu Lys Gly Ser

CAA GGA GAA AAA GCC GGA CGC ATA CCT CGT CGG TGA GAT ATG GAC GCT CTC
Gln Gly Glu Lys Ala Gly Arg Ile Pro Arg Arg End Asp Met Asp Ala Leu
```

FIG. 1P-3

```
CCC TGA GTG GGT GAA AGG AGA CCG CTT CGA CTC CCT CAT GAA CTA CGC CCT
Pro End Val Gly Glu Arg Arg Pro Leu Arg Leu Pro His Glu Leu Arg Pro

CGG GAG GGA CAT CCT CCT GAA CTA CGC GAA GGG CCT GCT CAG TGG AGA AAG
Arg Glu Gly His Pro Pro Glu Leu Arg Glu Gly Pro Ala Gln Trp Arg Lys

TGC AAT GAA AAT GAT GGG ACG TTA CTA TGC TTC CTA CGG CGA GAA CGT ATT
Cys Asn Glu Asn Asp Gly Thr Leu Leu Cys Phe Leu Arg Arg Glu Arg Ile

GCG ATG GGC TTC AAC CTC GTT GAT TCG CAC GAC ACT TCG AGG GTT CTC ACT
Ala Met Gly Phe Asn Leu Val Asp Ser His Asp Thr Ser Arg Val Leu Thr

GAT CTC GGT GGG GGG AGT CTC GGT GAC ACA CCG TCA AAC GAG TCA ATT CAG
Asp Leu Gly Gly Gly Ser Leu Gly Asp Thr Pro Ser Asn Glu Ser Ile Gln

AGA CTC AAG CTC CTC TCA ACG TCC TCT ATG CCC TGC CTG GAA CTC CGG TCA
Arg Leu Lys Leu Leu Ser Thr Ser Ser Met Pro Cys Leu Glu Leu Arg Ser

CCT TCC AGG GGA TGA GAG AGG ACT GCT CGG AGA CAA GGG GCA CTA CGA CGA
Pro Ser Arg Gly End Glu Arg Thr Ala Arg Arg Gln Gly Ala Leu Arg Arg

ACA GCG CTA CCC AAT ACA GTG GGA TAC TGT GAA CGA AGA CGT CCT GAA CCA
```

FIG. 1P-4

```
Thr Ala Leu Pro Asn Thr Val Gly Tyr Cys Glu Arg Arg Arg Pro Glu Pro

TTA CAG GGC ATT GGC GGA GCT CAG AAA AAG AGT TCC TGC ATT GAG GAG CAG
Leu Gln Gly Ile Gly Gly Ala Gln Lys Lys Ser Ser Cys Ile Glu Glu Gln

CGC AAT AAG GTT CTA CAC TGC CAA AGG CGG CGT TAT GGC CTT CTT CAG GGG
Arg Asn Lys Val Leu His Cys Gln Arg Arg Arg Tyr Gly Leu Leu Gln Gly

GCA TCA TGA CGA GGT TCT TGT CGT TGC CAA CAG CTG GAA GAA GCC AGC CCT
Ala Ser End Arg Gly Ser Cys Arg Cys Gln Gln Leu Glu Glu Ala Ser Pro

ACT AAA GCT TCC TGA GGG AGA GTG GAA AGT AAT CTG GCC TGA GAA TTT CAG
Thr Lys Ala Ser End Gly Arg Val Glu Ser Asn Leu Ala End Glu Phe Gln

CCC GGA ACT GCT TCG CGG CAA AGT TGA AGT GCC AGC CAT ACG GAT AAT CAT
Pro Gly Thr Ala Ser Arg Gln Ser End Ser Ala Ser His Arg Asp Asn His

CCT TGA GCG GAG TTG          1443
Pro End Ala Glu Leu
```

FIG. 1P-5

(SEQ ID NO:33 - nucleotide sequence and SEQ ID NO:34 - amino acid sequence)
Bacillus thermoloeovorans (Clone # 68GC1) Glycosidase

```
1
ATG ACT GAA TTA TAT ATA AAA AAT CCC CTG ATC GAA CAG CGG GCA GAT CCC
Met Thr Glu Leu Tyr Ile Lys Asn Pro Leu Ile Glu Gln Arg Ala Asp Pro

TGG ATC TAT AAA CAT ACC GAT GGT TAT TAT TAC TTT ACC GGT TCC GTG CCG
Trp Ile Tyr Lys His Thr Asp Gly Tyr Tyr Tyr Phe Thr Gly Ser Val Pro

GAG TAC GAC CGA ATT GAG CTT AGA CGC TCG CAA ACG ATT CAA GGG CTT GCG
Glu Tyr Asp Arg Ile Glu Leu Arg Arg Ser Gln Thr Ile Gln Gly Leu Ala

GAT GCC GAA GGA ATT ACG ATC TGG CGC AAG CAT GAG TCA GGC CTG ATG AGT
Asp Ala Glu Gly Ile Thr Ile Trp Arg Lys His Glu Ser Gly Leu Met Ser

GCC AAC ATA TGG GCA CCC GAG ATT CAT TAT ATG GAT GGC AAA TGG TAT GTG
Ala Asn Ile Trp Ala Pro Glu Ile His Tyr Met Asp Gly Lys Trp Tyr Val

TAT TAC GCC GCT GCC CAT ACT TCA GAA ACG AGG GAC GGA TTG TTC GAT CAC
Tyr Tyr Ala Ala Ala His Thr Ser Glu Thr Arg Asp Gly Leu Phe Asp His

CGC ATG TTC GTA TTG GAG AAC GCT TCG GCG AAC CCG CTC GAA GGG GAA TGG
Arg Met Phe Val Leu Glu Asn Ala Ser Ala Asn Pro Leu Glu Gly Glu Trp
```

FIG. 1Q-1

```
GTG GAG AAG GGG CAA GTG ATC ACG AAG TGG GAA TCT TTC GCC TTG GAC GCA
Val Glu Lys Gly Gln Val Ile Thr Lys Trp Glu Ser Phe Ala Leu Asp Ala

ACG ACG TTC GAG CAT AAA GGC AAA CGG TAC TAT GTA TGG GCT CAG AAA GAT
Thr Thr Phe Glu His Lys Gly Lys Arg Tyr Tyr Val Trp Ala Gln Lys Asp

CCG GGC ATT CCA GGC AAT TCC AAT CTG TAT ATC TCA TTG ATG GAA GAC CCG
Pro Gly Ile Pro Gly Asn Ser Asn Leu Tyr Ile Ser Leu Met Glu Asp Pro

TGG ACC CTG ACA GGG GAA CAG GTA TGC ATA TCG GTT CCC GAG TAC GAT TGG
Trp Thr Leu Thr Gly Glu Gln Val Cys Ile Ser Val Pro Glu Tyr Asp Trp

GAG AAG ATC GGG TAT CTT GTG AAT GAA GGG GCC GCC GTT CTT AAG CGA AAC
Glu Lys Ile Gly Tyr Leu Val Asn Glu Gly Ala Ala Val Leu Lys Arg Asn

GGG CGA ATA TTC ATG ACC TAT TCC GCG AGC GCC ACG GAC CAC AAC TAT GCG
Gly Arg Ile Phe Met Thr Tyr Ser Ala Ser Ala Thr Asp His Asn Tyr Ala

ATG GGG CTG CTG ACA GCC GAT GAA GAC AGT GAT TTG CTG AAT CCG AGC TCC
Met Gly Leu Leu Thr Ala Asp Glu Asp Ser Asp Leu Leu Asn Pro Ser Ser

TGG GTC AAG TCG CCT GTA CCT GTA TTT ACG ACA TCT GAA GCC AAT GGC CAA
Trp Val Lys Ser Pro Val Pro Val Phe Thr Thr Ser Glu Ala Asn Gly Gln
```

FIG. 1Q-2

```
TAT GGT CCG GGG CAC AAC AGC TTC ACG ATT TCC GAG GAC GGC TTG CAG GAC
Tyr Gly Pro Gly His Asn Ser Phe Thr Ile Ser Glu Asp Gly Leu Gln Asp

ATT TTG GTA TAC CAT GCA AGA AGT TAC AAG GAG ATC GTC GGG ATC CAC TAT
Ile Leu Val Tyr His Ala Arg Ser Tyr Lys Glu Ile Val Gly Ile His Tyr

ATG ATC CGA ACC GTC ATA CGC GTG TAC AGG TCA TCC GAT GGA ACG AAG ACG
Met Ile Arg Thr Val Ile Arg Val Tyr Arg Ser Ser Asp Gly Thr Lys Thr

GAA CGC CGA ATT TCG GGG TGC CAA GAG CGG ATC ATG AAC CGG TCT CCA AGC
Glu Arg Arg Ile Ser Gly Cys Gln Glu Arg Ile Met Asn Arg Ser Pro Ser

CAT GAT GCC GAC TTT GTC ATT GGG GTT GTG ACC GGA AGG ATT AAC AAA CAT
His Asp Ala Asp Phe Val Ile Gly Val Val Thr Gly Arg Ile Asn Lys His

CAG ACC GAC TGA        1031
Gln Thr Asp END
```

FIG. 1Q-3

Figure 1R
(SEQ ID NO:35 - nucleotide sequence and SEQ ID NO:36 - amino acid sequence)
Thermotoga maritima (Clone # 6GA2) Glycosidase

```
1
TTG AAT AAC ACC ATT CCA AGA TGG CGT GGT TTC AAC CTT CTG GAG GCC TTT
Leu Asn Asn Thr Ile Pro Arg Trp Arg Gly Phe Asn Leu Leu Glu Ala Phe

TCC ATT AAA AGT ACA GGA AAT TTT AAA GAG GAA GAT TTT TTG TGG ATG GCT
Ser Ile Lys Ser Thr Gly Asn Phe Lys Glu Glu Asp Phe Leu Trp Met Ala

CAG TGG GAC TTT AAT TTT GTT AGA ATC CCT ATG TGT CAT CTT CTC TGG TCA
Gln Trp Asp Phe Asn Phe Val Arg Ile Pro Met Cys His Leu Leu Trp Ser

GAC CGG GGC AAC CCA TTT ATT ATC AGA GAA GAT TTT TTT GAG AAA ATC GAT
Asp Arg Gly Asn Pro Phe Ile Ile Arg Glu Asp Phe Phe Glu Lys Ile Asp

CGT GTA ATT TTC TGG GGA GAG AAA TAT GGA ATA CAT ATA TGT ATT TCT CTT
Arg Val Ile Phe Trp Gly Glu Lys Tyr Gly Ile His Ile Cys Ile Ser Leu

CAC AGG GCA CCT GGC TAT TCT GTT AAC AAG GAA GTA GAA GAG AAA ACC AAT
His Arg Ala Pro Gly Tyr Ser Val Asn Lys Glu Val Glu Glu Lys Thr Asn

CTG TGG AAA GAT GAA ACA GCT CAA GAA GCG TTC ATT CAT CAC TGG TCT TTT
Leu Trp Lys Asp Glu Thr Ala Gln Glu Ala Phe Ile His His Trp Ser Phe
```

FIG. 1R-1

```
ATC GCA CGT CGT TAC AAA GGA ATT TCT TCC ACA CAC CTG AGT TTT AAC TTA
Ile Ala Arg Arg Tyr Lys Gly Ile Ser Ser Thr His Leu Ser Phe Asn Leu

ATA AAT GAG CCT CCA TTT CCT GAT CCA CAA ATC ATG AGT GTT GAA GAT CAC
Ile Asn Glu Pro Pro Phe Pro Asp Pro Gln Ile Met Ser Val Glu Asp His

AAC TCT CTT ATC AAG AGA ACT ATT ACA GAA ATT CGA AAA ATA GAT CCC GAA
Asn Ser Leu Ile Lys Arg Thr Ile Thr Glu Ile Arg Lys Ile Asp Pro Glu

AGA TTA ATT ATA ATA GAT GGA TTA GGC TAT GGG AAT ATT CCA GTG GAT GAT
Arg Leu Ile Ile Ile Asp Gly Leu Gly Tyr Gly Asn Ile Pro Val Asp Asp

TTA ACA ATT GAG AAT ACA GTG CAA TCA TGC AGA GGG TAC ATT CCC TTC AGT
Leu Thr Ile Glu Asn Thr Val Gln Ser Cys Arg Gly Tyr Ile Pro Phe Ser

GTT ACT CAT TAC AAA GCG GAA TGG GTG GAT AGT AAG GAC TTT CCT GTT CCT
Val Thr His Tyr Lys Ala Glu Trp Val Asp Ser Lys Asp Phe Pro Val Pro

GAG TGG CCA AAT GGA TGG CAT TTT GGG GAA TAC TGG AAC AGA GAA AAG TTA
Glu Trp Pro Asn Gly Trp His Phe Gly Glu Tyr Trp Asn Arg Glu Lys Leu

TTG GAA CAT TAT TTA ACG TGG ATA AAA CTC AGA CAA AAA GGA ATA GAA GTA
Leu Glu His Tyr Leu Thr Trp Ile Lys Leu Arg Gln Lys Gly Ile Glu Val
```

FIG. 1R-2

```
TTC TGT GGA GAA ATG GGA GCT TAC AAC AAA ACA CCT CAC GAT GTG GTT TTA
Phe Cys Gly Glu Met Gly Ala Tyr Asn Lys Thr Pro His Asp Val Val Leu

AAA TGG CTT GAA GAT CTT TTA GAA ATT TTT AAA ACT TTG AAC ATA GGG TTT
Lys Trp Leu Glu Asp Leu Leu Glu Ile Phe Lys Thr Leu Asn Ile Gly Phe

GCC TTA TGG AAT TTT AGA GGT CCT TTT GGT ATT TTA GAT TCG GAA AGG AAA
Ala Leu Trp Asn Phe Arg Gly Pro Phe Gly Ile Leu Asp Ser Glu Arg Lys

GAC GTT GAA TAC GAA GAA TGG TAT GGA CAT AAA CTG GAT AGG AAA ATG TTG
Asp Val Glu Tyr Glu Glu Trp Tyr Gly His Lys Leu Asp Arg Lys Met Leu

GAA CTA TTG AGA AAA TAT TAG      990
Glu Leu Leu Arg Lys Tyr End
```

FIG. 1R-3

(SEQ ID NO:37 - nucleotide sequence and SEQ ID NO:38 - amino acid sequence)
Thermotoga maritima MSB8 (Clone # 6GC17) Glycosidase

```
  1
ATG CTC TCA GAG ATT GTT CCG TAT ACT GTT CTG AGA AGA GAA AGA ATA GAA
Met Leu Ser Glu Ile Val Pro Tyr Thr Val Leu Arg Arg Glu Arg Ile Glu

AGC TGG ATT TTC TCC GAT GAT GCT GTT GAG AGA ATC GTG GAT CCT TCC TTC
Ser Trp Ile Phe Ser Asp Asp Ala Val Glu Arg Ile Val Asp Pro Ser Phe

GAA TGG GAC TTC AGC TCC GCT CCC GTC CGG TTC AGG AAA GAG CTA GAG CCT
Glu Trp Asp Phe Ser Ser Ala Pro Val Arg Phe Arg Lys Glu Leu Glu Pro

TTC TCC GTC GCT GGA GAG CAG AGG GCC TAC CTG AAA CTC TGG TTC GGT GGT
Phe Ser Val Ala Gly Glu Gln Arg Ala Tyr Leu Lys Leu Trp Phe Gly Gly

GAA ACA CTC GTT CTG ATA GAT GGG AAG CCT TAC GGT GAG ATC AAC GAG TAT
Glu Thr Leu Val Leu Ile Asp Gly Lys Pro Tyr Gly Glu Ile Asn Glu Tyr

CAT AGG ATG TTG AAC ATC ACC CCC CTT GCT GAT GGA AAA CCA CAC ACG ATA
His Arg Met Leu Asn Ile Thr Pro Leu Ala Asp Gly Lys Pro His Thr Ile

GAA GCT CAG GTG ATG CCA AGG GGT CTC TTT GGA AAA CCA GAA AAG CCG GTG
Glu Ala Gln Val Met Pro Arg Gly Leu Phe Gly Lys Pro Glu Lys Pro Val
```

FIG. 1S-1

```
TTC ACG GAA GCT TTC TTC ATC GTC GTT GAT GAA GCA CTG ATG AAG GTG GTG
Phe Thr Glu Ala Phe Phe Ile Val Val Asp Glu Ala Leu Met Lys Val Val

AAA ACT CTC GAA CTC ACT ATA AAA ACG GCA GAA GTG ATA GAA GAC GAG TCG
Lys Thr Leu Glu Leu Thr Ile Lys Thr Ala Glu Val Ile Glu Asp Glu Ser

CTT TCT AAG AAA CTT CTG GAC ATC TCC GAG GAG TTT CTC TCG AAA GTA TGG
Leu Ser Lys Lys Leu Leu Asp Ile Ser Glu Glu Phe Leu Ser Lys Val Trp

ATC CCA AGA GAC ACA GGT ACC TAT CTG ATG ACA GCA CTG GAG GAT CCG GGA
Ile Pro Arg Asp Thr Gly Thr Tyr Leu Met Thr Ala Leu Glu Asp Pro Gly

ATA AAA GAT GAG ATC AAA AAC ACC TGG AAC ACA CCG GAG TTC AAA GAG TTC
Ile Lys Asp Glu Ile Lys Asn Thr Trp Asn Thr Pro Glu Phe Lys Glu Phe

ACA GGT GTG AAG CTT CCT GAA GAG TTG AGA AAT CAG ATT CTG GAA GAG TTC
Thr Gly Val Lys Leu Pro Glu Glu Leu Arg Asn Gln Ile Leu Glu Glu Phe

GAA AAA TTC AAA GAA AAG CTG GAT AGA ATA AGA AAA AAC CAT CCG GGT TTT
Glu Lys Phe Lys Glu Lys Leu Asp Arg Ile Arg Lys Asn His Pro Gly Phe

GGA ACG ATT CAC CTT GTG GGG CAC GCG CAC ATA GAC TAC GCC TGG CTC TGG
Gly Thr Ile His Leu Val Gly His Ala His Ile Asp Tyr Ala Trp Leu Trp
```

FIG. 1S-2

CCA GTT GAG GAG ACG AAG AGA AAG ATC CTA CGC ACT TTC GCA AAC TCT GTG
Pro Val Glu Glu Thr Lys Arg Lys Ile Leu Arg Thr Phe Ala Asn Ser Val

TTG CTC TCT AAG CTT TAT CCG GAG TTC GTT TAC ACT CAG TCT TCT GCT CAG
Leu Leu Ser Lys Leu Tyr Pro Glu Phe Val Tyr Thr Gln Ser Ser Ala Gln

ATG TAC GAG GAT CTC AAG CAA AAT TCA CCA GAG CTT TTC GAG GAA GTG AGA
Met Tyr Glu Asp Leu Lys Gln Asn Ser Pro Glu Leu Phe Glu Glu Val Arg

AAG CTC GTA GAA GAG GGG AGA TGG GAG CCA GTC GGT GGC ATG TGG GTG GAG
Lys Leu Val Glu Glu Gly Arg Trp Glu Pro Val Gly Gly Met Trp Val Glu

TCG GAC TGC AAC GTT CCA TCG ATA GAG TCG CTT GTG AGA CAG TTC TAC TAT
Ser Asp Cys Asn Val Pro Ser Ile Glu Ser Leu Val Arg Gln Phe Tyr Tyr

GGG CAA AAA TTC TTC GAA AGA GAA TTC GGG AAA AAG AGC AAG GTG TGC TGG
Gly Gln Lys Phe Phe Glu Arg Glu Phe Gly Lys Lys Ser Lys Val Cys Trp

CTT CCG GAT GTG TTT GGG TTT TCC TGG GTG CTT CCC CAA ATT CTG AAA GAA
Leu Pro Asp Val Phe Gly Phe Ser Trp Val Leu Pro Gln Ile Leu Lys Glu

GCC GGG ATA AAA TAC TTC GTC ACC ACG AAA CTC AAC TGG AAC GAC ACG AAC

FIG. 1S-3

```
Ala Gly Ile Lys Tyr Phe Val Thr Thr Lys Leu Asn Trp Asn Asp Thr Asn

GAG TTT CCG TAC GAT CTG TGC CGC TGG AGG GGA ATA GAT GGA TCC GAA GTG
Glu Phe Pro Tyr Asp Leu Cys Arg Trp Arg Gly Ile Asp Gly Ser Glu Val

ATC TAT TTC AGT TTC AAA AAT CCC AAC GAG GGG TAC AAC GGA AAG ATA GAT
Ile Tyr Phe Ser Phe Lys Asn Pro Asn Glu Gly Tyr Asn Gly Lys Ile Asp

CCC GAT ACG GTC TAC AAA ACC TGG AAG AAC TTC AGG CAG AAA GAT CTC ACA
Pro Asp Thr Val Tyr Lys Thr Trp Lys Asn Phe Arg Gln Lys Asp Leu Thr

AAC AGA GTT CTT CTT TCG TTC GGA CAC GGT GAT GGT GGC GGT CCA ACC
Asn Arg Val Leu Leu Ser Phe Gly His Gly Asp Gly Gly Gly Gly Pro Thr

GAA GAG ATG CTG GAA AAT TAC GAG GTT CTG AAG GAT TTC CCT GGA CTA CCG
Glu Glu Met Leu Glu Asn Tyr Glu Val Leu Lys Asp Phe Pro Gly Leu Pro

CAC CTT GAA ATG GGA ACT GTG GAA GAA TTT TTC AAG AAG GTG GAG ATC GAC
His Leu Glu Met Gly Thr Val Glu Glu Phe Phe Lys Lys Val Glu Ile Asp

GAA GAA CTC CCT GTG TGG GAC GGA GAG CTT TAC CTT GAA CTT CAC AGG GGA
Glu Glu Leu Pro Val Trp Asp Gly Glu Leu Tyr Leu Glu Leu His Arg Gly
```

FIG. 1S-4

```
ACC TAC ACT TCT CAG TTC AGG ACA AAG AAA CTT CAC AAA GAA GCG GAA GAC
Thr Tyr Thr Ser Gln Phe Arg Thr Lys Lys Leu His Lys Glu Ala Glu Asp

AGT CTT TAT CTT GCA GAG TTG ATC TCG GCT TTC ACG GAT AAA GAT TTT TCG
Ser Leu Tyr Leu Ala Glu Leu Ile Ser Ala Phe Thr Asp Lys Asp Phe Ser

GAC GAA ATA GAC GAA CTC TGG AAG ATT CTG TTG AGA AAC GAA TTT CAC GAT
Asp Glu Ile Asp Glu Leu Trp Lys Ile Leu Leu Arg Asn Glu Phe His Asp

ATT CTA CCT GGA TCT TCT ATA AAG GAA GTC TAT GAA GAT ACA GAA AAA GAG
Ile Leu Pro Gly Ser Ser Ile Lys Glu Val Tyr Glu Asp Thr Glu Lys Glu

CTC AGA CAT GTG ATA GAA AAA TCA AAA GAC ATC GTT ATC GAA TCT CTC AAA
Leu Arg His Val Ile Glu Lys Ser Lys Asp Ile Val Ile Glu Ser Leu Lys

GTT CTT TCC TCT GAG AAC AAA GAT GTT CTA ACC ATT TTG AAC GCT TCA TCG
Val Leu Ser Ser Glu Asn Lys Asp Val Leu Thr Ile Leu Asn Ala Ser Ser

TTT CCA AAG AAG TGT CTT TTC TTC CTC AAC GAA GAT CTC GCG ATT TCC TTT
Phe Pro Lys Lys Cys Leu Phe Phe Leu Asn Glu Asp Leu Ala Ile Ser Phe

GAA GGA GAA GCA CTC TTG AAA CAG AAA ACT CAC GAT GGA AGG TAT GTG TAC
Glu Gly Glu Ala Leu Leu Lys Gln Lys Thr His Asp Gly Arg Tyr Val Tyr
```

FIG. 1S-5

```
TTC ATA GAC AGG GAG ATT CCT CCG TTC ACG AAA GTA GAA CTG AAA GTT CGC
Phe Ile Asp Arg Glu Ile Pro Pro Phe Thr Lys Val Glu Leu Lys Val Arg

AAA GCC ACG TCT GAG GAA ACT CCA AGT GAG TTG AGA GAA ACA AAC ATC ATG
Lys Ala Thr Ser Glu Glu Thr Pro Ser Glu Leu Arg Glu Thr Asn Ile Met

GAG AAC GAA TTT CTC AGG GTG CAC GTC AAC GAT GAC GGA ACA ATT CAA ATC
Glu Asn Glu Phe Leu Arg Val His Val Asn Asp Asp Gly Thr Ile Gln Ile

TAC GAC AAA GAA CTG GAC AGG TAC GTT TTC GAA GAG AAG GGA AAC ATC TTG
Tyr Asp Lys Glu Leu Asp Arg Tyr Val Phe Glu Glu Lys Gly Asn Ile Leu

AAA CTT CAT AAA AAC ATC CCT GCT TAC TGG GAC AAC TGG GAT ATC GCA GAA
Lys Leu His Lys Asn Ile Pro Ala Tyr Trp Asp Asn Trp Asp Ile Ala Glu

AAC GTG GAA AAG ACA GGA TAT ACC CTG AGG GCG AAA AAC ATA GAA AAA ATA
Asn Val Glu Lys Thr Gly Tyr Thr Leu Arg Ala Lys Asn Ile Glu Lys Ile

GAG TCT GGC CCT GTT CGA GAA GTG ATC CGT GTT GAA CAT GAA TCA GAA GGA
Glu Ser Gly Pro Val Arg Glu Val Ile Arg Val Glu His Glu Ser Glu Gly

AGC AGG ATC ACG CAG CAT TAC ATC CTT TAC AGA AAG AGT AGA AGG CTC GAT
```

FIG. 1S-6

Ser Arg Ile Thr Gln His Tyr Ile Leu Tyr Arg Lys Ser Arg Arg Leu Asp

ATA GAA ACG AAG GTA GAC TGG CAC ACA AGG CGT GCG CTT CTC AGA GCC TAC
Ile Glu Thr Lys Val Asp Trp His Thr Arg Arg Ala Leu Leu Arg Ala Tyr

TTC CCA ACA ACT GTT CTG TCG AGA AAG GCT AGG TTC GAT ATC TCC GGT GGT
Phe Pro Thr Thr Val Leu Ser Arg Lys Ala Arg Phe Asp Ile Ser Gly Gly

TTC ATC GAA AGG CCC ACA CAC AGA AAC ACC AGT TTC GAA CAG GCG CGT TTC
Phe Ile Glu Arg Pro Thr His Arg Asn Thr Ser Phe Glu Gln Ala Arg Phe

GAG GTG CCG TTT CAC AGG TGG ATG GAT CTT TCC CAG ACA GAC TTC GGC GTG
Glu Val Pro Phe His Arg Trp Met Asp Leu Ser Gln Thr Asp Phe Gly Val

TCC ATT CTG AAC GAC GGA AAA TAC GGT GGC AGT GTT CAT CAG GGT ATC ATG
Ser Ile Leu Asn Asp Gly Lys Tyr Gly Gly Ser Val His Gln Gly Ile Met

GCG CTT TCA CTG ATA AAA GCG GGT ATT TTC CCC GAT TTT CTC TGT GAC GAA
Ala Leu Ser Leu Ile Lys Ala Gly Ile Phe Pro Asp Phe Leu Cys Asp Glu

GGC GAA CAC ACT TTC ACC TAT TCT GTC TAC GTA CAC CCT GGA GAC AGC TTG
Gly Glu His Thr Phe Thr Tyr Ser Val Tyr Val His Pro Gly Asp Ser Leu

FIG. 1S-7

```
AGA GAT GTT GTA AAA GGA TCA GAA GAT CTC AAC AGA TCT TTC ATC GTT CAT
Arg Asp Val Val Lys Gly Ser Glu Asp Leu Asn Arg Ser Phe Ile Val His

CGC GGG GTG TTG AAC CTC CCC TCT CCT TTA CTG GAG ATC TCT CCT CAA AAC
Arg Gly Val Leu Asn Leu Pro Ser Pro Leu Leu Glu Ile Ser Pro Gln Asn

TTC CGT CTC ACC TCA CTG AGA AGG GTG AAG GAC AAA ATT GTT TTG AGG CTT
Phe Arg Leu Thr Ser Leu Arg Arg Val Lys Asp Lys Ile Val Leu Arg Leu

GTT GAG ATT TTC GGA ACA TCA GGG AAA CTT TCC ATT AAA CTC CCA TGG CAT
Val Glu Ile Phe Gly Thr Ser Gly Lys Leu Ser Ile Lys Leu Pro Trp His

GGT GAA ATC TAT CAG ACG AAC GTT CTG GAA GAG AAA AAA CAG AAA GTC ACC
Gly Glu Ile Tyr Gln Thr Asn Val Leu Glu Glu Lys Lys Gln Lys Val Thr

TTC CCA GTG GTT TAC CAT CCG TTC AAG ATC TAC ACT TTT GTT GTA GAA GGT
Phe Pro Val Val Tyr His Pro Phe Lys Ile Tyr Thr Phe Val Val Glu Gly

TGA     3011
END
```

FIG. 1S-8

(SEQ ID NO:39 - nucleotide sequence and SEQ ID NO:40 - amino acid sequence)
Thermotoga maritima MSB8 (Clone # 6GC18) Glycosidase

```
1
ATG GAA CTG TAC AGG GAT CCT TCG CAA CCC ATC GAA GTG AGA GTG AGA GAT
Met Glu Leu Tyr Arg Asp Pro Ser Gln Pro Ile Glu Val Arg Val Arg Asp

CTT CTT TCC AGA ATG ACG CTG GAA GAG AAA GTG GCC CAG CTT GGG TCT GTC
Leu Leu Ser Arg Met Thr Leu Glu Glu Lys Val Ala Gln Leu Gly Ser Val

TGG GGT TAC GAA CTG ATA GAC GAG AGG GGA AAG TTC AGT AGA GAA AAA GCA
Trp Gly Tyr Glu Leu Ile Asp Glu Arg Gly Lys Phe Ser Arg Glu Lys Ala

AAA GAA CTC CTC AAA AAT GGT ATA GGC CAG ATC ACA AGG CCT GGT GGA TCA
Lys Glu Leu Leu Lys Asn Gly Ile Gly Gln Ile Thr Arg Pro Gly Gly Ser

ACG AAC CTT GAA CCT CAA GAA GCC GCG GAA CTT GTG AAC GAA ATA CAG AGA
Thr Asn Leu Glu Pro Gln Glu Ala Ala Glu Leu Val Asn Glu Ile Gln Arg

TTT CTT GTG GAA GAA ACA CGC CTT GGA ATT CCT GCG ATG ATA CAC GAA GAA
Phe Leu Val Glu Glu Thr Arg Leu Gly Ile Pro Ala Met Ile His Glu Glu

TGT CTC ACC GGT TAC ATG GGA CTT GGA GGA ACC AAC TTC CCT CAG GCG ATA
Cys Leu Thr Gly Tyr Met Gly Leu Gly Gly Thr Asn Phe Pro Gln Ala Ile
```

FIG. 1T-1

```
GCA ATG GCG AGT ACA TGG GAT CCA GAT CTC ATA GAA AAA ATG ACC ACC GCC
Ala Met Ala Ser Thr Trp Asp Pro Asp Leu Ile Glu Lys Met Thr Thr Ala

GTC AGA GAG GAT ATG AGA AAG ATA GGG GCA CAT CAG GGT CTC GCA CCT GTT
Val Arg Glu Asp Met Arg Lys Ile Gly Ala His Gln Gly Leu Ala Pro Val

CTG GAT GTC GCA AGA GAT CCA AGG TGG GGG AGA ACA GAA GAG ACG TTC GGA
Leu Asp Val Ala Arg Asp Pro Arg Trp Gly Arg Thr Glu Glu Thr Phe Gly

GAA TCT CCC TAT CTG GTG GCG AGG ATG GGA GTC TCT TAC GTG AAA GGC CTC
Glu Ser Pro Tyr Leu Val Ala Arg Met Gly Val Ser Tyr Val Lys Gly Leu

CAG GGG GAA GAT ATC AAA AAA GGT GTC GTT GCC ACA GTG AAA CAC TTC GCC
Gln Gly Glu Asp Ile Lys Lys Gly Val Val Ala Thr Val Lys His Phe Ala

GGA TAC AGC GCT TCT GAA GGT GGA AAG AAC TGG GCA CCA ACG AAC ATT CCG
Gly Tyr Ser Ala Ser Glu Gly Gly Lys Asn Trp Ala Pro Thr Asn Ile Pro

GAG AGG GAA TTC AAA GAG GTC TTT CTC TTT CCG TTC GAA GCG GCC GTT AAA
Glu Arg Glu Phe Lys Glu Val Phe Leu Phe Pro Phe Glu Ala Ala Val Lys

GAA GCG AAT GTG CTT TCT GTG ATG AAC TCC TAC AGC GAA ATA GAC GGT GTC
Glu Ala Asn Val Leu Ser Val Met Asn Ser Tyr Ser Glu Ile Asp Gly Val
```

FIG. 1T-2

```
CCA TGT GCA GCG AAC AGG AAA CTC CTC ACA GAC ATT CTC AGA AAA GAC TGG
Pro Cys Ala Ala Asn Arg Lys Leu Leu Thr Asp Ile Leu Arg Lys Asp Trp

GGA TTC GAA GGA ATC GTC GTT TCT GAC TAT TTT GCT GTG AAA GTT CTG GAA
Gly Phe Glu Gly Ile Val Val Ser Asp Tyr Phe Ala Val Lys Val Leu Glu

GAT TAT CAC AGA ATA GCA AGG GAT AAG TCA GAA GCC GCA AGA CTC GCA CTT
Asp Tyr His Arg Ile Ala Arg Asp Lys Ser Glu Ala Ala Arg Leu Ala Leu

GAA GCG GGG ATA GAT GTT GAA CTT CCG AAG ACA GAA TGT TAT CAA TAT TTG
Glu Ala Gly Ile Asp Val Glu Leu Pro Lys Thr Glu Cys Tyr Gln Tyr Leu

AAA GAC CTT GTT GAA AAA GGC ATC ATC TCC GAA GCT TTG ATC GAC GAG GCA
Lys Asp Leu Val Glu Lys Gly Ile Ile Ser Glu Ala Leu Ile Asp Glu Ala

GTC ACC AGG GTG CTG AGG CTG AAG TTC ATG CTC GGG CTC TTC GAA AAT CCC
Val Thr Arg Val Leu Arg Leu Lys Phe Met Leu Gly Leu Phe Glu Asn Pro

TAC GTT GAG GTG GAA AAA GCA AAG ATA GAA AGT CAC AGA GAC ATC GCA CTC
Tyr Val Glu Val Glu Lys Ala Lys Ile Glu Ser His Arg Asp Ile Ala Leu

GAG ATA GCA AGG AAA TCC ATT ATC CTT CTC AAG AAT GAT GGA ATT CTG CCT
```

FIG. 1T-3

```
                Glu Ile Ala Arg Lys Ser Ile Ile Leu Leu Lys Asn Asp Gly Ile Leu Pro

CTT CAG AAA AAC AAA AAA GTT GCC CTG ATC GGA CCG AAC GCG GGT GAG GTG
Leu Gln Lys Asn Lys Lys Val Ala Leu Ile Gly Pro Asn Ala Gly Glu Val

AGA AAT CTC CTC GGA GAT TAC ATG TAC CTT GCA CAC ATA AGG GCT CTC CTC
Arg Asn Leu Leu Gly Asp Tyr Met Tyr Leu Ala His Ile Arg Ala Leu Leu

GAC AAC ATA GAC GAC GTC TTT GGA AAT CCT CAG ATC CCG AGA GAA AAC TAC
Asp Asn Ile Asp Asp Val Phe Gly Asn Pro Gln Ile Pro Arg Glu Asn Tyr

GAA AGA CTG AAG AAG AGC ATA GAA GAA CAT ATG AAG AGC ATT CCG AGT GTT
Glu Arg Leu Lys Lys Ser Ile Glu Glu His Met Lys Ser Ile Pro Ser Val

CTC GAT GCC TTC AAA GAA GAA GGG ATC GAA TTC GAA TAT GCA AAA GGC TGT
Leu Asp Ala Phe Lys Glu Glu Gly Ile Glu Phe Glu Tyr Ala Lys Gly Cys

GAA GTG ACA GGG GAA GAC AGA AGC GGT TTC GAA GAG GCG ATA GAA ATT GCA
Glu Val Thr Gly Glu Asp Arg Ser Gly Phe Glu Glu Ala Ile Glu Ile Ala

AAG AAA TCC GAC GTT GCC ATC GTT GTC GTA GGG GAC AAA TCT GGA CTC ACC
Lys Lys Ser Asp Val Ala Ile Val Val Val Gly Asp Lys Ser Gly Leu Thr
```

FIG. 1T-4

```
CTT GAC TGC ACA ACC GGT GAG TCC AGA GAC ATG GCA AAC CTC AAG CTT CCA
Leu Asp Cys Thr Thr Gly Glu Ser Arg Asp Met Ala Asn Leu Lys Leu Pro

GGA GTC CAG GAA GAA CTC GTC CTC GAA GTT GCA AAG ACA GGA AAA CCC GTC
Gly Val Gln Glu Glu Leu Val Leu Glu Val Ala Lys Thr Gly Lys Pro Val

GTT CTT GTC CTC ATC ACG GGA AGA CCC TAT TCA CTC AAA AAC GTC GTC GAC
Val Leu Val Leu Ile Thr Gly Arg Pro Tyr Ser Leu Lys Asn Val Val Asp

AAG GTG AAC GCG ATC CTT CAG GTG TGG CTT CCT GGA GAA GCG GGA GGA AGA
Lys Val Asn Ala Ile Leu Gln Val Trp Leu Pro Gly Glu Ala Gly Gly Arg

GCG ATC GTT GAC ATC ATC TAT GGA AAG GTG AAT CCC TCT GGA AAA CTC CCG
Ala Ile Val Asp Ile Ile Tyr Gly Lys Val Asn Pro Ser Gly Lys Leu Pro

ATC AGC TTT CCA AGA AGC GCT GGT CAG ATT CCT GTC TTC CAC TAC GTC AAA
Ile Ser Phe Pro Arg Ser Ala Gly Gln Ile Pro Val Phe His Tyr Val Lys

CCA TCC GGG GGA AGG TCT CAC TGG CAC GGA GAC TAC GTG GAT GAG AGC ACA
Pro Ser Gly Gly Arg Ser His Trp His Gly Asp Tyr Val Asp Glu Ser Thr

AAG CCT CTC TTC CCG TTT GGG CAC GGT TTG TCT TAC ACG AAG TTC GAG TAC
Lys Pro Leu Phe Pro Phe Gly His Gly Leu Ser Tyr Thr Lys Phe Glu Tyr
```

FIG. 1T-5

```
AGC AAC CTC AGA ATC GAG CCG AAG GAA GTG CCA CCG GCC GGC GAA GTG GTG
Ser Asn Leu Arg Ile Glu Pro Lys Glu Val Pro Pro Ala Gly Glu Val Val

ATA AAG GTG GAC GTG GAA AAC ATC GGA GAC AGA GAC GGA GAC GAG GTG GTT
Ile Lys Val Asp Val Glu Asn Ile Gly Asp Arg Asp Gly Asp Glu Val Val

CAA CTT TAC ATC GGT CGT GAG TTT GCA AGC GTC ACA AGG CCT GTG AAA GAG
Gln Leu Tyr Ile Gly Arg Glu Phe Ala Ser Val Thr Arg Pro Val Lys Glu

CTG AAG GGC TTC AAG AGG GTT TCT TTG AAG GCG AAA GAG AAG AAG ACT GTT
Leu Lys Gly Phe Lys Arg Val Ser Leu Lys Ala Lys Glu Lys Lys Thr Val

GTG TTC AGG CTT CAC ATG GAC GTG CTC GCC TAC TAC AAC AGA GAC ATG AAA
Val Phe Arg Leu His Met Asp Val Leu Ala Tyr Tyr Asn Arg Asp Met Lys

CTC GTG GTT GAA CCC GGT GAG TTC AAA GTG ATG GTG GGA AGC TCT TCT GAA
Leu Val Val Glu Pro Gly Glu Phe Lys Val Met Val Gly Ser Ser Ser Glu

GAC ATC AGA CTC ACA GGT TCT TTC TCC GTC GTC GGT GAA AAA AGA GAA GTG
Asp Ile Arg Leu Thr Gly Ser Phe Ser Val Val Gly Glu Lys Arg Glu Val

GTG GGA ATG AGG AAA TTC TTC ACG GAA GCC TGC GAG GAG TGA        2336
Val Gly Met Arg Lys Phe Phe Thr Glu Ala Cys Glu Glu END
```

FIG. 1T-6

(SEQ ID NO:41 - nucleotide sequence and SEQ ID NO:42 - amino acid sequence)
Thermotoga maritima MSB8 (Clone # 6GP2) Glycosidase

```
1
ATG GGG ATT GGT GGC GAC GAC TCC TGG AGC CCG TCA GTA TCG GCG AAA TTC
Met Gly Ile Gly Gly Asp Asp Ser Trp Ser Pro Ser Val Ser Ala Glu Phe

CTT TTA TTG ATC GTT GAG CTC TCT TTC GTT CTC TTT GCA AGT GAC GAG TTC
Leu Leu Leu Ile Val Glu Leu Ser Phe Val Leu Phe Ala Ser Asp Glu Phe

GTG AAA GTG GAA AAC GGA AAA TTC GCT CTG AAC GGA AAA GAA TTC AGA TTC
Val Lys Val Glu Asn Gly Lys Phe Ala Leu Asn Gly Lys Glu Phe Arg Phe

ATT GGA AGC AAC AAC TAC TAC ATG CAC TAC AAG AGC AAC GGA ATG ATA GAC
Ile Gly Ser Asn Asn Tyr Tyr Met His Tyr Lys Ser Asn Gly Met Ile Asp

AGT GTT CTG GAG AGT GCC AGA GAC ATG GGT ATA AAG GTC CTC AGA ATC TGG
Ser Val Leu Glu Ser Ala Arg Asp Met Gly Ile Lys Val Leu Arg Ile Trp

GGT TTC CTC GAC GGG GAG AGT TAC TGC AGA GAC AAG AAC ACC TAC ATG CAT
Gly Phe Leu Asp Gly Glu Ser Tyr Cys Arg Asp Lys Asn Thr Tyr Met His

CCT GAG CCC GGT GTT TTC GGG GTG CCA GAA GGA ATA TCG AAC GCC CAG AGC
Pro Glu Pro Gly Val Phe Gly Val Pro Glu Gly Ile Ser Asn Ala Gln Ser
```

FIG. 1U-1

```
GGT TTC GAA AGA CTC GAC TAC ACA GTT GCG AAA GCG AAA GAA CTC GGT ATA
Gly Phe Glu Arg Leu Asp Tyr Thr Val Ala Lys Ala Lys Glu Leu Gly Ile

AAA CTT GTC ATT GTT CTT GTG AAC AAC TGG GAC GAC TTC GGT GGA ATG AAC
Lys Leu Val Ile Val Leu Val Asn Asn Trp Asp Asp Phe Gly Gly Met Asn

CAG TAC GTG AGG TGG TTT GGA GGA ACC CAT CAC GAC GAT TTC TAC AGA GAT
Gln Tyr Val Arg Trp Phe Gly Gly Thr His His Asp Asp Phe Tyr Arg Asp

GAG AAG ATC AAA GAA GAG TAC AAA AAG TAC GTC TCC TTT CTC GTA AAC CAT
Glu Lys Ile Lys Glu Glu Tyr Lys Lys Tyr Val Ser Phe Leu Val Asn His

GTC AAT ACC TAC ACG GGA GTT CCT TAC AGG GAA GAG CCC ACC ATC ATG GCC
Val Asn Thr Tyr Thr Gly Val Pro Tyr Arg Glu Glu Pro Thr Ile Met Ala

TGG GAG CTT GCA AAC GAA CCG CGC TGT GAG ACG GAC AAA TCG GGG AAC ACG
Trp Glu Leu Ala Asn Glu Pro Arg Cys Glu Thr Asp Lys Ser Gly Asn Thr

CTC GTT GAG TGG GTG AAG GAG ATG AGC TCC TAC ATA AAG AGT CTG GAT CCC
Leu Val Glu Trp Val Lys Glu Met Ser Ser Tyr Ile Lys Ser Leu Asp Pro

AAC CAC CTC GTG GCT GTG GGG GAC GAA GGA TTC TTC AGC AAC TAC GAA GGA
Asn His Leu Val Ala Val Gly Asp Glu Gly Phe Phe Ser Asn Tyr Glu Gly
```

FIG. 1U-2

```
TTC AAA CCT TAC GGT GGA GAA GCC GAG TGG GCC TAC AAC GGC TGG TCC GGT
Phe Lys Pro Tyr Gly Gly Glu Ala Glu Trp Ala Tyr Asn Gly Trp Ser Gly

GTT GAC TGG AAG AAG CTC CTT TCG ATA GAG ACG GTG GAC TTC GGC ACG TTC
Val Asp Trp Lys Lys Leu Leu Ser Ile Glu Thr Val Asp Phe Gly Thr Phe

CAC CTC TAT CCG TCC CAC TGG GGT GTC AGT CCA GAG AAC TAT GCC CAG TGG
His Leu Tyr Pro Ser His Trp Gly Val Ser Pro Glu Asn Tyr Ala Gln Trp

GGA GCG AAG TGG ATA GAA GAC CAC ATA AAG ATC GCA AAA GAG ATC GGA AAA
Gly Ala Lys Trp Ile Glu Asp His Ile Lys Ile Ala Lys Glu Ile Gly Lys

CCC GTT GTT CTG GAA GAA TAT GGA ATT CCA AAG AGT GCG CCA GTT AAC AGA
Pro Val Val Leu Glu Glu Tyr Gly Ile Pro Lys Ser Ala Pro Val Asn Arg

ACG GCC ATC TAC AGA CTC TGG AAC GAT CTG GTC TAC GAT CTC GGT GGA GAT
Thr Ala Ile Tyr Arg Leu Trp Asn Asp Leu Val Tyr Asp Leu Gly Gly Asp

GGA GCG ATG TTC TGG ATG CTC GCG GGA ATC GGG GAA GGT TCG GAC AGA GAC
Gly Ala Met Phe Trp Met Leu Ala Gly Ile Gly Glu Gly Ser Asp Arg Asp

GAG AGA GGG TAC TAT CCG GAC TAC GAC GGT TTC AGA ATA GTG AAC GAC GAC
```

FIG. 1U-3

```
Glu Arg Gly Tyr Tyr Pro Asp Tyr Asp Gly Phe Arg Ile Val Asn Asp Asp

AGT CCA GAA GCG GAA CTG ATA AGA GAA TAC GCG AAG CTG TTC AAC ACA GGT
Ser Pro Glu Ala Glu Leu Ile Arg Glu Tyr Ala Lys Leu Phe Asn Thr Gly

GAA GAC ATA AGA GAA GAC ACC TGC TCT TTC ATC CTT CCA AAA GAC GGC ATG
Glu Asp Ile Arg Glu Asp Thr Cys Ser Phe Ile Leu Pro Lys Asp Gly Met

GAG ATC AAA AAG ACC GTG GAA GTG AGG GCT GGT GTT TTC GAC TAC AGC AAC
Glu Ile Lys Lys Thr Val Glu Val Arg Ala Gly Val Phe Asp Tyr Ser Asn

ACG TTT GAA AAG TTG TCT GTC AAA GTC GAA GAT CTG GTT TTT GAA AAT GAG
Thr Phe Glu Lys Leu Ser Val Lys Val Glu Asp Leu Val Phe Glu Asn Glu

ATA GAG CAT CTC GGA TAC GGA ATT TAC GGC TTT GAT CTC GAC ACA ACC CGG
Ile Glu His Leu Gly Tyr Gly Ile Tyr Gly Phe Asp Leu Asp Thr Thr Arg

ATC CCG GAT GGA GAA CAT GAA ATG TTC CTT GAA GGC CAC TTT CAG GGA AAA
Ile Pro Asp Gly Glu His Glu Met Phe Leu Glu Gly His Phe Gln Gly Lys

ACG GTG AAA GAC TCT ATC AAA GCG AAA GTG GTG AAC GAA GCA CGG TAC GTG
Thr Val Lys Asp Ser Ile Lys Ala Lys Val Val Asn Glu Ala Arg Tyr Val
```

FIG. 1U-4

```
CTC GCA GAG GAA GTT GAT TTT TCC TCT CCA GAA GAG GTG AAA AAC TGG TGG
Leu Ala Glu Glu Val Asp Phe Ser Ser Pro Glu Glu Val Lys Asn Trp Trp

AAC AGC GGA ACC TGG CAG GCA GAG TTC GGG TCA CCT GAC ATT GAA TGG AAC
Asn Ser Gly Thr Trp Gln Ala Glu Phe Gly Ser Pro Asp Ile Glu Trp Asn

GGT GAG GTG GGA AAT GGA GCA CTG CAG CTG AAC GTG AAA CTG CCC GGA AAG
Gly Glu Val Gly Asn Gly Ala Leu Gln Leu Asn Val Lys Leu Pro Gly Lys

AGC GAC TGG GAA GAA GTG AGA GTA GCA AGG AAG TTC GAA AGA CTC TCA GAA
Ser Asp Trp Glu Glu Val Arg Val Ala Arg Lys Phe Glu Arg Leu Ser Glu

TGT GAG ATC CTC GAG TAC GAC ATC TAC ATT CCA AAC GTC GAG GGA CTC AAG
Cys Glu Ile Leu Glu Tyr Asp Ile Tyr Ile Pro Asn Val Glu Gly Leu Lys

GGA AGG TTG AGG CCG TAC GCG GTT CTG AAC CCC GGC TGG GTG AAG ATA GGC
Gly Arg Leu Arg Pro Tyr Ala Val Leu Asn Pro Gly Trp Val Lys Ile Gly

CTC GAC ATG AAC AAC GCG AAC GTG GAA AGT GCG GAG ATC ATC ACT TTC GGC
Leu Asp Met Asn Asn Ala Asn Val Glu Ser Ala Glu Ile Ile Thr Phe Gly

GGA AAA GAG TAC AGA AGA TTC CAT GTA AGA ATT GAG TTC GAC AGA ACA GCG
Gly Lys Glu Tyr Arg Arg Phe His Val Arg Ile Glu Phe Asp Arg Thr Ala
```

FIG. 1U-5

```
GGG GTG AAA GAA CTT CAC ATA GGA GTT GTC GGT GAT CAT CTG AGG TAC GAT

Gly Val Lys Glu Leu His Ile Gly Val Val Gly Asp His Leu Arg Tyr Asp

GGA CCG ATT TTC ATC GAT AAT GTG AGA CTT TAT AAA AGA ACA GGA GGT ATG

Gly Pro Ile Phe Ile Asp Asn Val Arg Leu Tyr Lys Arg Thr Gly Gly Met

TGA        2042
END
```

FIG. 1U-6

(SEQ ID NO:43 - nucleotide sequence and SEQ ID NO:44 - amino acid sequence)
Polyangium brachysporum (Clone # 78GA1) Glycosidase

```
1
ATG TTC CTG CAT CCG AGG GGT CGC ATG ACC CGC CTA GCG CTC GGC TGT GCC
Met Phe Leu His Pro Arg Gly Arg Met Thr Arg Leu Ala Leu Gly Cys Ala

GTG CTG TGT CTG GCC GTC GCA GGC TGC GGT GGT GGT GAT GAC GAC GGC GAC
Val Leu Cys Leu Ala Val Ala Gly Cys Gly Gly Gly Asp Asp Asp Gly Asp

GAC AAC GGC ACC GCC CCC CAG CCC GCA CCT GGT CAA CCC GAG CCC CCG ACT
Asp Asn Gly Thr Ala Pro Gln Pro Ala Pro Gly Gln Pro Glu Pro Pro Thr

GAC ACC GTG CTG AAA GAC TGG CCT CGC ATC AAC AGC AGC ATC ACC GCC GAC
Asp Thr Val Leu Lys Asp Trp Pro Arg Ile Asn Ser Ser Ile Thr Ala Asp

GCA GCG ATC GAA AGC CGC GTC AAC TCA CTC GTC GCG GCG ATG ACG CTG GAA
Ala Ala Ile Glu Ser Arg Val Asn Ser Leu Val Ala Ala Met Thr Leu Glu

GAA AAA GTC GGC CAG ATG ACG CAG GTC GAA ATC CAG GAG GTG ACG CCG GAG
Glu Lys Val Gly Gln Met Thr Gln Val Glu Ile Gln Glu Val Thr Pro Glu

GAG ATC CGG CAG TAC CAC ATC GGC TCC GTG CTC AAC GGC GGT GGT TCG TTC
Glu Ile Arg Gln Tyr His Ile Gly Ser Val Leu Asn Gly Gly Gly Ser Phe
```

FIG. 1V-1

```
CCG AAG CAG GAC AAG GGC GCG GCG GTG ACC GAC TGG CTG GCG GTG GCC GAC
Pro Lys Gln Asp Lys Gly Ala Ala Val Thr Asp Trp Leu Ala Val Ala Asp

GCC TTG TGG GCC GCG TCG ATG GAT CCC GCC AAG CCG CGG CGC ATC CCG CTC
Ala Leu Trp Ala Ala Ser Met Asp Pro Ala Lys Pro Arg Arg Ile Pro Leu

ATC TGG GGC ACC GAC GCC GTC CAC GGC CAC AAC AAC GTC AAG GGC GCG ACC
Ile Trp Gly Thr Asp Ala Val His Gly His Asn Asn Val Lys Gly Ala Thr

ATC TTC CCG CAC AAC ATC GGC CTG GGC GCC GCG CGC GAC CCC GAC TTG GTC
Ile Phe Pro His Asn Ile Gly Leu Gly Ala Ala Arg Asp Pro Asp Leu Val

GCC CGC ATC GGC GCC GCC ACG GCG CTG GAA GTG GCA CGC ACC GGC ATC GAC
Ala Arg Ile Gly Ala Ala Thr Ala Leu Glu Val Ala Arg Thr Gly Ile Asp

TGG GTG TTC GCG CCA ACG CTG GCG GTC GTG CGC GAC GAC CGC TGG GGC CGC
Trp Val Phe Ala Pro Thr Leu Ala Val Val Arg Asp Asp Arg Trp Gly Arg

AGC TAC GAA GGC TAT TCG GAA GAC CCC GAA ATC GTC GTC TCC TAT GCC GGC
Ser Tyr Glu Gly Tyr Ser Glu Asp Pro Glu Ile Val Val Ser Tyr Ala Gly

AAG ATG GTC GAA GGC CTG CAG GGC CGA TTG GCG CAG GAC GCG AAG GCC AAC
Lys Met Val Glu Gly Leu Gln Gly Arg Leu Ala Gln Asp Ala Lys Ala Asn
```

FIG. 1V-2

```
GAG AAG GTG GTG GCC ACC GCC AAG CAT TTC GTC GGC GAC GGC GGC ACC GAC
Glu Lys Val Val Ala Thr Ala Lys His Phe Val Gly Asp Gly Gly Thr Asp

CAG GGC AAG GAC CAG GGG GTC ACC CGG GTC ACC GAG CGC GAC CTG TTG AAC
Gln Gly Lys Asp Gln Gly Val Thr Arg Val Thr Glu Arg Asp Leu Leu Asn

GTC CAT GCG CGC GGC TAC ATC CCC GCG CTC GAG GCG GGC GCG CAA ACC GTG
Val His Ala Arg Gly Tyr Ile Pro Ala Leu Glu Ala Gly Ala Gln Thr Val

ATG GCC TCC TTC AAC AGC TGG CAG GAC CCG TCG CAG GGC GAG GGC GCC AAG
Met Ala Ser Phe Asn Ser Trp Gln Asp Pro Ser Gln Gly Glu Gly Ala Lys

GCC TTC AAG ATG CAT GGC AGC CGC TAC CTG CTC ACC GAG GCC CTC AAG CAG
Ala Phe Lys Met His Gly Ser Arg Tyr Leu Leu Thr Glu Ala Leu Lys Gln

AAG ATG GGC TTC GAC GGT TTC GTG GTG TCC GAC TGG AAC GGC ATC GGC CAG
Lys Met Gly Phe Asp Gly Phe Val Val Ser Asp Trp Asn Gly Ile Gly Gln

GTC ACC ACC GAG AAC AGC AAC GCG ACG CGC AAC TGC AGC AAC AGC GAC TGC
Val Thr Thr Glu Asn Ser Asn Ala Thr Arg Asn Cys Ser Asn Ser Asp Cys

CCC GAG GCC ATC AAC GCT GGC ATC GAC ATG GTG ATG GTG CCG TAC CGG GCC
```

FIG. 1V-3

```
            Pro Glu Ala Ile Asn Ala Gly Ile Asp Met Val Met Val Pro Tyr Arg Ala

GAC TGG AAG GCC TTC ATC ACC AAC ACA ATT GCA ATT GTC CGC AAA GGC GAG
Asp Trp Lys Ala Phe Ile Thr Asn Thr Ile Ala Ile Val Arg Lys Gly Glu

ATC GCG CAG GAG CGC ATC GAC AAC GCG GTG CGG CGC ATC CTG CGC GTC AAG
Ile Ala Gln Glu Arg Ile Asp Asn Ala Val Arg Arg Ile Leu Arg Val Lys

TTG CGC GCC GGT CTG TTC GAC AAG CCC ACA CCC TCC GCC CGT CTG GCC TCG
Leu Arg Ala Gly Leu Phe Asp Lys Pro Thr Pro Ser Ala Arg Leu Ala Ser

CGC GAG GTC GGC AGC GCC GAA CAC CGG GCG CTC GCG CGT GAA GCG GTG CGC
Arg Glu Val Gly Ser Ala Glu His Arg Ala Leu Ala Arg Glu Ala Val Arg

AAG TCG TTG GTG CTG TTG AAG AAC AAC GGC CGG GTG CTG CCG CTG GCA CGC
Lys Ser Leu Val Leu Leu Lys Asn Asn Gly Arg Val Leu Pro Leu Ala Arg

AAT GCC AAG GTC CTG GTG GCC GGC AAG AGC GCC AAC AGC CTC GAG AAC CAG
Asn Ala Lys Val Leu Val Ala Gly Lys Ser Ala Asn Ser Leu Glu Asn Gln

ACC GGC GGC TGG TCG CTC AGC TGG CAA GGC ACC GGC AAC GCC AAC GCC GAT
Thr Gly Gly Trp Ser Leu Ser Trp Gln Gly Thr Gly Asn Ala Asn Ala Asp
```

FIG. 1V-4

```
TTC GGC GGC GGC ACG ACC GTG TGG CAG GCG ATC CAG AAG ATC GCC CCG AAT
Phe Gly Gly Gly Thr Thr Val Trp Gln Ala Ile Gln Lys Ile Ala Pro Asn

GCC GAA CTC GAC ACC AGC GCC GAC GGC GCC AAG GGC AGC GAT GCC TAC GAC
Ala Glu Leu Asp Thr Ser Ala Asp Gly Ala Lys Gly Ser Asp Ala Tyr Asp

GCC GCG ATC GTC GTG ATC GGT GAA ACA CCG TAC GCC GAA GGT GTC GGA GAC
Ala Ala Ile Val Val Ile Gly Glu Thr Pro Tyr Ala Glu Gly Val Gly Asp

ATC GGC CGC AGC AAG ACG CTG GAA CTC ACC AAG CTG CGT CCA GAA GAC CTC
Ile Gly Arg Ser Lys Thr Leu Glu Leu Thr Lys Leu Arg Pro Glu Asp Leu

GCC GTG ATC GAA GGC CTG CGC GCC AAG GGC GTG AAG AAA ATC GTC ACG CTG
Ala Val Ile Glu Gly Leu Arg Ala Lys Gly Val Lys Lys Ile Val Thr Leu

CTG GTC TCC GGC CGC CCG CTC TAC GTC AAC AAG GAG CTG AAC CGC TCG GAC
Leu Val Ser Gly Arg Pro Leu Tyr Val Asn Lys Glu Leu Asn Arg Ser Asp

GCC TTC GTG GCG GCG TGG CTG CCC GGC ACC GAA GGC GAC GGC GTC GCC GAC
Ala Phe Val Ala Ala Trp Leu Pro Gly Thr Glu Gly Asp Gly Val Ala Asp

GTG CTG TTC CGT GCG GCC GAC GGC AGC GTC GCG CAT GGC TTC AGC GGC AAG
Val Leu Phe Arg Ala Ala Asp Gly Ser Val Ala His Gly Phe Ser Gly Lys
```

FIG. 1V-5

```
CTG TCG TTC TCG TGG CCG AAG TCG GCC TGC CAG ACG CCG CTC AAC CGT GGC
Leu Ser Phe Ser Trp Pro Lys Ser Ala Cys Gln Thr Pro Leu Asn Arg Gly

GAC GCC ACC TAC GAC CCG CTC TAC GCT TAT GGC TAC GGC CTT CAA TAC GGC
Asp Ala Thr Tyr Asp Pro Leu Tyr Ala Tyr Gly Tyr Gly Leu Gln Tyr Gly

GAG GAG ACC GAT CAG AGC GCG TAC GAC GAA AGC AGT GCC ACG GTC GGC TGC
Glu Glu Thr Asp Gln Ser Ala Tyr Asp Glu Ser Ser Ala Thr Val Gly Cys

GGC ATC CAG GAC GGC GGC GGC ACC ACG GCC GAG CCG CTG GCG GTG TTC GAA
Gly Ile Gln Asp Gly Gly Gly Thr Thr Ala Glu Pro Leu Ala Val Phe Glu

GGC GGA GCC AAC CAG GGC AAC TGG AAG CTG CGC ATC GGC GCC GAG TCG AGC
Gly Gly Ala Asn Gln Gly Asn Trp Lys Leu Arg Ile Gly Ala Glu Ser Ser

TGG AGC AAC GAT GTG ACG CTG GCC AGC AGC GCG GTG ACG TCG ACG CCG TCC
Trp Ser Asn Asp Val Thr Leu Ala Ser Ser Ala Val Thr Ser Thr Pro Ser

AAC GAA CTG CAG GCC GTG CCG GTG GAC GAC AAG GCC GGG CGG CAA TGG GCG
Asn Glu Leu Gln Ala Val Pro Val Asp Asp Lys Ala Gly Arg Gln Trp Ala

GCG GTG AAG GCG ACC TGG AAC GAC AAG CCC GGC CAG CTC TAC ATG CAA AGC
```

FIG. 1V-6

Ala Val Lys Ala Thr Trp Asn Asp Lys Pro Gly Gln Leu Tyr Met Gln Ser

GCC AAC CCC GGC GAC CTG GTG GAC CTG ATG GCC TAT CAG AAC TCC GGT GGC
Ala Asn Pro Gly Asp Leu Val Asp Leu Met Ala Tyr Gln Asn Ser Gly Gly

GCG CTG GTG TTC GAC CTG CGT GTC GTC AGT GCG CCG ACC GAC CCG GTC AAG
Ala Leu Val Phe Asp Leu Arg Val Val Ser Ala Pro Thr Asp Pro Val Lys

CTG CGC GTC GAT TGC GGC TGG CCC TGT CTG GGC GAG ATC GAC GTC ACC AGC
Leu Arg Val Asp Cys Gly Trp Pro Cys Leu Gly Glu Ile Asp Val Thr Ser

GCC GTC AAG GCC CAG CCG GTC AAC GCC TGG AAG GAA GTG GCG GTG TCG CTG
Ala Val Lys Ala Gln Pro Val Asn Ala Trp Lys Glu Val Ala Val Ser Leu

CAG TGT TTC GCC GAC GCC GGC ACC GAC CTG GCC ATC GTC AAC ACG CCC TTC
Gln Cys Phe Ala Asp Ala Gly Thr Asp Leu Ala Ile Val Asn Thr Pro Phe

CTG ATG TAC ACG TCT GGC CGC TTC GAA GCT GCC GTC GCG AAC ATC CGT TGG
Leu Met Tyr Thr Ser Gly Arg Phe Glu Ala Ala Val Ala Asn Ile Arg Trp

GAG CCC AAG CGC ACG CCC AAC GTG GGG TGC AAC GGC GCA CCG ATC GCC GCC
Glu Pro Lys Arg Thr Pro Asn Val Gly Cys Asn Gly Ala Pro Ile Ala Ala

FIG. 1V-7

GCG CCT TGA    2711
Ala Pro END

FIG. 1V-8

(SEQ ID NO:45 - nucleotide sequence and SEQ ID NO:46 - amino acid sequence)
Pyrococcus furiosus (Clone # 7EG1) Glycosidase

```
  1
ATG AGC AAG AAA AAG TTC GTC ATC GTA TCT ATC TTA ACA ATC CTT TTA GTA
Met Ser Lys Lys Lys Phe Val Ile Val Ser Ile Leu Thr Ile Leu Leu Val

CAG GCA ATA TAT TTT GTA GAA AAG TAT CAT ACC TCT GAG GAC AAG TCA ACT
Gln Ala Ile Tyr Phe Val Glu Lys Tyr His Thr Ser Glu Asp Lys Ser Thr

TCA AAT ACC TCA TCT ACA CCA CCC CAA ACA ACA CTT TCC ACT ACC AAG GTT
Ser Asn Thr Ser Ser Thr Pro Pro Gln Thr Thr Leu Ser Thr Thr Lys Val

CTC AAG ATT AGA TAC CCT GAT GAC GGT GAG TGG CCA GGA GCT CCT ATT GAT
Leu Lys Ile Arg Tyr Pro Asp Asp Gly Glu Trp Pro Gly Ala Pro Ile Asp

AAG GAT GGT GAT GGG AAC CCA GAA TTC TAC ATT GAA ATA AAC CTA TGG AAC
Lys Asp Gly Asp Gly Asn Pro Glu Phe Tyr Ile Glu Ile Asn Leu Trp Asn

ATT CTT AAT GCT ACT GGA TTT GCT GAG ATG ACG TAC AAT TTA ACC AGC GGC
Ile Leu Asn Ala Thr Gly Phe Ala Glu Met Thr Tyr Asn Leu Thr Ser Gly

GTC CTT CAC TAC GTC CAA CAA CTT GAC AAC ATT GTC TTG AGG GAT AGA AGT
Val Leu His Tyr Val Gln Gln Leu Asp Asn Ile Val Leu Arg Asp Arg Ser
```

FIG. 1W-1

AAT TGG GTG CAT GGA TAC CCC GAA ATA TTC TAT GGA AAC AAG CCA TGG AAT
Asn Trp Val His Gly Tyr Pro Glu Ile Phe Tyr Gly Asn Lys Pro Trp Asn

GCA AAC TAC GCA ACT GAT GGC CCA ATA CCA TTA CCC AGT AAA GTT TCA AAC
Ala Asn Tyr Ala Thr Asp Gly Pro Ile Pro Leu Pro Ser Lys Val Ser Asn

CTA ACA GAC TTC TAT CTA ACA ATC TCC TAT AAA CTT GAG CCC AAG AAC GGC
Leu Thr Asp Phe Tyr Leu Thr Ile Ser Tyr Lys Leu Glu Pro Lys Asn Gly

CTG CCA ATT AAC TTC GCA ATA GAA TCC TGG TTA ACG AGA GAA GCT TGG AGA
Leu Pro Ile Asn Phe Ala Ile Glu Ser Trp Leu Thr Arg Glu Ala Trp Arg

ACA ACA GGA ATT AAC AGC GAT GAG CAA GAA GTA ATG ATA TGG ATT TAC TAT
Thr Thr Gly Ile Asn Ser Asp Glu Gln Glu Val Met Ile Trp Ile Tyr Tyr

GAC GGA TTA CAA CCG GCT GGC TCC AAA GTT AAG GAG ATT GTA GTC CCA ATA
Asp Gly Leu Gln Pro Ala Gly Ser Lys Val Lys Glu Ile Val Val Pro Ile

ATA GTT AAC GGA ACA CCA GTA AAT GCT ACA TTT GAA GTA TGG AAG GCA AAC
Ile Val Asn Gly Thr Pro Val Asn Ala Thr Phe Glu Val Trp Lys Ala Asn

ATT GGT TGG GAG TAT GTT GCA TTT AGA ATA AAG ACC CCA ATC AAA GAG GGA
Ile Gly Trp Glu Tyr Val Ala Phe Arg Ile Lys Thr Pro Ile Lys Glu Gly

FIG. 1W-2

ACA GTG ACA ATT CCA TAC GGA GCA TTT ATA AGT GTT GCA GCC AAC ATT TCA
Thr Val Thr Ile Pro Tyr Gly Ala Phe Ile Ser Val Ala Ala Asn Ile Ser

AGC TTA CCA AAT TAC ACA GAA CTT TAC TTA GAG GAC GTG GAG ATT GGA ACT
Ser Leu Pro Asn Tyr Thr Glu Leu Tyr Leu Glu Asp Val Glu Ile Gly Thr

GAG TTT GGA ACG CCA AGC ACT ACC TCC GCC CAC CTA GAG TGG TGG ATC ACA
Glu Phe Gly Thr Pro Ser Thr Thr Ser Ala His Leu Glu Trp Trp Ile Thr

AAC ATA ACA CTA ACT CCT CTA GAT AGA CCT CTT ATT TCC TAA      960
Asn Ile Thr Leu Thr Pro Leu Asp Arg Pro Leu Ile Ser End

FIG. 1W-3

(SEQ ID NO:47 - nucleotide sequence and SEQ ID NO:48 - amino acid sequence)
Vibrio Harveyi (Clone # 91GP2) Glycosidase

```
  1
ATG AGA GGT AAC ACG ATG AAG CAA AAA GCG CTA TAT CGA GCA GTA GCA ATG
Met Arg Gly Asn Thr Met Lys Gln Lys Ala Leu Tyr Arg Ala Val Ala Met

GGT TTG AGT GGT CTT GCG AAC GTC GCA TCC GCT AAT GAG ATG GTA AAT CCT
Gly Leu Ser Gly Leu Ala Asn Val Ala Ser Ala Asn Glu Met Val Asn Pro

GAT GGT GGT GTC GTA GTG GGT TAC TGG CAT AAC TGG TGC GAT GGC GCT GGT
Asp Gly Gly Val Val Val Gly Tyr Trp His Asn Trp Cys Asp Gly Ala Gly

TAC AAG GGA GGT AAT GCA CCG TGT GTA ACA TTG GAT GAA GTT GAT CCT ATG
Tyr Lys Gly Gly Asn Ala Pro Cys Val Thr Leu Asp Glu Val Asp Pro Met

TAC AAT GTG GTT AAC GTC TCC TTT ATG AAG GTA TTC AAT ACC AGT GAA GGT
Tyr Asn Val Val Asn Val Ser Phe Met Lys Val Phe Asn Thr Ser Glu Gly

CGT ATT CCA ACC TTT AAG CTC GAT CCA AAT ATC GGC CTT TCA GAA CAA CAA
Arg Ile Pro Thr Phe Lys Leu Asp Pro Asn Ile Gly Leu Ser Glu Gln Gln

TTT TTT GAC CAA ATT GAA GCT CTA AAC CAA CAA GGA CGT GCC GTT CTC ATC
Phe Phe Asp Gln Ile Glu Ala Leu Asn Gln Gln Gly Arg Ala Val Leu Ile
```

FIG. 1X-1

```
GCT CTT GGT GGC GCA GAT GCT CAC GTT GAA CTT AGA ACT GGT GAC GAA CAA
Ala Leu Gly Gly Ala Asp Ala His Val Glu Leu Arg Thr Gly Asp Glu Gln

GCG TTC GCA CAA GAG ATT ATT CGT TTA ACG GAT AAG TTC GGT TTT GAT GGT
Ala Phe Ala Gln Glu Ile Ile Arg Leu Thr Asp Lys Phe Gly Phe Asp Gly

CTA GAT ATC GAT TTA GAG CAG TCA GCA GTA ACG GCA GAG AAC AAC CAA ACC
Leu Asp Ile Asp Leu Glu Gln Ser Ala Val Thr Ala Glu Asn Asn Gln Thr

GTA ATT CCA GCT GCA CTT CGC CTT GTA AAA GAG CAT TAT CAA CAA CAA GGT
Val Ile Pro Ala Ala Leu Arg Leu Val Lys Glu His Tyr Gln Gln Gln Gly

AAG AAC TTC CTA ATT ACG ATG GCG CCT GAA TTC CCT TAT CTA ACA GAA GGT
Lys Asn Phe Leu Ile Thr Met Ala Pro Glu Phe Pro Tyr Leu Thr Glu Gly

GGC AAG TAT GTT CCT TAC ATT ACT GGT TTA GAA GGG TAC TAC GAT TGG ATC
Gly Lys Tyr Val Pro Tyr Ile Thr Gly Leu Glu Gly Tyr Tyr Asp Trp Ile

AAC CCT CAG TTT TAC AAT CAA GGT GGT GAC GGT ATT TGG GTT GAT GGC GTG
Asn Pro Gln Phe Tyr Asn Gln Gly Gly Asp Gly Ile Trp Val Asp Gly Val

GGT TGG ATA GCG CAA AAC AAT GAT GAG TTA AAA CAA GAG TTT ATT TAC TAC
Gly Trp Ile Ala Gln Asn Asn Asp Glu Leu Lys Gln Glu Phe Ile Tyr Tyr
```

FIG. 1X-2

ATT TCG GAC GCT CTA TCG AAC GGT ACA CGC GGT TTC CAC AAA ATC CCG CAT
Ile Ser Asp Ala Leu Ser Asn Gly Thr Arg Gly Phe His Lys Ile Pro His

GAC AAA CTG GTG TTT GGT ATC CCA TCT AAC ATT GAT GCT GCT GCA ACG GGC
Asp Lys Leu Val Phe Gly Ile Pro Ser Asn Ile Asp Ala Ala Ala Thr Gly

TTT GTT CAA AAC CCT CAA GAC CTT TAC GAC GCG TTT GAT CAA CTT AAA GCG
Phe Val Gln Asn Pro Gln Asp Leu Tyr Asp Ala Phe Asp Gln Leu Lys Ala

CAA GGG CAG GCA CTT CGT GGC GTA ATG ACA TGG TCG GTG AAC TGG GAT ATG
Gln Gly Gln Ala Leu Arg Gly Val Met Thr Trp Ser Val Asn Trp Asp Met

GGC ACC GAT AAA AAT GGC CAA GCG TAC GGT GAA AAA TTC GTG AAG GAT TAC
Gly Thr Asp Lys Asn Gly Gln Ala Tyr Gly Glu Lys Phe Val Lys Asp Tyr

GGT CCG TTT ATC CAC GGG CAG ACT CCA CCA CCA AGT GAA GGT GAA CCA GTT
Gly Pro Phe Ile His Gly Gln Thr Pro Pro Pro Ser Glu Gly Glu Pro Val

TTT AGT GGC CTC AAC GAT GTT CGT GTG CAT CAC GGT AGT TCA TTT GAC CCG
Phe Ser Gly Leu Asn Asp Val Arg Val His His Gly Ser Ser Phe Asp Pro

TAT GCA GGT GTT ACT GCG TCT GAT AAA GAA GAT GGA GAC CTA ACC AAC AGC

FIG. 1X-3

```
Tyr Ala Gly Val Thr Ala Ser Asp Lys Glu Asp Gly Asp Leu Thr Asn Ser

ATC ACT GTC GAA GGT TCA GTT GAT GTG AAC ACG GTA GGC ACA TAT GTT TTG
Ile Thr Val Glu Gly Ser Val Asp Val Asn Thr Val Gly Thr Tyr Val Leu

GTT TAC AGT GTA AAA GAC AGC GAC AAC AAT GAA ACC AAG CAA AGT AGA ACG
Val Tyr Ser Val Lys Asp Ser Asp Asn Asn Glu Thr Lys Gln Ser Arg Thr

GTT GTT GTT TAC AGC CTA GTG CCT GAG TTT GAA GGT GTC GCA GAT ACG ACC
Val Val Val Tyr Ser Leu Val Pro Glu Phe Glu Gly Val Ala Asp Thr Thr

ATC CAG CTT GGT GAC GCT TTT GAC CCA ATG GCA GGC GTA AAA GCG ACG GAT
Ile Gln Leu Gly Asp Ala Phe Asp Pro Met Ala Gly Val Lys Ala Thr Asp

GCA GAA GAC GGT GAT TTG ACT GAT CGG TAT CTA CGC CGC CTA AGG TCA CTT
Ala Glu Asp Gly Asp Leu Thr Asp Arg Tyr Leu Arg Arg Leu Arg Ser Leu

CTG CGG TGC GAT AGC CTT CTG TGC CAT TTG GTG CAA CCG CCC AGT TTT CCA
Leu Arg Cys Asp Ser Leu Leu Cys His Leu Val Gln Pro Pro Ser Phe Pro

GAC GCT CAA CGA TGG TTG CCA TCT CTT TCT GGT TGA         1514
Asp Ala Gln Arg Trp Leu Pro Ser Leu Ser Gly END
```

ENDOGLUCANASES

CROSS-REFERENCE TO RELATED APPLICATIONS

This application is a national phase application claiming benefit of priority under 35 U.S.C. §371 to Patent Convention Treaty (PCT) International Application Serial No.: PCT/US97/08793, filed May 22, 1997, which claims benefit of priority to U.S. patent application Ser. No. 08/651,572, ("USSN") filed May 22, 1996, now U.S. Pat. No. 5,789,228, issued Aug. 4, 1998. The aforementioned applications are explicitly incorporated herein by reference in their entirety and for all purposes.

FIELD OF THE INVENTION

This invention relates to newly identified polynucleotides, polypeptides encoded by such polynucleotides, the use of such polynucleotides and polypeptides, as well as the production and isolation of such polynucleotides and polypeptides. More particularly, the polypeptides of the present invention have been identified as endoglucanases and in particular, enzymes having carboxymethyl cellulase activity.

BACKGROUND

Cellulose, a fibrous, tough, water-insoluble substance is found in the cell walls of plants, particularly, in stalks, stems, trunks and all the woody portions of plant tissues. Cellulose constitutes much of the mass of wood, and cotton is almost pure cellulose. Because cellulose is a linear, unbranched homopolysaccharide of 10,000 to 15,000 D-glucose units, it resembles amylose and the main chains of glycogen. But there is a very important difference, in cellulose, the glucose residues have the beta configuration, whereas in amylose, amylopectin and glycogen, the glucose is in the alpha configuration. The glucose residues in cellulose are linked by (beta 1→4) glycosidic bonds. This difference gives cellulose and amylose very different 3-dimensional structures and physical properties.

Cellulose cannot be used by most animals as a source of stored fuel, because the (beta 1→4) linkages of cellulose are not hydrolyzed by alpha-amylases. Termites readily digest cellulose but only because their intestinal tract harbors a symbiotic microorganism, *trichonympha*, which secretes cellulase, an enzyme that hydrolyses (beta 1→4) linkages between glucose units. The only vertebrates able to use cellulose as food are cattle and other ruminant animals (sheep, goats, camels and giraffes). The extra stomachs "rumens" of those animals teem with bacteria and protists that secrete cellulase.

The enzymatic hydrolysis of cellulose is considered to require the action of both endoglucanases (1,4-beta-D-glucan glucanohydrolase) and exoglucanases (1,4-beta-D-glucan cellobichydrolase). A synergistic interaction of these enzymes is necessary for the complete hydrolysis of crystalline cellulose. (Caughlin, M. P., Genet. Eng. Rev., 3:39-109 (1985)). For the complete degradation of cellulose (cellulose to glucose), β-glucosidase might be required if the "exo" enzyme does not release glucose. 1,4-β-D-glucan glucohydrolase is another type of "exo" cellulase.

Thermophilic bacteria have received considerable attention as sources of highly active and thermostable cellulolytic and xylanolytic enzymes (Bronneomeier, K. and Staudenbauer, W. L., D. R. Woods (Ed.), The Clostridia and Biotechnology, Butterworth Publishers, Stoneham, Mass. (1993).

Recently, the most extremely thermophilic organotrophic eubacteria presently known have been isolated and characterized. These bacteria, which belong to the genus *thermotoga*, are fermentative microorganisms metabolizing a variety of carbohydrates (Huber, R. and Stetter, K. O., in Ballows, et al., (Ed.), The Procaryotes, 2nd Ed., Springer-Verlaz, New York, pgs. 3809-3819 (1992)).

In Huber et al., 1986, Arch. Microbiol. 144:324-333, the isolation of the bacterium *Thermotoga maritima* is described. *T. maritima* is a eubacterium that is strictly anaerobic, rod-shaped, fermentative, hyperthermophilic, and grows between 55° C. and 90° C., with an optimum growth temperature of about 80° C. This eubacterium has been isolated from geothermally heated sea floors in Italy and the Azores. *T. maritima* cells have a sheath-like structure and monotrichous flagellation. *T. maritima* is classified in the eubacterium kingdom by virtue of having murein and fatty acid-containing lipids, diphtheria-toxin-resistant elongation factor 2, an RNA polymerase subunit pattern, and sensitivity to antibiotics.

Since, to date, most organisms identified from the archaeal domain are thermophiles or hyperthermophiles, archaeal bacteria are also considered a fertile source of thermophilic enzymes.

SUMMARY OF THE INVENTION

The present invention provides polynucleotides and polypeptides encoded thereby which have been identified as endoglucanase enzymes having carboxymethyl cellulase activity (CMC).

In accordance with one aspect of the present invention, there is provided novel enzymes, as well as active fragments, analogs and derivatives thereof.

In accordance with another aspect of the present invention, there are provided isolated nucleic acid molecules encoding enzymes of the present invention including mRNAs, DNAs, cDNAs, genomic DNAs as well as active analogs and fragments of such enzymes.

In accordance with another aspect of the present invention there are provided isolated nucleic acid molecules encoding mature polypeptides expressed by the DNA contained in ATCC Deposit No. 97516.

In accordance with yet a further aspect of the present invention, there is provided a process for producing such polypeptide by recombinant techniques comprising culturing recombinant prokaryotic and/or eukaryotic host cells, containing a nucleic acid sequence encoding an enzyme of the present invention, under conditions promoting expression of said enzyme and subsequent recovery of said enzyme.

In accordance with yet a further aspect of the present invention, there is provided a process for utilizing such enzymes, or polynucleotide encoding such enzymes for degradation of cellulose for the conversion of plant biomass into fuels and chemicals, for use in detergents, the textile industry, in animal feed, in waste treatment, and in the fruit juice/brewing industry for the clarification and extraction of juices.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A-1X (FIG. 1A: SEQ ID NO:1—nucleotide sequence and SEQ ID NO:2—amino acid sequence; FIG. 1B: SEQ ID NO:3—nucleotide sequence and SEQ ID NO:4—amino acid sequence; FIG. 1C: SEQ ID NO:5—nucleotide sequence and SEQ ID NO:6—amino acid sequence; FIG. 1D: SEQ ID NO:7—nucleotide sequence and SEQ ID NO:8—amino acid sequence; FIG. 1E: SEQ ID NO:9—nucleotide sequence and SEQ ID NO:10—amino acid sequence; FIG. 1F: SEQ ID NO:11—nucleotide sequence and SEQ ID NO:12—amino acid sequence; FIG. 1G: SEQ ID NO:13—nucleotide sequence and SEQ ID NO:14—amino acid sequence; FIG. 1H: SEQ ID NO:15—nucleotide sequence and SEQ ID NO:16—amino acid sequence; FIG. 1I: SEQ ID NO:17—nucleotide sequence and SEQ ID NO:18—amino acid sequence; FIG. 1J: SEQ ID NO:19—nucleotide sequence and SEQ ID NO:20—amino acid sequence; FIG. 1K: SEQ ID NO:21—nucleotide sequence and SEQ ID NO:22—amino acid sequence; FIG. 1L: SEQ ID NO:23—nucleotide sequence and SEQ ID NO:24—amino acid sequence; FIG. 1M: SEQ ID NO:25—nucleotide sequence and SEQ ID NO:26—amino acid sequence; FIG. 1N: SEQ ID NO:27—nucleotide sequence and SEQ ID NO:28—amino acid sequence; FIG. 1O: SEQ ID NO:29—nucleotide sequence and SEQ ID NO:30—amino acid sequence; FIG. 1P: SEQ ID NO:31—nucleotide sequence and SEQ ID NO:32—amino acid sequence; FIG. 1Q: SEQ ID NO:33—nucleotide sequence and SEQ ID NO:34—amino acid sequence; FIG. 1R: SEQ ID NO:35—nucleotide sequence and SEQ ID NO:36—amino acid sequence; FIG. 1S: SEQ ID NO:37—nucleotide sequence and SEQ ID NO:38—amino acid sequence; FIG. 1T: SEQ ID NO:39—nucleotide sequence and SEQ ID NO:40—amino acid sequence; FIG. 1U: SEQ ID NO:41—nucleotide sequence and SEQ ID NO:42—amino acid sequence; FIG. 1V: SEQ ID NO:43—nucleotide sequence and SEQ ID NO:44—amino acid sequence; FIG. 1W: SEQ ID NO:45—nucleotide sequence and SEQ ID NO:46—amino acid sequence; and FIG. 1X: SEQ ID NO:47—nucleotide sequence and SEQ ID NO:48—amino acid sequence) show the nucleotide and deduced amino acid sequences of the enzymes of the present invention. Sequencing was performed using a 378 automated DNA sequencer (Applied Biosystems, Inc.).

DETAILED DESCRIPTION OF THE INVENTION

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The present invention provides purified thermostable enzymes that catalyze the hydrolysis of the beta 1,4 glycosidic bonds in cellulose to thereby degrade cellulose. An exemplary purified enzyme is an endoglucanase derived from an organism referred herein as "AEPII1a" which is a thermophilic archaeal bacteria which has a very high temperature optimum. The organism is strictly anaerobic, rod-shaped and fermentative, and grows between 55 and 90° C. (optimally at 85° C.). AEPII1a was discovered in a shallow marine hydrothermal area in Vulcano, Italy. The organism has coccoid cells occurring in singlets or pairs. AEPII1a grows optimally at 85° C. and pH 6.5 in a marine medium with cellulose as a substrate and nitrogen in gas phase. This exemplary enzyme is shown in FIG. 1A, SEQ ID NO:2.

The polynucleotide encoding SEQ ID NO:2 was originally recovered from a genomic gene library derived from AEPII1a as described below. It contains an open reading frame encoding a protein of 553 amino acid residues.

In one embodiment, the endoglucanase enzyme of SEQ ID NO:2 of the present invention has a molecular weight of about 60.9 kilodaltons as measured by SDS-PAGE gel electrophoresis and an inferred molecular weight from the nucleotide sequence of the gene. This purified enzyme may be used to catalyze the enzymatic degradation of cellulose where desired. The endoglucanase enzyme of the present invention has a very high thermostability and has the closest homology to endo-1,4-beta-glucanase from *Xanthomonas campestris* with 50% identity and 71% similarity at the amino acid level.

In accordance with an aspect of the present invention, there are provided isolated nucleic acid molecules (polynucleotides) which encode for the mature enzymes having the deduced amino acid sequence of FIGS. 1A-1X (FIG. 1A: SEQ ID NO:1—nucleotide sequence and SEQ ID NO:2—amino acid sequence; FIG. 1B: SEQ ID NO:3—nucleotide sequence and SEQ ID NO:4—amino acid sequence; FIG. 1C: SEQ ID NO:5—nucleotide sequence and SEQ ID NO:6—amino acid sequence; FIG. 1D: SEQ ID NO:7—nucleotide sequence and SEQ ID NO:8—amino acid sequence; FIG. 1E: SEQ ID NO:9—nucleotide sequence and SEQ ID NO:10—amino acid sequence; FIG. 1F: SEQ ID NO:11—nucleotide sequence and SEQ ID NO:12—amino acid sequence; FIG. 1G: SEQ ID NO:13—nucleotide sequence and SEQ ID NO:14—amino acid sequence; FIG. 1H: SEQ ID NO:15—nucleotide sequence and SEQ ID NO:16—amino acid sequence; FIG. 1I: SEQ ID NO:17—nucleotide sequence and SEQ ID NO:18—amino acid sequence; FIG. 1J: SEQ ID NO:19—nucleotide sequence and SEQ ID NO:20—amino acid sequence; FIG. 1K: SEQ ID NO:21—nucleotide sequence and SEQ ID NO:22—amino acid sequence; FIG. 1L: SEQ ID NO:23—nucleotide sequence and SEQ ID NO:24—amino acid sequence; FIG. 1M: SEQ ID NO:25—nucleotide sequence and SEQ ID NO:26—amino acid sequence; FIG. 1N: SEQ ID NO:27—nucleotide sequence and SEQ ID NO:28—amino acid sequence; FIG. 1O: SEQ ID NO:29—nucleotide sequence and SEQ ID NO:30—amino acid sequence; FIG. 1P: SEQ ID NO:31—nucleotide sequence and SEQ ID NO:32—amino acid sequence; FIG. 1Q: SEQ ID NO:33—nucleotide sequence and SEQ ID NO:34—amino acid sequence; FIG. 1R: SEQ ID NO:35—nucleotide sequence and SEQ ID NO:36—amino acid sequence; FIG. 1S: SEQ ID NO:37—nucleotide sequence and SEQ ID NO:38—amino acid sequence; FIG. 1T: SEQ ID NO:39—nucleotide sequence and SEQ ID NO:40—amino acid sequence; FIG. 1U: SEQ ID NO:41—nucleotide sequence and SEQ ID NO:42—amino acid sequence; FIG. 1V: SEQ ID NO:43—nucleotide sequence and SEQ ID NO:44—amino acid sequence; FIG. 1W: SEQ ID NO:45—nucleotide sequence and SEQ ID NO:46—amino acid sequence; and FIG. 1X: SEQ ID NO:47—nucleotide sequence and SEQ ID NO:48—amino acid sequence).

This invention, in addition to the isolated nucleic acid molecule encoding an endoglucanase enzyme disclosed in FIG. 1 (SEQ ID NO:1), also provides substantially similar sequences. Isolated nucleic acid sequences are substantially similar if: (i) they are capable of hybridizing under stringent conditions, hereinafter described, to SEQ ID NO:1; or (ii) they encode DNA sequences which are degenerate to SEQ ID NO:1. Degenerate DNA sequences encode the amino acid sequence of SEQ ID NO:2, but have variations in the nucleotide coding sequences. As used herein, "substantially similar" refers to the sequences having similar identity to the sequences of the instant invention. The nucleotide sequences that are substantially similar can be identified by hybridization or by sequence comparison. Enzyme sequences that are substantially similar can be identified by one or more of the following: proteolytic digestion, gel electrophoresis and/or microsequencing.

One means for isolating a nucleic acid molecule encoding an endoglucanase enzyme is to probe a genomic gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated to one skilled in the art that SEQ ID NO:1, or fragments thereof (comprising at least 15 contiguous nucleotides), is a particularly useful probe. Other particular useful probes for this purpose are hybridizable fragments to the sequences of SEQ ID NO:1 (i.e., comprising at least 15 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acid is first prehybridized for 30 minutes at 45° C. in a solution consisting of 0.9 M NaCl, 50 mM $NaH_2PO_4$, pH 7.0, 5.0 mM $Na_2$ EDTA, 0.5% SDS, 10× Denhardt's, and 0.5 mg/mL polyriboadenylic acid. Approximately $2\times10^7$ cpm (specific activity $4-9\times10^8$ cpm/ug) of $^{32}P$ end-labeled oligonucleotide probe are then added to the solution. After 12-16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at Tm-10° C. for the oligonucleotide probe. The membrane is then exposed to autoradiographic film for detection of hybridization signals.

Stringent conditions means hybridization will occur only if there is at least 90% identity, preferably at least 95% identity and most preferably at least 97% identity between the sequences. See J. Sambrook et al., Molecular Cloning, A Laboratory Manual (2d Ed. 1989) (Cold Spring Harbor Laboratory) which is hereby incorporated by reference in its entirety.

"Identity" as the term is used herein, refers to a polynucleotide sequence which comprises a percentage of the same bases as a reference polynucleotide (SEQ ID NO:1). For example, a polynucleotide which is at least 90% identical to a reference polynucleotide, has polynucleotide bases which are identical in 90% of the bases which make up the reference polynucleotide and may have different bases in 10% of the bases which comprise that polynucleotide sequence.

The present invention also relates to polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the enzyme encoded by the reference polynucleotide (SEQ ID NO:1). In a preferred aspect of the invention these enzymes retain the same biological action as the enzyme encoded by the reference polynucleotide.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other animal sources or to screen such sources for related sequences.

The present invention provides substantially pure endoglucanase enzymes. The term "substantially pure" is used herein to describe a molecule, such as a polypeptide (e.g., an endoglucanase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

Endoglucanase polypeptides included in the invention can have one of the amino acid sequences of Endoglucanases shown in FIGS. 1A through 1X (FIG. 1A: SEQ ID NO:1—nucleotide sequence and SEQ ID NO:2—amino acid sequence; FIG. 1B: SEQ ID NO:3—nucleotide sequence and SEQ ID NO:4—amino acid sequence; FIG. 1C: SEQ ID NO:5—nucleotide sequence and SED ID NO:6—amino acid sequence; FIG. 1D: SEQ ID NO:7—nucleotide sequence and SEQ ID NO:8—amino acid sequence; FIG. 1E: SEQ ID NO:9—nucleotide sequence and SEQ ID NO:10—amino acid sequence; FIG. 1F: SEQ ID NO:11—nucleotide sequence and SEQ ID NO:12—amino acid sequence; FIG. 1G: SEQ ID NO:13—nucleotide sequence and SEQ ID NO:14—amino acid sequence; FIG. 1H: SEQ ID NO:15—nucleotide sequence and SEQ ID NO:16—amino acid sequence; FIG. 1I: SEQ ID NO:17—nucleotide sequence and SEQ ID NO:18—amino acid sequence; FIG. 1J: SEQ ID NO:19—nucleotide sequence and SEW ID NO:20—amino acid sequence; FIG. 1K: SEQ ID NO:21—nucleotide sequence and SEQ ID NO:22—amino acid sequence; FIG. 1L: SEQ ID NO:23—nucleotide sequence and SEQ ID NO:24—amino acid sequence; FIG. 1M: SEQ ID NO:25—nucleotide sequence and SEQ ID NO:26—amino acid sequence; FIG. 1N: SEQ ID NO:27—nucleotide sequence and SEQ ID NO:28—amino acid sequence; FIG. 1O: SEQ ID NO:29—nucleotide sequence and SEQ ID NO:30—amino acid sequence; FIG. 1P: SEQ ID NO:31—nucleotide sequence and SEQ ID NO:32—amino acid sequence; FIG. 1Q: SEQ ID NO:33—nucleotide sequence and SEQ ID NO:34—amino acid sequence; FIG. 1R: SEQ ID NO:35—nucleotide sequence and SEQ ID NO:36—amino acid sequence; FIG. 1S: SEQ ID NO:37—nucleotide sequence and SEQ ID NO:38—amino acid sequence; FIG. 1T: SEQ ID NO:39—nucleotide sequence and SEQ ID NO:40—amino acid sequence; FIG. 1U: SEQ ID NO:41—nucleotide sequence and SEQ ID NO:42—amino acid sequence; FIG. 1V: SEQ ID NO:43—nucleotide sequence and SEQ ID NO:44—amino acid sequence; FIG. 1W: SEQ ID NO:45—nucleotide sequence and SEQ ID NO:46—amino acid sequence; and FIG. 1X: SEQ ID NO:47—nucleotide sequence and SEQ ID NO:48—amino acid sequence). Endoglucanase polypeptides, such as those isolated from AEPII1a, can be characterized by catalyzing the hydrolysis of the beta 1,4 glycosidic bonds in cellulose.

Also included in the invention are polypeptides having sequences that are "substantially identical" to the sequence of an endoglucanase polypeptide, such as one of SEQ ID NO:NO:2, 4, 6, 8, 10, 12, 14, 16, 18, 20, 22, 24, 26, 28, 30, 32, 36, 38, 40, 42, 44, 46, and 48, e.g., SEQ ID NO:2. A "substantially identical" amino acid sequence is a sequence that differs from a reference sequence only by conservative amino acid substitutions, for example, substitutions of one amino acid for another of the same class (e.g., substitution of one hydropholic amino acid, such as isoleucine, valine, leucine, or methionine, for another, or substitution of one polar amino acid for another, such as substitution of arginine for lysine, glutamic acid for aspartic acid, or glutamine for asparagine), or by one or more non-conservative substitution, deletions, or insertions, provided that the polypeptide retains at least one endoglucanase-specific activity or an endoglucanase-specific epitope. For example, one or more amino acids can be deleted from an endoglucanase polypeptide, resulting in modification of the structure of the polypeptide, without significantly altering its biological activity. For example, amino- or carboxyl-terminal amino acids that are not required for endoglucanase biological activity, can be removed. Such modifications can result in the development of smaller active endoglucanase polypeptides.

Other endoglucanase polypeptides included in the invention are polypeptides having amino acid sequences that are at least 50% identical to the amino acid sequence of an endoglucanase polypeptide, such as any of endoglucanases in SEQ ID NO:NO:2, 4, 6, 8, 10, 12, 14, 16, 18, 20, 22, 24, 26, 28, 30, 32, 36, 38, 40, 42, 44, 46, and 48, e.g., SEQ ID NO:2. The length of comparison in determining amino acid sequence homology can be, for example, at least 15 amino acids, for example, at least 20, 25, or 35 amino acids. Homology can be measured using standard sequence analysis software (e.g., Sequence Analysis Software Package of the Genetics Computer Group, University of Wisconsin Biotechnology Center, 1710 University Avenue, Madison, Wis. 53705; also see Ausubel, et al., supra).

The invention also includes fragments of endoglucanase polypeptides that retain at least one endoglucanase-specific activity or epitope. Endoglucanase activity can be assayed by examining the catalysis of beta 1,4 glycosidic bonds in cellulose. For example, an endoglucanase polypeptide fragment containing, e.g., at least 8-10 amino acids can be used as an immunogen in the production of endoglucanase-specific antibodies. The fragment can contain, for example, an amino acid sequence that is conserved in endoglucanases, and this amino acid sequence can contain amino acids that are conserved in endoglucanases. Such fragments can easily be identified by comparing the sequences of endoglucanases found in FIGS. 1A-1X (FIG. 1A: SEQ ID NO:1—nucleotide sequence and SEQ ID NO:2—amino acid sequence; FIG. 1B: SEQ ID NO:3—nucleotide sequence and SEQ ID NO:4—amino acid sequence; FIG. 1C: SEQ ID NO:5—nucleotide sequence and SEQ ID NO:6—amino acid sequence; FIG. 1D: SEQ ID NO:7—nucleotide sequence and SEQ ID NO:8—amino acid sequence; FIG. 1E: SEQ ID NO:9—nucleotide sequence and SEQ ID NO:10—amino acid sequence; FIG. 1F: SEQ ID NO:11—nucleotide sequence and SEQ ID NO:12—amino acid sequence; FIG. 1G: SEQ ID NO:13—nucleotide sequence and SEQ ID NO:14—amino acid sequence; FIG. 1H: SEQ ID NO:15—nucleotide sequence and SEQ ID NO:16—amino acid sequence; FIG. 1I: SEQ ID NO:17—nucleotide sequence and SEQ ID NO:18—amino acid sequence; FIG. 1J: SEQ ID NO:19—nucleotide sequence and SEQ ID NO:20—amino acid sequence; FIG. 1K: SEQ ID NO:21—nucleotide sequence and SEQ ID NO:22—amino acid sequence; FIG. 1L: SEQ ID NO:23—nucleotide sequence and SEQ ID NO:24—amino acid sequence; FIG. 1M: SEQ ID NO:25—nucleotide sequence and SEQ ID NO:26—amino acid sequence; FIG. 1N: SEQ ID NO:27—nucleotide sequence and SEQ ID NO:28—amino acid sequence; FIG. 1O: SEQ ID NO:29—nucleotide sequence and SEQ ID NO:30—amino acid sequence; FIG. 1P: SEQ ID NO:31—nucleotide sequence and SEQ ID NO:32—amino acid sequence; FIG. 1Q: SEQ ID NO:33—nucleotide sequence and SEQ ID NO:34—amino acid sequence; FIG. 1R: SEQ ID NO:35—nucleotide sequence and SEQ ID NO:36—amino acid sequence; FIG. 1S: SEQ ID NO:37—nucleotide sequence and SEQ ID NO:38—amino acid sequence; FIG. 1T: SEQ ID NO:39—nucleotide sequence and SEQ ID NO:40—amino acid sequence; FIG. 1U: SEQ ID NO:41—nucleotide sequence and SEQ ID NO:42—amino acid sequence; FIG. 1V: SEQ ID NO:43—nucleotide sequence and SEQ ID NO:44—amino acid sequence; FIG. 1W: SEQ ID NO:45—nucleotide sequence and SEQ ID NO:46—amino acid sequence; and FIG. 1X: SEQ ID NO:47—nucleotide sequence and SEQ ID NO:48—amino acid sequence). In addition to their use as peptide immunogens, the above-described endoglucanase fragments can be used in immunoassays, such as ELISAs, to detect the presence of endoglucanase-specific antibodies in samples.

The endoglucanase polypeptides of the invention can be obtained using any of several standard methods. For example, endoglucanase polypeptides can be produced in a standard recombinant expression systems (see below), chemically synthesized (this approach may be limited to small endoglucanase peptide fragments), or purified from organisms in which they are naturally expressed.

The invention also provides isolated nucleic acid molecules that encode the endoglucanase polypeptides described above, as well as fragments thereof. For example, nucleic acids that encode any of SEQ ID NO:NO:2, 4, 6, 8, 10, 12, 14, 16, 18, 20, 22, 24, 26, 28, 30, 32, 36, 38, 40, 42, 44, 46, and 48, are included in the invention. These nucleic acids can contain naturally occurring nucleotide sequences, or sequences that differ from those of the naturally occurring nucleic acids that encode endoglucanases, but encode the same amino acids, due to the degeneracy of the genetic code. The nucleic acids of the invention can contain DNA or RNA nucleotides, or combinations or modifications thereof. Exemplary nucleic acids of the invention are shown in SEQ ID NO:1, 3, 5, 7, 9, 11, 13, 15, 17, 19, 21, 23, 25, 27, 29, 31, 33, 35, 37, 39, 41, 43, 45, and 47.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

The nucleic acid molecules of the invention can be used as templates in standard methods for production of endoglucanase gene products (e.g., endoglucanase RNAs and endoglucanase polypeptides). In addition, the nucleic acid molecules that encode endoglucanase polypeptides (and fragments thereof) and related nucleic acids, such as (1) nucleic acids containing sequences that are complementary to, or that hybridize to, nucleic acids encoding endoglucanase polypeptides, or fragments thereof (e.g., fragments containing at least 12, 15, 20, or 25 nucleotides); and (2) nucleic acids containing sequences that hybridize to sequences that are complementary to nucleic acids encoding endoglucanase polypeptides, or fragments thereof (e.g., fragments containing at least 12, 15, 20, or 25 nucleotides); can be used in methods focused on their hybridization properties. For example, as is described in further detail below, such nucleic acid molecules can be used in the following methods: PCR methods for synthesizing endoglucanase nucleic acids, methods for detecting the presence of an endoglucanase nucleic acid in a sample, screening methods for identifying nucleic acids encoding new endoglucanase family members.

The invention also includes methods for identifying nucleic acid molecules that encode members of the endoglucanase polypeptide family in addition to SEQ ID NO:NO:2, 4, 6, 8, 10, 12, 14, 16, 18, 20, 22, 24, 26, 28, 30, 32, 36, 38, 40, 42, 44, 46, and 48. In these methods, a sample, e.g., a nucleic acid library, such as a cDNA library, that contains a nucleic acid encoding an endoglucanase polypeptide is screened with an endoglucanase-specific probe, e.g., an endoglucanase-specific nucleic acid probe. Endoglucanase-specific nucleic acid probes are nucleic acid molecules (e.g., molecules containing DNA or RNA nucleotides, or combinations or modifications thereof) that specifically hybridize to nucleic acids encoding endoglucanase polypeptides, or to complementary sequences thereof. The term "endoglucanase-specific probe," in the context of this method of invention, refers to probes that bind to nucleic acids encoding endoglucanase polypeptides, or to complementary sequences thereof, to a detectably greater extent than to nucleic acids encoding other enzymes, or to complementary sequences thereof.

The invention facilitates production of endoglucanase-specific nucleic acid probes. Methods for obtaining such probes can be designed based on the amino acid sequences shown in FIG. 1. The probes, which can contain at least 12, e.g., at least 15, 25, 35, 50, 100, or 150 nucleotides, can be produced using any of several standard methods (see, e.g., Ausubel, et al., supra). For example, preferably, the probes are generated using PCR amplification methods. In these methods, primers are designed that correspond to endoglucanase-conserved sequences (see FIG. 1), which can include endoglucanase-specific amino acids, and the resulting PCR product is used as a probe to screen a nucleic acid library, such as a cDNA library.

In accordance with another aspect of the present invention, there is provided an isolated polynucleotide encoding an exemplary enzyme of the present invention (SEQ ID NO:1) which has been deposited with an appropriate depository for the deposit of biological material. The deposited material is a pQET (Qiagen, Inc.) plasmid comprising the DNA of FIG. 1A. The deposit has been deposited with the American Type Culture Collection, 12301 Parklawn Drive, Rockville, Md. 20852, USA, on Apr. 22, 1996 and assigned ATCC Deposit No. 97516.

The deposit has been made under the terms of the Budapest Treaty on the International Recognition of the deposit of micro-organisms for purposes of patent procedure. The strain will be irrevocably and without restriction or condition released to the public upon the issuance of a patent. The deposit is provided merely as convenience to those of skill in the art and are not an admission that a deposit be required under 35 U.S.C. §112. The sequences of the polynucleotides contained in the deposited materials, as well as the amino acid sequences of the polypeptides encoded thereby, are controlling in the event of any conflict with any description of sequences herein. A license may be required to make, use or sell the deposited materials, and no such license is hereby granted.

The coding sequences for the endoglucanase enzymes of the present invention were identified by preparing an AEPII1a genomic DNA library, for example, and screening the library for the clones having endoglucanase activity. Such methods for constructing a genomic gene library are well-known in the art. One means, for example, comprises shearing DNA isolated from AEPII1a by physical disruption. A small amount of the sheared DNA is checked on an agarose gel to verify that the majority of the DNA is in the desired size range (approximately 3-6 kb). The DNA is then blunt ended using Mung Bean Nuclease, incubated at 37° C. and phenol/chloroform extracted. The DNA is then methylated using Eco RI Methylase. Eco RI linkers are then ligated to the blunt ends through the use of T4 DNA ligase and incubation at 4° C. The ligation reaction is then terminated and the DNA is cut-back with Eco RI restriction enzyme. The DNA is then size fractionated on a sucrose gradient following procedures known in the art, for example, Maniatis, T., et al., *Molecular Cloning*, Cold Spring Harbor Press, New York, 1982, which is hereby incorporated by reference in its entirety.

A plate assay is then performed to get an approximate concentration of the DNA. Ligation reactions are then performed and 1 μl of the ligation reaction is packaged to construct a library. Packaging, for example, may occur through the use of purified λgt11 phage arms cut with EcoRI and DNA cut with EcoRI after attaching EcoRI linkers. The DNA and λgt11 arms are ligated with DNA ligase. The ligated DNA is then packaged into infectious phage particles. The packaged phages are used to infect *E. coli* cultures and the infected cells are spread on agar plates to yield plates carrying thousands of individual phage plaques. The library is then amplified.

In a preferred embodiment, the enzyme of the present invention, was isolated from an AEPII1a library by the following technique:

1. λgt11 AEPII1a library was plated onto 6 LB/GelRite/ 0.1% CMC/NZY agar plates (~4,800 plaque forming units/ plate) in *E. coli* Y1090 host with LB agarose containing 1 mM IPTG as top agarose. The plates were incubated at 37° C. overnight.

2. Plates were chilled at 4° C. for one hour.

3. The plates were overlayed with Duralon membranes (Stratagene) at room temperature for one hour and the membranes were oriented and lifted off the plates and stored at 4° C.

4. The top agarose layer was removed and plates were incubated at 72° C. for ~3 hours.

5. The plate surface was rinsed with NaCl.

6. The plate was stained with 0.1% Congo Red for 15 minutes.

7. The plate was destained with 1M NaCl.

8. The putative positives identified on plate were isolated from the Duralon membrane (positives are identified by clearing zones around clones). The phage was eluted from the membrane by incubating in 500 μl SM+25 μl CHCl$_3$ to elute.

9. Insert DNA was subcloned into pBluescript II SK(+) cloning vector (Stratagene), and subclones were reassayed for CMCase activity using the following protocol:

i) Spin 1 ml overnight miniprep of clone at maximum speed for 3 minutes.
  ii) Decant the supernatant and use it to fill "wells" that have been made in an LB/GelRite/0.1% CMC plate.
  iii) Incubate at 72° C. for 2 hours.
  iv) Stain with 0.1% Congo Red for 15 minutes.
  v) Destain with 1M NaCl for 15 minutes.
  vi) Identify positives by clearing zone around clone.

Fragments of the full length gene of the present invention may be used as a hybridization probe for a cDNA or a genomic library to isolate the full length DNA and to isolate other DNAs which have a high sequence similarity to the gene or similar biological activity. Probes of this type have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns.

The isolated acid sequences and other enzymes may then be measured for retention of biological activity characteristic to the enzyme of the present invention, for example, in an assay for detecting enzymatic endoglucanase activity. Such enzymes include truncated forms of endoglucanase, and variants such as deletion and insertion variants.

Examples of such assays include an assay for the detection of endoglucanase activity based on specific interaction of direct dyes such as Congo red with polysaccharides. This colorant reacts with beta-1,4-glucans causing a visible red shift (Wood, P. J., Carbohydr. Res., 85:271 (1980) and Wood, P. J., Carbohydr. Res., 94:c19 (1981)). The preferred substrate for the test is carboxymethylcellulose (CMC) which can be obtained from different sources (Hercules Inc., Wilmington, Del., Type 4M6F or Sigma Chemical Company, St. Louis, Mo., Medium Viscosity). The CMC is incorporated as the main carbon sources into a minimal agar medium in quantities of 0.1-1.0%. The microorganisms can be screened directly on these plates, but the replica plating technique from a master plate is preferable since the visualization of the activity requires successive flooding with the reagents, which would render the reisolation of active colonies difficult. Such endoglucanase-producing colonies are detectable after a suitable incubation time (1-3 days depending on the growth), by flooding the plate with 10 ml of a 0.1% aqueous solution of Congo Red. The coloration is terminated after 20 minutes by pouring off the dye and flooding the plates with 10 ml of 5M NaCl solution (commercial salt can be used). After an additional 20 minutes, the salt solution is discarded and endoglucanase activity is revealed by a pale-orange zone around the active microorganisms. In some cases, these zones can be enhanced by treating the plates with 1 N acetic acid, causing the dye to change its color to blue.

The same technique can be used as a cup-plate diffusion assay with excellent sensitivity for the determination of endoglucanase activity in culture filtrates or during enzyme purification steps (Carger, J. H., Anal. Biochem., 153:75 (1986)). See generally, Methods for Measuring Cellulase Activities, Methods in Enzymology, Vol. 160, pgs. 87-116.

The enzyme of the present invention has enzymatic activity with respect to the hydrolysis of the beta 1,4 glycosidic bonds in carboxymethylcellulose, since the halos discussed above are shown around the colonies.

The polynucleotide of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequence which encodes the mature enzyme may be identical to the coding sequences shown in FIG. 1 and/or that of the deposited clone (SEQ ID NO:1), or may be a different coding sequence which coding sequence, as a result of the redundancy or degeneracy of the genetic code, encodes the same mature enzyme as the DNA of FIG. 1 (e.g., SEQ ID NO:1).

The polynucleotide which encodes for the mature enzyme of FIG. 1 (e.g., SEQ ID NO:2) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzyme having the deduced amino acid sequence of FIG. 1 (e.g., SEQ ID NO:2). The variant of the polynucleotide may be a naturally occurring allelic variant of the polynucleotide or a non-naturally occurring variant of the polynucleotide.

Thus, the present invention includes polynucleotides encoding the same mature enzyme as shown in FIG. 1 as well as variants of such polynucleotides which variants encode for a fragment, derivative or analog of the enzyme of FIG. 1. Such nucleotide variants include deletion variants, substitution variants and addition or insertion variants.

As hereinabove indicated, the polynucleotide may have a coding sequence which is a naturally occurring allelic variant of the coding sequence shown in FIG. 1. As known in the art, an allelic variant is an alternate form of a polynucleotide sequence which may have a substitution, deletion or addition of one or more nucleotides, which does not substantially alter the function of the encoded enzyme.

The present invention also includes polynucleotides, wherein the coding sequence for the mature enzyme may be fused in the same reading frame to a polynucleotide sequence which aids in expression and secretion of an enzyme from a host cell, for example, a leader sequence which functions to control transport of an enzyme from the cell. The enzyme having a leader sequence is a preprotein and may have the leader sequence cleaved by the host cell to form the mature form of the enzyme. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature enzyme, or for an enzyme having a prosequence or for an enzyme having both a prosequence and a presequence (leader sequence).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIG. 1.

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a PCR primer.

Thus, the present invention is directed to polynucleotides having at least a 70% identity, preferably at least 90% identity and more preferably at least a 95% identity to a polynucleotide which encodes the enzyme of SEQ ID NO:2, 4, 6, 8, 10, 12, 14, 16, 18, 20, 22, 24, 26, 28, 30, 32, 36, 38, 40, 42, 44, 46, or 48 as well as fragments thereof, which fragments have at least 30 bases and preferably at least 50 bases and to enzymes encoded by such polynucleotides.

The present invention further relates to a enzyme which has the deduced amino acid sequence of FIG. 1, as well as fragments, analogs and derivatives of such enzyme.

The terms "fragment," "derivative" and "analog" when referring to the enzyme of FIG. 1 means a enzyme which retains essentially the same biological function or activity as such enzyme. Thus, an analog includes a proprotein which can be activated by cleavage of the proprotein portion to produce an active mature enzyme.

The enzyme of the present invention may be a recombinant enzyme, a natural enzyme or a synthetic enzyme, preferably a recombinant enzyme.

The fragment, derivative or analog of the enzyme of FIG. 1 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention include an enzyme of FIGS. 1A-1X (FIG. 1A: SEQ ID NO:1—nucleotide sequence and SEQ ID NO:2—amino acid sequence; FIG. 1B: SEQ ID NO:3—nucleotide sequence and SEQ ID NO:4—amino acid sequence; FIG. 1C: SEQ ID NO:5—nucleotide sequence and SEQ ID NO:6—amino acid sequence; FIG. 1D: SEQ ID NO:7—nucleotide sequence and SEQ ID NO:8—amino acid sequence; FIG. 1E: SEQ ID NO:9—nucleotide sequence and SEQ ID NO:10—amino acid sequence; FIG. 1F: SEQ ID NO:11—nucleotide sequence and SEQ ID NO:12—amino acid sequence; FIG. 1G: SEQ ID NO:13—nucleotide sequence and SEQ ID NO:14—amino acid sequence; FIG. 1H: SEQ ID NO:15—nucleotide sequence and SEQ ID NO:16—amino acid sequence; FIG. 1I: SEQ ID NO:17—nucleotide sequence and SEQ ID NO:18—amino acid sequence; FIG. 1J: SEQ ID NO:19—nucleotide sequence and SEQ ID NO:20—amino acid sequence; FIG. 1K: SEQ ID NO:21—nucleotide sequence and SEQ ID NO:22—amino acid sequence; FIG. 1L: SEQ ID NO:23—nucleotide sequence and SEQ ID NO:24—amino acid sequence; FIG. 1M: SEQ ID NO:25—nucleotide sequence and SEQ ID NO:26—amino acid sequence; FIG. 1N: SEQ ID NO:27—nucleotide sequence and SEQ ID NO:28—amino acid sequence; FIG. 1O: SEQ ID NO:29—nucleotide sequence and SEQ ID NO:30—amino acid sequence; FIG. 1P: SEQ ID NO:31—nucleotide sequence and SEQ ID NO:32—amino acid sequence; FIG. 1Q: SEQ ID NO:33—nucleotide sequence and SEQ ID NO:34—amino acid sequence; FIG. 1R: SEQ ID NO:35—nucleotide sequence and SEQ ID NO:36—amino acid sequence; FIG. 1S: SEQ ID NO:37—nucleotide sequence and SEQ ID NO:38—amino acid sequence; FIG. 1T: SEQ ID NO:39—nucleotide sequence and SEQ ID NO:40—amino acid sequence; FIG. 1U: SEQ ID NO:41—nucleotide sequence and SEQ ID NO:42—amino acid sequence; FIG. 1V: SEQ ID NO:43—nucleotide sequence and SEQ ID NO:44—amino acid sequence; FIG. 1W: SEQ ID NO:45—nucleotide sequence and SEQ ID NO:46—amino acid sequence; and FIG. 1X: SEQ ID NO:47—nucleotide sequence and SEQ ID NO:48—amino acid sequence), in particular the mature enzyme, as well as enzymes which have at least 70% similarity (preferably at least 70% identity) to an enzyme of the invention and more preferably at least 90% similarity (more preferably at least 90% identity) to an enzyme of the invention and still more preferably at least 95% similarity (still more preferably at least 95% identity) to an enzyme of the invention and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Cneter for Biological Information).

A variant, i.e. a "fragment", "analog" or "derivative" enzyme, and reference enzyme may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors containing the polynucleotides of this invention. Such vectors may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phase DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtillis; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II (Stratagene); pTRC99a, pKK223-3, pDR540, pRIT2T (Pharmacia); Eukaryotic: pXT1, pSG5 (Stratagene) pSVK3, pBPV, pMSG, pSVLSV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battery, I., Basic Methods in Molecular Biology, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the general Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylaptite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

The enzyme of this invention may be employed for any purpose in which such enzyme activity is necessary or desired. In a preferred embodiment the enzyme is employed for catalyzing the hydrolysis of cellulose. The degradation of cellulose may be used for the conversion of plant biomass into fuels and chemicals.

The enzyme of the present invention may also be employed in the detergent and textile industry, in the production of animal feed, in waste treatment and in the fruit juice/brewing industry for the clarification and extraction of juices.

In a preferred embodiment, the enzyme of the present invention is a thermostable enzyme which is stable to heat and is heat resistant and catalyzes the enzymatic hydrolysis of cellulose, i.e., the enzyme is able to renature and regain activity after a brief (i.e., 5 to 30 seconds), or longer period, of example, minutes or hours, exposure to temperatures of 80° C. to 105° C. and has a temperature optimum above 60° C.

The enzymes, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art, for example, one such screening assay is described in "Methods for Measuring Cellulase Activities", *Methods in Enzymology*, Vol 160, pp. 87-116, which is hereby incorporated by reference in its entirety. Antibodies may also be employed as a probe to screen gene libraries generated from this or other organisms to identify this or cross reactive activities.

Isolation and purification of polypeptides produced in the systems described above can be carried out using conventional methods, appropriate for the particular system. For example, preparative chromatography and immunological separations employing antibodies, such as monoclonal or polyclonal antibodies, can be used.

The term "antibody," as used herein, refers to intact immunoglobulin molecules, as well as fragments of immunoglobulin molecules, such as Fab, Fab', (Fab')$_2$, Fv, and SCA fragments, that are capable of binding to an epitope of an endoglucanase polypeptide. These antibody fragments, which retain some ability to selectively bind to the antigen (e.g., an endoglucanase antigen) of the antibody from which they are derived, can be made using well known methods in the art (see, e.g., Harlow and Lane, supra), and are described further, as follows.

(1) A Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) A Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) A (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As used in this invention, the term "epitope" refers to an antigenic determinant on an antigen, such as an endoglucanase polypeptide, to which the paratope of an antibody, such as an endoglucanase-specific antibody, binds. Antigenic determinants usually consist of chemically active surface groupings of molecules, such as amino acids or sugar side chains, and can have specific three-dimensional structural characteristics, as well as specific charge characteristics.

As in mentioned above, antigens that can be used in producing endoglucanase-specific antibodies include endoglucanase polypeptides, e.g., any of the endoglucanases shown in FIGS. 1A-1X polypeptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

Endoglucanase-specific polyclonal and monoclonal antibodies can be purified, for example, by binding to, and elution from, a matrix containing an endoglucanase polypeptide, e.g., the endoglucanase polypeptide (or fragment thereof) to which the antibodies were raised. Additional methods for antibody purification and concentration are well known in the art and can be practiced with the endoglucanase-specific antibodies of the invention (see, for example, C-oligan, et al., Unit 9, *Current Protocols in Immunology*, Wiley Interscience, 1994).

Anti-idiotype antibodies corresponding to endoglucanase-specific antigens are also included in the invention, and can be produced using standard methods. These antibodies are raised to endoglucanase-specific antibodies, and thus mimic endoglucanase-specific epitopes.

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

The present invention is further described with reference to the following examples; however, it is to be understood that the present invention is not limited to such examples. All parts or amounts, unless otherwise specified, are by weight.

In one aspect of the invention, a method for producing an endoglucanase enzyme, such as those shown in FIGS. 1A-1X (FIG. 1A: SEQ ID NO:1—nucleotide sequence and SEQ ID NO:2—amino acid sequence; FIG. 1B: SEQ ID NO:3—nucleotide sequence and SEQ ID NO:4—amino acid sequence; FIG. 1C: SEQ ID NO:5—nucleotide sequence and SEQ ID NO:6—amino acid sequence; FIG. 1D: SEQ ID NO:7—nucleotide sequence and SEQ ID NO:8—amino acid sequence; FIG. 1E: SEQ ID NO:9—nucleotide sequence and SEQ ID NO:10—amino acid sequence; FIG. 1F: SEQ ID NO:11—nucleotide sequence and SEQ ID NO:12—amino acid sequence; FIG. 1G: SEQ ID NO:13—nucleotide sequence and SEQ ID NO:14—amino acid sequence; FIG. 1H: SEQ ID NO:15—nucleotide sequence and SEQ ID NO:16—amino acid sequence; FIG. 1I: SEQ ID NO:17—nucleotide sequence and SEQ ID NO:18—amino acid sequence; FIG. 1J: SEQ ID NO:19—nucleotide sequence and SEQ ID NO:20—amino acid sequence; FIG. 1K: SEQ ID NO:21—nucleotide sequence and SEQ ID NO:22—amino acid sequence; FIG. 1L: SEQ ID NO:23—nucleotide sequence and SEQ ID NO:24—amino acid sequence; FIG. 1M: SEQ ID NO:25—nucleotide sequence and SEQ ID NO:26—amino acid sequence; FIG. 1N: SEQ ID NO:27—nucleotide sequence and SEQ ID NO:28—amino acid sequence; FIG. 1O: SEQ ID NO:29—nucleotide sequence and SEQ ID NO:30—amino acid sequence; FIG. 1P: SEQ ID NO:31—nucleotide sequence and SEQ ID NO:32—amino acid sequence; FIG. 1Q: SEQ ID NO:33—nucleotide sequence and SEQ ID NO:34—amino acid sequence; FIG. 1R: SEQ ID NO:35—nucleotide sequence and SEQ ID NO:36—amino acid sequence; FIG. 1S: SEQ ID NO:37—nucleotide sequence and SEQ ID NO:38—amino acid sequence; FIG. 1T: SEQ ID NO:39—nucleotide sequence and SEQ ID NO:40—amino acid sequence; FIG. 1U: SEQ ID NO:41—nucleotide sequence and SEQ ID NO:42—amino acid sequence; FIG. 1V: SEQ ID NO:43—nucleotide sequence and SEQ ID NO:44—amino acid sequence; FIG. 1W: SEQ ID NO:45—nucleotide sequence and SEQ ID NO:46—amino acid sequence; and FIG. 1X: SEQ ID NO:47—nucleotide sequence and SEQ ID NO:48—amino acid sequence), is provided. The method includes growing a host cell which contains a polynucleotide encoding the enzyme (e.g., SEQ ID NO:1, 3, 5, 7, 9, 11, 13, 15, 17, 19, 21, 23, 25, 27, 29, 31, 33, 35, 37, 39, 41, 43, 45, or 47), under conditions which allow the expression of the nucleic acid, and isolating the enzyme encoded by the nucleic acid. Methods of culturing the host cell are described in the Examples and are known by those of skill in the art.

In another embodiment, the invention provides a method for degrading carboxymethylcellulose. The method includes contacting carboxymethylcellulose with a degrading effective amount of an enzyme of the invention, such as the enzyme shown in SEQ ID NO:2, 4, 6, 8, 10, 12, 14, 16, 18, 20, 22, 24, 26, 28, 30, 32, 36, 38, 40, 42, 44, 46, or 48. The term "degrading effective" amount refers to the amount of enzyme which is required to degrade at least 50% of the carboxymethylcellulose, as compared to carboxymethylcellulose not contacted with the enzyme. Preferably, at least 80% of the carboxymethylcellulose is degraded.

In another embodiment, the invention provides a method for hydrolyzing the beta 1,4 glycosidic bond in cellulose, the method including administering an effective amount of an enzyme of the invention (e.g., SEQ ID NO:2, 4, 6, 8, 10, 12, 14, 16, 18, 20, 22, 24, 26, 28, 30, 32, 36, 38, 40, 42, 44, 46, or 48) to cellulose, to hydrolyze the glycosidic bond. An "effective" amount refers to the amount of enzyme which is required to hydrolyze at least 50% of the glycosidic bonds, as compared to carboxymethylcellulose not contacted with the enzyme. Preferably, at least 80% of the glycosidic bonds are hydrolyzed.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is generally performed using 8 percent polyacrylamide gel described by Goeddel, D. et al., Nucleic Acids Res., 8:4057 (1980), for example.

"Oligonucleotides" refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Sambrook, Fritsch and Maniatus, 1989. The following examples are intended to illustrate, but not to limit, the invention. While the procedures described in the examples are typical of those that can be used to carry out certain aspects of the invention, other procedures known to those skilled in the art can also be used. The following materials and methods were used in carrying out the experiments described in the examples.

Example 1

Bacterial Expression and Purification of Endoglucanase

An AEPII1a genomic library was constructed in the Lambda gt11 cloning vector (Stratagene Cloning Systems). The library was screened in Y1090 E. coli cells (Stratagene) for endoglucanase activity and a positive clone was identified and isolated. DNA of this clone was used as a template in a 100 ul PCT reaction using the following primer sequences: 5' primer: AATAGCGGCCGCAAGCTTATCGACG-GTTTCCATATGGGGATTGGTG (SEQ ID NO:49). 3' primer: AATAGCGGCCGCGGATCCAGACCAACTGG
TAATGGTAGCGAC (SEQ ID NO:50).

The PCR reaction product was purified and digested with Not I restriction enzyme. The digested product was subcloned into the pBluescript II SK cloning vector (Stratagene) and sequenced. The sequence information was used in the generation of primer sequences which were subsequently used to PCR amplify the target gene encoding the endoglucanase. The primer sequences used were as follows: 5' primer: TTTATTCAATTGATTAAAGAGGAGAAAT-
TAACTATGATAAACGTTGCAACGGGAGAGGAG (SEQ ID NO:51) and 3' primer: TTTATTGGATCCTACTTTGT-
GTCAACGAAGTATCC (SEQ ID NO:52).

The amplification product was digested with the restriction enzymes MfeI and BamHI. The digested product was then ligated to pQET cloning vector, a modified form of a pQE vector (Qiagen, Inc.) which was previously digested with BamHI and EcoRI compatible with MfeI. The pQE vector encodes antibiotic resistance (Amp$^r$), a bacterial origin of replication (ori), an IPTG-regulatable promoter operator (P/O), a ribosome binding site (RBS), a 6-His tag and restriction enzyme sites.

The amplified sequences were inserted in frame with the sequence encoding for the RBS. The ligation mixture was then used to transform the E. coli strain M15/pREP4 (Qiagen, Inc.) by electroporation. M15/pREP4 contains multiple copies of the plasmid pREP4, which expresses the lacI repressor and also confers kanamycin resistance (Kan$^r$). Positive recombinant transformants were identified as having thermostable CMCase/endoglucanase activity by the assay described above. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

Numerous modifications and variations of the present invention are possible in light of the above teachings and, therefore, within the scope of the appended claims, the invention may be practiced otherwise than as particularly described. It is to be understood that, while the invention has been described with reference to the above detailed description, the foregoing description is intended to illustrate, but not to limit, the scope of the invention. Other aspects, advantages, and modifications of the invention are within the scope of the following claims. All publications, patent applications, patents, and other references mentioned herein are incorporated by reference in their entirety.

What is claimed is:

1. An isolated, synthetic or recombinant polypeptide having endoglucanase or cellulase activity comprising an amino acid sequence having at least 95% sequence identity to the amino acid sequence of SEQ ID NO:46, or encoded by a nucleic acid encoding a polypeptide having endoglucanase or cellulase activity and having at least 95% sequence identity to the polynucleotide sequence of SEQ ID NO:45.

2. An isolated, synthetic or recombinant polynucleotide comprising a sequence encoding the endoglucanase or cellulase of claim 1, or comprising a nucleic acid sequence encoding a polypeptide having endoglucanase or cellulase activity and having at least 95% sequence identity to the polynucleotide sequence of SEQ ID NO:45.

3. The isolated, synthetic or recombinant polynucleotide of claim 2, wherein the polynucleotide is isolated from a prokaryote.

4. A vector comprising a nucleic acid having a sequence as set forth in claim 2.

5. The vector of claim 4, wherein the vector comprises a plasmid.

6. The vector of claim 4, wherein the vector comprises virus-derived sequences.

7. An isolated host cell comprising the vector of claim 4.

8. A method for producing an enzyme comprising (a) (i) growing a host cell of claim 7 under conditions which allow the expression of the enzyme-encoding nucleic acid and (ii) isolating the enzyme encoded by the nucleic acid, or (b) the method of (a), wherein the cell is a plant cell, a yeast cell, a bacterial cell, a fungal cell, an insect cell or an animal cell.

9. The host cell of claim 7, wherein the cell is a plant cell.

10. The host cell of claims 7, wherein the cell is a yeast cell, a bacterial cell, a fungal cell, an insect cell or an animal cell.

11. The host cell of claim 7, wherein the cell is prokaryotic.

12. The isolated, synthetic or recombinant polypeptide of claim 1, wherein the polypeptide has the amino acid sequence of SEQ ID NO:46.

13. The isolated, synthetic or recombinant polypeptide of claim 1, wherein the polypeptide has endoglucanase activity.

14. The isolated, synthetic or recombinant polypeptide of claim 1, wherein the polypeptide has cellulase activity.

15. The isolated, synthetic or recombinant polypeptide of claim 14, wherein the cellulase activity comprises a carboxymethyl cellulase activity.

16. The isolated, synthetic or recombinant polypeptide of claim 1, wherein the cellulase activity comprises a carboxymethylcellulase.

17. An isolated, synthetic or recombinant polypeptide having endoglucanase or cellulase activity comprising (a) a polypeptide having at least 95% sequence identity to the amino acid sequence of SEQ ID NO:46, (b) a polypeptide encoded by a nucleic acid encoding a polypeptide having endoglucanase or cellulase activity and having at least 95% sequence identity to the polynucleotide sequence of SEQ ID NO:45, or (c) enzymatically active fragments of (a) or (b).

18. A method for degrading carboxymethylcellulose comprising contacting a carboxymethylcellulose with an effective amount of the polypeptide of claim 17.

19. A method for hydrolyzing a beta 1,4 glycosidic bond in a cellulose comprising contacting an effective amount of the polypeptide of claim 17 with the cellulose to hydrolyze the glycosidic bond.

20. The method of claim 19, wherein the method comprises contacting the cellulose with a detergent comprising an effective amount of the polypeptide.

21. The method of claim 19, wherein the method comprises contacting a textile comprising the cellulose with an effective amount of the polypeptide in.

22. The method of claim 19, wherein the method comprises contacting an animal feed comprising the cellulose with an effective amount of the polypeptide in.

23. The method of claim 19, wherein the method comprises contacting a waste comprising the cellulose with an effective amount of the polypeptide.

24. The method of claim 19, wherein the method comprises contacting a juice or a brew comprising the cellulose with an effective amount of the polypeptide for the clarification or extraction of juices or brews.

25. A method for converting plant biomass into fuels or chemicals comprising contacting a plant biomass comprising cellulose with an effective amount of a polypeptide of claim 17, thereby hydrolyzing the cellulose for converting the plant biomass into a fuel or a chemical.

26. A composition comprising the isolated, synthetic or recombinant polypeptide of claim 17, and a textile.

27. A composition comprising the isolated, synthetic or recombinant polypeptide of claim 17, and a feed.

28. A composition comprising the isolated, synthetic or recombinant polypeptide of claim 17, and a detergent.

29. A composition comprising the isolated, synthetic or recombinant polypeptide of claim 17, and a juice or a brew.

30. An isolated, synthetic or recombinant polynucleotide sequence encoding an endoglucanase or cellulase of claim 17.

31. A composition comprising the isolated, synthetic or recombinant polypeptide of claim 17, and a plant biomass.

32. An isolated, synthetic or recombinant polypeptide having endoglucanase or cellulase activity comprising a polypeptide having the amino acid sequence of SEQ ID NO:46, or enzymatically active fragments thereof.

33. An isolated, synthetic or recombinant nucleic acid encoding the polypeptide of claim 32.

34. A vector comprising a nucleic acid having the nucleic acid sequence of claim 33.

35. An isolated host cell comprising (a) the nucleic acid of claim 33, or (b) the host cell of (a), wherein the cell is a plant cell, a yeast cell, a bacterial cell, a fungal cell, an insect cell or an animal cell.

36. An isolated, synthetic or recombinant polypeptide having endoglucanase or cellulase activity comprising the amino acid sequence of SEQ ID NO:46 and having at least one conservative amino acid substitution, wherein the conservative amino acid substitution comprises: a replacement, one for another, among the aliphatic amino acids Ala, Val, Leu and Ile; or an interchange of the hydroxyl residues Ser and Thr; or an exchange of the acidic residues Asp and Glu; or a substitution between the amide residues Asn and Gln; or an exchange of the basic residues Lys and Arg; or a replacement among the aromatic residues Phe, Tyr,
   wherein the polypeptide has an amino acid sequence having at least 95% sequence identity to the amino acid sequence of SEQ ID NO:46, or the polypeptide is encoded by a nucleic acid having at least 95% sequence identity to the polynucleotide sequence of SEQ ID NO:45.

37. An isolated, synthetic or recombinant nucleic acid encoding a polypeptide having endoglucanase or cellulase activity, wherein the nucleic acid hybridizes under stringent conditions to the polynucleotide sequence of SEQ ID NO:45, and the stringent conditions comprise a wash step comprising a wash for 30 minutes at room temperature in a solution comprising 150 mM NaCl, 20 mM Tris hydrochloride, pH 7.8, 1 mM $Na_2EDTA$, 0.5% SDS, followed by 30 minute wash in fresh solution at Tm-10° C.

38. The isolated, synthetic or recombinant nucleic acid of claim 37, wherein the nucleic acid that hybridizes under stringent conditions to the polynucleotide sequence of SEQ ID NO:45 has at least 97% sequence identity to the polynucleotide of SEQ ID NO:45.

39. The isolated, synthetic or recombinant nucleic acid of claim 38, wherein the nucleic acid has the polynucleotide sequence of SEQ ID NO:45.

40. An isolated host cell comprising (a) a heterologous nucleic acid having the sequence of claim 37, or (b) the host cell of (a), wherein the cell is a plant cell, a yeast cell, a bacterial cell, a fungal cell, an insect cell or an animal cell.

41. A method for producing an enzyme comprising growing a host cell of claim 40 under conditions which allow the expression of the nucleic acid and isolating the enzyme encoded by the nucleic acid.

42. The isolated, synthetic or recombinant nucleic acid claim 37, wherein the nucleic acid that hybridizes under stringent conditions to the polynucleotide sequence SEQ ID NO:45 has at least 95% sequence identity to the polynucleotide of SEQ ID NO:45.

43. A method for degrading carboxymethylcellulose comprising (i) expressing the nucleic acid of claim 37 to generate a recombinant enzyme, and (ii) contacting a carboxymethylcellulose with an effective amount of the recombinant enzyme of (i).

44. A method for hydrolyzing a beta 1,4 glycosidic bond in a cellulose comprising (i) expressing the nucleic acid of claim 37 to generate a recombinant enzyme, and (ii) contacting an effective amount of the recombinant enzyme of (i) with the cellulose to hydrolyze the glycosidic bond.

45. A composition comprising the isolated, synthetic or recombinant polypeptide encoded by the nucleic acid of claim 37, and a textile.

46. A composition comprising the isolated, synthetic or recombinant polypeptide encoded by the nucleic acid of claim 37, and a feed.

47. A composition comprising the isolated, synthetic or recombinant polypeptide encoded by the nucleic acid of claim 37, and a detergent.

48. A vector comprising a nucleic acid having the nucleic acid sequence of claim 37.

49. A composition comprising the isolated, synthetic or recombinant polypeptide encoded by the nucleic acid of claim 37, and a juice or a brew.

50. A composition comprising the isolated, synthetic or recombinant polypeptide encoded by the nucleic acid of claim 37, and a plant biomass.

* * * * *

UNITED STATES PATENT AND TRADEMARK OFFICE
CERTIFICATE OF CORRECTION

PATENT NO. : 7,465,571 B1  
APPLICATION NO. : 09/914543  
DATED : December 16, 2008  
INVENTOR(S) : David Lam and Eric J. Mathur It is certified that error appears in the above-identified patent and that said Letters Patent is hereby corrected as shown below:

In Column 195
Line 54 in Claim 8, after "comprising" delete "(a)"
Line 57 and 58 in Claim 8, delete "or (b) the method of (a),"
Line 62 in Claim 10, delete "claims" and insert --claim--, therefor

In Column 196
Line 35 in Claim 15, delete "a"
Line 38 in Claim 16, delete "a"
Line 39 in Claim 16, after "carboxymethylcellulase" insert --activity--
Line 49 in Claim 18, delete "a"
Line 61 in Claim 21, delete "in"
Line 64 in Claim 22, delete "in"

In Column 197, Lines 5 to 9 in Claim 25
delete "A method for converting plant biomass into fuels or chemicals comprising contacting a plant biomass comprising cellulose with an effective amount of a poly peptide of claim 17, thereby hydrolyzing the cellulose for converting the plant biomass into a fuel or a chemical."
and insert --A method for enzymatically converting plant biomass into a precursor for producing fuels or chemicals comprising: (a) providing a plant biomass comprising cellulose; (b) providing a cellulase comprising the polypeptide of claim 27; and (c) contacting the plant biomass with an effective amount of the polypeptide of (b), thereby enzymatically hydrolyzing the cellulose into a precursor for producing a fuel or a chemical.--, therefor

In Column 197
Line 30 in Claim 35, delete "(a)"
Line 31 in Claim 35, delete "or (b) the host cell of (a),"

UNITED STATES PATENT AND TRADEMARK OFFICE
CERTIFICATE OF CORRECTION

PATENT NO. : 7,465,571 B1
APPLICATION NO. : 09/914543
DATED : December 16, 2008
INVENTOR(S) : David Lam and Eric J. Mathur It is certified that error appears in the above-identified patent and that said Letters Patent is hereby corrected as shown below:

In Column 198
Line 14 in Claim 40, delete "(a)"
Line 15 and 16 in Claim 40, delete "or (b) the host cell of (a),"
Line 29 in Claim 43, after "contacting" delete "a"

Signed and Sealed this

Fifth Day of May, 2009

JOHN DOLL
*Acting Director of the United States Patent and Trademark Office*

SEQUENCE LISTING

```
<160> NUMBER OF SEQ ID NOS: 52

<210> SEQ ID NO 1
<211> LENGTH: 2529
<212> TYPE: DNA
<213> ORGANISM: Thermotoga maritima
<220> FEATURE:
<221> NAME/KEY: CDS
<222> LOCATION: (1)...(2523)
<223> OTHER INFORMATION: AEPII 1a Archaeal Endoglucanase

<400> SEQUENCE: 1 atg ata aac gtt gca acg gga gag gag acc cca ata cac ctc ttt gga      48
Met Ile Asn Val Ala Thr Gly Glu Glu Thr Pro Ile His Leu Phe Gly
1               5                   10                  15 gtc aac tgg ttc ggc ttt gag aca ccg aac tac gtt gtt cac ggc cta      96
Val Asn Trp Phe Gly Phe Glu Thr Pro Asn Tyr Val Val His Gly Leu
            20                  25                  30 tgg agt agg aac tgg gag gac atg ctc ctc cag atc aag agc ctt ggc     144
Trp Ser Arg Asn Trp Glu Asp Met Leu Leu Gln Ile Lys Ser Leu Gly
        35                  40                  45 ttc aat gcg ata agg ctt ccc ttc tgt acc cag tca gta aaa ccg ggg     192
Phe Asn Ala Ile Arg Leu Pro Phe Cys Thr Gln Ser Val Lys Pro Gly
    50                  55                  60 acg atg cca acg gcg att gac tac gcc aag aac cca gac ctc cag ggt     240
Thr Met Pro Thr Ala Ile Asp Tyr Ala Lys Asn Pro Asp Leu Gln Gly
65                  70                  75                  80 ctt gac agc gtc cag ata atg gag aaa ata atc aag aag gct gga gac     288
Leu Asp Ser Val Gln Ile Met Glu Lys Ile Ile Lys Lys Ala Gly Asp
                85                  90                  95 ctg ggc ata ttc gtg ctc ctc gac tac cac aga ata gga tgc aac ttc     336
Leu Gly Ile Phe Val Leu Leu Asp Tyr His Arg Ile Gly Cys Asn Phe
```

```
                    100                 105                 110
ata gaa ccc cta tgg tac acc gac agc ttc tcg gag cag gac tac ata        384
Ile Glu Pro Leu Trp Tyr Thr Asp Ser Phe Ser Glu Gln Asp Tyr Ile
            115                 120                 125 aac acc tgg gtt gaa gtc gcc cag agg ttc ggc aag tac tgg aac gtt        432
Asn Thr Trp Val Glu Val Ala Gln Arg Phe Gly Lys Tyr Trp Asn Val
    130                 135                 140 atc ggc gcg gac ctg aag aac gaa ccc cac agc tca agc ccc gca cct        480
Ile Gly Ala Asp Leu Lys Asn Glu Pro His Ser Ser Ser Pro Ala Pro
145                 150                 155                 160 gcc gcc tac act gac gga agt ggg gcc acg tgg gga atg ggc aac aac        528
Ala Ala Tyr Thr Asp Gly Ser Gly Ala Thr Trp Gly Met Gly Asn Asn
                165                 170                 175 gcc acc gac tgg aac ctg gcg gct gag agg ata gga agg gca att ctg        576
Ala Thr Asp Trp Asn Leu Ala Ala Glu Arg Ile Gly Arg Ala Ile Leu
            180                 185                 190 gag gtt gcc cca caa tgg gtt ata ttt gtt gag gga acc cag ttc acc        624
Glu Val Ala Pro Gln Trp Val Ile Phe Val Glu Gly Thr Gln Phe Thr
    195                 200                 205 acc ccc gag ata gac ggt agg tac aag tgg ggc cac aac gcc tgg tgg        672
Thr Pro Glu Ile Asp Gly Arg Tyr Lys Trp Gly His Asn Ala Trp Trp
210                 215                 220 ggc gga aac ctt atg ggt gtt agg aag tac cca gtt aac ctg ccc agg        720
Gly Gly Asn Leu Met Gly Val Arg Lys Tyr Pro Val Asn Leu Pro Arg
225                 230                 235                 240 gac aag gtt gtt tac agc ccc caa gtt tac ggt tca gaa gtt tac gac        768
Asp Lys Val Val Tyr Ser Pro Gln Val Tyr Gly Ser Glu Val Tyr Asp
                245                 250                 255 cag ccc tac ttt gac ccc ggt gag ggg ttc ccc gac aac ctc ccc gaa        816
Gln Pro Tyr Phe Asp Pro Gly Glu Gly Phe Pro Asp Asn Leu Pro Glu
            260                 265                 270 ata tgg tac cac cac ttc ggc tac gta aag ctt gat ctc ggt tac cct        864
Ile Trp Tyr His His Phe Gly Tyr Val Lys Leu Asp Leu Gly Tyr Pro
    275                 280                 285 gtt gtt ata ggt gag ttc gga ggc aag tac ggc cat ggg gga gac ccg        912
Val Val Ile Gly Glu Phe Gly Gly Lys Tyr Gly His Gly Gly Asp Pro
290                 295                 300 agg gat gtc act tgg cag aac aag ata ata gac tgg atg atc cag aac        960
Arg Asp Val Thr Trp Gln Asn Lys Ile Ile Asp Trp Met Ile Gln Asn
305                 310                 315                 320 aaa ttc tgt gac ttc ttc tac tgg agc tgg aac cca aac agc ggt gac       1008
Lys Phe Cys Asp Phe Phe Tyr Trp Ser Trp Asn Pro Asn Ser Gly Asp
                325                 330                 335 acc ggt gga att ctg aag gat gac tgg acg aca ata tgg gag gac aag       1056
Thr Gly Gly Ile Leu Lys Asp Asp Trp Thr Thr Ile Trp Glu Asp Lys
            340                 345                 350 tac aac aac ctg aag agg ctc atg gac agc tgt tct gga aac gcc act       1104
Tyr Asn Asn Leu Lys Arg Leu Met Asp Ser Cys Ser Gly Asn Ala Thr
    355                 360                 365 gcc ccg tcc gtc ccc acg aca act aca aca agc aca ccg cca acg       1152
Ala Pro Ser Val Pro Thr Thr Thr Thr Thr Ser Thr Pro Pro Thr
370                 375                 380 acc aca acg act aca aca tcc act cca acg acc act acc cag acc ccg       1200
Thr Thr Thr Thr Thr Thr Ser Thr Pro Thr Thr Thr Gln Thr Pro
385                 390                 395                 400 acc acc act act cca act acg aca acc acc acg acc aca act cct tca       1248
Thr Thr Thr Thr Pro Thr Thr Thr Thr Thr Thr Thr Thr Pro Ser
                405                 410                 415 aat aac gtc cca ttt gaa att gtg aac gtt ctc ccg act agc tcc cag       1296
```

```
                Asn Asn Val Pro Phe Glu Ile Val Asn Val Leu Pro Thr Ser Ser Gln
                            420                 425                 430 tac gag gga acc agc gtg gag gtt gta tgt gat gga acc cag tgt gcc            1344
Tyr Glu Gly Thr Ser Val Glu Val Val Cys Asp Gly Thr Gln Cys Ala
            435                 440                 445 tcc agc gtt tgg gga gct ccg aac ctc tgg gga gtc gtt aaa atc gga            1392
Ser Ser Val Trp Gly Ala Pro Asn Leu Trp Gly Val Val Lys Ile Gly
450                 455                 460 aac gcc acc atg gac ccc aac gtt tgg ggc tgg gag gac gtt tac aag            1440
Asn Ala Thr Met Asp Pro Asn Val Trp Gly Trp Glu Asp Val Tyr Lys
465                 470                 475                 480 act gca ccc cag gac att gga acc ggc agc aca aag atg gag ata agg            1488
Thr Ala Pro Gln Asp Ile Gly Thr Gly Ser Thr Lys Met Glu Ile Arg
                485                 490                 495 aac ggg gtg ctc aag gtt aca aac ctc tgg aac atc aac atg cat ccg            1536
Asn Gly Val Leu Lys Val Thr Asn Leu Trp Asn Ile Asn Met His Pro
            500                 505                 510 aag tat aac aca atg gca tac ccg gag gtc ata tac ggc gcc aag cct            1584
Lys Tyr Asn Thr Met Ala Tyr Pro Glu Val Ile Tyr Gly Ala Lys Pro
            515                 520                 525 tgg ggc aac cag cca ata aac gct ccg aac ttc gtg ctc ccg ata aag            1632
Trp Gly Asn Gln Pro Ile Asn Ala Pro Asn Phe Val Leu Pro Ile Lys
530                 535                 540 gtc tcc cag ctt ccg agg ata ctc gtt gac aca aag tac acg ctc gaa            1680
Val Ser Gln Leu Pro Arg Ile Leu Val Asp Thr Lys Tyr Thr Leu Glu
545                 550                 555                 560 aag agc ttc ccg gga aac aac ttc gcc ttt gag gcc tgg ctc ttc aag            1728
Lys Ser Phe Pro Gly Asn Asn Phe Ala Phe Glu Ala Trp Leu Phe Lys
                565                 570                 575 gat gcc aac aac atg agg gca cca ggc cag ggg gac tac gag ata atg            1776
Asp Ala Asn Asn Met Arg Ala Pro Gly Gln Gly Asp Tyr Glu Ile Met
            580                 585                 590 gta cag ctc tac atc gag ggc ggc tat cct gcg ggc tac gac aag ggg            1824
Val Gln Leu Tyr Ile Glu Gly Gly Tyr Pro Ala Gly Tyr Asp Lys Gly
            595                 600                 605 cca gtt ctc acc gtt gat gtt ccg ata atc gtc gat gga agg ctt gta            1872
Pro Val Leu Thr Val Asp Val Pro Ile Ile Val Asp Gly Arg Leu Val
            610                 615                 620 aac cag act ttt gag ctc tac gac gtc ata gcg gat gcc gga tgg agg            1920
Asn Gln Thr Phe Glu Leu Tyr Asp Val Ile Ala Asp Ala Gly Trp Arg
625                 630                 635                 640 ttc ttc acc ttc aag cca act aag aac tac aac ggc tca gag gtt gtg            1968
Phe Phe Thr Phe Lys Pro Thr Lys Asn Tyr Asn Gly Ser Glu Val Val
                645                 650                 655 ttc gac tac acc aaa ttc ata gaa ata gtt gac aac tac ctc ggc ggt            2016
Phe Asp Tyr Thr Lys Phe Ile Glu Ile Val Asp Asn Tyr Leu Gly Gly
            660                 665                 670 ggc agc ctc acg aac cac tac ctg atg tcc ctg gaa ttc ggt acc gag            2064
Gly Ser Leu Thr Asn His Tyr Leu Met Ser Leu Glu Phe Gly Thr Glu
            675                 680                 685 ata tac acc aac ggg tgc acc tca ttc cca tgc aca gtg gac gta agg            2112
Ile Tyr Thr Asn Gly Cys Thr Ser Phe Pro Cys Thr Val Asp Val Arg
            690                 695                 700 tgg acc ctt gac aag tac agg ttc atc ctg gcc cca gga aca atg gcc            2160
Trp Thr Leu Asp Lys Tyr Arg Phe Ile Leu Ala Pro Gly Thr Met Ala
705                 710                 715                 720 act gag gag gcc atg aga gtt ctc gtc gga gag gtc cag cct ccc gct            2208
Thr Glu Glu Ala Met Arg Val Leu Val Gly Glu Val Gln Pro Pro Ala
                725                 730                 735
```

```
tcc aca aca aca tcg cag acg act act tca acc aca acc cca acg ccc    2256
Ser Thr Thr Thr Ser Gln Thr Thr Thr Ser Thr Thr Thr Pro Thr Pro
            740                 745                 750 act acc act act acg act cag act tca acc acc act aca acc acc tca    2304
Thr Thr Thr Thr Thr Thr Gln Thr Ser Thr Thr Thr Thr Thr Thr Ser
        755                 760                 765 ccg ccg aca acc acc gca cct gct cag gac gta att aag ctc agg tac    2352
Pro Pro Thr Thr Thr Ala Pro Ala Gln Asp Val Ile Lys Leu Arg Tyr
770                 775                 780 ccg gac gat ggg cag tgg ccc gag gcc cca att gac agg gat gga gac    2400
Pro Asp Asp Gly Gln Trp Pro Glu Ala Pro Ile Asp Arg Asp Gly Asp
785                 790                 795                 800 gga aac cca gag ttc tac ata gaa ata aac ccg tgg aac ata ctg agc    2448
Gly Asn Pro Glu Phe Tyr Ile Glu Ile Asn Pro Trp Asn Ile Leu Ser
                805                 810                 815 gct gaa agc tac gcc gag atg acc tac aac ttg agc agc ggg gtt ctc    2496
Ala Glu Ser Tyr Ala Glu Met Thr Tyr Asn Leu Ser Ser Gly Val Leu
            820                 825                 830 cac tac gtc cag gcc ctg gat agt ata tgatga                         2529
His Tyr Val Gln Ala Leu Asp Ser Ile
        835                 840

<210> SEQ ID NO 2
<211> LENGTH: 841
<212> TYPE: PRT
<213> ORGANISM: Thermotoga maritima

<400> SEQUENCE: 2

Met Ile Asn Val Ala Thr Gly Glu Glu Thr Pro Ile His Leu Phe Gly
1               5                   10                  15

Val Asn Trp Phe Gly Phe Glu Thr Pro Asn Tyr Val Val His Gly Leu
            20                  25                  30

Trp Ser Arg Asn Trp Glu Asp Met Leu Leu Gln Ile Lys Ser Leu Gly
        35                  40                  45

Phe Asn Ala Ile Arg Leu Pro Phe Cys Thr Gln Ser Val Lys Pro Gly
    50                  55                  60

Thr Met Pro Thr Ala Ile Asp Tyr Ala Lys Asn Pro Asp Leu Gln Gly
65                  70                  75                  80

Leu Asp Ser Val Gln Ile Met Glu Lys Ile Ile Lys Lys Ala Gly Asp
                85                  90                  95

Leu Gly Ile Phe Val Leu Leu Asp Tyr His Arg Ile Gly Cys Asn Phe
            100                 105                 110

Ile Glu Pro Leu Trp Tyr Thr Asp Ser Phe Ser Glu Gln Asp Tyr Ile
        115                 120                 125

Asn Thr Trp Val Glu Val Ala Gln Arg Phe Gly Lys Tyr Trp Asn Val
    130                 135                 140

Ile Gly Ala Asp Leu Lys Asn Glu Pro His Ser Ser Ser Pro Ala Pro
145                 150                 155                 160

Ala Ala Tyr Thr Asp Gly Ser Gly Ala Thr Trp Gly Met Gly Asn Asn
                165                 170                 175

Ala Thr Asp Trp Asn Leu Ala Ala Glu Arg Ile Gly Arg Ala Ile Leu
            180                 185                 190

Glu Val Ala Pro Gln Trp Val Ile Phe Val Glu Gly Thr Gln Phe Thr
        195                 200                 205

Thr Pro Glu Ile Asp Gly Arg Tyr Lys Trp Gly His Asn Ala Trp Trp
    210                 215                 220

Gly Gly Asn Leu Met Gly Val Arg Lys Tyr Pro Val Asn Leu Pro Arg
```

-continued

```
            225                 230                 235                 240
Asp Lys Val Val Tyr Ser Pro Gln Val Tyr Gly Ser Glu Val Tyr Asp
                    245                 250                 255
Gln Pro Tyr Phe Asp Pro Gly Glu Gly Phe Pro Asp Asn Leu Pro Glu
                260                 265                 270
Ile Trp Tyr His His Phe Gly Tyr Val Lys Leu Asp Leu Gly Tyr Pro
            275                 280                 285
Val Val Ile Gly Glu Phe Gly Lys Tyr Gly His Gly Gly Asp Pro
        290                 295                 300
Arg Asp Val Thr Trp Gln Asn Lys Ile Ile Asp Trp Met Ile Gln Asn
305                 310                 315                 320
Lys Phe Cys Asp Phe Phe Tyr Trp Ser Trp Asn Pro Asn Ser Gly Asp
                325                 330                 335
Thr Gly Gly Ile Leu Lys Asp Asp Trp Thr Thr Ile Trp Glu Asp Lys
            340                 345                 350
Tyr Asn Asn Leu Lys Arg Leu Met Asp Ser Cys Ser Gly Asn Ala Thr
            355                 360                 365
Ala Pro Ser Val Pro Thr Thr Thr Thr Thr Ser Thr Pro Pro Thr
370                 375                 380
Thr Thr Thr Thr Thr Thr Ser Thr Pro Thr Thr Thr Thr Gln Thr Pro
385                 390                 395                 400
Thr Thr Thr Thr Pro Thr Thr Thr Thr Thr Thr Thr Thr Pro Ser
                405                 410                 415
Asn Asn Val Pro Phe Glu Ile Val Asn Val Leu Pro Thr Ser Ser Gln
                420                 425                 430
Tyr Glu Gly Thr Ser Val Glu Val Val Cys Asp Gly Thr Gln Cys Ala
            435                 440                 445
Ser Ser Val Trp Gly Ala Pro Asn Leu Trp Gly Val Val Lys Ile Gly
        450                 455                 460
Asn Ala Thr Met Asp Pro Asn Val Trp Gly Trp Glu Asp Val Tyr Lys
465                 470                 475                 480
Thr Ala Pro Gln Asp Ile Gly Thr Gly Ser Thr Lys Met Glu Ile Arg
                485                 490                 495
Asn Gly Val Leu Lys Val Thr Asn Leu Trp Asn Ile Asn Met His Pro
            500                 505                 510
Lys Tyr Asn Thr Met Ala Tyr Pro Glu Val Ile Tyr Gly Ala Lys Pro
            515                 520                 525
Trp Gly Asn Gln Pro Ile Asn Ala Pro Asn Phe Val Leu Pro Ile Lys
        530                 535                 540
Val Ser Gln Leu Pro Arg Ile Leu Val Asp Thr Lys Tyr Thr Leu Glu
545                 550                 555                 560
Lys Ser Phe Pro Gly Asn Asn Phe Ala Phe Glu Ala Trp Leu Phe Lys
                565                 570                 575
Asp Ala Asn Asn Met Arg Ala Pro Gly Gln Gly Asp Tyr Glu Ile Met
                580                 585                 590
Val Gln Leu Tyr Ile Glu Gly Gly Tyr Pro Ala Gly Tyr Asp Lys Gly
            595                 600                 605
Pro Val Leu Thr Val Asp Val Pro Ile Val Asp Gly Arg Leu Val
        610                 615                 620
Asn Gln Thr Phe Glu Leu Tyr Asp Val Ile Ala Asp Ala Gly Trp Arg
625                 630                 635                 640
Phe Phe Thr Phe Lys Pro Thr Lys Asn Tyr Asn Gly Ser Glu Val Val
                645                 650                 655
```

```
Phe Asp Tyr Thr Lys Phe Ile Glu Ile Val Asp Asn Tyr Leu Gly Gly
            660                 665                 670

Gly Ser Leu Thr Asn His Tyr Leu Met Ser Leu Glu Phe Gly Thr Glu
            675                 680                 685

Ile Tyr Thr Asn Gly Cys Thr Ser Phe Pro Cys Thr Val Asp Val Arg
            690                 695                 700

Trp Thr Leu Asp Lys Tyr Arg Phe Ile Leu Ala Pro Gly Thr Met Ala
705                 710                 715                 720

Thr Glu Glu Ala Met Arg Val Leu Val Gly Glu Val Gln Pro Pro Ala
                725                 730                 735

Ser Thr Thr Thr Ser Gln Thr Thr Ser Thr Thr Thr Pro Thr Pro
            740                 745                 750

Thr Thr Thr Thr Thr Thr Gln Thr Ser Thr Thr Thr Thr Thr Ser
            755                 760                 765

Pro Pro Thr Thr Thr Ala Pro Ala Gln Asp Val Ile Lys Leu Arg Tyr
            770                 775                 780

Pro Asp Gly Gln Trp Pro Glu Ala Pro Ile Asp Arg Asp Gly Asp
785                 790                 795                 800

Gly Asn Pro Glu Phe Tyr Ile Glu Ile Asn Pro Trp Asn Ile Leu Ser
                805                 810                 815

Ala Glu Ser Tyr Ala Glu Met Thr Tyr Asn Leu Ser Ser Gly Val Leu
            820                 825                 830

His Tyr Val Gln Ala Leu Asp Ser Ile
            835                 840

<210> SEQ ID NO 3
<211> LENGTH: 1959
<212> TYPE: DNA
<213> ORGANISM: Artificial Sequence
<220> FEATURE:
<223> OTHER INFORMATION: OC9a Glycosidase (clone #27GA1)
<220> FEATURE:
<221> NAME/KEY: CDS
<222> LOCATION: (1)...(1959)

<400> SEQUENCE: 3 atg cca acc aat gta ttt ttc aac gcc cat cac tcg ccg gtt ggg gcg     48
Met Pro Thr Asn Val Phe Phe Asn Ala His His Ser Pro Val Gly Ala
 1               5                  10                  15 ttt gcc agc ttt acg cta ggg ttt ccg gga aaa agc gga gga ctg gac     96
Phe Ala Ser Phe Thr Leu Gly Phe Pro Gly Lys Ser Gly Gly Leu Asp
                20                  25                  30 ttg gaa ctt gcc cga ccg cca cgg caa aat gtc ttt att ggc gtt gag    144
Leu Glu Leu Ala Arg Pro Pro Arg Gln Asn Val Phe Ile Gly Val Glu
            35                  40                  45 tcg ccg cat gag ccg ggg ctg tat cat atc ctt cca ttc gcg gaa aca    192
Ser Pro His Glu Pro Gly Leu Tyr His Ile Leu Pro Phe Ala Glu Thr
        50                  55                  60 gca ggc gag gat gaa agc aaa cga tat gac att gaa aat cct gat ccg    240
Ala Gly Glu Asp Glu Ser Lys Arg Tyr Asp Ile Glu Asn Pro Asp Pro
65                  70                  75                  80 aat ccg caa aaa cca aac atc ctg att cca ttt gcg aaa gag cgg atc    288
Asn Pro Gln Lys Pro Asn Ile Leu Ile Pro Phe Ala Lys Glu Arg Ile
                85                  90                  95 gaa cgc gaa ttt cgc gtt gcc acg gat aca tgg aag gcc ggg gac ttg    336
Glu Arg Glu Phe Arg Val Ala Thr Asp Thr Trp Lys Ala Gly Asp Leu
            100                 105                 110 acg ttg acg att tat tca ccg gtg aag gcc gta cca gat ccg gaa acg    384
```

```
                Thr Leu Thr Ile Tyr Ser Pro Val Lys Ala Val Pro Asp Pro Glu Thr
                        115                 120                 125 gcc tcc gag gaa gaa ctc aag ttg gcg ttg gtt cca gct gtc att gtc        432
Ala Ser Glu Glu Glu Leu Lys Leu Ala Leu Val Pro Ala Val Ile Val
130                 135                 140 gag atg acg atc gat aat acg aac gga aca aga aca cga cgg gcg ttt        480
Glu Met Thr Ile Asp Asn Thr Asn Gly Thr Arg Thr Arg Arg Ala Phe
145                 150                 155                 160 ttc gga ttc gaa ggc act gac ccg tat acc tcg atg cgg ggg atc gat        528
Phe Gly Phe Glu Gly Thr Asp Pro Tyr Thr Ser Met Arg Gly Ile Asp
                165                 170                 175 gat aca tgc ccg cag ctg cgc ggt gtc ggt caa ggg cgg att ttg ggc        576
Asp Thr Cys Pro Gln Leu Arg Gly Val Gly Gln Gly Arg Ile Leu Gly
            180                 185                 190 ata gca tcc aag gat gag ggc gtt cgt tca gca ctg cat ttt agc atg        624
Ile Ala Ser Lys Asp Glu Gly Val Arg Ser Ala Leu His Phe Ser Met
        195                 200                 205 gag gat atc tta acg gcg act ctc gaa gaa aac tgg acg ttt ggg ctc        672
Glu Asp Ile Leu Thr Ala Thr Leu Glu Glu Asn Trp Thr Phe Gly Leu
    210                 215                 220 ggg aaa gtc ggt gca tta att gcg gat gtg ccg gcg gga gaa aag aaa        720
Gly Lys Val Gly Ala Leu Ile Ala Asp Val Pro Ala Gly Glu Lys Lys
225                 230                 235                 240 acg tat caa ttt gct gtt tgc ttc tat cgt ggg ggt tgt gtg acg gcg        768
Thr Tyr Gln Phe Ala Val Cys Phe Tyr Arg Gly Gly Cys Val Thr Ala
                245                 250                 255 gga atg gat gcc tct tat ttt tac acc cgt ttc ttc cat aat atc gaa        816
Gly Met Asp Ala Ser Tyr Phe Tyr Thr Arg Phe Phe His Asn Ile Glu
            260                 265                 270 gaa gtc ggt ctt tat gcg tta gag cag gcc gag gtg tta aaa gag cag        864
Glu Val Gly Leu Tyr Ala Leu Glu Gln Ala Glu Val Leu Lys Glu Gln
        275                 280                 285 gcg ttc cgt tcg aat gaa ctc att gaa aaa gaa tgg ctc tcc gat gat        912
Ala Phe Arg Ser Asn Glu Leu Ile Glu Lys Glu Trp Leu Ser Asp Asp
    290                 295                 300 caa aag ttt atg atg gcg cac gcg atc cgt agc tac tat ggc aat aca        960
Gln Lys Phe Met Met Ala His Ala Ile Arg Ser Tyr Tyr Gly Asn Thr
305                 310                 315                 320 cag ctg ctt gag cat gaa gga aag ccg att tgg gtc gtc aat gaa ggc       1008
Gln Leu Leu Glu His Glu Gly Lys Pro Ile Trp Val Val Asn Glu Gly
                325                 330                 335 gag tac cgg atg atg aat acg ttt gat ctc acc gtc gac cag ctc ttt       1056
Glu Tyr Arg Met Met Asn Thr Phe Asp Leu Thr Val Asp Gln Leu Phe
            340                 345                 350 ttt gaa ttg aaa atg aat ccg tgg acg gtg aaa aat gtg ctt gac ttt       1104
Phe Glu Leu Lys Met Asn Pro Trp Thr Val Lys Asn Val Leu Asp Phe
        355                 360                 365 tat gtc gag cgc tac agc tat gag gat cgt gtc cgt ttc cca gga gat       1152
Tyr Val Glu Arg Tyr Ser Tyr Glu Asp Arg Val Arg Phe Pro Gly Asp
    370                 375                 380 gag acg gaa tac ccc ggc ggc atc agc ttc act cac gat atg gga gtc       1200
Glu Thr Glu Tyr Pro Gly Gly Ile Ser Phe Thr His Asp Met Gly Val
385                 390                 395                 400 gcc aac acg ttc tca cgc ccg cat tac tcg tca tat gag cta tac ggg       1248
Ala Asn Thr Phe Ser Arg Pro His Tyr Ser Ser Tyr Glu Leu Tyr Gly
                405                 410                 415 atc agc ggc tgc ttt tca cat atg acg cac gaa cag ctc gtc aac tgg       1296
Ile Ser Gly Cys Phe Ser His Met Thr His Glu Gln Leu Val Asn Trp
            420                 425                 430
```

```
gtg ctt tgc gca gcg gta tac atc gaa caa acg aaa gac tgg gca tgg      1344
Val Leu Cys Ala Ala Val Tyr Ile Glu Gln Thr Lys Asp Trp Ala Trp
            435                 440                 445 cgc gac cgg cgg ctt acg atc ttg gaa caa tgt ctc gaa agc atg gtg      1392
Arg Asp Arg Arg Leu Thr Ile Leu Glu Gln Cys Leu Glu Ser Met Val
        450                 455                 460 cgc cgc gat cat ccg gat cca gaa aag cgg aac ggc gtg atg ggg ctt      1440
Arg Arg Asp His Pro Asp Pro Glu Lys Arg Asn Gly Val Met Gly Leu
465                 470                 475                 480 gac agc acc cgc acg atg ggt gga gcg gaa atc aca acg tat gat agt      1488
Asp Ser Thr Arg Thr Met Gly Gly Ala Glu Ile Thr Thr Tyr Asp Ser
                485                 490                 495 ttg gat gtt tct ctt ggc cag gcg cgc aac aat tta tat ttg gca gga      1536
Leu Asp Val Ser Leu Gly Gln Ala Arg Asn Asn Leu Tyr Leu Ala Gly
            500                 505                 510 aaa tgt tgg gct gcc tat gtg gcg ctc gaa aag ttg ttc cgc gat gtc      1584
Lys Cys Trp Ala Ala Tyr Val Ala Leu Glu Lys Leu Phe Arg Asp Val
        515                 520                 525 ggc aaa gaa gaa ctg gct gca ttg gca agg gag cag gcg gaa aaa tgc      1632
Gly Lys Glu Glu Leu Ala Ala Leu Ala Arg Glu Gln Ala Glu Lys Cys
530                 535                 540 gcc gcg acg att gtc agt cac gtg acg gag gac ggg tat atc cca gcc      1680
Ala Ala Thr Ile Val Ser His Val Thr Glu Asp Gly Tyr Ile Pro Ala
545                 550                 555                 560 gtg atg gga gaa gga aat gac tcg aaa atc att ccg gct att gag ggg      1728
Val Met Gly Glu Gly Asn Asp Ser Lys Ile Ile Pro Ala Ile Glu Gly
                565                 570                 575 ctt gtg ttt cct tac ttt acg aac tgc cat gag gcg tta aga gaa gac      1776
Leu Val Phe Pro Tyr Phe Thr Asn Cys His Glu Ala Leu Arg Glu Asp
            580                 585                 590 gga cgt ttt gga gac tat att cgt gca ctg cga caa cat ttg caa tat      1824
Gly Arg Phe Gly Asp Tyr Ile Arg Ala Leu Arg Gln His Leu Gln Tyr
        595                 600                 605 gtg ttg cgg gaa gga att tac cta ttc ccg gac ggg gga tgg aaa att      1872
Val Leu Arg Glu Gly Ile Tyr Leu Phe Pro Asp Gly Gly Trp Lys Ile
610                 615                 620 tgc ctc gac aag caa caa ctc gtg gtt gag caa aat tta ctt atg cca      1920
Cys Leu Asp Lys Gln Gln Leu Val Val Glu Gln Asn Leu Leu Met Pro
625                 630                 635                 640 gtt tat tgc ccg ccg cat ttt agg gtg gga atg gga tga                  1959
Val Tyr Cys Pro Pro His Phe Arg Val Gly Met Gly  *
                645                 650
```

<210> SEQ ID NO 4
<211> LENGTH: 652
<212> TYPE: PRT
<213> ORGANISM: Artificial Sequence
<220> FEATURE:
<223> OTHER INFORMATION: OC9a Glycosidase (clone #27GA1)

<400> SEQUENCE: 4

```
Met Pro Thr Asn Val Phe Phe Asn Ala His His Ser Pro Val Gly Ala
 1               5                  10                  15

Phe Ala Ser Phe Thr Leu Gly Phe Pro Gly Lys Ser Gly Gly Leu Asp
            20                  25                  30

Leu Glu Leu Ala Arg Pro Pro Arg Gln Asn Val Phe Ile Gly Val Glu
        35                  40                  45

Ser Pro His Glu Pro Gly Leu Tyr His Ile Leu Pro Phe Ala Glu Thr
    50                  55                  60

Ala Gly Glu Asp Glu Ser Lys Arg Tyr Asp Ile Glu Asn Pro Asp Pro
```

```
                65                  70                  75                  80
Asn Pro Gln Lys Pro Asn Ile Leu Ile Pro Phe Ala Lys Glu Arg Ile
                    85                  90                  95

Glu Arg Glu Phe Arg Val Ala Thr Asp Thr Trp Lys Ala Gly Asp Leu
                    100                 105                 110

Thr Leu Thr Ile Tyr Ser Pro Val Lys Ala Val Pro Asp Pro Glu Thr
                    115                 120                 125

Ala Ser Glu Glu Leu Lys Leu Ala Leu Val Pro Ala Val Ile Val
    130                 135                 140

Glu Met Thr Ile Asp Asn Thr Asn Gly Thr Arg Thr Arg Ala Phe
145                 150                 155                 160

Phe Gly Phe Glu Gly Thr Asp Pro Tyr Thr Ser Met Arg Gly Ile Asp
                    165                 170                 175

Asp Thr Cys Pro Gln Leu Arg Gly Val Gly Gln Gly Arg Ile Leu Gly
                    180                 185                 190

Ile Ala Ser Lys Asp Glu Gly Val Arg Ser Ala Leu His Phe Ser Met
                    195                 200                 205

Glu Asp Ile Leu Thr Ala Thr Leu Glu Glu Asn Trp Thr Phe Gly Leu
                    210                 215                 220

Gly Lys Val Gly Ala Leu Ile Ala Asp Val Pro Ala Gly Glu Lys Lys
225                 230                 235                 240

Thr Tyr Gln Phe Ala Val Cys Phe Tyr Arg Gly Gly Cys Val Thr Ala
                    245                 250                 255

Gly Met Asp Ala Ser Tyr Phe Tyr Thr Arg Phe Phe His Asn Ile Glu
                    260                 265                 270

Glu Val Gly Leu Tyr Ala Leu Glu Gln Ala Glu Val Leu Lys Glu Gln
                    275                 280                 285

Ala Phe Arg Ser Asn Glu Leu Ile Glu Lys Glu Trp Leu Ser Asp Asp
                    290                 295                 300

Gln Lys Phe Met Met Ala His Ala Ile Arg Ser Tyr Tyr Gly Asn Thr
305                 310                 315                 320

Gln Leu Leu Glu His Glu Gly Lys Pro Ile Trp Val Val Asn Glu Gly
                    325                 330                 335

Glu Tyr Arg Met Met Asn Thr Phe Asp Leu Thr Val Asp Gln Leu Phe
                    340                 345                 350

Phe Glu Leu Lys Met Asn Pro Trp Thr Val Lys Asn Val Leu Asp Phe
                    355                 360                 365

Tyr Val Glu Arg Tyr Ser Tyr Glu Asp Arg Val Arg Phe Pro Gly Asp
                    370                 375                 380

Glu Thr Glu Tyr Pro Gly Gly Ile Ser Phe Thr His Asp Met Gly Val
385                 390                 395                 400

Ala Asn Thr Phe Ser Arg Pro His Tyr Ser Ser Tyr Glu Leu Tyr Gly
                    405                 410                 415

Ile Ser Gly Cys Phe Ser His Met Thr His Glu Gln Leu Val Asn Trp
                    420                 425                 430

Val Leu Cys Ala Ala Val Tyr Ile Glu Gln Thr Lys Asp Trp Ala Trp
                    435                 440                 445

Arg Asp Arg Arg Leu Thr Ile Leu Glu Gln Cys Leu Glu Ser Met Val
                    450                 455                 460

Arg Arg Asp His Pro Asp Pro Glu Lys Arg Asn Gly Val Met Gly Leu
465                 470                 475                 480

Asp Ser Thr Arg Thr Met Gly Gly Ala Glu Ile Thr Thr Tyr Asp Ser
                    485                 490                 495
```

```
Leu Asp Val Ser Leu Gly Gln Ala Arg Asn Asn Leu Tyr Leu Ala Gly
            500                 505                 510

Lys Cys Trp Ala Ala Tyr Val Ala Leu Glu Lys Leu Phe Arg Asp Val
            515                 520                 525

Gly Lys Glu Glu Leu Ala Ala Leu Ala Arg Glu Gln Ala Glu Lys Cys
            530                 535                 540

Ala Ala Thr Ile Val Ser His Val Thr Glu Asp Gly Tyr Ile Pro Ala
545                 550                 555                 560

Val Met Gly Glu Gly Asn Asp Ser Lys Ile Ile Pro Ala Ile Glu Gly
            565                 570                 575

Leu Val Phe Pro Tyr Phe Thr Asn Cys His Glu Ala Leu Arg Glu Asp
            580                 585                 590

Gly Arg Phe Gly Asp Tyr Ile Arg Ala Leu Arg Gln His Leu Gln Tyr
            595                 600                 605

Val Leu Arg Glu Gly Ile Tyr Leu Phe Pro Asp Gly Gly Trp Lys Ile
            610                 615                 620

Cys Leu Asp Lys Gln Gln Leu Val Val Glu Gln Asn Leu Leu Met Pro
625                 630                 635                 640

Val Tyr Cys Pro Pro His Phe Arg Val Gly Met Gly
            645                 650
```

```
<210> SEQ ID NO 5
<211> LENGTH: 2628
<212> TYPE: DNA
<213> ORGANISM: Bankia gouldi
<220> FEATURE:
<221> NAME/KEY: CDS
<222> LOCATION: (1)...(2628)
<223> OTHER INFORMATION: clone #37GP2

<400> SEQUENCE: 5
```

```
atg ttg aaa aaa ctg gct tta gca gcc ggg atc gca gca aca ctg         48
Met Leu Lys Lys Leu Ala Leu Ala Ala Gly Ile Ala Ala Ala Thr Leu
 1               5                  10                  15 gct gca tcc ggt tcc cat ggg cag acg ttc gcg tac ggc gaa gct ctg    96
Ala Ala Ser Gly Ser His Gly Gln Thr Phe Ala Tyr Gly Glu Ala Leu
                 20                  25                  30 caa aaa tcc atc tat ttt tat gag gct caa cag gcc ggc cca ctc ccg   144
Gln Lys Ser Ile Tyr Phe Tyr Glu Ala Gln Gln Ala Gly Pro Leu Pro
             35                  40                  45 gaa tgg aac cgc gtt gcc tgg cgt ggc gac tca gtt cct gat gac ggt   192
Glu Trp Asn Arg Val Ala Trp Arg Gly Asp Ser Val Pro Asp Asp Gly
 50                  55                  60 gcc gac gtc gga ctg gat tta cgc ggt ggc tgg ttc gat gcg ggc gac   240
Ala Asp Val Gly Leu Asp Leu Arg Gly Gly Trp Phe Asp Ala Gly Asp
 65                  70                  75                  80 cac gtt aag ttt ggc ttt cca atg gcc gcg tca gcg aca ctc gtc gcc   288
His Val Lys Phe Gly Phe Pro Met Ala Ala Ser Ala Thr Leu Val Ala
                 85                  90                  95 tgg gga ggc gtc gat tac aaa gac gcg tac gaa cag tcg ggg caa atg   336
Trp Gly Gly Val Asp Tyr Lys Asp Ala Tyr Glu Gln Ser Gly Gln Met
                100                 105                 110 gaa cat ctg cgc aac aac ctg cgc ttc gtc aat gac tac ttt atc agc   384
Glu His Leu Arg Asn Asn Leu Arg Phe Val Asn Asp Tyr Phe Ile Ser
            115                 120                 125 gcg cac ccc gct ccg aac gtg ctt tac ggg cag gtt ggc gat ggc agt   432
Ala His Pro Ala Pro Asn Val Leu Tyr Gly Gln Val Gly Asp Gly Ser
        130                 135                 140
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gca | gac | cat | acc | ttc | tgg | ggt | ccc | gct | gag | gtt | ctg | cac | cac | aag | atc | 480 |
| Ala | Asp | His | Thr | Phe | Trp | Gly | Pro | Ala | Glu | Val | Leu | His | His | Lys | Ile |     |
| 145 |     |     |     | 150 |     |     |     |     | 155 |     |     |     |     | 160 |     |     |
| ccc | ggc | tcg | cgc | att | tct | atg | aag | att | gac | gaa | agc | tgc | ccg | ggt | acc | 528 |
| Pro | Gly | Ser | Arg | Ile | Ser | Met | Lys | Ile | Asp | Glu | Ser | Cys | Pro | Gly | Thr |     |
|     |     |     |     | 165 |     |     |     |     | 170 |     |     |     |     | 175 |     |     |
| gat | ctg | gcc | gca | gag | acc | gca | gca | gcg | atg | gcc | gcg | tct | gcg | atg | gtt | 576 |
| Asp | Leu | Ala | Ala | Glu | Thr | Ala | Ala | Ala | Met | Ala | Ala | Ser | Ala | Met | Val |     |
|     |     |     | 180 |     |     |     |     | 185 |     |     |     |     | 190 |     |     |     |
| ttt | cag | ggt | gag | gac | gat | gct | tac | gca | gca | acc | ctg | atc | act | cac | gcc | 624 |
| Phe | Gln | Gly | Glu | Asp | Asp | Ala | Tyr | Ala | Ala | Thr | Leu | Ile | Thr | His | Ala |     |
|     |     | 195 |     |     |     |     | 200 |     |     |     |     | 205 |     |     |     |     |
| aaa | cag | ctg | tgg | caa | ttt | gct | gat | tca | acc | aaa | ggc | aca | acc | ggt | aca | 672 |
| Lys | Gln | Leu | Trp | Gln | Phe | Ala | Asp | Ser | Thr | Lys | Gly | Thr | Thr | Gly | Thr |     |
| 210 |     |     |     |     | 215 |     |     |     |     | 220 |     |     |     |     |     |     |
| gat | aca | gcc | tat | tcc | aat | tgc | ata | aca | ggt | gca | cag | ggc | ttt | tat | acg | 720 |
| Asp | Thr | Ala | Tyr | Ser | Asn | Cys | Ile | Thr | Gly | Ala | Gln | Gly | Phe | Tyr | Thr |     |
| 225 |     |     |     | 230 |     |     |     |     | 235 |     |     |     |     | 240 |     |     |
| tcg | acg | tat | ggc | gtt | tac | tac | gat | gaa | ctt | gcc | tgg | ggt | gct | ctc | tgg | 768 |
| Ser | Thr | Tyr | Gly | Val | Tyr | Tyr | Asp | Glu | Leu | Ala | Trp | Gly | Ala | Leu | Trp |     |
|     |     |     |     | 245 |     |     |     |     | 250 |     |     |     |     | 255 |     |     |
| tta | tgg | cgc | gca | act | gga | gaa | gac | ttc | tac | ctg | gaa | caa | gcc | aag | cat | 816 |
| Leu | Trp | Arg | Ala | Thr | Gly | Glu | Asp | Phe | Tyr | Leu | Glu | Gln | Ala | Lys | His |     |
|     |     |     | 260 |     |     |     |     | 265 |     |     |     |     | 270 |     |     |     |
| tac | tac | ggt | ttg | atg | ggc | ttt | gaa | aac | cag | acg | aca | act | ccg | gta | tat | 864 |
| Tyr | Tyr | Gly | Leu | Met | Gly | Phe | Glu | Asn | Gln | Thr | Thr | Thr | Pro | Val | Tyr |     |
|     |     | 275 |     |     |     |     | 280 |     |     |     |     | 285 |     |     |     |     |
| acc | tgg | tcg | ctt | ggc | tgg | aac | gat | aaa | gcg | tat | gcc | gtt | tat | gta | ctt | 912 |
| Thr | Trp | Ser | Leu | Gly | Trp | Asn | Asp | Lys | Ala | Tyr | Ala | Val | Tyr | Val | Leu |     |
| 290 |     |     |     |     | 295 |     |     |     |     | 300 |     |     |     |     |     |     |
| atg | gcc | gca | ctt | gta | ggt | gac | gag | gtt | tac | cac | gca | gat | gca | cag | cgc | 960 |
| Met | Ala | Ala | Leu | Val | Gly | Asp | Glu | Val | Tyr | His | Ala | Asp | Ala | Gln | Arg |     |
| 305 |     |     |     | 310 |     |     |     |     | 315 |     |     |     |     | 320 |     |     |
| tac | ctg | gat | cac | tgg | agc | gtc | ggc | gag | ggt | aac | cgc | aca | ccc | aat | ggg | 1008 |
| Tyr | Leu | Asp | His | Trp | Ser | Val | Gly | Glu | Gly | Asn | Arg | Thr | Pro | Asn | Gly |     |
|     |     |     | 325 |     |     |     |     | 330 |     |     |     |     | 335 |     |     |     |
| ctg | att | ctg | gtc | gac | tcc | tgg | ggg | gta | aac | cgc | tat | gcg | gcc | aac | gcg | 1056 |
| Leu | Ile | Leu | Val | Asp | Ser | Trp | Gly | Val | Asn | Arg | Tyr | Ala | Ala | Asn | Ala |     |
|     |     | 340 |     |     |     |     | 345 |     |     |     |     | 350 |     |     |     |     |
| ggt | tat | ctc | gca | ctc | ttt | tat | gca | gat | gcg | att | ggc | agt | gac | cac | ccc | 1104 |
| Gly | Tyr | Leu | Ala | Leu | Phe | Tyr | Ala | Asp | Ala | Ile | Gly | Ser | Asp | His | Pro |     |
| 355 |     |     |     |     | 360 |     |     |     |     | 365 |     |     |     |     |     |     |
| ctt | tat | gat | cgt | tac | cac | aat | ttt | ggt | aag | aag | cag | atc | gat | cat | atc | 1152 |
| Leu | Tyr | Asp | Arg | Tyr | His | Asn | Phe | Gly | Lys | Lys | Gln | Ile | Asp | His | Ile |     |
|     | 370 |     |     |     |     | 375 |     |     |     |     | 380 |     |     |     |     |     |
| ctg | ggc | gac | aac | cct | gac | aac | caa | agc | tac | gtc | gtc | ggc | ttt | ggc | gat | 1200 |
| Leu | Gly | Asp | Asn | Pro | Asp | Asn | Gln | Ser | Tyr | Val | Val | Gly | Phe | Gly | Asp |     |
| 385 |     |     |     |     | 390 |     |     |     |     | 395 |     |     |     |     | 400 |     |
| aat | ttc | cca | atc | aat | gtt | cac | cac | cgt | ggc | tcc | cac | ggt | tcc | tgg | tcc | 1248 |
| Asn | Phe | Pro | Ile | Asn | Val | His | His | Arg | Gly | Ser | His | Gly | Ser | Trp | Ser |     |
|     |     |     |     | 405 |     |     |     |     | 410 |     |     |     |     | 415 |     |     |
| gac | agc | att | tcc | aac | ccg | gtt | aat | caa | cgc | cat | gtg | cta | tac | ggc | gca | 1296 |
| Asp | Ser | Ile | Ser | Asn | Pro | Val | Asn | Gln | Arg | His | Val | Leu | Tyr | Gly | Ala |     |
|     |     |     | 420 |     |     |     |     | 425 |     |     |     |     | 430 |     |     |     |
| gtt | gcc | ggt | ggt | ccg | cag | ggc | gat | aca | ggc | tat | gaa | gaa | gac | cgc | aat | 1344 |
| Val | Ala | Gly | Gly | Pro | Gln | Gly | Asp | Thr | Gly | Tyr | Glu | Glu | Asp | Arg | Asn |     |
|     |     | 435 |     |     |     |     | 440 |     |     |     |     | 445 |     |     |     |     |
| gac | tat | gtc | cag | aat | gag | gtc | gca | aca | gac | tac | aac | tca | ggc | ttc | acc | 1392 |
| Asp | Tyr | Val | Gln | Asn | Glu | Val | Ala | Thr | Asp | Tyr | Asn | Ser | Gly | Phe | Thr |     |
| 450 |     |     |     |     | 455 |     |     |     |     | 460 |     |     |     |     |     |     |

-continued

| | | |
|---|---|---|
| agt gcc gtc gct gca ctt tat gat cac tat ggt ggc gcg ccc ctg gcg<br>Ser Ala Val Ala Ala Leu Tyr Asp His Tyr Gly Gly Ala Pro Leu Ala<br>465                        470                        475                        480 | 1440 |
| aac ttc ccg cct ccc gaa cca gag tcg gtg gag tat ctg gtg ggg gcc<br>Asn Phe Pro Pro Pro Glu Pro Glu Ser Val Glu Tyr Leu Val Gly Ala<br>                        485                        490                        495 | 1488 |
| aag atc aat tcc tct ggc aac cgc ttc gtg gaa atg aaa gcc gtt att<br>Lys Ile Asn Ser Ser Gly Asn Arg Phe Val Glu Met Lys Ala Val Ile<br>                500                        505                        510 | 1536 |
| caa aac cac agc aca aca ccc gcc caa ggt aaa gac gac ctt tac atg<br>Gln Asn His Ser Thr Thr Pro Ala Gln Gly Lys Asp Asp Leu Tyr Met<br>                  515                        520                        525 | 1584 |
| cgc tat ttc tat gat ctg agc gaa gta ttt gcc gca ggc tac agt ttg<br>Arg Tyr Phe Tyr Asp Leu Ser Glu Val Phe Ala Ala Gly Tyr Ser Leu<br>530                        535                        540 | 1632 |
| aat gat cta acg gtg gcg tcc gga tac aac caa gcc tcg gat gtg aat<br>Asn Asp Leu Thr Val Ala Ser Gly Tyr Asn Gln Ala Ser Asp Val Asn<br>545                        550                        555                        560 | 1680 |
| ggc ctg caa cat tgg gat ggc aac gtc tac tat gtg gaa gcc cag ttc<br>Gly Leu Gln His Trp Asp Gly Asn Val Tyr Tyr Val Glu Ala Gln Phe<br>                  565                        570                        575 | 1728 |
| tat gac gat gtg gta ttt ccc ggt ggt cag tcc gcg cac cga cgg gaa<br>Tyr Asp Asp Val Val Phe Pro Gly Gly Gln Ser Ala His Arg Arg Glu<br>                        580                        585                        590 | 1776 |
| gta caa ttt cgc gtg tcc ctg cca acc aca tcc aat ctt gcc gag tgg<br>Val Gln Phe Arg Val Ser Leu Pro Thr Thr Ser Asn Leu Ala Glu Trp<br>                595                        600                        605 | 1824 |
| gac aac acg aac gac ccc tcg ttt gat cca agt tat tta acg gtc gat<br>Asp Asn Thr Asn Asp Pro Ser Phe Asp Pro Ser Tyr Leu Thr Val Asp<br>610                        615                        620 | 1872 |
| agt agt ctg act tac ggt atc gac gcg ccg aaa att cca ctc tac gac<br>Ser Ser Leu Thr Tyr Gly Ile Asp Ala Pro Lys Ile Pro Leu Tyr Asp<br>625                        630                        635                        640 | 1920 |
| gcc aac ggc ctg ctc tgg ggc gag gag cca ccc cgt ggc gga act tcc<br>Ala Asn Gly Leu Leu Trp Gly Glu Glu Pro Pro Arg Gly Gly Thr Ser<br>                  645                        650                        655 | 1968 |
| tcc agc tca tcg tcg agc agt tcg tcc tct agc tca tcc agc agt tca<br>Ser Ser Ser Ser Ser Ser Ser Ser Ser Ser Ser Ser Ser Ser Ser Ser<br>                        660                        665                        670 | 2016 |
| tcg tcg agc agc tcc tcg agc agt tcg tcc tcg agt aat tcg tcc tct<br>Ser Ser Ser Ser Ser Ser Ser Ser Ser Ser Ser Ser Asn Ser Ser Ser<br>                675                        680                        685 | 2064 |
| agc tcg tcc agc tct tcg tcg aat tct tcg tcg tct aac agc agt tcc<br>Ser Ser Ser Ser Ser Ser Ser Asn Ser Ser Ser Ser Asn Ser Ser Ser<br>            690                        695                        700 | 2112 |
| tcg tcc agc tca agc tca tcg agc agt tcc agt tcg tcg agt tcg ggc<br>Ser Ser Ser Ser Ser Ser Ser Ser Ser Ser Ser Ser Ser Ser Ser Gly<br>705                        710                        715                        720 | 2160 |
| ggc acc tgt gcg gac gtg aac gta tac ccc aac tgg acc gca cgt gac<br>Gly Thr Cys Ala Asp Val Asn Val Tyr Pro Asn Trp Thr Ala Arg Asp<br>                        725                        730                        735 | 2208 |
| tgg gcc ggt gga gta ccg aac cac gcg gaa gcc ggt gat ttg atg gtt<br>Trp Ala Gly Gly Val Pro Asn His Ala Glu Ala Gly Asp Leu Met Val<br>                740                        745                        750 | 2256 |
| tac caa ggt act gtc tac caa gct aat tgg tac acc aac agt gtg cct<br>Tyr Gln Gly Thr Val Tyr Gln Ala Asn Trp Tyr Thr Asn Ser Val Pro<br>                755                        760                        765 | 2304 |
| ggc agt gat gca tcc tgg acc aac caa ggg tta tgt gcc ggc ggc gga<br>Gly Ser Asp Ala Ser Trp Thr Asn Gln Gly Leu Cys Ala Gly Gly Gly | 2352 |

-continued

```
          770                 775                 780
tcc agc tcc agc agc tca tca tcc agc tca agc agc tct tcg tcc agc     2400
Ser Ser Ser Ser Ser Ser Ser Ser Ser Ser Ser Ser Ser Ser Ser Ser
785                 790                 795                 800 agc agc tca agc tcg tcc agt ggt gcg tcc ggt tca tcc tcc agc tcg     2448
Ser Ser Ser Ser Ser Ser Gly Ala Ser Gly Ser Ser Ser Ser Ser Ser
            805                 810                 815 agc agt tcg tcc tcg tca agt tcg agc agc agc tct tcg agt tcg tct     2496
Ser Ser Ser Ser Ser Ser Ser Ser Ser Ser Ser Ser Ser Ser Ser Ser
        820                 825                 830 tct ggt ggc ggc gcc atg tgt aac tgg tat ggc tgg caa gta cct att     2544
Ser Gly Gly Gly Ala Met Cys Asn Trp Tyr Gly Trp Gln Val Pro Ile
    835                 840                 845 tgt gaa aac acc cca tct ggc tgg ggc aac gaa aat ggc caa aca tgt     2592
Cys Glu Asn Thr Pro Ser Gly Trp Gly Asn Glu Asn Gly Gln Thr Cys
850                 855                 860 gtc ggc ccc gat act tgc caa gag gtc gtc aac taa                     2628
Val Gly Pro Asp Thr Cys Gln Glu Val Val Asn *
865                 870                 875

<210> SEQ ID NO 6
<211> LENGTH: 875
<212> TYPE: PRT
<213> ORGANISM: Bankia gouldi

<400> SEQUENCE: 6

Met Leu Lys Lys Leu Ala Leu Ala Ala Gly Ile Ala Ala Ala Thr Leu
 1               5                   10                  15

Ala Ala Ser Gly Ser His Gly Gln Thr Phe Ala Tyr Gly Glu Ala Leu
            20                  25                  30

Gln Lys Ser Ile Tyr Phe Tyr Glu Ala Gln Gln Ala Gly Pro Leu Pro
        35                  40                  45

Glu Trp Asn Arg Val Ala Trp Arg Gly Asp Ser Val Pro Asp Asp Gly
    50                  55                  60

Ala Asp Val Gly Leu Asp Leu Arg Gly Gly Trp Phe Asp Ala Gly Asp
65                  70                  75                  80

His Val Lys Phe Gly Phe Pro Met Ala Ala Ser Ala Thr Leu Val Ala
                85                  90                  95

Trp Gly Gly Val Asp Tyr Lys Asp Ala Tyr Glu Gln Ser Gly Gln Met
            100                 105                 110

Glu His Leu Arg Asn Asn Leu Arg Phe Val Asn Asp Tyr Phe Ile Ser
        115                 120                 125

Ala His Pro Ala Pro Asn Val Leu Tyr Gly Gln Val Gly Asp Gly Ser
    130                 135                 140

Ala Asp His Thr Phe Trp Gly Pro Ala Glu Val Leu His His Lys Ile
145                 150                 155                 160

Pro Gly Ser Arg Ile Ser Met Lys Ile Asp Glu Ser Cys Pro Gly Thr
                165                 170                 175

Asp Leu Ala Ala Glu Thr Ala Ala Met Ala Ser Ala Met Val
            180                 185                 190

Phe Gln Gly Glu Asp Ala Tyr Ala Ala Thr Leu Ile Thr His Ala
        195                 200                 205

Lys Gln Leu Trp Gln Phe Ala Asp Ser Thr Lys Gly Thr Thr Gly Thr
    210                 215                 220

Asp Thr Ala Tyr Ser Asn Cys Ile Thr Gly Ala Gln Gly Phe Tyr Thr
225                 230                 235                 240
```

-continued

```
Ser Thr Tyr Gly Val Tyr Tyr Asp Glu Leu Ala Trp Gly Ala Leu Trp
            245                 250                 255

Leu Trp Arg Ala Thr Gly Glu Asp Phe Tyr Leu Glu Gln Ala Lys His
        260                 265                 270

Tyr Tyr Gly Leu Met Gly Phe Glu Asn Gln Thr Thr Thr Pro Val Tyr
                275                 280                 285

Thr Trp Ser Leu Gly Trp Asn Asp Lys Ala Tyr Ala Val Tyr Val Leu
290                 295                 300

Met Ala Ala Leu Val Gly Asp Glu Val Tyr His Ala Asp Ala Gln Arg
305                 310                 315                 320

Tyr Leu Asp His Trp Ser Val Gly Glu Gly Asn Arg Thr Pro Asn Gly
                325                 330                 335

Leu Ile Leu Val Asp Ser Trp Gly Val Asn Arg Tyr Ala Ala Asn Ala
                340                 345                 350

Gly Tyr Leu Ala Leu Phe Tyr Ala Asp Ala Ile Gly Ser Asp His Pro
            355                 360                 365

Leu Tyr Asp Arg Tyr His Asn Phe Gly Lys Lys Gln Ile Asp His Ile
370                 375                 380

Leu Gly Asp Asn Pro Asp Asn Gln Ser Tyr Val Val Gly Phe Gly Asp
385                 390                 395                 400

Asn Phe Pro Ile Asn Val His His Arg Gly Ser His Gly Ser Trp Ser
                405                 410                 415

Asp Ser Ile Ser Asn Pro Val Asn Gln Arg His Val Leu Tyr Gly Ala
            420                 425                 430

Val Ala Gly Gly Pro Gln Gly Asp Thr Gly Tyr Glu Glu Asp Arg Asn
            435                 440                 445

Asp Tyr Val Gln Asn Glu Val Ala Thr Asp Tyr Asn Ser Gly Phe Thr
450                 455                 460

Ser Ala Val Ala Ala Leu Tyr Asp His Tyr Gly Gly Ala Pro Leu Ala
465                 470                 475                 480

Asn Phe Pro Pro Pro Glu Pro Glu Ser Val Glu Tyr Leu Val Gly Ala
                485                 490                 495

Lys Ile Asn Ser Ser Gly Asn Arg Phe Val Glu Met Lys Ala Val Ile
            500                 505                 510

Gln Asn His Ser Thr Thr Pro Ala Gln Gly Lys Asp Asp Leu Tyr Met
            515                 520                 525

Arg Tyr Phe Tyr Asp Leu Ser Glu Val Phe Ala Ala Gly Tyr Ser Leu
530                 535                 540

Asn Asp Leu Thr Val Ala Ser Gly Tyr Asn Gln Ala Ser Asp Val Asn
545                 550                 555                 560

Gly Leu Gln His Trp Asp Gly Asn Val Tyr Tyr Val Glu Ala Gln Phe
                565                 570                 575

Tyr Asp Asp Val Val Phe Pro Gly Gly Gln Ser Ala His Arg Arg Glu
            580                 585                 590

Val Gln Phe Arg Val Ser Leu Pro Thr Thr Ser Asn Leu Ala Glu Trp
            595                 600                 605

Asp Asn Thr Asn Asp Pro Ser Phe Asp Pro Ser Tyr Leu Thr Val Asp
            610                 615                 620

Ser Ser Leu Thr Tyr Gly Ile Asp Ala Pro Lys Ile Pro Leu Tyr Asp
625                 630                 635                 640

Ala Asn Gly Leu Leu Trp Gly Glu Glu Pro Arg Gly Gly Thr Ser
                645                 650                 655

Ser Ser Ser Ser Ser Ser Ser Ser Ser Ser Ser Ser Ser Ser Ser
```

-continued

```
                        660                 665                 670
Ser Ser Ser Ser Ser Ser Ser Ser Ser Ser Asn Ser Ser
            675                 680                 685

Ser Ser Ser Ser Ser Ser Asn Ser Ser Ser Asn Ser Ser
            690                 695                 700

Ser Ser Ser Ser Ser Ser Ser Ser Ser Ser Ser Ser Gly
705                 710                 715                 720

Gly Thr Cys Ala Asp Val Asn Val Tyr Pro Asn Trp Thr Ala Arg Asp
                725                 730                 735

Trp Ala Gly Gly Val Pro Asn His Ala Glu Ala Gly Asp Leu Met Val
            740                 745                 750

Tyr Gln Gly Thr Val Tyr Gln Ala Asn Trp Tyr Thr Asn Ser Val Pro
        755                 760                 765

Gly Ser Asp Ala Ser Trp Thr Asn Gln Gly Leu Cys Ala Gly Gly Gly
    770                 775                 780

Ser Ser Ser Ser Ser Ser Ser Ser Ser Ser Ser Ser Ser Ser Ser Ser
785                 790                 795                 800

Ser Ser Ser Ser Ser Ser Ser Gly Ala Ser Gly Ser Ser Ser Ser Ser
                805                 810                 815

Ser Ser Ser Ser Ser Ser Ser Ser Ser Ser Ser Ser Ser Ser Ser Ser
            820                 825                 830

Ser Gly Gly Gly Ala Met Cys Asn Trp Tyr Gly Trp Gln Val Pro Ile
        835                 840                 845

Cys Glu Asn Thr Pro Ser Gly Trp Gly Asn Asn Gly Gln Thr Cys
    850                 855                 860

Val Gly Pro Asp Thr Cys Gln Glu Val Val Asn
865                 870                 875
```

<210> SEQ ID NO 7
<211> LENGTH: 849
<212> TYPE: DNA
<213> ORGANISM: Bankia gouldi
<220> FEATURE:
<221> NAME/KEY: CDS
<222> LOCATION: (1)...(849)
<223> OTHER INFORMATION: clone # 37GP3

<400> SEQUENCE: 7

```
atg aag atg acc tac atg cat ccg gct gaa gat act tac tcg ttt ggt      48
Met Lys Met Thr Tyr Met His Pro Ala Glu Asp Thr Tyr Ser Phe Gly
1               5                  10                  15 caa gcg gat cag ttg gtc aac tgg gcg aaa gcg aat ggt att ggc gtg      96
Gln Ala Asp Gln Leu Val Asn Trp Ala Lys Ala Asn Gly Ile Gly Val
            20                  25                  30 cac ggc cac act ctg gtt tgg cac tcc gaa tac cag gta ccc aat tgg     144
His Gly His Thr Leu Val Trp His Ser Glu Tyr Gln Val Pro Asn Trp
        35                  40                  45 atg aaa aat tac tct ggt gat gca act gca ttc caa acc atg ctc aac     192
Met Lys Asn Tyr Ser Gly Asp Ala Thr Ala Phe Gln Thr Met Leu Asn
    50                  55                  60 acc cat gtg aaa act gtg gct gag cat ttt gct ggc gaa ctg gac agc     240
Thr His Val Lys Thr Val Ala Glu His Phe Ala Gly Glu Leu Asp Ser
65                  70                  75                  80 tgg gac gtt gtg aat gaa gtg ctg gag ccg ggc tcc aat ggt tgc tgg     288
Trp Asp Val Val Asn Glu Val Leu Glu Pro Gly Ser Asn Gly Cys Trp
                85                  90                  95 cgt gaa aac tct ctg ttc tac cag aag ctt ggc aaa gac ttt gtc gcg     336
Arg Glu Asn Ser Leu Phe Tyr Gln Lys Leu Gly Lys Asp Phe Val Ala
```

-continued

```
                 100                 105                 110
aac gca ttc cgt gca gct cgc gag ggc gat ccc aat gca gac ttg tat    384
Asn Ala Phe Arg Ala Ala Arg Glu Gly Asp Pro Asn Ala Asp Leu Tyr
            115                 120                 125 tac aac gat tac tcg act gaa aat ggt gta act tcc gat gag aag ttc    432
Tyr Asn Asp Tyr Ser Thr Glu Asn Gly Val Thr Ser Asp Glu Lys Phe
130                 135                 140 agt tgt ttg ttg gaa cta gtc gat gag ctt ctg gaa gcg gac gtg ccg    480
Ser Cys Leu Leu Glu Leu Val Asp Glu Leu Leu Glu Ala Asp Val Pro
145                 150                 155                 160 att aca ggt gtt ggt ttc caa atg cac gtg cag gcg acg tgg cct agc    528
Ile Thr Gly Val Gly Phe Gln Met His Val Gln Ala Thr Trp Pro Ser
                165                 170                 175 aat gcc aac atc ggc aag gca ttc aaa gcc atc gcg gat cgc ggt ctg    576
Asn Ala Asn Ile Gly Lys Ala Phe Lys Ala Ile Ala Asp Arg Gly Leu
            180                 185                 190 aaa gtt aaa att tct gag ctc gat gtt cct gtt aac aac cct tac gga    624
Lys Val Lys Ile Ser Glu Leu Asp Val Pro Val Asn Asn Pro Tyr Gly
        195                 200                 205 acc act aat ttc ccg caa tac agc agt ttt acc gcg gaa gcc gcc gag    672
Thr Thr Asn Phe Pro Gln Tyr Ser Ser Phe Thr Ala Glu Ala Ala Glu
    210                 215                 220 ctg cag aag cag cgc tac aag ggc att atg caa gcg tac ctt gat aac    720
Leu Gln Lys Gln Arg Tyr Lys Gly Ile Met Gln Ala Tyr Leu Asp Asn
225                 230                 235                 240 gta ccg gcc aac ctg cgt ggt ggt ttc acc gtg tgg ggc gtt tgg gat    768
Val Pro Ala Asn Leu Arg Gly Gly Phe Thr Val Trp Gly Val Trp Asp
                245                 250                 255 ggc gat agc tgg atc atg acg ttc agc cag tac acc aac gct aac gcc    816
Gly Asp Ser Trp Ile Met Thr Phe Ser Gln Tyr Thr Asn Ala Asn Ala
            260                 265                 270 aac gac tgg cca ctg ttg ttc acc ggg ccg taa                        849
Asn Asp Trp Pro Leu Leu Phe Thr Gly Pro *
        275                 280

<210> SEQ ID NO 8
<211> LENGTH: 282
<212> TYPE: PRT
<213> ORGANISM: Bankia gouldi

<400> SEQUENCE: 8

Met Lys Met Thr Tyr Met His Pro Ala Glu Asp Thr Tyr Ser Phe Gly
1               5                   10                  15

Gln Ala Asp Gln Leu Val Asn Trp Ala Lys Ala Asn Gly Ile Gly Val
            20                  25                  30

His Gly His Thr Leu Val Trp His Ser Glu Tyr Gln Val Pro Asn Trp
        35                  40                  45

Met Lys Asn Tyr Ser Gly Asp Ala Thr Ala Phe Gln Thr Met Leu Asn
    50                  55                  60

Thr His Val Lys Thr Val Ala Glu His Phe Ala Gly Glu Leu Asp Ser
65                  70                  75                  80

Trp Asp Val Val Asn Glu Val Leu Glu Pro Gly Ser Asn Gly Cys Trp
                85                  90                  95

Arg Glu Asn Ser Leu Phe Tyr Gln Lys Leu Gly Lys Asp Phe Val Ala
            100                 105                 110

Asn Ala Phe Arg Ala Ala Arg Glu Gly Asp Pro Asn Ala Asp Leu Tyr
        115                 120                 125

Tyr Asn Asp Tyr Ser Thr Glu Asn Gly Val Thr Ser Asp Glu Lys Phe
```

-continued

```
                130                 135                 140
Ser Cys Leu Leu Glu Leu Val Asp Glu Leu Leu Glu Ala Asp Val Pro
145                 150                 155                 160

Ile Thr Gly Val Gly Phe Gln Met His Val Gln Ala Thr Trp Pro Ser
                165                 170                 175

Asn Ala Asn Ile Gly Lys Ala Phe Lys Ala Ile Ala Asp Arg Gly Leu
                180                 185                 190

Lys Val Lys Ile Ser Glu Leu Asp Val Pro Val Asn Pro Tyr Gly
                195                 200                 205

Thr Thr Asn Phe Pro Gln Tyr Ser Ser Phe Thr Ala Glu Ala Ala Glu
                210                 215                 220

Leu Gln Lys Gln Arg Tyr Lys Gly Ile Met Gln Ala Tyr Leu Asp Asn
225                 230                 235                 240

Val Pro Ala Asn Leu Arg Gly Gly Phe Thr Val Trp Gly Val Trp Asp
                245                 250                 255

Gly Asp Ser Trp Ile Met Thr Phe Ser Gln Tyr Thr Asn Ala Asn Ala
                260                 265                 270

Asn Asp Trp Pro Leu Leu Phe Thr Gly Pro
                275                 280
```

<210> SEQ ID NO 9
<211> LENGTH: 3033
<212> TYPE: DNA
<213> ORGANISM: Teredinibacter
<220> FEATURE:
<221> NAME/KEY: CDS
<222> LOCATION: (1)...(3033)
<223> OTHER INFORMATION: clone # 42GP1

<400> SEQUENCE: 9

```
atg gga aca tct ctt atg atc aaa tct aca ctg aca ggt atg att act      48
Met Gly Thr Ser Leu Met Ile Lys Ser Thr Leu Thr Gly Met Ile Thr
1               5                   10                  15 gct gtt gcc gcc gca gtt ttc acc acc tct gca gct ttc gcg gat gta     96
Ala Val Ala Ala Ala Val Phe Thr Thr Ser Ala Ala Phe Ala Asp Val
                20                  25                  30 cct ccg ttg aca gtg agc gga aat cag gtt tta agt ggc ggt gaa gca    144
Pro Pro Leu Thr Val Ser Gly Asn Gln Val Leu Ser Gly Gly Glu Ala
            35                  40                  45 aaa agc ttc gct ggt aac agc ttc ttt tgg agc aat acc gga tgg ggc    192
Lys Ser Phe Ala Gly Asn Ser Phe Phe Trp Ser Asn Thr Gly Trp Gly
        50                  55                  60 cag gaa cgt ttt tac aac gca gaa act gtg cgt tgg ttg aaa gac gac    240
Gln Glu Arg Phe Tyr Asn Ala Glu Thr Val Arg Trp Leu Lys Asp Asp
65                  70                  75                  80 tgg aac gca acc att gtc cgc gcc gct atg ggc gta gac ttt gat ggc    288
Trp Asn Ala Thr Ile Val Arg Ala Ala Met Gly Val Asp Phe Asp Gly
                85                  90                  95 agc tat atc ccc gag cat gaa gac gcc gac ccc gag ggt aac gtc gct    336
Ser Tyr Ile Pro Glu His Glu Asp Ala Asp Pro Glu Gly Asn Val Ala
                100                 105                 110 cgc gta cgt gca ttg gtg gat gca gcc atc gca gaa gac atg tac gtg    384
Arg Val Arg Ala Leu Val Asp Ala Ala Ile Ala Glu Asp Met Tyr Val
            115                 120                 125 att atc gat ttt cac act cac cac gca gaa gat tac caa gcc gaa tct    432
Ile Ile Asp Phe His Thr His His Ala Glu Asp Tyr Gln Ala Glu Ser
        130                 135                 140 atc gag ttc ttc gaa gaa atg gcc aca ctg tac ggt ggg tac gac aat    480
Ile Glu Phe Phe Glu Glu Met Ala Thr Leu Tyr Gly Gly Tyr Asp Asn
```

```
                145                 150                 155                 160
gtt att tat gaa atc tat aac gag ccc ctg caa atc agc tgg gac aat         528
Val Ile Tyr Glu Ile Tyr Asn Glu Pro Leu Gln Ile Ser Trp Asp Asn
                    165                 170                 175 gtt att aaa cct tat gca gaa tcg gtg att ggc gct atc cgc gca atc         576
Val Ile Lys Pro Tyr Ala Glu Ser Val Ile Gly Ala Ile Arg Ala Ile
                    180                 185                 190 gac ccg gac aac ctg att atc gtc ggc acg ccc act tgg tca cag gac         624
Asp Pro Asp Asn Leu Ile Ile Val Gly Thr Pro Thr Trp Ser Gln Asp
                    195                 200                 205 gtg gac gcc gct gcg cgc aat cca atc acc agc tac agc aat att gcg         672
Val Asp Ala Ala Ala Arg Asn Pro Ile Thr Ser Tyr Ser Asn Ile Ala
            210                 215                 220 tac acc ctg cac ttt tac gca ggc act cac ggt tca tgg ttg cgc gat         720
Tyr Thr Leu His Phe Tyr Ala Gly Thr His Gly Ser Trp Leu Arg Asp
    225                 230                 235                 240 aaa gcg cgt aac gct atg aac agt ggt att gcg ctg ttt gtg act gag         768
Lys Ala Arg Asn Ala Met Asn Ser Gly Ile Ala Leu Phe Val Thr Glu
                    245                 250                 255 tgg ggc acc gtt aat gca gat ggc gat ggt gcg cct gca gtt aac gaa         816
Trp Gly Thr Val Asn Ala Asp Gly Asp Gly Ala Pro Ala Val Asn Glu
            260                 265                 270 act cag caa tgg atg gac ttc ctc aag cag aac aat atc tct cac ttg         864
Thr Gln Gln Trp Met Asp Phe Leu Lys Gln Asn Asn Ile Ser His Leu
        275                 280                 285 aac tgg tcc gtg agt gat aaa ttg gaa ggt gcg tct atc gta caa cct         912
Asn Trp Ser Val Ser Asp Lys Leu Glu Gly Ala Ser Ile Val Gln Pro
    290                 295                 300 ggc acg ccc att agc ggc tgg aac gct tct gac ctt acg gcc tcc ggc         960
Gly Thr Pro Ile Ser Gly Trp Asn Ala Ser Asp Leu Thr Ala Ser Gly
305                 310                 315                 320 aca ctg gtt aag aac atc gtt tcc aac tgg ggc acc aca atc ggt aac        1008
Thr Leu Val Lys Asn Ile Val Ser Asn Trp Gly Thr Thr Ile Gly Asn
                    325                 330                 335 ggc agc tcc tca agt tca tcc agc tcc tct tcc agc tct tca agc agt        1056
Gly Ser Ser Ser Ser Ser Ser Ser Ser Ser Ser Ser Ser Ser Ser Ser
                    340                 345                 350 tct tct tcg agc agt tcc tcc tcc agc agc tct tcc tcg tca agc agc        1104
Ser Ser Ser Ser Ser Ser Ser Ser Ser Ser Ser Ser Ser Ser Ser Ser
            355                 360                 365 tcc gga tca act ggt ggc ggc aac tgt gct gga gtg aat gtg tac ccg        1152
Ser Gly Ser Thr Gly Gly Gly Asn Cys Ala Gly Val Asn Val Tyr Pro
    370                 375                 380 aac tgg acc gcg cgt gac tgg tct ggc ggc gcc tac aac cat gcg aac        1200
Asn Trp Thr Ala Arg Asp Trp Ser Gly Gly Ala Tyr Asn His Ala Asn
385                 390                 395                 400 gct ggc gac caa atg gtc tat caa aac agc ctg tat cgt gcc aac tgg        1248
Ala Gly Asp Gln Met Val Tyr Gln Asn Ser Leu Tyr Arg Ala Asn Trp
                    405                 410                 415 tac acc aac agc gtg cct ggc agc gac gcc tcc tgg act agc ctt ggc        1296
Tyr Thr Asn Ser Val Pro Gly Ser Asp Ala Ser Trp Thr Ser Leu Gly
                    420                 425                 430 gcc tgc gga ggc aac gga agt acg acc tca tcc agc tca agc agc tcc        1344
Ala Cys Gly Gly Asn Gly Ser Thr Thr Ser Ser Ser Ser Ser Ser Ser
            435                 440                 445 tcg tca agc agc agc tct tct tcc agc agc tcc tcg tct act ggc ggt        1392
Ser Ser Ser Ser Ser Ser Ser Ser Ser Ser Ser Ser Ser Thr Gly Gly
    450                 455                 460 ggc tcc agc tcc tcc agc agt tca tct tct tca tcg tcg tct tcc agc        1440
```

```
Gly Ser Ser Ser Ser Ser Ser Ser Ser Ser Ser Ser Ser Ser
465                 470                 475                 480 agc tct agc agc act ggt ggc ggt caa tgt acc gaa gtg tgc aac tgg      1488
Ser Ser Ser Ser Thr Gly Gly Gly Gln Cys Thr Glu Val Cys Asn Trp
                    485                 490                 495 tac ggt cag gga acc tac cca ctg tgt aac aac acc agt ggt tgg ggt      1536
Tyr Gly Gln Gly Thr Tyr Pro Leu Cys Asn Asn Thr Ser Gly Trp Gly
                500                 505                 510 tgg gaa aac aat cag agc tgt atc ggc cgt caa acc tgt gag tca cag      1584
Trp Glu Asn Asn Gln Ser Cys Ile Gly Arg Gln Thr Cys Glu Ser Gln
            515                 520                 525 aac ggt ggc gct ggc ggc gtg gtg agc aac tgc acc ggt tcg agt aca      1632
Asn Gly Gly Ala Gly Gly Val Val Ser Asn Cys Thr Gly Ser Ser Thr
        530                 535                 540 tcc agc agc tcc tct tcc agc agt agt tct tcc tca agt agc agc tcc      1680
Ser Ser Ser Ser Ser Ser Ser Ser Ser Ser Ser Ser Ser Ser Ser Ser
545                 550                 555                 560 agt tca tcc agc agc tct tca tct ggc act ggt agc agt aca tct tcc      1728
Ser Ser Ser Ser Ser Ser Ser Gly Thr Gly Ser Ser Thr Ser Ser
                565                 570                 575 agc agc agc tct tcc agc agc tcc agc tca agt acc ggt tcc tcc ggt      1776
Ser Ser Ser Ser Ser Ser Ser Ser Ser Thr Gly Ser Ser Gly
                580                 585                 590 atg cct gga cca cgc gtg gac aac ccc ttc gcc gct gcg cag aag tgg      1824
Met Pro Gly Pro Arg Val Asp Asn Pro Phe Ala Ala Ala Gln Lys Trp
            595                 600                 605 tac ata aac cca atg tgg tca gcg agt gct gca aac gaa ccc ggc ggc      1872
Tyr Ile Asn Pro Met Trp Ser Ala Ser Ala Ala Asn Glu Pro Gly Gly
        610                 615                 620 tct gtc att gcc aac gaa ccc tcg ttt gta tgg atg gac cgt atc ggc      1920
Ser Val Ile Ala Asn Glu Pro Ser Phe Val Trp Met Asp Arg Ile Gly
625                 630                 635                 640 gca atc gaa ggg cct gct gac ggt atg ggc ctg cgc gac cac ttg aac      1968
Ala Ile Glu Gly Pro Ala Asp Gly Met Gly Leu Arg Asp His Leu Asn
                645                 650                 655 gaa gcc ctt gca caa ggc gcc gac ctg ttc atg ttt gtt gtg tac gac      2016
Glu Ala Leu Ala Gln Gly Ala Asp Leu Phe Met Phe Val Val Tyr Asp
            660                 665                 670 ctg cca aac cgt gac tgt gct gca ctc gcc tcc aac ggt gaa ctg cgc      2064
Leu Pro Asn Arg Asp Cys Ala Ala Leu Ala Ser Asn Gly Glu Leu Arg
        675                 680                 685 atc tcc gaa gat ggc ttc aac atc tac aag tcc gac tac atc gca cct      2112
Ile Ser Glu Asp Gly Phe Asn Ile Tyr Lys Ser Asp Tyr Ile Ala Pro
                690                 695                 700 atc gtt gaa atc atc agc gac cct gca tac gca ggt atc aaa atc gct      2160
Ile Val Glu Ile Ile Ser Asp Pro Ala Tyr Ala Gly Ile Lys Ile Ala
705                 710                 715                 720 gcg gtt atc gag gtg gac tca ctg cct aac ctg gtt acc aat ctg agc      2208
Ala Val Ile Glu Val Asp Ser Leu Pro Asn Leu Val Thr Asn Leu Ser
                725                 730                 735 gaa cct gac tgt cag gaa gca aat ggt cct ggc ggc tac cgc gac ggc      2256
Glu Pro Asp Cys Gln Glu Ala Asn Gly Pro Gly Gly Tyr Arg Asp Gly
            740                 745                 750 att cgt cac gct atc act gaa ctg ggc aaa atc ccc aac gta tac tcc      2304
Ile Arg His Ala Ile Thr Glu Leu Gly Lys Ile Pro Asn Val Tyr Ser
        755                 760                 765 tac gtg gat att gca cac tca ggc tgg ctg ggc tgg aac gac aac ttc      2352
Tyr Val Asp Ile Ala His Ser Gly Trp Leu Gly Trp Asn Asp Asn Phe
                770                 775                 780
```

```
gcg caa ggc gtt aac ctg att tat gaa gtg gtt gcc aac ctc ggt tcc       2400
Ala Gln Gly Val Asn Leu Ile Tyr Glu Val Val Ala Asn Leu Gly Ser
785                 790                 795                 800 ggc att aac cca atc gcc ggt ttc gtc agt aac tcc gct aac tac acg       2448
Gly Ile Asn Pro Ile Ala Gly Phe Val Ser Asn Ser Ala Asn Tyr Thr
                805                 810                 815 cct gtg gaa gaa ccc ttc ttg cca gac gcc aac ctg cag gtc ggt ggt       2496
Pro Val Glu Glu Pro Phe Leu Pro Asp Ala Asn Leu Gln Val Gly Gly
            820                 825                 830 cag ccc gtt cgc tct tcc gat ttc tat gag tgg aac agc tac ctg gca       2544
Gln Pro Val Arg Ser Ser Asp Phe Tyr Glu Trp Asn Ser Tyr Leu Ala
        835                 840                 845 gag aaa ccc ttc gtg acc gat tgg cgt tct gcc atg atc tcg aaa ggt       2592
Glu Lys Pro Phe Val Thr Asp Trp Arg Ser Ala Met Ile Ser Lys Gly
850                 855                 860 atg cca agc tcc atc ggt atg ctg atc gat acc gca cgt aac ggc tgg       2640
Met Pro Ser Ser Ile Gly Met Leu Ile Asp Thr Ala Arg Asn Gly Trp
865                 870                 875                 880 ggt ggc cct gag cgt cca act gcg cag tct acc tcc aac aac ctg aac       2688
Gly Gly Pro Glu Arg Pro Thr Ala Gln Ser Thr Ser Asn Asn Leu Asn
                885                 890                 895 acc ttc gtt aac gaa tca cgt atc gac cgt cgt gag cac cgc ggc aac       2736
Thr Phe Val Asn Glu Ser Arg Ile Asp Arg Arg Glu His Arg Gly Asn
            900                 905                 910 tgg tgt aac cag cct ggt ggt gtc ggc tac cgt cca acc gct gca cct       2784
Trp Cys Asn Gln Pro Gly Gly Val Gly Tyr Arg Pro Thr Ala Ala Pro
        915                 920                 925 tct cca ggt att gat gcc tac gtt tgg gtg aaa cca cag ggt gag tct       2832
Ser Pro Gly Ile Asp Ala Tyr Val Trp Val Lys Pro Gln Gly Glu Ser
930                 935                 940 gac ggt gtt tcc gat cct aac ttc gag atc gat cct aac gac ccg aac       2880
Asp Gly Val Ser Asp Pro Asn Phe Glu Ile Asp Pro Asn Asp Pro Asn
945                 950                 955                 960 aaa cag cac gac cca atg tgt gat ccg ttc gcc agc aac tcg tcc aac       2928
Lys Gln His Asp Pro Met Cys Asp Pro Phe Ala Ser Asn Ser Ser Asn
                965                 970                 975 agt gca tac ggc acc ggc gct atg cca aat gct ccg cac gct ggt cgc       2976
Ser Ala Tyr Gly Thr Gly Ala Met Pro Asn Ala Pro His Ala Gly Arg
            980                 985                 990 tgg ttc cct gaa gcc ttc cag tta ctg ctt gaa aac gct tac cca cca       3024
Trp Phe Pro Glu Ala Phe Gln Leu Leu Leu Glu Asn Ala Tyr Pro Pro
        995                 1000                1005 att aac taa                                                            3033
Ile Asn *
    1010

<210> SEQ ID NO 10
<211> LENGTH: 1010
<212> TYPE: PRT
<213> ORGANISM: Teredinibacter

<400> SEQUENCE: 10

Met Gly Thr Ser Leu Met Ile Lys Ser Thr Leu Thr Gly Met Ile Thr
1               5                   10                  15

Ala Val Ala Ala Ala Val Phe Thr Thr Ser Ala Ala Phe Ala Asp Val
                20                  25                  30

Pro Pro Leu Thr Val Ser Gly Asn Gln Val Leu Ser Gly Gly Glu Ala
            35                  40                  45

Lys Ser Phe Ala Gly Asn Ser Phe Phe Trp Ser Asn Thr Gly Trp Gly
        50                  55                  60
```

-continued

```
Gln Glu Arg Phe Tyr Asn Ala Glu Thr Val Arg Trp Leu Lys Asp Asp
 65                  70                  75                  80

Trp Asn Ala Thr Ile Val Arg Ala Ala Met Gly Val Asp Phe Asp Gly
                 85                  90                  95

Ser Tyr Ile Pro Glu His Glu Asp Ala Asp Pro Glu Gly Asn Val Ala
            100                 105                 110

Arg Val Arg Ala Leu Val Asp Ala Ile Ala Glu Asp Met Tyr Val
        115                 120                 125

Ile Ile Asp Phe His Thr His His Ala Glu Asp Tyr Gln Ala Glu Ser
130                 135                 140

Ile Glu Phe Phe Glu Glu Met Ala Thr Leu Tyr Gly Gly Tyr Asp Asn
145                 150                 155                 160

Val Ile Tyr Glu Ile Tyr Asn Glu Pro Leu Gln Ile Ser Trp Asp Asn
                165                 170                 175

Val Ile Lys Pro Tyr Ala Glu Ser Val Ile Gly Ala Ile Arg Ala Ile
            180                 185                 190

Asp Pro Asp Asn Leu Ile Ile Val Gly Thr Pro Thr Trp Ser Gln Asp
        195                 200                 205

Val Asp Ala Ala Arg Asn Pro Ile Thr Ser Tyr Ser Asn Ile Ala
    210                 215                 220

Tyr Thr Leu His Phe Tyr Ala Gly Thr His Gly Ser Trp Leu Arg Asp
225                 230                 235                 240

Lys Ala Arg Asn Ala Met Asn Ser Gly Ile Ala Leu Phe Val Thr Glu
                245                 250                 255

Trp Gly Thr Val Asn Ala Asp Gly Asp Gly Ala Pro Ala Val Asn Glu
            260                 265                 270

Thr Gln Gln Trp Met Asp Phe Leu Lys Gln Asn Asn Ile Ser His Leu
        275                 280                 285

Asn Trp Ser Val Ser Asp Lys Leu Glu Gly Ala Ser Ile Val Gln Pro
290                 295                 300

Gly Thr Pro Ile Ser Gly Trp Asn Ala Ser Asp Leu Thr Ala Ser Gly
305                 310                 315                 320

Thr Leu Val Lys Asn Ile Val Ser Asn Trp Gly Thr Thr Ile Gly Asn
                325                 330                 335

Gly Ser Ser Ser Ser Ser Ser Ser Ser Ser Ser Ser Ser Ser Ser
            340                 345                 350

Ser Ser Ser Ser Ser Ser Ser Ser Ser Ser Ser Ser Ser Ser Ser
        355                 360                 365

Ser Gly Ser Thr Gly Gly Gly Asn Cys Ala Gly Val Asn Val Tyr Pro
    370                 375                 380

Asn Trp Thr Ala Arg Asp Trp Ser Gly Gly Ala Tyr Asn His Ala Asn
385                 390                 395                 400

Ala Gly Asp Gln Met Val Tyr Gln Asn Ser Leu Tyr Arg Ala Asn Trp
                405                 410                 415

Tyr Thr Asn Ser Val Pro Gly Ser Asp Ala Ser Trp Thr Ser Leu Gly
            420                 425                 430

Ala Cys Gly Gly Asn Gly Ser Thr Thr Ser Ser Ser Ser Ser Ser
        435                 440                 445

Ser Ser Ser Ser Ser Ser Ser Ser Ser Ser Ser Ser Thr Gly Gly
    450                 455                 460

Gly Ser Ser Ser Ser Ser Ser Ser Ser Ser Ser Ser Ser Ser Ser
465                 470                 475                 480
```

-continued

```
Ser Ser Ser Ser Thr Gly Gly Gln Cys Thr Glu Val Cys Asn Trp
            485             490             495

Tyr Gly Gln Gly Thr Tyr Pro Leu Cys Asn Asn Thr Ser Gly Trp Gly
            500             505             510

Trp Glu Asn Asn Gln Ser Cys Ile Gly Arg Gln Thr Cys Glu Ser Gln
            515             520             525

Asn Gly Gly Ala Gly Gly Val Val Ser Asn Cys Thr Gly Ser Ser Thr
        530             535             540

Ser Ser Ser Ser Ser Ser Ser Ser Ser Ser Ser Ser Ser Ser Ser Ser
545             550             555             560

Ser Ser Ser Ser Ser Ser Ser Gly Thr Gly Ser Ser Thr Ser Ser
            565             570             575

Ser Ser Ser Ser Ser Ser Ser Ser Ser Thr Gly Ser Ser Gly
        580             585             590

Met Pro Gly Pro Arg Val Asp Asn Pro Phe Ala Ala Ala Gln Lys Trp
        595             600             605

Tyr Ile Asn Pro Met Trp Ser Ala Ser Ala Ala Asn Glu Pro Gly Gly
        610             615             620

Ser Val Ile Ala Asn Glu Pro Ser Phe Val Trp Met Asp Arg Ile Gly
625             630             635             640

Ala Ile Glu Gly Pro Ala Asp Gly Met Gly Leu Arg Asp His Leu Asn
            645             650             655

Glu Ala Leu Ala Gln Gly Ala Asp Leu Phe Met Phe Val Val Tyr Asp
            660             665             670

Leu Pro Asn Arg Asp Cys Ala Ala Leu Ala Ser Asn Gly Glu Leu Arg
            675             680             685

Ile Ser Glu Asp Gly Phe Asn Ile Tyr Lys Ser Asp Tyr Ile Ala Pro
        690             695             700

Ile Val Glu Ile Ile Ser Asp Pro Ala Tyr Ala Gly Ile Lys Ile Ala
705             710             715             720

Ala Val Ile Glu Val Asp Ser Leu Pro Asn Leu Val Thr Asn Leu Ser
            725             730             735

Glu Pro Asp Cys Gln Glu Ala Asn Gly Pro Gly Gly Tyr Arg Asp Gly
            740             745             750

Ile Arg His Ala Ile Thr Glu Leu Gly Lys Ile Pro Asn Val Tyr Ser
        755             760             765

Tyr Val Asp Ile Ala His Ser Gly Trp Leu Gly Trp Asn Asp Asn Phe
    770             775             780

Ala Gln Gly Val Asn Leu Ile Tyr Glu Val Val Ala Asn Leu Gly Ser
785             790             795             800

Gly Ile Asn Pro Ile Ala Gly Phe Val Ser Asn Ser Ala Asn Tyr Thr
            805             810             815

Pro Val Glu Glu Pro Phe Leu Pro Asp Ala Asn Leu Gln Val Gly Gly
            820             825             830

Gln Pro Val Arg Ser Ser Asp Phe Tyr Glu Trp Asn Ser Tyr Leu Ala
        835             840             845

Glu Lys Pro Phe Val Thr Asp Trp Arg Ser Ala Met Ile Ser Lys Gly
    850             855             860

Met Pro Ser Ser Ile Gly Met Leu Ile Asp Thr Ala Arg Asn Gly Trp
865             870             875             880

Gly Gly Pro Glu Arg Pro Thr Ala Gln Ser Thr Ser Asn Asn Leu Asn
            885             890             895

Thr Phe Val Asn Glu Ser Arg Ile Asp Arg Arg Glu His Arg Gly Asn
```

-continued

```
                900             905             910
Trp Cys Asn Gln Pro Gly Gly Val Gly Tyr Arg Pro Thr Ala Ala Pro
            915             920             925

Ser Pro Gly Ile Asp Ala Tyr Val Trp Val Lys Pro Gln Gly Glu Ser
        930             935             940

Asp Gly Val Ser Asp Pro Asn Phe Glu Ile Asp Pro Asn Asp Pro Asn
945             950             955             960

Lys Gln His Asp Pro Met Cys Asp Pro Phe Ala Ser Asn Ser Ser Asn
                965             970             975

Ser Ala Tyr Gly Thr Gly Ala Met Pro Asn Ala Pro His Ala Gly Arg
            980             985             990

Trp Phe Pro Glu Ala Phe Gln Leu Leu Leu Glu Asn Ala Tyr Pro Pro
        995             1000            1005

Ile Asn
    1010

<210> SEQ ID NO 11
<211> LENGTH: 1683
<212> TYPE: DNA
<213> ORGANISM: Microscilla furvescens
<220> FEATURE:
<221> NAME/KEY: CDS
<222> LOCATION: (1)...(1683)
<223> OTHER INFORMATION: clone # 53GC1

<400> SEQUENCE: 11 atg aac aag aag tgg tgg aaa gaa gcc gtg gtg tat caa gtc tac ccg      48
Met Asn Lys Lys Trp Trp Lys Glu Ala Val Val Tyr Gln Val Tyr Pro
  1               5                  10                  15 cgg agc ttc aaa gac agc aat gga gat ggt gta ggc gat ctg cct ggg      96
Arg Ser Phe Lys Asp Ser Asn Gly Asp Gly Val Gly Asp Leu Pro Gly
                 20                  25                  30 gtt att gaa aag ctt gat tac atc aaa agc ctt ggg gtg gat gtt atc     144
Val Ile Glu Lys Leu Asp Tyr Ile Lys Ser Leu Gly Val Asp Val Ile
             35                  40                  45 tgg cta tgc ccg gtg tac gat tcc ccc aat gat gac aat ggt tac gat     192
Trp Leu Cys Pro Val Tyr Asp Ser Pro Asn Asp Asp Asn Gly Tyr Asp
         50                  55                  60 att cgt gac tac tac gat atc atg gct gat ttc ggc acg atg gct gat     240
Ile Arg Asp Tyr Tyr Asp Ile Met Ala Asp Phe Gly Thr Met Ala Asp
 65                  70                  75                  80 ttt gat cag ctg ctc gag gga ata cat cag cgt ggg atg aaa ctg cta     288
Phe Asp Gln Leu Leu Glu Gly Ile His Gln Arg Gly Met Lys Leu Leu
                 85                  90                  95 atg gac ctg gtg gta aac cac tgc tct gat gag cac aaa tgg ttt cag     336
Met Asp Leu Val Val Asn His Cys Ser Asp Glu His Lys Trp Phe Gln
            100                 105                 110 gag tcc cgc aag agt aaa gac aac cct tac cgg gac tac ttc atc tgg     384
Glu Ser Arg Lys Ser Lys Asp Asn Pro Tyr Arg Asp Tyr Phe Ile Trp
        115                 120                 125 aag cct ggc aaa aac gga ggc cca cct aac aac tgg cag tcc ttt ttt     432
Lys Pro Gly Lys Asn Gly Gly Pro Pro Asn Asn Trp Gln Ser Phe Phe
    130                 135                 140 agt ggt aat gcc tgg gaa tac gat gag gcc act gac gag tat tac cta     480
Ser Gly Asn Ala Trp Glu Tyr Asp Glu Ala Thr Asp Glu Tyr Tyr Leu
145                 150                 155                 160 cat ctt ttc acc aaa aag caa cca gac ctc aat tgg gaa aac ccg aaa     528
His Leu Phe Thr Lys Lys Gln Pro Asp Leu Asn Trp Glu Asn Pro Lys
                165                 170                 175
```

|  |  |
|---|---|
| gta cgt gag gag gtg cac aag ctg atg aag tat tgg ctg gac aaa gga<br>Val Arg Glu Glu Val His Lys Leu Met Lys Tyr Trp Leu Asp Lys Gly<br>180 185 190 | 576 |
| gta gat ggg ttc cgg atg gat gtg att tcc gtg att tca aaa aga aac<br>Val Asp Gly Phe Arg Met Asp Val Ile Ser Val Ile Ser Lys Arg Asn<br>195 200 205 | 624 |
| ttc gaa gat tca cct tac aag gac ttc aac aag acc atc gat aac gtc<br>Phe Glu Asp Ser Pro Tyr Lys Asp Phe Asn Lys Thr Ile Asp Asn Val<br>210 215 220 | 672 |
| tac gcc aat ggc ccg cgt gtg cag gag ttt ctc cag gaa atg aac cgt<br>Tyr Ala Asn Gly Pro Arg Val Gln Glu Phe Leu Gln Glu Met Asn Arg<br>225 230 235 240 | 720 |
| gaa gta ctg agt aag tac gat gtg atg aca gta ggt gag ggt cca ggt<br>Glu Val Leu Ser Lys Tyr Asp Val Met Thr Val Gly Glu Gly Pro Gly<br>245 250 255 | 768 |
| atc aat ctg gaa agc ggc ctg caa tat gta tcc agc tca gcg gag gct<br>Ile Asn Leu Glu Ser Gly Leu Gln Tyr Val Ser Ser Ser Ala Glu Ala<br>260 265 270 | 816 |
| ctt aat atg att ttt cat ttt ggg cac atg ttt atg gat cat gga ccc<br>Leu Asn Met Ile Phe His Phe Gly His Met Phe Met Asp His Gly Pro<br>275 280 285 | 864 |
| gga ggt aga ttt gat ccc aag ccc atc gat ttt ctg gaa ttc aaa aaa<br>Gly Gly Arg Phe Asp Pro Lys Pro Ile Asp Phe Leu Glu Phe Lys Lys<br>290 295 300 | 912 |
| gtc ttc agg ctg tgg gat gag tac ctt aaa gaa gag ggc tgg ggt agc<br>Val Phe Arg Leu Trp Asp Glu Tyr Leu Lys Glu Glu Gly Trp Gly Ser<br>305 310 315 320 | 960 |
| gtc ttt cta ggg aat cat gat ttt cag cga atc gtt tct cgc ttt ggg<br>Val Phe Leu Gly Asn His Asp Phe Gln Arg Ile Val Ser Arg Phe Gly<br>325 330 335 | 1008 |
| gat gac gga gcg tac tgg aaa gag tcc gcc aaa ctg ctg agc ttg ttg<br>Asp Asp Gly Ala Tyr Trp Lys Glu Ser Ala Lys Leu Leu Ser Leu Leu<br>340 345 350 | 1056 |
| cta ttt agc atg cgc ggc acg gtc tac gtt tac cag ggt gat gaa ata<br>Leu Phe Ser Met Arg Gly Thr Val Tyr Val Tyr Gln Gly Asp Glu Ile<br>355 360 365 | 1104 |
| ggt atg acc aat gtg gct ttt gac acc ata gaa gaa tat gac gat gtg<br>Gly Met Thr Asn Val Ala Phe Asp Thr Ile Glu Glu Tyr Asp Asp Val<br>370 375 380 | 1152 |
| gag atc aaa aat gct tac aag gag tgg aaa gct gaa gga aaa gac ctg<br>Glu Ile Lys Asn Ala Tyr Lys Glu Trp Lys Ala Glu Gly Lys Asp Leu<br>385 390 395 400 | 1200 |
| gat cag ttt tta aag aac gtc cat atc aat ggc cgt gac aat gcc cgt<br>Asp Gln Phe Leu Lys Asn Val His Ile Asn Gly Arg Asp Asn Ala Arg<br>405 410 415 | 1248 |
| aca ccg ctg caa tgg aat gat gct gag cag gct ggt ttt acc tca ggc<br>Thr Pro Leu Gln Trp Asn Asp Ala Glu Gln Ala Gly Phe Thr Ser Gly<br>420 425 430 | 1296 |
| act cca tgg ctc aaa gtc aac cct aac tat acg gca atc aat gtg gct<br>Thr Pro Trp Leu Lys Val Asn Pro Asn Tyr Thr Ala Ile Asn Val Ala<br>435 440 445 | 1344 |
| agt cag gaa gga gat gag aac tct att ctg gca ttt tat cgc cgg atg<br>Ser Gln Glu Gly Asp Glu Asn Ser Ile Leu Ala Phe Tyr Arg Arg Met<br>450 455 460 | 1392 |
| gtg gcg atg cga aag gag cac ccg aca ctt gtt tat ggt gat ttt gcc<br>Val Ala Met Arg Lys Glu His Pro Thr Leu Val Tyr Gly Asp Phe Ala<br>465 470 475 480 | 1440 |
| ccc att cag gaa gat cat ccg agt gta ttt gct ttt tgg aga tgg gat<br>Pro Ile Gln Glu Asp His Pro Ser Val Phe Ala Phe Trp Arg Trp Asp<br>485 490 495 | 1488 |

```
gaa gag gct gca tat tta gtc tta ctc aat ttt tct gag gag act cag    1536
Glu Glu Ala Ala Tyr Leu Val Leu Leu Asn Phe Ser Glu Glu Thr Gln
            500                 505                 510 gaa ttt ggg ctg gac gat cga ttt gat agt agt aag ctt cgc ata gta    1584
Glu Phe Gly Leu Asp Asp Arg Phe Asp Ser Ser Lys Leu Arg Ile Val
        515                 520                 525 gag gcc aat gac ttt gac ttt ggt gag cca caa agt gga aaa gtg aaa    1632
Glu Ala Asn Asp Phe Asp Phe Gly Glu Pro Gln Ser Gly Lys Val Lys
    530                 535                 540 cta aaa ccg tgg cag gcg gtg ttg gcg cgt gtt cgg cat att gaa ttg    1680
Leu Lys Pro Trp Gln Ala Val Leu Ala Arg Val Arg His Ile Glu Leu
545                 550                 555                 560 taa                                                                 1683
*

<210> SEQ ID NO 12
<211> LENGTH: 560
<212> TYPE: PRT
<213> ORGANISM: Microscilla furvescens

<400> SEQUENCE: 12

Met Asn Lys Lys Trp Lys Glu Ala Val Val Tyr Gln Val Tyr Pro
 1               5                  10                  15

Arg Ser Phe Lys Asp Ser Asn Gly Asp Gly Val Gly Asp Leu Pro Gly
            20                  25                  30

Val Ile Glu Lys Leu Asp Tyr Ile Lys Ser Leu Gly Val Asp Val Ile
        35                  40                  45

Trp Leu Cys Pro Val Tyr Asp Ser Pro Asn Asp Asp Asn Gly Tyr Asp
    50                  55                  60

Ile Arg Asp Tyr Tyr Asp Ile Met Ala Asp Phe Gly Thr Met Ala Asp
65                  70                  75                  80

Phe Asp Gln Leu Leu Glu Gly Ile His Gln Arg Gly Met Lys Leu Leu
                85                  90                  95

Met Asp Leu Val Val Asn His Cys Ser Asp Glu His Lys Trp Phe Gln
            100                 105                 110

Glu Ser Arg Lys Ser Lys Asp Asn Pro Tyr Arg Asp Tyr Phe Ile Trp
        115                 120                 125

Lys Pro Gly Lys Asn Gly Gly Pro Pro Asn Asn Trp Gln Ser Phe Phe
    130                 135                 140

Ser Gly Asn Ala Trp Glu Tyr Asp Glu Ala Thr Asp Glu Tyr Tyr Leu
145                 150                 155                 160

His Leu Phe Thr Lys Lys Gln Pro Asp Leu Asn Trp Glu Asn Pro Lys
                165                 170                 175

Val Arg Glu Glu Val His Lys Leu Met Lys Tyr Trp Leu Asp Lys Gly
            180                 185                 190

Val Asp Gly Phe Arg Met Asp Val Ile Ser Val Ile Ser Lys Arg Asn
        195                 200                 205

Phe Glu Asp Ser Pro Tyr Lys Asp Phe Asn Lys Thr Ile Asp Asn Val
    210                 215                 220

Tyr Ala Asn Gly Pro Arg Val Gln Glu Phe Leu Gln Glu Met Asn Arg
225                 230                 235                 240

Glu Val Leu Ser Lys Tyr Asp Val Met Thr Val Gly Glu Gly Pro Gly
                245                 250                 255

Ile Asn Leu Glu Ser Gly Leu Gln Tyr Val Ser Ser Ser Ala Glu Ala
            260                 265                 270
```

```
Leu Asn Met Ile Phe His Phe Gly His Met Phe Met Asp His Gly Pro
            275                 280                 285
Gly Gly Arg Phe Asp Pro Lys Pro Ile Asp Phe Leu Glu Phe Lys Lys
        290                 295                 300
Val Phe Arg Leu Trp Asp Glu Tyr Leu Lys Glu Glu Gly Trp Gly Ser
305                 310                 315                 320
Val Phe Leu Gly Asn His Asp Phe Gln Arg Ile Val Ser Arg Phe Gly
                325                 330                 335
Asp Asp Gly Ala Tyr Trp Lys Glu Ser Ala Lys Leu Leu Ser Leu Leu
            340                 345                 350
Leu Phe Ser Met Arg Gly Thr Val Tyr Val Tyr Gln Gly Asp Glu Ile
        355                 360                 365
Gly Met Thr Asn Val Ala Phe Asp Thr Ile Glu Glu Tyr Asp Asp Val
    370                 375                 380
Glu Ile Lys Asn Ala Tyr Lys Glu Trp Lys Ala Glu Gly Lys Asp Leu
385                 390                 395                 400
Asp Gln Phe Leu Lys Asn Val His Ile Asn Gly Arg Asp Asn Ala Arg
                405                 410                 415
Thr Pro Leu Gln Trp Asn Asp Ala Glu Gln Ala Gly Phe Thr Ser Gly
            420                 425                 430
Thr Pro Trp Leu Lys Val Asn Pro Asn Tyr Thr Ala Ile Asn Val Ala
        435                 440                 445
Ser Gln Glu Gly Asp Glu Asn Ser Ile Leu Ala Phe Tyr Arg Arg Met
    450                 455                 460
Val Ala Met Arg Lys Glu His Pro Thr Leu Val Tyr Gly Asp Phe Ala
465                 470                 475                 480
Pro Ile Gln Glu Asp His Pro Ser Val Phe Ala Phe Trp Arg Trp Asp
                485                 490                 495
Glu Glu Ala Ala Tyr Leu Val Leu Leu Asn Phe Ser Glu Glu Thr Gln
            500                 505                 510
Glu Phe Gly Leu Asp Asp Arg Phe Asp Ser Ser Lys Leu Arg Ile Val
        515                 520                 525
Glu Ala Asn Asp Phe Asp Phe Gly Glu Pro Gln Ser Gly Lys Val Lys
    530                 535                 540
Leu Lys Pro Trp Gln Ala Val Leu Ala Arg Val Arg His Ile Glu Leu
545                 550                 555                 560

<210> SEQ ID NO 13
<211> LENGTH: 1857
<212> TYPE: DNA
<213> ORGANISM: Thermotoga neapolitana
<220> FEATURE:
<221> NAME/KEY: CDS
<222> LOCATION: (1)...(1857)
<223> OTHER INFORMATION: clone # 56GC2

<400> SEQUENCE: 13 tct tct gaa cga ttc tcc act gag cag aaa aga cca gat cat act ctt      48
Ser Ser Glu Arg Phe Ser Thr Glu Gln Lys Arg Pro Asp His Thr Leu
1               5                   10                  15 tgt gga cgg aaa aga aca ttc ggc aaa gaa ggt ggt tat acc acc ctt      96
Cys Gly Arg Lys Arg Thr Phe Gly Lys Glu Gly Gly Tyr Thr Thr Leu
            20                  25                  30 caa aga gga aac gct ggt ctt caa agt gaa cgg act gaa gag gga aga     144
Gln Arg Gly Asn Ala Gly Leu Gln Ser Glu Arg Thr Glu Glu Gly Arg
        35                  40                  45 gca cct cgt atc cac cag tct gaa cac ggg aaa aac cat cta tgt gag     192
```

```
            Ala Pro Arg Ile His Gln Ser Glu His Gly Lys Asn His Leu Cys Glu
                50                  55                  60 gtg atc tgt gtg gag atc ttc aaa aga ccg ttc aga gaa ggg agc ttc         240
Val Ile Cys Val Glu Ile Phe Lys Arg Pro Phe Arg Glu Gly Ser Phe
 65                  70                  75                  80 gtt ctg aaa gag aag gac tac acc gtt gag ttc gag gtg gag aag atc         288
Val Leu Lys Glu Lys Asp Tyr Thr Val Glu Phe Glu Val Glu Lys Ile
                 85                  90                  95 cat ctt gga tgg aag att tca ggg aga gtg aag gga aat ccc gga agg         336
His Leu Gly Trp Lys Ile Ser Gly Arg Val Lys Gly Asn Pro Gly Arg
            100                 105                 110 ctt gag atc ttt cgg aca aac gca ccg aag aaa ctc ctc gtg aac aac         384
Leu Glu Ile Phe Arg Thr Asn Ala Pro Lys Lys Leu Leu Val Asn Asn
        115                 120                 125 tgg cag tcc tgg gga ccc tgc agg gtg gtg gat ctt cca tcc ttc acc         432
Trp Gln Ser Trp Gly Pro Cys Arg Val Val Asp Leu Pro Ser Phe Thr
    130                 135                 140 cca ccc gag ata gat cca aac tgg cag tac acg gcc tct gtg gta ccg         480
Pro Pro Glu Ile Asp Pro Asn Trp Gln Tyr Thr Ala Ser Val Val Pro
145                 150                 155                 160 gat gtg atc aaa aac cgt ctt cag agt gac tac ttc gtg gca gag gaa         528
Asp Val Ile Lys Asn Arg Leu Gln Ser Asp Tyr Phe Val Ala Glu Glu
                165                 170                 175 ggg aga gta tac ggt ttt ttg agt tcg aag atc gca cat cct ttc ttt         576
Gly Arg Val Tyr Gly Phe Leu Ser Ser Lys Ile Ala His Pro Phe Phe
            180                 185                 190 gcg gca gag aat gga gaa ctt gtt gcg tat ctt gag tac ttc gat gtg         624
Ala Ala Glu Asn Gly Glu Leu Val Ala Tyr Leu Glu Tyr Phe Asp Val
        195                 200                 205 aat ttc gat gac ttc gtc ccg ata gaa cct ttt gtc gtc ctt gaa aat         672
Asn Phe Asp Asp Phe Val Pro Ile Glu Pro Phe Val Val Leu Glu Asn
    210                 215                 220 cca atc acc tct ctc ctt ctg gaa aag tac gct gaa ctc gtc ggg aag         720
Pro Ile Thr Ser Leu Leu Leu Glu Lys Tyr Ala Glu Leu Val Gly Lys
225                 230                 235                 240 gaa aac agc gcg agg att cca aaa cgt aca ccg gtt gga tgg tgc agc         768
Glu Asn Ser Ala Arg Ile Pro Lys Arg Thr Pro Val Gly Trp Cys Ser
                245                 250                 255 tgg tac cac tat ttc ctc gat ctc acc tgg gag gag act ttg aag aat         816
Trp Tyr His Tyr Phe Leu Asp Leu Thr Trp Glu Glu Thr Leu Lys Asn
            260                 265                 270 ctg gaa ctt gca gga gag ttt ccc ttc gag gtc ttt cag ata gac gac         864
Leu Glu Leu Ala Gly Glu Phe Pro Phe Glu Val Phe Gln Ile Asp Asp
        275                 280                 285 gcg tat gaa aaa gac atc gga gac tgg ctc gtc acg aag aaa gac ttc         912
Ala Tyr Glu Lys Asp Ile Gly Asp Trp Leu Val Thr Lys Lys Asp Phe
    290                 295                 300 cca tct gtg gac gag atg gca agg acg ata cag gag aaa ggc ttt gtt         960
Pro Ser Val Asp Glu Met Ala Arg Thr Ile Gln Glu Lys Gly Phe Val
305                 310                 315                 320 cct ggt ata tgg acc gca ccg ttc agt gtt tca gaa aca tcg gat gtg        1008
Pro Gly Ile Trp Thr Ala Pro Phe Ser Val Ser Glu Thr Ser Asp Val
                325                 330                 335 ttc aac tcc tat ccg gac tgg gtc gtg aag gaa aac gga atg cca aag        1056
Phe Asn Ser Tyr Pro Asp Trp Val Val Lys Glu Asn Gly Met Pro Lys
            340                 345                 350 atg gcg tac agg aac tgg aac aga aag atc tac gct ctt gac ctt tca        1104
Met Ala Tyr Arg Asn Trp Asn Arg Lys Ile Tyr Ala Leu Asp Leu Ser
        355                 360                 365
```

```
aac aaa gaa gtc ctg gac tgg ctc ttc gac ctc ttc agc tct ctc aag    1152
Asn Lys Glu Val Leu Asp Trp Leu Phe Asp Leu Phe Ser Ser Leu Lys
    370                 375                 380 aag atg ggc tac aga tac ttc aag atc gac ttt ctc ttt gca gga gcg    1200
Lys Met Gly Tyr Arg Tyr Phe Lys Ile Asp Phe Leu Phe Ala Gly Ala
385                 390                 395                 400 att ccg ggt gag agg aaa gaa aac atc aca ccc gtt cag gcg ttc aga    1248
Ile Pro Gly Glu Arg Lys Glu Asn Ile Thr Pro Val Gln Ala Phe Arg
                405                 410                 415 aag ggg atg gag gtg atc aga aag gcg gtt gga gac ttg ttc ata ctc    1296
Lys Gly Met Glu Val Ile Arg Lys Ala Val Gly Asp Leu Phe Ile Leu
            420                 425                 430 gga tgt ggc tct ccc ctt ctt cct gcg gtg ggc tac gtt gac ggc atg    1344
Gly Cys Gly Ser Pro Leu Leu Pro Ala Val Gly Tyr Val Asp Gly Met
        435                 440                 445 agg ata ggg ccg gac acc aca ccc ttc tgg ggt gat caa ata gaa gac    1392
Arg Ile Gly Pro Asp Thr Thr Pro Phe Trp Gly Asp Gln Ile Glu Asp
    450                 455                 460 aac gga gca ccc gct gca aga tgg gct ctg aga aat gcc atc aca cgt    1440
Asn Gly Ala Pro Ala Ala Arg Trp Ala Leu Arg Asn Ala Ile Thr Arg
465                 470                 475                 480 tac ttc atg cac gac aga ctc tgg ctg aac gat ccg gac tgc ctc atc    1488
Tyr Phe Met His Asp Arg Leu Trp Leu Asn Asp Pro Asp Cys Leu Ile
                485                 490                 495 ctg aga gag gaa aaa aca gaa ctg acc cca aaa gag aga gag ctc tac    1536
Leu Arg Glu Glu Lys Thr Glu Leu Thr Pro Lys Glu Arg Glu Leu Tyr
            500                 505                 510 tcg tac acc tgt ggg atc ctc gac aac atg atc ata gaa agt gac gac    1584
Ser Tyr Thr Cys Gly Ile Leu Asp Asn Met Ile Ile Glu Ser Asp Asp
        515                 520                 525 ctg tca ctt gtg aaa gag cac gga agg aag gtt ctg aga gag aca ctc    1632
Leu Ser Leu Val Lys Glu His Gly Arg Lys Val Leu Arg Glu Thr Leu
    530                 535                 540 gat ctt ctc ggg gga aag ccc cgt gtt ctg aac atc atg aca gag gat    1680
Asp Leu Leu Gly Gly Lys Pro Arg Val Leu Asn Ile Met Thr Glu Asp
545                 550                 555                 560 ctg aag tac gag atc gtc tcg tct ggc acg atc tct gga aac acc agg    1728
Leu Lys Tyr Glu Ile Val Ser Ser Gly Thr Ile Ser Gly Asn Thr Arg
                565                 570                 575 ctc gtt gtc gat ctc aaa aac aga gag tac cat ctg gaa aaa gag gga    1776
Leu Val Val Asp Leu Lys Asn Arg Glu Tyr His Leu Glu Lys Glu Gly
            580                 585                 590 aag tcc tct ctg aga aag aag gtt gtc aaa aga gaa gac gga aga aac    1824
Lys Ser Ser Leu Arg Lys Lys Val Val Lys Arg Glu Asp Gly Arg Asn
        595                 600                 605 ttc tac ttc tac gaa gag ggt gag aga gaa tga                        1857
Phe Tyr Phe Tyr Glu Glu Gly Glu Arg Glu *
    610                 615
```

<210> SEQ ID NO 14
<211> LENGTH: 618
<212> TYPE: PRT
<213> ORGANISM: Thermotoga neapolitana

<400> SEQUENCE: 14

```
Ser Ser Glu Arg Phe Ser Thr Glu Gln Lys Arg Pro Asp His Thr Leu
1               5                   10                  15

Cys Gly Arg Lys Arg Thr Phe Gly Lys Glu Gly Gly Tyr Thr Thr Leu
            20                  25                  30

Gln Arg Gly Asn Ala Gly Leu Gln Ser Glu Arg Thr Glu Glu Gly Arg
```

```
                35                  40                  45
Ala Pro Arg Ile His Gln Ser Glu His Gly Lys Asn His Leu Cys Glu
 50                  55                  60

Val Ile Cys Val Glu Ile Phe Lys Arg Pro Phe Arg Glu Gly Ser Phe
 65                  70                  75                  80

Val Leu Lys Glu Lys Asp Tyr Thr Val Glu Phe Glu Val Glu Lys Ile
                 85                  90                  95

His Leu Gly Trp Lys Ile Ser Gly Arg Val Lys Gly Asn Pro Gly Arg
                100                 105                 110

Leu Glu Ile Phe Arg Thr Asn Ala Pro Lys Lys Leu Leu Val Asn Asn
                115                 120                 125

Trp Gln Ser Trp Gly Pro Cys Arg Val Val Asp Leu Pro Ser Phe Thr
130                 135                 140

Pro Pro Glu Ile Asp Pro Asn Trp Gln Tyr Thr Ala Ser Val Val Pro
145                 150                 155                 160

Asp Val Ile Lys Asn Arg Leu Gln Ser Asp Tyr Phe Val Ala Glu Glu
                165                 170                 175

Gly Arg Val Tyr Gly Phe Leu Ser Ser Lys Ile Ala His Pro Phe Phe
                180                 185                 190

Ala Ala Glu Asn Gly Glu Leu Val Ala Tyr Leu Glu Tyr Phe Asp Val
                195                 200                 205

Asn Phe Asp Asp Phe Val Pro Ile Glu Pro Phe Val Val Leu Glu Asn
210                 215                 220

Pro Ile Thr Ser Leu Leu Leu Glu Lys Tyr Ala Glu Leu Val Gly Lys
225                 230                 235                 240

Glu Asn Ser Ala Arg Ile Pro Lys Arg Thr Pro Val Gly Trp Cys Ser
                245                 250                 255

Trp Tyr His Tyr Phe Leu Asp Leu Thr Trp Glu Glu Thr Leu Lys Asn
                260                 265                 270

Leu Glu Leu Ala Gly Glu Phe Pro Phe Glu Val Phe Gln Ile Asp Asp
                275                 280                 285

Ala Tyr Glu Lys Asp Ile Gly Asp Trp Leu Val Thr Lys Lys Asp Phe
290                 295                 300

Pro Ser Val Asp Glu Met Ala Arg Thr Ile Gln Glu Lys Gly Phe Val
305                 310                 315                 320

Pro Gly Ile Trp Thr Ala Pro Phe Ser Val Ser Glu Thr Ser Asp Val
                325                 330                 335

Phe Asn Ser Tyr Pro Asp Trp Val Val Lys Glu Asn Gly Met Pro Lys
                340                 345                 350

Met Ala Tyr Arg Asn Trp Asn Arg Lys Ile Tyr Ala Leu Asp Leu Ser
                355                 360                 365

Asn Lys Glu Val Leu Asp Trp Leu Phe Asp Leu Phe Ser Ser Leu Lys
                370                 375                 380

Lys Met Gly Tyr Arg Tyr Phe Lys Ile Asp Phe Leu Phe Ala Gly Ala
385                 390                 395                 400

Ile Pro Gly Glu Arg Lys Glu Asn Ile Thr Pro Val Gln Ala Phe Arg
                405                 410                 415

Lys Gly Met Glu Val Ile Arg Lys Ala Val Gly Asp Leu Phe Ile Leu
                420                 425                 430

Gly Cys Gly Ser Pro Leu Leu Pro Ala Val Gly Tyr Val Asp Gly Met
                435                 440                 445

Arg Ile Gly Pro Asp Thr Thr Pro Phe Trp Gly Asp Gln Ile Glu Asp
450                 455                 460
```

-continued

```
Asn Gly Ala Pro Ala Ala Arg Trp Ala Leu Arg Asn Ala Ile Thr Arg
465                 470                 475                 480

Tyr Phe Met His Asp Arg Leu Trp Leu Asn Asp Pro Asp Cys Leu Ile
                485                 490                 495

Leu Arg Glu Glu Lys Thr Glu Leu Thr Pro Lys Glu Arg Glu Leu Tyr
            500                 505                 510

Ser Tyr Thr Cys Gly Ile Leu Asp Asn Met Ile Ile Glu Ser Asp Asp
            515                 520                 525

Leu Ser Leu Val Lys Glu His Gly Arg Lys Val Leu Arg Glu Thr Leu
        530                 535                 540

Asp Leu Leu Gly Gly Lys Pro Arg Val Leu Asn Ile Met Thr Glu Asp
545                 550                 555                 560

Leu Lys Tyr Glu Ile Val Ser Ser Gly Thr Ile Ser Gly Asn Thr Arg
                565                 570                 575

Leu Val Val Asp Leu Lys Asn Arg Glu Tyr His Leu Glu Lys Glu Gly
                580                 585                 590

Lys Ser Ser Leu Arg Lys Lys Val Val Lys Arg Glu Asp Gly Arg Asn
            595                 600                 605

Phe Tyr Phe Tyr Glu Glu Gly Glu Arg Glu
610                 615
```

<210> SEQ ID NO 15
<211> LENGTH: 2001
<212> TYPE: DNA
<213> ORGANISM: Thermotoga neapolitana
<220> FEATURE:
<221> NAME/KEY: CDS
<222> LOCATION: (1)...(2001)
<223> OTHER INFORMATION: clone # 56GP1

<400> SEQUENCE: 15

```
atg aga aaa ctt gtg ttc tca ttt ttg att gtg aca ttg ccc atc gtc        48
Met Arg Lys Leu Val Phe Ser Phe Leu Ile Val Thr Leu Pro Ile Val
 1               5                  10                  15 ctc ttt gca aac agt gat ttc gtg aaa gtg gaa aac ggc agg ttc ata        96
Leu Phe Ala Asn Ser Asp Phe Val Lys Val Glu Asn Gly Arg Phe Ile
                20                  25                  30 ctg aac gga gaa gag ttc aga ttc gtt gga agc aac aac tac tac atg       144
Leu Asn Gly Glu Glu Phe Arg Phe Val Gly Ser Asn Asn Tyr Tyr Met
            35                  40                  45 cac tac aag agc aat cga atg ata gac agt gtc ctt gaa agt gca aaa       192
His Tyr Lys Ser Asn Arg Met Ile Asp Ser Val Leu Glu Ser Ala Lys
        50                  55                  60 gcc atg ggg gtg aag gtg ctc aga att tgg gga ttc ctc gat ggt gag       240
Ala Met Gly Val Lys Val Leu Arg Ile Trp Gly Phe Leu Asp Gly Glu
 65                  70                  75                  80 agt tac tgc cgt gac aag aac acc tac atg cac ccc gca ccg gga gta       288
Ser Tyr Cys Arg Asp Lys Asn Thr Tyr Met His Pro Ala Pro Gly Val
                85                  90                  95 ttt gga ttg cca gag ggt acg aac gct cag gac ggt ttt gaa aga ctc       336
Phe Gly Leu Pro Glu Gly Thr Asn Ala Gln Asp Gly Phe Glu Arg Leu
            100                 105                 110 gac tac acg gta gcg aaa gca aaa gaa ctg ggc ata aag ctc ata atc       384
Asp Tyr Thr Val Ala Lys Ala Lys Glu Leu Gly Ile Lys Leu Ile Ile
        115                 120                 125 gtt ctt gtg aac aac tgg gac gac ttc ggt gga atg aat caa tac gtg       432
Val Leu Val Asn Asn Trp Asp Asp Phe Gly Gly Met Asn Gln Tyr Val
    130                 135                 140
```

```
aga tgg ttt ggg ggc atc cat cac gat gac ttc tac agg aac gag aag       480
Arg Trp Phe Gly Gly Ile His His Asp Asp Phe Tyr Arg Asn Glu Lys
145                 150                 155                 160 atc aaa gaa gaa tac aaa aag tac gtg tct ttc ctc ata aac agg gtg       528
Ile Lys Glu Glu Tyr Lys Lys Tyr Val Ser Phe Leu Ile Asn Arg Val
                165                 170                 175 aac acc tac acg ggt gtt cct tac agg gaa gag ccc acc atc atg gca       576
Asn Thr Tyr Thr Gly Val Pro Tyr Arg Glu Glu Pro Thr Ile Met Ala
            180                 185                 190 tgg gaa ctg gcg aac gag ccc agg tgt gaa acg gac aag tct ggt aac       624
Trp Glu Leu Ala Asn Glu Pro Arg Cys Glu Thr Asp Lys Ser Gly Asn
        195                 200                 205 aca ctc gtt gaa tgg gta gag gag atg agt gct tac ata aag agt ctg       672
Thr Leu Val Glu Trp Val Glu Glu Met Ser Ala Tyr Ile Lys Ser Leu
    210                 215                 220 gat cca aac cac ctg gtt gcc gtg gga gac gag gga ttc ttc aac aac       720
Asp Pro Asn His Leu Val Ala Val Gly Asp Glu Gly Phe Phe Asn Asn
225                 230                 235                 240 tac gaa ggc ttc aga cct tac ggt gga gag gct gag tgg gcc tac aac       768
Tyr Glu Gly Phe Arg Pro Tyr Gly Gly Glu Ala Glu Trp Ala Tyr Asn
                245                 250                 255 gga tgg tcc ggt gtt gac tgg aag aga ctt ctg gag ata gag acg gtg       816
Gly Trp Ser Gly Val Asp Trp Lys Arg Leu Leu Glu Ile Glu Thr Val
            260                 265                 270 gat ttt ggt acg ttc cat ctc tac ccc tcc cac tgg ggt gtg agc cct       864
Asp Phe Gly Thr Phe His Leu Tyr Pro Ser His Trp Gly Val Ser Pro
        275                 280                 285 gaa aac tac gca cag tgg ggg gca aag tgg ata gaa gat cac ata aag       912
Glu Asn Tyr Ala Gln Trp Gly Ala Lys Trp Ile Glu Asp His Ile Lys
    290                 295                 300 atc gca aaa gag gtt gga aaa ccc gtc gtt ctg gaa gag tac ggt att       960
Ile Ala Lys Glu Val Gly Lys Pro Val Val Leu Glu Glu Tyr Gly Ile
305                 310                 315                 320 ccc aaa agt gcc ccg gtc aac agg gtt gcc att tac aaa ttg tgg aac      1008
Pro Lys Ser Ala Pro Val Asn Arg Val Ala Ile Tyr Lys Leu Trp Asn
                325                 330                 335 gat ctg gtc tac aac ctc ggt gga aac ggt gcc atg ttc tgg atg ctc      1056
Asp Leu Val Tyr Asn Leu Gly Gly Asn Gly Ala Met Phe Trp Met Leu
            340                 345                 350 gca gga atc ggt gaa gga tgg gac aga gac gaa aag ggt tac tac ccc      1104
Ala Gly Ile Gly Glu Gly Trp Asp Arg Asp Glu Lys Gly Tyr Tyr Pro
        355                 360                 365 gat tac gac ggc ttc aga ata gtg aac gat gaa agt gaa gag gca aag      1152
Asp Tyr Asp Gly Phe Arg Ile Val Asn Asp Glu Ser Glu Glu Ala Lys
    370                 375                 380 ttg atc aga gag tac gcg aaa ctg ttc agc acg ggt gag gat acg agg      1200
Leu Ile Arg Glu Tyr Ala Lys Leu Phe Ser Thr Gly Glu Asp Thr Arg
385                 390                 395                 400 gaa gat acc tgc atg ttc atc aca cca aag gat ggt cag gag atc aaa      1248
Glu Asp Thr Cys Met Phe Ile Thr Pro Lys Asp Gly Gln Glu Ile Lys
                405                 410                 415 aag act gtg aag gtg aga gtg ggt gtc ttc gac tac agc aac acg ttc      1296
Lys Thr Val Lys Val Arg Val Gly Val Phe Asp Tyr Ser Asn Thr Phe
            420                 425                 430 aaa gga att tcc gtc ggg gtt gaa aat ctg ctc ttt gaa gat gag ata      1344
Lys Gly Ile Ser Val Gly Val Glu Asn Leu Leu Phe Glu Asp Glu Ile
        435                 440                 445 aaa cat ctc gga tat gga gtt tac gga ttc gaa ttt gac aca acg cgg      1392
Lys His Leu Gly Tyr Gly Val Tyr Gly Phe Glu Phe Asp Thr Thr Arg
    450                 455                 460
```

-continued

```
att tca gac gga gaa cac gag atg ttc ctt gag gca cat ttc agg gga      1440
Ile Ser Asp Gly Glu His Glu Met Phe Leu Glu Ala His Phe Arg Gly
465                 470                 475                 480 gaa acg gtg aaa gac aca atc agg gtg aaa gtt gtg aac aga gcg cag      1488
Glu Thr Val Lys Asp Thr Ile Arg Val Lys Val Val Asn Arg Ala Gln
                485                 490                 495 tat gta ctc gca gaa gaa gtg gat ttt tcc aga ccc gaa gaa gtc aag      1536
Tyr Val Leu Ala Glu Glu Val Asp Phe Ser Arg Pro Glu Glu Val Lys
            500                 505                 510 aac tgg tgg aac agc gga aca tgg cag gct gag ttc aaa aca ccc gat      1584
Asn Trp Trp Asn Ser Gly Thr Trp Gln Ala Glu Phe Lys Thr Pro Asp
        515                 520                 525 ata gag tgg aac ggt gag gtg ggg aac ggt gct ctc cag atg aac gtg      1632
Ile Glu Trp Asn Gly Glu Val Gly Asn Gly Ala Leu Gln Met Asn Val
    530                 535                 540 gtg ctt ccc gga aag ggt gac tgg gaa gag gtg agg gtg gtc agg aaa      1680
Val Leu Pro Gly Lys Gly Asp Trp Glu Glu Val Arg Val Val Arg Lys
545                 550                 555                 560 ttc gat caa ctc ccc gtg tgt gag atc ctc gag tac gat atc tac ata      1728
Phe Asp Gln Leu Pro Val Cys Glu Ile Leu Glu Tyr Asp Ile Tyr Ile
                565                 570                 575 cca gac gtt gaa ggg ctt aca gga agg ctc aga ccg tac gcg gtg ctg      1776
Pro Asp Val Glu Gly Leu Thr Gly Arg Leu Arg Pro Tyr Ala Val Leu
            580                 585                 590 aat ccc ggc tgg gtg aag ata ggg ctc gac atg aac aac acc tcg att      1824
Asn Pro Gly Trp Val Lys Ile Gly Leu Asp Met Asn Asn Thr Ser Ile
        595                 600                 605 gac agc gga gaa ctt gtc agt ttc gat ggc aaa aag tac aga aag ttc      1872
Asp Ser Gly Glu Leu Val Ser Phe Asp Gly Lys Lys Tyr Arg Lys Phe
    610                 615                 620 cat gtg agg atc gag ttc gac aag aca cct gga gtg aac gag ctc cac      1920
His Val Arg Ile Glu Phe Asp Lys Thr Pro Gly Val Asn Glu Leu His
625                 630                 635                 640 ata ggt gta gtt gga gac cac ctg gag tat gat ggg ccg att ttc atc      1968
Ile Gly Val Val Gly Asp His Leu Glu Tyr Asp Gly Pro Ile Phe Ile
                645                 650                 655 gat aat gtg agg ctc tat aaa aaa tct tct tga                          2001
Asp Asn Val Arg Leu Tyr Lys Lys Ser Ser *
            660                 665

<210> SEQ ID NO 16
<211> LENGTH: 666
<212> TYPE: PRT
<213> ORGANISM: Thermotoga neapolitana

<400> SEQUENCE: 16

Met Arg Lys Leu Val Phe Ser Phe Leu Ile Val Thr Leu Pro Ile Val
1               5                   10                  15

Leu Phe Ala Asn Ser Asp Phe Val Lys Val Glu Asn Gly Arg Phe Ile
            20                  25                  30

Leu Asn Gly Glu Glu Phe Arg Phe Val Gly Ser Asn Asn Tyr Tyr Met
        35                  40                  45

His Tyr Lys Ser Asn Arg Met Ile Asp Ser Val Leu Glu Ser Ala Lys
    50                  55                  60

Ala Met Gly Val Lys Val Leu Arg Ile Trp Gly Phe Leu Asp Gly Glu
65                  70                  75                  80

Ser Tyr Cys Arg Asp Lys Asn Thr Tyr Met His Pro Ala Pro Gly Val
                85                  90                  95
```

-continued

```
Phe Gly Leu Pro Glu Gly Thr Asn Ala Gln Asp Gly Phe Glu Arg Leu
            100                 105                 110
Asp Tyr Thr Val Ala Lys Ala Lys Glu Leu Gly Ile Lys Leu Ile Ile
            115                 120                 125
Val Leu Val Asn Asn Trp Asp Asp Phe Gly Gly Met Asn Gln Tyr Val
        130                 135                 140
Arg Trp Phe Gly Gly Ile His His Asp Asp Phe Tyr Arg Asn Glu Lys
145                 150                 155                 160
Ile Lys Glu Glu Tyr Lys Lys Tyr Val Ser Phe Leu Ile Asn Arg Val
                165                 170                 175
Asn Thr Tyr Thr Gly Val Pro Tyr Arg Glu Glu Pro Thr Ile Met Ala
            180                 185                 190
Trp Glu Leu Ala Asn Glu Pro Arg Cys Glu Thr Asp Lys Ser Gly Asn
        195                 200                 205
Thr Leu Val Glu Trp Val Glu Met Ser Ala Tyr Ile Lys Ser Leu
        210                 215                 220
Asp Pro Asn His Leu Val Ala Val Gly Asp Glu Gly Phe Phe Asn Asn
225                 230                 235                 240
Tyr Glu Gly Phe Arg Pro Tyr Gly Gly Glu Ala Glu Trp Ala Tyr Asn
                245                 250                 255
Gly Trp Ser Gly Val Asp Trp Lys Arg Leu Leu Glu Ile Glu Thr Val
            260                 265                 270
Asp Phe Gly Thr Phe His Leu Tyr Pro Ser His Trp Gly Val Ser Pro
        275                 280                 285
Glu Asn Tyr Ala Gln Trp Gly Ala Lys Trp Ile Glu Asp His Ile Lys
        290                 295                 300
Ile Ala Lys Glu Val Gly Lys Pro Val Val Leu Glu Glu Tyr Gly Ile
305                 310                 315                 320
Pro Lys Ser Ala Pro Val Asn Arg Val Ala Ile Tyr Lys Leu Trp Asn
                325                 330                 335
Asp Leu Val Tyr Asn Leu Gly Gly Asn Gly Ala Met Phe Trp Met Leu
            340                 345                 350
Ala Gly Ile Gly Glu Gly Trp Asp Arg Asp Glu Lys Gly Tyr Tyr Pro
        355                 360                 365
Asp Tyr Asp Gly Phe Arg Ile Val Asn Asp Glu Ser Glu Glu Ala Lys
        370                 375                 380
Leu Ile Arg Glu Tyr Ala Lys Leu Phe Ser Thr Gly Glu Asp Thr Arg
385                 390                 395                 400
Glu Asp Thr Cys Met Phe Ile Thr Pro Lys Asp Gly Gln Glu Ile Lys
                405                 410                 415
Lys Thr Val Lys Val Arg Val Gly Val Phe Asp Tyr Ser Asn Thr Phe
            420                 425                 430
Lys Gly Ile Ser Val Gly Val Glu Asn Leu Leu Phe Glu Asp Glu Ile
        435                 440                 445
Lys His Leu Gly Tyr Gly Val Tyr Gly Phe Glu Phe Asp Thr Thr Arg
        450                 455                 460
Ile Ser Asp Gly Glu His Gly Met Phe Leu Glu Ala His Phe Arg Gly
465                 470                 475                 480
Glu Thr Val Lys Asp Thr Ile Arg Val Lys Val Asn Arg Ala Gln
                485                 490                 495
Tyr Val Leu Ala Glu Glu Val Asp Phe Ser Arg Pro Glu Glu Val Lys
            500                 505                 510
Asn Trp Trp Asn Ser Gly Thr Trp Gln Ala Glu Phe Lys Thr Pro Asp
```

-continued

```
                515                 520                 525
Ile Glu Trp Asn Gly Glu Val Gly Asn Gly Ala Leu Gln Met Asn Val
        530                 535                 540

Val Leu Pro Gly Lys Gly Asp Trp Glu Glu Val Arg Val Val Arg Lys
545                 550                 555                 560

Phe Asp Gln Leu Pro Val Cys Glu Ile Leu Glu Tyr Asp Ile Tyr Ile
                565                 570                 575

Pro Asp Val Glu Gly Leu Thr Gly Arg Leu Arg Pro Tyr Ala Val Leu
                580                 585                 590

Asn Pro Gly Trp Val Lys Ile Gly Leu Asp Met Asn Asn Thr Ser Ile
                595                 600                 605

Asp Ser Gly Glu Leu Val Ser Phe Asp Gly Lys Lys Tyr Arg Lys Phe
                610                 615                 620

His Val Arg Ile Glu Phe Asp Lys Thr Pro Gly Val Asn Glu Leu His
625                 630                 635                 640

Ile Gly Val Val Gly Asp His Leu Glu Tyr Asp Gly Pro Ile Phe Ile
                645                 650                 655

Asp Asn Val Arg Leu Tyr Lys Lys Ser Ser
                660                 665
```

<210> SEQ ID NO 17
<211> LENGTH: 255
<212> TYPE: DNA
<213> ORGANISM: Artificial Sequence
<220> FEATURE:
<223> OTHER INFORMATION: Alum Rock sulfur spring (clone # 58GB3)
<220> FEATURE:
<221> NAME/KEY: CDS
<222> LOCATION: (1)...(255)

<400> SEQUENCE: 17

```
atg cat ttt agc cca cta caa ttg atc ctc gtc tta gtc att gtc att      48
Met His Phe Ser Pro Leu Gln Leu Ile Leu Val Leu Val Ile Val Ile
 1               5                  10                  15 ctg ctg ttt ggc acc aaa aaa tta cgc aat atg ggc ggc gat tta ggc      96
Leu Leu Phe Gly Thr Lys Lys Leu Arg Asn Met Gly Gly Asp Leu Gly
             20                  25                  30 gaa gcc ttc aag aat ttc aga aaa gca gtc aaa gac ggc gat gat gct     144
Glu Ala Phe Lys Asn Phe Arg Lys Ala Val Lys Asp Gly Asp Asp Ala
         35                  40                  45 gaa aca caa aaa gat gtt gct gtg caa aaa gtt gac caa cag cca cca     192
Glu Thr Gln Lys Asp Val Ala Val Gln Lys Val Asp Gln Gln Pro Pro
     50                  55                  60 gca cag ccc atc cca caa ggt cga gtc att gat tcg gaa gcc aag gaa     240
Ala Gln Pro Ile Pro Gln Gly Arg Val Ile Asp Ser Glu Ala Lys Glu
 65                  70                  75                  80 aag gat aag gtc taa                                                  255
Lys Asp Lys Val *
```

<210> SEQ ID NO 18
<211> LENGTH: 84
<212> TYPE: PRT
<213> ORGANISM: Artificial Sequence
<220> FEATURE:
<223> OTHER INFORMATION: Alum Rock sulfur spring (clone # 58GB3)

<400> SEQUENCE: 18

```
Met His Phe Ser Pro Leu Gln Leu Ile Leu Val Leu Val Ile Val Ile
 1               5                  10                  15

Leu Leu Phe Gly Thr Lys Lys Leu Arg Asn Met Gly Gly Asp Leu Gly
```

-continued

```
                      20                  25                  30
Glu Ala Phe Lys Asn Phe Arg Lys Ala Val Lys Asp Gly Asp Ala
            35                  40                  45
Glu Thr Gln Lys Asp Val Ala Val Gln Lys Val Asp Gln Gln Pro Pro
 50                  55                  60
Ala Gln Pro Ile Pro Gln Gly Arg Val Ile Asp Ser Glu Ala Lys Glu
 65                  70                  75                  80
Lys Asp Lys Val

<210> SEQ ID NO 19
<211> LENGTH: 1479
<212> TYPE: DNA
<213> ORGANISM: Artificial Sequence
<220> FEATURE:
<223> OTHER INFORMATION: AEPII 1a (clone # 63GA3)
<220> FEATURE:
<221> NAME/KEY: CDS
<222> LOCATION: (1)...(1479)

<400> SEQUENCE: 19 atg gaa gga ctt cga gga ggt gtg agg atg aag ttc cca tct aac ttt     48
Met Glu Gly Leu Arg Gly Gly Val Arg Met Lys Phe Pro Ser Asn Phe
 1               5                  10                  15 ctt ttt ggc tac tcc tgg tcg ggc ttc cag ttt gaa atg ggt tta cct     96
Leu Phe Gly Tyr Ser Trp Ser Gly Phe Gln Phe Glu Met Gly Leu Pro
             20                  25                  30 ggg agt gaa gtt gag agc gac tgg tgg gca tgg gtc cac gat aag gag    144
Gly Ser Glu Val Glu Ser Asp Trp Trp Ala Trp Val His Asp Lys Glu
         35                  40                  45 aac atc ttc tcg ggc cta gtt agc ggt gac cta cca gag aac ggg cct    192
Asn Ile Phe Ser Gly Leu Val Ser Gly Asp Leu Pro Glu Asn Gly Pro
     50                  55                  60 gct tac tgg cac ctc tac aag aaa gac cac gac ata gct gaa agc ctt    240
Ala Tyr Trp His Leu Tyr Lys Lys Asp His Asp Ile Ala Glu Ser Leu
 65                  70                  75                  80 ggc atg gac gcg ata aga ggc gga atc gag tgg gcg agg atc ttc cca    288
Gly Met Asp Ala Ile Arg Gly Gly Ile Glu Trp Ala Arg Ile Phe Pro
             85                  90                  95 aaa ccc acc ttt gac gtg aag gtt gac gtg gaa aag gac gaa aac ggg    336
Lys Pro Thr Phe Asp Val Lys Val Asp Val Glu Lys Asp Glu Asn Gly
            100                 105                 110 aac ata atc tcc att gac gtc ccg gag agc gcg ata gag gag cta gaa    384
Asn Ile Ile Ser Ile Asp Val Pro Glu Ser Ala Ile Glu Glu Leu Glu
        115                 120                 125 aag ctt gcc aac atg gat gcc ctc aac cac tac cgc gaa atc tac tcg    432
Lys Leu Ala Asn Met Asp Ala Leu Asn His Tyr Arg Glu Ile Tyr Ser
    130                 135                 140 gac tgg aag gag agg ggc aag acc ttc ata ttg aac ctc tat cac tgg    480
Asp Trp Lys Glu Arg Gly Lys Thr Phe Ile Leu Asn Leu Tyr His Trp
145                 150                 155                 160 ccc ctt ccc ctc tgg ctc cac gac ccg ata ggc gtt aga aag ctc ggc    528
Pro Leu Pro Leu Trp Leu His Asp Pro Ile Gly Val Arg Lys Leu Gly
                165                 170                 175 cct gat aga gct ccc tcg ggc tgg ctg gac gag agg agc gtg gtg gag    576
Pro Asp Arg Ala Pro Ser Gly Trp Leu Asp Glu Arg Ser Val Val Glu
            180                 185                 190 ttc acc aag ttc gct gca ttc atc gcc tac cac ttg gat gac ctc gtt    624
Phe Thr Lys Phe Ala Ala Phe Ile Ala Tyr His Leu Asp Asp Leu Val
        195                 200                 205 gac atg tgg agc acg atg aac gag ccg aat gtg gtt tac gag cag ggt    672
```

| | |
|---|---|
| Asp Met Trp Ser Thr Met Asn Glu Pro Asn Val Val Tyr Glu Gln Gly<br>210 215 220 | |
| tac acg agg cct cag tcg ggc ttt cca ccg ggt tat ctc agc cac gag<br>Tyr Thr Arg Pro Gln Ser Gly Phe Pro Pro Gly Tyr Leu Ser His Glu<br>225 230 235 240 | 720 |
| gcc gct gga aag gcg aag ctc aac ctc atg cag gct cac gct aga gct<br>Ala Ala Gly Lys Ala Lys Leu Asn Leu Met Gln Ala His Ala Arg Ala<br>245 250 255 | 768 |
| tac gat gcg ata aaa gag cac tcg gac aag ccc gtg ggg ttg ata tac<br>Tyr Asp Ala Ile Lys Glu His Ser Asp Lys Pro Val Gly Leu Ile Tyr<br>260 265 270 | 816 |
| tcc ttt gtc tgg cac gat gcc cta aac gag gaa gcg gag gag att gtg<br>Ser Phe Val Trp His Asp Ala Leu Asn Glu Glu Ala Glu Glu Ile Val<br>275 280 285 | 864 |
| aag gag ata agg agg aga cac tac gac ttc gta acc ggc ctt cac tcc<br>Lys Glu Ile Arg Arg Arg His Tyr Asp Phe Val Thr Gly Leu His Ser<br>290 295 300 | 912 |
| ggc tca tcg gag ttc ggg gag agg gag gac ttc aag ggg aag atc gac<br>Gly Ser Ser Glu Phe Gly Glu Arg Glu Asp Phe Lys Gly Lys Ile Asp<br>305 310 315 320 | 960 |
| tgg ata ggc gtg aac tac tac act agg gtt gct tac gag atg agg aac<br>Trp Ile Gly Val Asn Tyr Tyr Thr Arg Val Ala Tyr Glu Met Arg Asn<br>325 330 335 | 1008 |
| ggc cgc ttt atg gcc cta ccc ggg tac ggc tac atg tgc gag agg agt<br>Gly Arg Phe Met Ala Leu Pro Gly Tyr Gly Tyr Met Cys Glu Arg Ser<br>340 345 350 | 1056 |
| ggt tac gca aaa tcc gga agg ccc gcg agc gat ttt ggc tgg gag acc<br>Gly Tyr Ala Lys Ser Gly Arg Pro Ala Ser Asp Phe Gly Trp Glu Thr<br>355 360 365 | 1104 |
| tat cct gag ggc ctc gaa aac gtc ctg atg gat ctg aag gag ctc tac<br>Tyr Pro Glu Gly Leu Glu Asn Val Leu Met Asp Leu Lys Glu Leu Tyr<br>370 375 380 | 1152 |
| ggc ctg cca atg atg gtg acg gag aac ggg atg gcg gat atg gca gac<br>Gly Leu Pro Met Met Val Thr Glu Asn Gly Met Ala Asp Met Ala Asp<br>385 390 395 400 | 1200 |
| agg cac cgc tct tac tac ctc gtg agc cac ctc gcg gct atc cac agg<br>Arg His Arg Ser Tyr Tyr Leu Val Ser His Leu Ala Ala Ile His Arg<br>405 410 415 | 1248 |
| gcg atg gag aag ggt gcc gac gtt agg ggg tac ctc cac tgg tct ctg<br>Ala Met Glu Lys Gly Ala Asp Val Arg Gly Tyr Leu His Trp Ser Leu<br>420 425 430 | 1296 |
| acc gac aac tac gag tgg gcg cag ggc ttc aga atg cgc ttt ggg ctg<br>Thr Asp Asn Tyr Glu Trp Ala Gln Gly Phe Arg Met Arg Phe Gly Leu<br>435 440 445 | 1344 |
| gtg atg gtg gac ttc gag act aag aag cgc tac ata agg ccg agc gca<br>Val Met Val Asp Phe Glu Thr Lys Lys Arg Tyr Ile Arg Pro Ser Ala<br>450 455 460 | 1392 |
| ctc gtc ttc agg gag ata gcc acg cag aag gaa ata ccc gaa gag ctc<br>Leu Val Phe Arg Glu Ile Ala Thr Gln Lys Glu Ile Pro Glu Glu Leu<br>465 470 475 480 | 1440 |
| tcc cac cta gcg aac ctc gaa ctg gta acg aag aag taa<br>Ser His Leu Ala Asn Leu Glu Leu Val Thr Lys Lys *<br>485 490 | 1479 |

<210> SEQ ID NO 20
<211> LENGTH: 492
<212> TYPE: PRT
<213> ORGANISM: Artificial Sequence
<220> FEATURE:
<223> OTHER INFORMATION: AEPII 1a (clone # 63GP4)

<400> SEQUENCE: 20

```
Met Glu Gly Leu Arg Gly Gly Val Arg Met Lys Phe Pro Ser Asn Phe
 1               5                  10                  15

Leu Phe Gly Tyr Ser Trp Ser Gly Phe Gln Phe Glu Met Gly Leu Pro
             20                  25                  30

Gly Ser Glu Val Glu Ser Asp Trp Trp Ala Trp Val His Asp Lys Glu
             35                  40                  45

Asn Ile Phe Ser Gly Leu Val Ser Gly Asp Leu Pro Glu Asn Gly Pro
 50                  55                  60

Ala Tyr Trp His Leu Tyr Lys Lys Asp His Asp Ile Ala Glu Ser Leu
 65                  70                  75                  80

Gly Met Asp Ala Ile Arg Gly Ile Glu Trp Ala Arg Ile Phe Pro
             85                  90                  95

Lys Pro Thr Phe Asp Val Lys Val Asp Val Glu Lys Asp Glu Asn Gly
            100                 105                 110

Asn Ile Ile Ser Ile Asp Val Pro Glu Ser Ala Ile Glu Glu Leu Glu
            115                 120                 125

Lys Leu Ala Asn Met Asp Ala Leu Asn His Tyr Arg Glu Ile Tyr Ser
130                 135                 140

Asp Trp Lys Glu Arg Gly Lys Thr Phe Ile Leu Asn Leu Tyr His Trp
145                 150                 155                 160

Pro Leu Pro Leu Trp Leu His Asp Pro Ile Gly Val Arg Lys Leu Gly
                165                 170                 175

Pro Asp Arg Ala Pro Ser Gly Trp Leu Asp Glu Arg Ser Val Val Glu
            180                 185                 190

Phe Thr Lys Phe Ala Ala Phe Ile Ala Tyr His Leu Asp Asp Leu Val
            195                 200                 205

Asp Met Trp Ser Thr Met Asn Glu Pro Asn Val Val Tyr Glu Gln Gly
210                 215                 220

Tyr Thr Arg Pro Gln Ser Gly Phe Pro Pro Gly Tyr Leu Ser His Glu
225                 230                 235                 240

Ala Ala Gly Lys Ala Lys Leu Asn Leu Met Gln Ala His Ala Arg Ala
                245                 250                 255

Tyr Asp Ala Ile Lys Glu His Ser Asp Lys Pro Val Gly Leu Ile Tyr
            260                 265                 270

Ser Phe Val Trp His Asp Ala Leu Asn Glu Glu Ala Glu Glu Ile Val
            275                 280                 285

Lys Glu Ile Arg Arg His Tyr Asp Phe Val Thr Gly Leu His Ser
290                 295                 300

Gly Ser Ser Glu Phe Gly Glu Arg Glu Asp Phe Lys Gly Lys Ile Asp
305                 310                 315                 320

Trp Ile Gly Val Asn Tyr Tyr Thr Arg Val Ala Tyr Glu Met Arg Asn
                325                 330                 335

Gly Arg Phe Met Ala Leu Pro Gly Tyr Gly Tyr Met Cys Glu Arg Ser
            340                 345                 350

Gly Tyr Ala Lys Ser Gly Arg Pro Ala Ser Asp Phe Gly Trp Glu Thr
            355                 360                 365

Tyr Pro Glu Gly Leu Glu Asn Val Leu Met Asp Leu Lys Glu Leu Tyr
370                 375                 380

Gly Leu Pro Met Met Val Thr Glu Asn Gly Met Ala Asp Met Ala Asp
385                 390                 395                 400

Arg His Arg Ser Tyr Tyr Leu Val Ser His Leu Ala Ala Ile His Arg
                405                 410                 415
```

```
Ala Met Glu Lys Gly Ala Asp Val Arg Gly Tyr Leu His Trp Ser Leu
            420                 425                 430

Thr Asp Asn Tyr Glu Trp Ala Gln Gly Phe Arg Met Arg Phe Gly Leu
        435                 440                 445

Val Met Val Asp Phe Glu Thr Lys Lys Arg Tyr Ile Arg Pro Ser Ala
    450                 455                 460

Leu Val Phe Arg Glu Ile Ala Thr Gln Lys Glu Ile Pro Glu Glu Leu
465                 470                 475                 480

Ser His Leu Ala Asn Leu Glu Leu Val Thr Lys Lys
            485                 490

<210> SEQ ID NO 21
<211> LENGTH: 1455
<212> TYPE: DNA
<213> ORGANISM: Artificial Sequence
<220> FEATURE:
<223> OTHER INFORMATION: AEPII 1a (clone # 63GA4)
<220> FEATURE:
<221> NAME/KEY: CDS
<222> LOCATION: (1)...(1455)

<400> SEQUENCE: 21 atg aag ttc cca tct aac ttt ctt ttt ggc tac tcc tgg tcg ggc ttc      48
Met Lys Phe Pro Ser Asn Phe Leu Phe Gly Tyr Ser Trp Ser Gly Phe
 1               5                  10                  15 cag ttt gaa atg ggt tta cct ggg agt gaa gtt gag agc gac tgg tgg      96
Gln Phe Glu Met Gly Leu Pro Gly Ser Glu Val Glu Ser Asp Trp Trp
                20                  25                  30 gca tgg gtc cac gat aag gag aac atc ttc tcg ggc cta gtt agc ggt     144
Ala Trp Val His Asp Lys Glu Asn Ile Phe Ser Gly Leu Val Ser Gly
            35                  40                  45 gac cta cca gag aac ggg cct gct tac tgg cac ctc tac aag aaa gac     192
Asp Leu Pro Glu Asn Gly Pro Ala Tyr Trp His Leu Tyr Lys Lys Asp
        50                  55                  60 cac gac ata gct gaa agc ctt ggc atg gac gcg ata aga ggc gga atc     240
His Asp Ile Ala Glu Ser Leu Gly Met Asp Ala Ile Arg Gly Gly Ile
 65                  70                  75                  80 gag tgg gcg agg atc ttc cca aaa ccc acc ttt gac gtg aag gtt gac     288
Glu Trp Ala Arg Ile Phe Pro Lys Pro Thr Phe Asp Val Lys Val Asp
                85                  90                  95 gtg gaa aag gac gaa aac ggg aac ata atc tcc att gac gtc ccg gag     336
Val Glu Lys Asp Glu Asn Gly Asn Ile Ile Ser Ile Asp Val Pro Glu
                100                 105                 110 agc gcg ata gag gag cta gaa aag ctt gcc aac atg gat gcc ctc aac     384
Ser Ala Ile Glu Glu Leu Glu Lys Leu Ala Asn Met Asp Ala Leu Asn
            115                 120                 125 cac tac cgc gaa atc tac tcg gac tgg aag gag agg ggc aag acc ttc     432
His Tyr Arg Glu Ile Tyr Ser Asp Trp Lys Glu Arg Gly Lys Thr Phe
        130                 135                 140 ata ttg aac ctc tat cac tgg ccc ctt ccc ctc tgg ctc cac gac ccg     480
Ile Leu Asn Leu Tyr His Trp Pro Leu Pro Leu Trp Leu His Asp Pro
145                 150                 155                 160 ata ggc gtt aga aag ctc ggc cct gat aga gct ccc tcg ggc tgg ctg     528
Ile Gly Val Arg Lys Leu Gly Pro Asp Arg Ala Pro Ser Gly Trp Leu
                165                 170                 175 gac gag agg agc gtg gtg gag ttc acc aag ttc gct gca ttc atc gcc     576
Asp Glu Arg Ser Val Val Glu Phe Thr Lys Phe Ala Ala Phe Ile Ala
                180                 185                 190 tac cac ttg gat gac ctc gtt gac atg tgg agc acg atg aac gag ccg     624
Tyr His Leu Asp Asp Leu Val Asp Met Trp Ser Thr Met Asn Glu Pro
```

-continued

```
              195                 200                 205
aat gtg gtt tac gag cag ggt tac acg agg cct cag tcg ggc ttt cca        672
Asn Val Val Tyr Glu Gln Gly Tyr Thr Arg Pro Gln Ser Gly Phe Pro
        210                 215                 220 ccg ggt tat ctc agc cac gag gcc gct gga aag gcg aag ctc aac ctc        720
Pro Gly Tyr Leu Ser His Glu Ala Ala Gly Lys Ala Lys Leu Asn Leu
225                 230                 235                 240 atg cag gct cac gct aga gct tac gat gcg ata aaa gag cac tcg gac        768
Met Gln Ala His Ala Arg Ala Tyr Asp Ala Ile Lys Glu His Ser Asp
                245                 250                 255 aag cca gtt gga gtt atc tac gca tat aag tgg att gat gcg gag gat        816
Lys Pro Val Gly Val Ile Tyr Ala Tyr Lys Trp Ile Asp Ala Glu Asp
            260                 265                 270 gaa gct gca gag gaa tcc gtt ctg gaa ctc cgc agg agg gat tac gac        864
Glu Ala Ala Glu Glu Ser Val Leu Glu Leu Arg Arg Arg Asp Tyr Asp
        275                 280                 285 ttc gtt gat ggt ctc tac tca ggc aag tcc ctg act gca ggt gag agg        912
Phe Val Asp Gly Leu Tyr Ser Gly Lys Ser Leu Thr Ala Gly Glu Arg
    290                 295                 300 gag gac ttc aaa ggc agg gtc gac tgg gtt ggc gtc aac tac tac tcc        960
Glu Asp Phe Lys Gly Arg Val Asp Trp Val Gly Val Asn Tyr Tyr Ser
305                 310                 315                 320 cgc ctc ctc ttt gga aag gcc gga gat tca gtg aga tta ctt gag ggc       1008
Arg Leu Leu Phe Gly Lys Ala Gly Asp Ser Val Arg Leu Leu Glu Gly
                325                 330                 335 tac ggt ttt gtc tcc ccg agg ggt ggc tac gcc aaa tcg gga agg cct       1056
Tyr Gly Phe Val Ser Pro Arg Gly Gly Tyr Ala Lys Ser Gly Arg Pro
            340                 345                 350 gcg agc gat ttt ggc tgg gag att tat cct gag ggc ctc gaa aag ctc       1104
Ala Ser Asp Phe Gly Trp Glu Ile Tyr Pro Glu Gly Leu Glu Lys Leu
        355                 360                 365 ctg gtt gag ctg agt ggc agg tac gag ctt ccg ctc ttc ata acg gag       1152
Leu Val Glu Leu Ser Gly Arg Tyr Glu Leu Pro Leu Phe Ile Thr Glu
    370                 375                 380 aat ggt atg gct gat gct gtc gat agg tac agg cct tac tac ctc gtg       1200
Asn Gly Met Ala Asp Ala Val Asp Arg Tyr Arg Pro Tyr Tyr Leu Val
385                 390                 395                 400 agc cac ctc gcg gct atc cac agg gcg atg gag aag ggt gcc gac att       1248
Ser His Leu Ala Ala Ile His Arg Ala Met Glu Lys Gly Ala Asp Ile
                405                 410                 415 agg ggg tac ctc cac tgg tct ctg acc gac aac tac gag tgg gcg cag       1296
Arg Gly Tyr Leu His Trp Ser Leu Thr Asp Asn Tyr Glu Trp Ala Gln
            420                 425                 430 ggc ttc aga atg cgc ttt ggg ctg gtg atg gtg gac ttc gag act aag       1344
Gly Phe Arg Met Arg Phe Gly Leu Val Met Val Asp Phe Glu Thr Lys
        435                 440                 445 aag cgc tac ttg agg ccg agc gca ctc gtc ttc agg gaa ata gcc acg       1392
Lys Arg Tyr Leu Arg Pro Ser Ala Leu Val Phe Arg Glu Ile Ala Thr
    450                 455                 460 cgg aag gaa ata ccc gaa gag ctt gaa cac ctt gcc gat gtg gat gca       1440
Arg Lys Glu Ile Pro Glu Glu Leu Glu His Leu Ala Asp Val Asp Ala
465                 470                 475                 480 atc att gct cgg tga                                                   1455
Ile Ile Ala Arg *
```

<210> SEQ ID NO 22
<211> LENGTH: 484
<212> TYPE: PRT
<213> ORGANISM: Artificial Sequence
<220> FEATURE:

<223> OTHER INFORMATION: AEPII 1a (clone # 63GP4)

<400> SEQUENCE: 22

```
Met Lys Phe Pro Ser Asn Phe Leu Phe Gly Tyr Ser Trp Ser Gly Phe
 1               5                  10                  15

Gln Phe Glu Met Gly Leu Pro Gly Ser Glu Val Glu Ser Asp Trp Trp
            20                  25                  30

Ala Trp Val His Asp Lys Glu Asn Ile Phe Ser Gly Leu Val Ser Gly
        35                  40                  45

Asp Leu Pro Glu Asn Gly Pro Ala Tyr Trp His Leu Tyr Lys Lys Asp
    50                  55                  60

His Asp Ile Ala Glu Ser Leu Gly Met Asp Ala Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Asn Gly Asn Ile Ile Ser Ile Asp Val Pro Glu
            100                 105                 110

Ser Ala Ile Glu Glu Leu Glu Lys Leu Ala Asn Met Asp Ala Leu Asn
        115                 120                 125

His Tyr Arg Glu Ile Tyr Ser Asp Trp Lys Glu Arg Gly Lys Thr Phe
    130                 135                 140

Ile Leu Asn Leu Tyr His Trp Pro Leu Pro Leu Trp Leu His Asp Pro
145                 150                 155                 160

Ile Gly Val Arg Lys Leu Gly Pro Asp Arg Ala Pro Ser Gly Trp Leu
                165                 170                 175

Asp Glu Arg Ser Val Val Glu Phe Thr Lys Phe Ala Ala Phe Ile Ala
            180                 185                 190

Tyr His Leu Asp Asp Leu Val Asp Met Trp Ser Thr Met Asn Glu Pro
        195                 200                 205

Asn Val Val Tyr Glu Gln Gly Tyr Thr Arg Pro Gln Ser Gly Phe Pro
    210                 215                 220

Pro Gly Tyr Leu Ser His Glu Ala Ala Gly Lys Ala Lys Leu Asn Leu
225                 230                 235                 240

Met Gln Ala His Ala Arg Ala Tyr Asp Ala Ile Lys Glu His Ser Asp
                245                 250                 255

Lys Pro Val Gly Val Ile Tyr Ala Tyr Lys Trp Ile Asp Ala Glu Asp
            260                 265                 270

Glu Ala Ala Glu Glu Ser Val Leu Glu Leu Arg Arg Arg Asp Tyr Asp
        275                 280                 285

Phe Val Asp Gly Leu Tyr Ser Gly Lys Ser Leu Thr Ala Gly Glu Arg
    290                 295                 300

Glu Asp Phe Lys Gly Arg Val Asp Trp Val Gly Val Asn Tyr Tyr Ser
305                 310                 315                 320

Arg Leu Leu Phe Gly Lys Ala Gly Asp Ser Val Arg Leu Leu Glu Gly
                325                 330                 335

Tyr Gly Phe Val Ser Pro Arg Gly Gly Tyr Ala Lys Ser Gly Arg Pro
            340                 345                 350

Ala Ser Asp Phe Gly Trp Glu Ile Tyr Pro Glu Gly Leu Glu Lys Leu
        355                 360                 365

Leu Val Glu Leu Ser Gly Arg Tyr Glu Leu Pro Leu Phe Ile Thr Glu
    370                 375                 380

Asn Gly Met Ala Asp Ala Val Asp Arg Tyr Arg Pro Tyr Tyr Leu Val
385                 390                 395                 400
```

```
Ser His Leu Ala Ala Ile His Arg Ala Met Glu Lys Gly Ala Asp Ile
            405                 410                 415

Arg Gly Tyr Leu His Trp Ser Leu Thr Asp Asn Tyr Glu Trp Ala Gln
        420                 425                 430

Gly Phe Arg Met Arg Phe Gly Leu Val Met Val Asp Phe Glu Thr Lys
    435                 440                 445

Lys Arg Tyr Leu Arg Pro Ser Ala Leu Val Phe Arg Glu Ile Ala Thr
450                 455                 460

Arg Lys Glu Ile Pro Glu Leu Glu His Leu Ala Asp Val Asp Ala
465                 470                 475                 480

Ile Ile Ala Arg

<210> SEQ ID NO 23
<211> LENGTH: 1539
<212> TYPE: DNA
<213> ORGANISM: Artificial Sequence
<220> FEATURE:
<223> OTHER INFORMATION: AEPII 1a (clone # 63GA9)
<220> FEATURE:
<221> NAME/KEY: CDS
<222> LOCATION: (1)...(1539)

<400> SEQUENCE: 23 atg cta cca gaa gag ttc cta tgg ggc gtt ggg cag tca ggc ttt cag      48
Met Leu Pro Glu Glu Phe Leu Trp Gly Val Gly Gln Ser Gly Phe Gln
 1               5                  10                  15 ttc gaa atg ggc gac aag ctc agg agg cac atc gat cca aat acc gac      96
Phe Glu Met Gly Asp Lys Leu Arg Arg His Ile Asp Pro Asn Thr Asp
                20                  25                  30 tgg tgg aag tgg gtt cgc gat cct ttc aac ata aaa aag gag ctt gtg     144
Trp Trp Lys Trp Val Arg Asp Pro Phe Asn Ile Lys Lys Glu Leu Val
            35                  40                  45 agt ggg gac ctt ccc gag gac ggc atc aac aac tac gaa ctt ttt gaa     192
Ser Gly Asp Leu Pro Glu Asp Gly Ile Asn Asn Tyr Glu Leu Phe Glu
        50                  55                  60 aac gat cac aag ctc gct aaa ggc ctt gga ctc aac gca tac agg att     240
Asn Asp His Lys Leu Ala Lys Gly Leu Gly Leu Asn Ala Tyr Arg Ile
 65                  70                  75                  80 gga ata gag tgg agc aga atc ttt ccc tgg ccg acg tgg acg tcg gat     288
Gly Ile Glu Trp Ser Arg Ile Phe Pro Trp Pro Thr Trp Thr Val Asp
                85                  90                  95 acc gag gtc gag ttc gac act tac ggt tta gta aag gac gtt aag ata     336
Thr Glu Val Glu Phe Asp Thr Tyr Gly Leu Val Lys Asp Val Lys Ile
                100                 105                 110 gac aag tcc acc ctt gct gaa ctc gac agg ctg gcc aac aag gag gag     384
Asp Lys Ser Thr Leu Ala Glu Leu Asp Arg Leu Ala Asn Lys Glu Glu
            115                 120                 125 gta atg tac tac agg cgc gtt att cag cat ttg agg gag ctc ggc ttc     432
Val Met Tyr Tyr Arg Arg Val Ile Gln His Leu Arg Glu Leu Gly Phe
        130                 135                 140 aag gtc ttc gtt aac ctc aac cac ttc acg ctt cca ata tgg ctc cac     480
Lys Val Phe Val Asn Leu Asn His Phe Thr Leu Pro Ile Trp Leu His
145                 150                 155                 160 gac ccg ata gtg gca agg gag aag gcc ctc aca aac gac aga atc ggc     528
Asp Pro Ile Val Ala Arg Glu Lys Ala Leu Thr Asn Asp Arg Ile Gly
                165                 170                 175 tgg gtc tcc cag agg aca gtt gtt gag ttt gcc aag tat gct gct tac     576
Trp Val Ser Gln Arg Thr Val Val Glu Phe Ala Lys Tyr Ala Ala Tyr
            180                 185                 190 atc gcc cat gcg ctc gga gac ctc gtg gac aca tgg agc acc ttc aac     624
```

```
Ile Ala His Ala Leu Gly Asp Leu Val Asp Thr Trp Ser Thr Phe Asn
        195                 200                 205 gaa cct atg gta gtt gtg gag ctc ggc tac ctc gcc ccc tac tca gga        672
Glu Pro Met Val Val Val Glu Leu Gly Tyr Leu Ala Pro Tyr Ser Gly
    210                 215                 220 ttt ccc ccg gga gtc atg aac ccc gag gcc gcg aag ctg gcg atc ctc        720
Phe Pro Pro Gly Val Met Asn Pro Glu Ala Ala Lys Leu Ala Ile Leu
225                 230                 235                 240 aac atg ata aac gcc cac gcc ttg gca tat aag atg ata aag agg ttc        768
Asn Met Ile Asn Ala His Ala Leu Ala Tyr Lys Met Ile Lys Arg Phe
                245                 250                 255 gac acc aag aag gcc gat gag gat agc aag tcc cct gcg gac gtt ggc        816
Asp Thr Lys Lys Ala Asp Glu Asp Ser Lys Ser Pro Ala Asp Val Gly
            260                 265                 270 ata atc tac aac aac atc ggt gtt gcc tac cct aaa gac cct aac gat        864
Ile Ile Tyr Asn Asn Ile Gly Val Ala Tyr Pro Lys Asp Pro Asn Asp
        275                 280                 285 ccc aag gac gtt aaa gca gcc gaa aac gac aac tac ttc cac agc gga        912
Pro Lys Asp Val Lys Ala Ala Glu Asn Asp Asn Tyr Phe His Ser Gly
    290                 295                 300 ctg ttc ttt gat gcc atc cac aag ggt aag ctc aac ata gag ttc gac        960
Leu Phe Phe Asp Ala Ile His Lys Gly Lys Leu Asn Ile Glu Phe Asp
305                 310                 315                 320 ggc gaa aac ttt gta aaa gtt aga cac cta aaa ggc aat gac tgg ata       1008
Gly Glu Asn Phe Val Lys Val Arg His Leu Lys Gly Asn Asp Trp Ile
                325                 330                 335 ggc ctc aac tac tac acc cgc gag gtt gtt aga tat tcg gag ccc aag       1056
Gly Leu Asn Tyr Tyr Thr Arg Glu Val Val Arg Tyr Ser Glu Pro Lys
            340                 345                 350 ttc cca agt ata ccc ctc ata tcc ttc aag ggc gtt ccc aac tac ggc       1104
Phe Pro Ser Ile Pro Leu Ile Ser Phe Lys Gly Val Pro Asn Tyr Gly
        355                 360                 365 tac tcc tgc agg ccc ggc acg acc tcc gcc gat ggc atg ccc gtc agc       1152
Tyr Ser Cys Arg Pro Gly Thr Thr Ser Ala Asp Gly Met Pro Val Ser
    370                 375                 380 gat atc ggc tgg gaa gtc tat ccc cag gga atc tac gac tcg ata gtc       1200
Asp Ile Gly Trp Glu Val Tyr Pro Gln Gly Ile Tyr Asp Ser Ile Val
385                 390                 395                 400 gag gcc acc aag tac agt gtt cct gtt tac gtc acc gag aac ggt gtt       1248
Glu Ala Thr Lys Tyr Ser Val Pro Val Tyr Val Thr Glu Asn Gly Val
                405                 410                 415 gcg gat tcc gcg gac acg ctg agg cca tac tac ata gtc agc cac gtc       1296
Ala Asp Ser Ala Asp Thr Leu Arg Pro Tyr Tyr Ile Val Ser His Val
            420                 425                 430 tca aag ata gag gaa gcc att gag aat gga tac ccc gta aaa ggc tac       1344
Ser Lys Ile Glu Glu Ala Ile Glu Asn Gly Tyr Pro Val Lys Gly Tyr
        435                 440                 445 atg tac tgg gcg ctt acg gat aac tac gag tgg gcc ctc ggc ttc agc       1392
Met Tyr Trp Ala Leu Thr Asp Asn Tyr Glu Trp Ala Leu Gly Phe Ser
    450                 455                 460 atg agg ttt ggt ctc tac aag gtc gac ctc atc tcc aag gag agg atc       1440
Met Arg Phe Gly Leu Tyr Lys Val Asp Leu Ile Ser Lys Glu Arg Ile
465                 470                 475                 480 ccg agg gag aga agc gtt gag ata tat cgc agg ata gtg cag tcc aac       1488
Pro Arg Glu Arg Ser Val Glu Ile Tyr Arg Arg Ile Val Gln Ser Asn
                485                 490                 495 ggt gtt cct aag gat atc aaa gag gag ttc ctg aag ggt gag gag aaa       1536
Gly Val Pro Lys Asp Ile Lys Glu Glu Phe Leu Lys Gly Glu Glu Lys
            500                 505                 510
```

-continued tga                                                                                         1539
*

<210> SEQ ID NO 24
<211> LENGTH: 512
<212> TYPE: PRT
<213> ORGANISM: Artificial Sequence
<220> FEATURE:
<223> OTHER INFORMATION: AEPII 1a (clone # 63GP4)

<400> SEQUENCE: 24

Met Leu Pro Glu Glu Phe Leu Trp Gly Val Gly Gln Ser Gly Phe Gln
1               5                   10                  15

Phe Glu Met Gly Asp Lys Leu Arg Arg His Ile Asp Pro Asn Thr Asp
            20                  25                  30

Trp Trp Lys Trp Val Arg Asp Pro Phe Asn Ile Lys Lys Glu Leu Val
        35                  40                  45

Ser Gly Asp Leu Pro Glu Asp Gly Ile Asn Asn Tyr Glu Leu Phe Glu
    50                  55                  60

Asn Asp His Lys Leu Ala Lys Gly Leu Gly Leu Asn Ala Tyr Arg Ile
65                  70                  75                  80

Gly Ile Glu Trp Ser Arg Ile Phe Pro Trp Pro Thr Trp Thr Val Asp
                85                  90                  95

Thr Glu Val Glu Phe Asp Thr Tyr Gly Leu Val Lys Asp Val Lys Ile
            100                 105                 110

Asp Lys Ser Thr Leu Ala Glu Leu Asp Arg Leu Ala Asn Lys Glu Glu
        115                 120                 125

Val Met Tyr Tyr Arg Arg Val Ile Gln His Leu Arg Glu Leu Gly Phe
    130                 135                 140

Lys Val Phe Val Asn Leu Asn His Phe Thr Leu Pro Ile Trp Leu His
145                 150                 155                 160

Asp Pro Ile Val Ala Arg Glu Lys Ala Leu Thr Asn Asp Arg Ile Gly
                165                 170                 175

Trp Val Ser Gln Arg Thr Val Val Glu Phe Ala Lys Tyr Ala Ala Tyr
            180                 185                 190

Ile Ala His Ala Leu Gly Asp Leu Val Asp Thr Trp Ser Thr Phe Asn
        195                 200                 205

Glu Pro Met Val Val Glu Leu Gly Tyr Leu Ala Pro Tyr Ser Gly
    210                 215                 220

Phe Pro Pro Gly Val Met Asn Pro Glu Ala Ala Lys Leu Ala Ile Leu
225                 230                 235                 240

Asn Met Ile Asn Ala His Ala Leu Ala Tyr Lys Met Ile Lys Arg Phe
                245                 250                 255

Asp Thr Lys Lys Ala Asp Glu Asp Ser Lys Ser Pro Ala Asp Val Gly
            260                 265                 270

Ile Ile Tyr Asn Asn Ile Gly Val Ala Tyr Pro Lys Asp Pro Asn Asp
        275                 280                 285

Pro Lys Asp Val Lys Ala Ala Glu Asn Asp Asn Tyr Phe His Ser Gly
    290                 295                 300

Leu Phe Phe Asp Ala Ile His Lys Gly Lys Leu Asn Ile Glu Phe Asp
305                 310                 315                 320

Gly Glu Asn Phe Val Lys Val Arg His Leu Lys Gly Asn Asp Trp Ile
                325                 330                 335

Gly Leu Asn Tyr Tyr Thr Arg Glu Val Val Arg Tyr Ser Glu Pro Lys
            340                 345                 350

```
Phe Pro Ser Ile Pro Leu Ile Ser Phe Lys Gly Val Pro Asn Tyr Gly
            355                 360                 365

Tyr Ser Cys Arg Pro Gly Thr Thr Ser Ala Asp Gly Met Pro Val Ser
    370                 375                 380

Asp Ile Gly Trp Glu Val Tyr Pro Gln Gly Ile Tyr Asp Ser Ile Val
385                 390                 395                 400

Glu Ala Thr Lys Tyr Ser Val Pro Val Tyr Val Thr Glu Asn Gly Val
                405                 410                 415

Ala Asp Ser Ala Asp Thr Leu Arg Pro Tyr Tyr Ile Val Ser His Val
            420                 425                 430

Ser Lys Ile Glu Glu Ala Ile Glu Asn Gly Tyr Pro Val Lys Gly Tyr
        435                 440                 445

Met Tyr Trp Ala Leu Thr Asp Asn Tyr Glu Trp Ala Leu Gly Phe Ser
    450                 455                 460

Met Arg Phe Gly Leu Tyr Lys Val Asp Leu Ile Ser Lys Glu Arg Ile
465                 470                 475                 480

Pro Arg Glu Arg Ser Val Gly Ile Tyr Arg Arg Ile Val Gln Ser Asn
                485                 490                 495

Gly Val Pro Lys Asp Ile Lys Glu Glu Phe Leu Lys Gly Glu Glu Lys
            500                 505                 510

<210> SEQ ID NO 25
<211> LENGTH: 1539
<212> TYPE: DNA
<213> ORGANISM: Artificial Sequence
<220> FEATURE:
<223> OTHER INFORMATION: AEPII 1a (clone # 63GB1)
<220> FEATURE:
<221> NAME/KEY: CDS
<222> LOCATION: (1)...(1536)

<400> SEQUENCE: 25 atg cta cca gaa gag ttc cta tgg ggc gtt ggg cag tca ggc ttt cag      48
Met Leu Pro Glu Glu Phe Leu Trp Gly Val Gly Gln Ser Gly Phe Gln
  1               5                  10                  15 ttc gaa atg ggc gac aag ctc agg agg cac atc gat cca aat acc gac      96
Phe Glu Met Gly Asp Lys Leu Arg Arg His Ile Asp Pro Asn Thr Asp
                 20                  25                  30 tgg tgg aag tgg gtt cgc gat cct ttc aac ata aaa aag gag ctt gtg     144
Trp Trp Lys Trp Val Arg Asp Pro Phe Asn Ile Lys Lys Glu Leu Val
             35                  40                  45 agt ggg gac ctt ccc gag gac ggc atc aac aac tac gaa ctt ttt gaa     192
Ser Gly Asp Leu Pro Glu Asp Gly Ile Asn Asn Tyr Glu Leu Phe Glu
         50                  55                  60 aac gat cac aag ctc gct aaa ggc ctt gga ctc aac gca tac ggg att     240
Asn Asp His Lys Leu Ala Lys Gly Leu Gly Leu Asn Ala Tyr Gly Ile
 65                  70                  75                  80 gga ata gag tgg agc aga atc ttt ccc tgg ccg acg tgg acg gtc gat     288
Gly Ile Glu Trp Ser Arg Ile Phe Pro Trp Pro Thr Trp Thr Val Asp
                 85                  90                  95 acc gag gtc gag ttc gac act tac ggt tta gta aag gac gtt aag ata     336
Thr Glu Val Glu Phe Asp Thr Tyr Gly Leu Val Lys Asp Val Lys Ile
                100                 105                 110 gac aag tcc acc ctt gct gaa ctc gac agg ctg gcc aac aag gag gag     384
Asp Lys Ser Thr Leu Ala Glu Leu Asp Arg Leu Ala Asn Lys Glu Glu
            115                 120                 125 gta atg tac tac agg cgc gtt att cag cat ttg agg gag ctc ggc ttc     432
Val Met Tyr Tyr Arg Arg Val Ile Gln His Leu Arg Glu Leu Gly Phe
        130                 135                 140
```

```
aag gtc ttc gtt aac ctc aac cac ttc acg ctt cca ata tgg ctc cac      480
Lys Val Phe Val Asn Leu Asn His Phe Thr Leu Pro Ile Trp Leu His
145                 150                 155                 160 gac ccg ata gtg gca agg gag aag gcc ctc aca aac gac aga atc ggc      528
Asp Pro Ile Val Ala Arg Glu Lys Ala Leu Thr Asn Asp Arg Ile Gly
                165                 170                 175 tgg gtc tcc cag agg aca gtt gtt gag ttt gcc aag tat gct gct tac      576
Trp Val Ser Gln Arg Thr Val Val Glu Phe Ala Lys Tyr Ala Ala Tyr
            180                 185                 190 atc gcc cat gcg ctc gga gac ctc gtg gac aca tgg agc acc ttc aac      624
Ile Ala His Ala Leu Gly Asp Leu Val Asp Thr Trp Ser Thr Phe Asn
        195                 200                 205 gaa cct atg gta gtt gtg gag ctc gga tac ctc gcc ccc tac tca gga      672
Glu Pro Met Val Val Val Glu Leu Gly Tyr Leu Ala Pro Tyr Ser Gly
    210                 215                 220 ttt ccc ccg gga gtc atg aac ccc gag gcc gcg aag ctg gcg atc ctc      720
Phe Pro Pro Gly Val Met Asn Pro Glu Ala Ala Lys Leu Ala Ile Leu
225                 230                 235                 240 aac atg ata aac gcc cac gcc ttg gca tat aag atg ata aag agg ttc      768
Asn Met Ile Asn Ala His Ala Leu Ala Tyr Lys Met Ile Lys Arg Phe
                245                 250                 255 gac acc aag aag gcc gat gag gat agc aag tcc cct gcg gac gtt ggc      816
Asp Thr Lys Lys Ala Asp Glu Asp Ser Lys Ser Pro Ala Asp Val Gly
            260                 265                 270 ata atc tac aac aac atc ggt gtt gcc tac cct aaa gac cct aac gat      864
Ile Ile Tyr Asn Asn Ile Gly Val Ala Tyr Pro Lys Asp Pro Asn Asp
        275                 280                 285 ccc aag gac gtt aaa gca gcc gaa aac gac aac tac ttc cac agc gga      912
Pro Lys Asp Val Lys Ala Ala Glu Asn Asp Asn Tyr Phe His Ser Gly
    290                 295                 300 ctg ttc ttt gat gcc atc cac aag ggt aag ctc aac ata gag ttc gac      960
Leu Phe Phe Asp Ala Ile His Lys Gly Lys Leu Asn Ile Glu Phe Asp
305                 310                 315                 320 ggc gaa aac ttt gta aaa gtt aga cac cta aaa ggc aat gac tgg ata     1008
Gly Glu Asn Phe Val Lys Val Arg His Leu Lys Gly Asn Asp Trp Ile
                325                 330                 335 ggc ctc aac tac tac acc cgc gag gtt gtt aga tat tcg gag ccc aag     1056
Gly Leu Asn Tyr Tyr Thr Arg Glu Val Val Arg Tyr Ser Glu Pro Lys
            340                 345                 350 ttc cca agt ata ccc ctc ata tcc ttc aag ggc gtt ccc aac tac ggc     1104
Phe Pro Ser Ile Pro Leu Ile Ser Phe Lys Gly Val Pro Asn Tyr Gly
        355                 360                 365 tac tcc tgc agg ccc ggc acg acc tcc gcc gat ggc atg ccc gtc agc     1152
Tyr Ser Cys Arg Pro Gly Thr Thr Ser Ala Asp Gly Met Pro Val Ser
    370                 375                 380 gat atc ggc tgg gaa gtc tat ccc cag gga atc tac gac tcg ata gtc     1200
Asp Ile Gly Trp Glu Val Tyr Pro Gln Gly Ile Tyr Asp Ser Ile Val
385                 390                 395                 400 gag gcc acc aag tac agt gtt cct gtt tac gtc acc gag aac ggt gtt     1248
Glu Ala Thr Lys Tyr Ser Val Pro Val Tyr Val Thr Glu Asn Gly Val
                405                 410                 415 gcg gat tcc gcg gac acg ctg agg cca tac tac ata gtc agc cac gtc     1296
Ala Asp Ser Ala Asp Thr Leu Arg Pro Tyr Tyr Ile Val Ser His Val
            420                 425                 430 tca aag ata gag gaa gcc att gag aat gga tac ccc gta aaa ggc tac     1344
Ser Lys Ile Glu Glu Ala Ile Glu Asn Gly Tyr Pro Val Lys Gly Tyr
        435                 440                 445 atg tac tgg gcg ctt acg gat aac tac gag tgg gcc ctc ggc ttc agc     1392
Met Tyr Trp Ala Leu Thr Asp Asn Tyr Glu Trp Ala Leu Gly Phe Ser
    450                 455                 460
```

```
atg agg ttt ggt ctc tac aag gtc gac ctc atc tcc aag gag agg atc      1440
Met Arg Phe Gly Leu Tyr Lys Val Asp Leu Ile Ser Lys Glu Arg Ile
465                 470                 475                 480 ccg agg gag aga agc gtt gag ata tat cgc agg ata gtg cag tcc aac      1488
Pro Arg Glu Arg Ser Val Glu Ile Tyr Arg Arg Ile Val Gln Ser Asn
                485                 490                 495 ggt gtt cct aag gat atc aaa gag gag ttc ctg aag ggt gag gag aaa      1536
Gly Val Pro Lys Asp Ile Lys Glu Glu Phe Leu Lys Gly Glu Glu Lys
            500                 505                 510 tga                                                                   1539
```

<210> SEQ ID NO 26
<211> LENGTH: 512
<212> TYPE: PRT
<213> ORGANISM: Artificial Sequence
<220> FEATURE:
<223> OTHER INFORMATION: AEPII 1a (clone # 63GP4)

<400> SEQUENCE: 26

```
Met Leu Pro Glu Glu Phe Leu Trp Gly Val Gly Gln Ser Gly Phe Gln
1               5                   10                  15

Phe Glu Met Gly Asp Lys Leu Arg Arg His Ile Asp Pro Asn Thr Asp
            20                  25                  30

Trp Trp Lys Trp Val Arg Asp Pro Phe Asn Ile Lys Lys Glu Leu Val
        35                  40                  45

Ser Gly Asp Leu Pro Glu Asp Gly Ile Asn Asn Tyr Glu Leu Phe Glu
    50                  55                  60

Asn Asp His Lys Leu Ala Lys Gly Leu Gly Leu Asn Ala Tyr Gly Ile
65              70                  75                  80

Gly Ile Glu Trp Ser Arg Ile Phe Pro Trp Pro Thr Trp Thr Val Asp
                85                  90                  95

Thr Glu Val Glu Phe Asp Thr Tyr Gly Leu Val Lys Asp Val Lys Ile
            100                 105                 110

Asp Lys Ser Thr Leu Ala Glu Leu Asp Arg Leu Ala Asn Lys Glu Glu
        115                 120                 125

Val Met Tyr Tyr Arg Arg Val Ile Gln His Leu Arg Glu Leu Gly Phe
    130                 135                 140

Lys Val Phe Val Asn Leu Asn His Phe Thr Leu Pro Ile Trp Leu His
145             150                 155                 160

Asp Pro Ile Val Ala Arg Glu Lys Ala Leu Thr Asn Asp Arg Ile Gly
                165                 170                 175

Trp Val Ser Gln Arg Thr Val Val Glu Phe Ala Lys Tyr Ala Ala Tyr
            180                 185                 190

Ile Ala His Ala Leu Gly Asp Leu Val Asp Thr Trp Ser Thr Phe Asn
        195                 200                 205

Glu Pro Met Val Val Glu Leu Gly Tyr Leu Ala Pro Tyr Ser Gly
    210                 215                 220

Phe Pro Pro Gly Val Met Asn Pro Glu Ala Ala Lys Leu Ala Ile Leu
225             230                 235                 240

Asn Met Ile Asn Ala His Ala Leu Ala Tyr Lys Met Ile Lys Arg Phe
                245                 250                 255

Asp Thr Lys Lys Ala Asp Glu Asp Ser Lys Ser Pro Ala Asp Val Gly
            260                 265                 270

Ile Ile Tyr Asn Asn Ile Gly Val Ala Tyr Pro Lys Asp Pro Asn Asp
        275                 280                 285
```

```
Pro Lys Asp Val Lys Ala Ala Glu Asn Asp Asn Tyr Phe His Ser Gly
    290                 295                 300

Leu Phe Phe Asp Ala Ile His Lys Gly Lys Leu Asn Ile Glu Phe Asp
305                 310                 315                 320

Gly Glu Asn Phe Val Lys Val Arg His Leu Lys Gly Asn Asp Trp Ile
                325                 330                 335

Gly Leu Asn Tyr Tyr Thr Arg Glu Val Val Arg Tyr Ser Glu Pro Lys
                340                 345                 350

Phe Pro Ser Ile Pro Leu Ile Ser Phe Lys Gly Val Pro Asn Tyr Gly
                355                 360                 365

Tyr Ser Cys Arg Pro Gly Thr Thr Ser Ala Asp Gly Met Pro Val Ser
    370                 375                 380

Asp Ile Gly Trp Glu Val Tyr Pro Gln Gly Ile Tyr Asp Ser Ile Val
385                 390                 395                 400

Glu Ala Thr Lys Tyr Ser Val Pro Val Tyr Val Thr Glu Asn Gly Val
                405                 410                 415

Ala Asp Ser Ala Asp Thr Leu Arg Pro Tyr Tyr Ile Val Ser His Val
                420                 425                 430

Ser Lys Ile Glu Glu Ala Ile Glu Asn Gly Tyr Pro Val Lys Gly Tyr
                435                 440                 445

Met Tyr Trp Ala Leu Thr Asp Asn Tyr Glu Trp Ala Leu Gly Phe Ser
    450                 455                 460

Met Arg Phe Gly Leu Tyr Lys Val Asp Leu Ile Ser Lys Glu Arg Ile
465                 470                 475                 480

Pro Arg Glu Arg Ser Val Glu Ile Tyr Arg Arg Ile Val Gln Ser Asn
                485                 490                 495

Gly Val Pro Lys Asp Ile Lys Glu Glu Phe Leu Lys Gly Glu Glu Lys
                500                 505                 510
```

<210> SEQ ID NO 27
<211> LENGTH: 1575
<212> TYPE: DNA
<213> ORGANISM: Artificial Sequence
<220> FEATURE:
<223> OTHER INFORMATION: AEPII 1a (clone # 63GP1)
<220> FEATURE:
<221> NAME/KEY: CDS
<222> LOCATION: (1)...(1572)

<400> SEQUENCE: 27

```
atg cgt cca ttc ttg tta att tct att ttg gac ttt cga gtt gct gac    48
Met Arg Pro Phe Leu Leu Ile Ser Ile Leu Asp Phe Arg Val Ala Asp
  1               5                  10                  15 tac ctc caa cgt aac ata aag aca caa aac caa tat tgg gca ttg tgc    96
Tyr Leu Gln Arg Asn Ile Lys Thr Gln Asn Gln Tyr Trp Ala Leu Cys
             20                  25                  30 gta gta atg ttc tcc aat gtt ctt aga tgg caa aac tta aat att tca   144
Val Val Met Phe Ser Asn Val Leu Arg Trp Gln Asn Leu Asn Ile Ser
         35                  40                  45 cca gcg gtg ata cat aga gac acc gct gaa cac aga ggt gat tcc atg   192
Pro Ala Val Ile His Arg Asp Thr Ala Glu His Arg Gly Asp Ser Met
     50                  55                  60 aag aag ttt gtc gcc ctg ttc ata acc atg ttt ttc gta gtg agc atg   240
Lys Lys Phe Val Ala Leu Phe Ile Thr Met Phe Phe Val Val Ser Met
 65                  70                  75                  80 gca gtc gtt gca cag cca gct agc gcc gca aag tat tcc gag ctc gaa   288
Ala Val Val Ala Gln Pro Ala Ser Ala Ala Lys Tyr Ser Glu Leu Glu
                 85                  90                  95
```

```
gaa ggc ggc gtt ata atg cag gcc ttc tac tgg gac gtc cca ggt gga    336
Glu Gly Gly Val Ile Met Gln Ala Phe Tyr Trp Asp Val Pro Gly Gly
            100                 105                 110 gga atc tgg tgg gac acc atc agg agc aag ata ccg gag tgg tac gag    384
Gly Ile Trp Trp Asp Thr Ile Arg Ser Lys Ile Pro Glu Trp Tyr Glu
        115                 120                 125 gcg gga ata tcc gcc att tgg att ccg cca gcc agc aag ggg atg agc    432
Ala Gly Ile Ser Ala Ile Trp Ile Pro Pro Ala Ser Lys Gly Met Ser
    130                 135                 140 ggc ggt tac tcg atg ggc tac gat ccc tac gat ttc ttt gac ctc ggc    480
Gly Gly Tyr Ser Met Gly Tyr Asp Pro Tyr Asp Phe Phe Asp Leu Gly
145                 150                 155                 160 gag tac aac cag aag gga acc atc gaa acg cgc ttt ggc tct aaa cag    528
Glu Tyr Asn Gln Lys Gly Thr Ile Glu Thr Arg Phe Gly Ser Lys Gln
                165                 170                 175 gag ctc atc aat atg ata aac acg gcc cat gcc tac ggc ata aag gtc    576
Glu Leu Ile Asn Met Ile Asn Thr Ala His Ala Tyr Gly Ile Lys Val
            180                 185                 190 ata gcg gac atc gtc ata aac cac cgc gca ggc gga gac ctc gag tgg    624
Ile Ala Asp Ile Val Ile Asn His Arg Ala Gly Gly Asp Leu Glu Trp
        195                 200                 205 aac ccg ttc gtt ggg gac tac acc tgg acg gac ttc tca aag gtg gcc    672
Asn Pro Phe Val Gly Asp Tyr Thr Trp Thr Asp Phe Ser Lys Val Ala
    210                 215                 220 tcg ggc aaa tat act gcc aac tac ctc gac ttc cac ccc aac gag gtc    720
Ser Gly Lys Tyr Thr Ala Asn Tyr Leu Asp Phe His Pro Asn Glu Val
225                 230                 235                 240 aag tgc tgt gac gag ggc aca ttt gga ggc ttc cca gac ata gcc cac    768
Lys Cys Cys Asp Glu Gly Thr Phe Gly Gly Phe Pro Asp Ile Ala His
                245                 250                 255 gag aag agc tgg gac cag cac tgg ctc tgg gcg agc gat gag agc tac    816
Glu Lys Ser Trp Asp Gln His Trp Leu Trp Ala Ser Asp Glu Ser Tyr
            260                 265                 270 gcc gcc tac cta agg agc atc ggc gtt gat gcc tgg cgc ttt gac tac    864
Ala Ala Tyr Leu Arg Ser Ile Gly Val Asp Ala Trp Arg Phe Asp Tyr
        275                 280                 285 gtg aag ggc tac gga gcg tgg gtc gtc aag gac tgg ctc aac tgg tgg    912
Val Lys Gly Tyr Gly Ala Trp Val Val Lys Asp Trp Leu Asn Trp Trp
    290                 295                 300 ggc ggc tgg gcc gtt ggc gag tac tgg gac acc aac gtt gat gca ctc    960
Gly Gly Trp Ala Val Gly Glu Tyr Trp Asp Thr Asn Val Asp Ala Leu
305                 310                 315                 320 ctc aac tgg gcc tac tcg agc ggc gcc aag gtc ttc gac ttc ccg ctc   1008
Leu Asn Trp Ala Tyr Ser Ser Gly Ala Lys Val Phe Asp Phe Pro Leu
                325                 330                 335 tac tac aag atg gat gag gcc ttt gac aac aaa aac att cca gcg ctc   1056
Tyr Tyr Lys Met Asp Glu Ala Phe Asp Asn Lys Asn Ile Pro Ala Leu
            340                 345                 350 gtc tct gcc ctt cag aac ggc cag act gtt gtc tcc cgc gac ccg ttc   1104
Val Ser Ala Leu Gln Asn Gly Gln Thr Val Val Ser Arg Asp Pro Phe
        355                 360                 365 aag gcc gta acc ttt gta gca aac cac gac acc gat ata atc tgg aac   1152
Lys Ala Val Thr Phe Val Ala Asn His Asp Thr Asp Ile Ile Trp Asn
    370                 375                 380 aag tac ctt gct tat gct ttc atc ctc acc tac gaa ggc cag ccc gtc   1200
Lys Tyr Leu Ala Tyr Ala Phe Ile Leu Thr Tyr Glu Gly Gln Pro Val
385                 390                 395                 400 ata ttt tac cgc gac tac gag gag tgg ctc aac aag gac agg ttg aac   1248
Ile Phe Tyr Arg Asp Tyr Glu Glu Trp Leu Asn Lys Asp Arg Leu Asn
                405                 410                 415
```

-continued

| | | | | | | | | | | | | | | |
|---|---|---|---|---|---|---|---|---|---|---|---|---|---|---|
| aac | ctc | ata | tgg | ata | cac | gac | cac | ctc | gca | ggt | gga | agc | acg | agc | ata | 1296 |
| Asn | Leu | Ile | Trp | Ile | His | Asp | His | Leu | Ala | Gly | Gly | Ser | Thr | Ser | Ile | |
| | | 420 | | | | 425 | | | | 430 | | | | | |

```
aac ctc ata tgg ata cac gac cac ctc gca ggt gga agc acg agc ata      1296
Asn Leu Ile Trp Ile His Asp His Leu Ala Gly Gly Ser Thr Ser Ile
            420                 425                 430 gtt tac tac gac agc gac gag atg att ttc gtg agg aac ggc tat gga      1344
Val Tyr Tyr Asp Ser Asp Glu Met Ile Phe Val Arg Asn Gly Tyr Gly
            435                 440                 445 agc aag cct ggc ctt ata act tac atc aac ctc ggc tcg agc aag gtt      1392
Ser Lys Pro Gly Leu Ile Thr Tyr Ile Asn Leu Gly Ser Ser Lys Val
            450                 455                 460 gga agg tgg gtt tat gtg ccg aag ttc gcg ggc gcg tgc atc cac gag      1440
Gly Arg Trp Val Tyr Val Pro Lys Phe Ala Gly Ala Cys Ile His Glu
465                 470                 475                 480 tat act ggt aac ctc gga ggc tgg gta gac aag tac gtc tac tca agc      1488
Tyr Thr Gly Asn Leu Gly Gly Trp Val Asp Lys Tyr Val Tyr Ser Ser
            485                 490                 495 ggc tgg gtc tat ttc gaa gct cca gct tac gac cct gcc aac ggg cag      1536
Gly Trp Val Tyr Phe Glu Ala Pro Ala Tyr Asp Pro Ala Asn Gly Gln
            500                 505                 510 tat ggc tac tcc gtg tgg agc tat tgc ggt gtt ggg tga                  1575
Tyr Gly Tyr Ser Val Trp Ser Tyr Cys Gly Val Gly
            515                 520
```

<210> SEQ ID NO 28
<211> LENGTH: 524
<212> TYPE: PRT
<213> ORGANISM: Artificial Sequence
<220> FEATURE:
<223> OTHER INFORMATION: AEPII 1a (clone # 63GP4)

<400> SEQUENCE: 28

```
Met Arg Pro Phe Leu Leu Ile Ser Ile Leu Asp Phe Arg Val Ala Asp
 1               5                  10                  15

Tyr Leu Gln Arg Asn Ile Lys Thr Gln Asn Gln Tyr Trp Ala Leu Cys
                20                  25                  30

Val Val Met Phe Ser Asn Val Leu Arg Trp Gln Asn Leu Asn Ile Ser
            35                  40                  45

Pro Ala Val Ile His Arg Asp Thr Ala Glu His Arg Gly Asp Ser Met
        50                  55                  60

Lys Lys Phe Val Ala Leu Phe Ile Thr Met Phe Phe Val Val Ser Met
65                  70                  75                  80

Ala Val Val Ala Gln Pro Ala Ser Ala Lys Tyr Ser Glu Leu Glu
                85                  90                  95

Glu Gly Gly Val Ile Met Gln Ala Phe Tyr Trp Asp Val Pro Gly Gly
                100                 105                 110

Gly Ile Trp Trp Asp Thr Ile Arg Ser Lys Ile Pro Glu Trp Tyr Glu
            115                 120                 125

Ala Gly Ile Ser Ala Ile Trp Ile Pro Pro Ala Ser Lys Gly Met Ser
        130                 135                 140

Gly Gly Tyr Ser Met Gly Tyr Asp Pro Tyr Asp Phe Phe Asp Leu Gly
145                 150                 155                 160

Glu Tyr Asn Gln Lys Gly Thr Ile Glu Thr Arg Phe Gly Ser Lys Gln
                165                 170                 175

Glu Leu Ile Asn Met Ile Asn Thr Ala His Ala Tyr Gly Ile Lys Val
            180                 185                 190

Ile Ala Asp Ile Val Ile Asn His Arg Ala Gly Gly Asp Leu Glu Trp
        195                 200                 205

Asn Pro Phe Val Gly Asp Tyr Thr Trp Thr Asp Phe Ser Lys Val Ala
```

-continued

| | | 210 | | | 215 | | | 220 | | | |
|---|---|---|---|---|---|---|---|---|---|---|---|
Ser Gly Lys Tyr Thr Ala Asn Tyr Leu Asp Phe His Pro Asn Glu Val
225                 230                 235                 240

Lys Cys Cys Asp Glu Gly Thr Phe Gly Gly Phe Pro Asp Ile Ala His
            245                 250                 255

Glu Lys Ser Trp Asp Gln His Trp Leu Trp Ala Ser Asp Glu Ser Tyr
        260                 265                 270

Ala Ala Tyr Leu Arg Ser Ile Gly Val Asp Ala Trp Arg Phe Asp Tyr
    275                 280                 285

Val Lys Gly Tyr Gly Ala Trp Val Val Lys Asp Trp Leu Asn Trp Trp
290                 295                 300

Gly Gly Trp Ala Val Gly Glu Tyr Trp Asp Thr Asn Val Asp Ala Leu
305                 310                 315                 320

Leu Asn Trp Ala Tyr Ser Ser Gly Ala Lys Val Phe Asp Phe Pro Leu
            325                 330                 335

Tyr Tyr Lys Met Asp Glu Ala Phe Asp Asn Lys Asn Ile Pro Ala Leu
        340                 345                 350

Val Ser Ala Leu Gln Asn Gly Gln Thr Val Val Ser Arg Asp Pro Phe
    355                 360                 365

Lys Ala Val Thr Phe Val Ala Asn His Asp Thr Asp Ile Ile Trp Asn
370                 375                 380

Lys Tyr Leu Ala Tyr Ala Phe Ile Leu Thr Tyr Glu Gly Gln Pro Val
385                 390                 395                 400

Ile Phe Tyr Arg Asp Tyr Glu Glu Trp Leu Asn Lys Asp Arg Leu Asn
            405                 410                 415

Asn Leu Ile Trp Ile His Asp His Leu Ala Gly Gly Ser Thr Ser Ile
        420                 425                 430

Val Tyr Tyr Asp Ser Asp Glu Met Ile Phe Val Arg Asn Gly Tyr Gly
    435                 440                 445

Ser Lys Pro Gly Leu Ile Thr Tyr Ile Asn Leu Gly Ser Ser Lys Val
450                 455                 460

Gly Arg Trp Val Tyr Val Pro Lys Phe Ala Gly Ala Cys Ile His Glu
465                 470                 475                 480

Tyr Thr Gly Asn Leu Gly Gly Trp Val Asp Lys Tyr Val Tyr Ser Ser
            485                 490                 495

Gly Trp Val Tyr Phe Glu Ala Pro Ala Tyr Asp Pro Ala Asn Gly Gln
        500                 505                 510

Tyr Gly Tyr Ser Val Trp Ser Tyr Cys Gly Val Gly
    515                 520

<210> SEQ ID NO 29
<211> LENGTH: 1887
<212> TYPE: DNA
<213> ORGANISM: Artificial Sequence
<220> FEATURE:
<223> OTHER INFORMATION: AEPII 1a (clone # 63GP2)
<220> FEATURE:
<221> NAME/KEY: CDS
<222> LOCATION: (1)...(1884)

<400> SEQUENCE: 29

```
atg ata aac gtt gca acg gga gag gag acc cca ata cac ctc ttt gga    48
Met Ile Asn Val Ala Thr Gly Glu Glu Thr Pro Ile His Leu Phe Gly
 1               5                  10                  15 gtc aac tgg ttc ggc ttt gag aca ccg aac tac gtt gtt cac ggc cta    96
Val Asn Trp Phe Gly Phe Glu Thr Pro Asn Tyr Val Val His Gly Leu
            20                  25                  30
```

|     |     |     |     |     |     |     |     |     |     |     |     |     |     |     |     |     |
|---|---|---|---|---|---|---|---|---|---|---|---|---|---|---|---|---|
| tgg | agt | agg | aac | tgg | gag | gac | atg | ctc | ctc | cag | atc | aag | agc | ctt | ggc | 144 |
| Trp | Ser | Arg | Asn | Trp | Glu | Asp | Met | Leu | Leu | Gln | Ile | Lys | Ser | Leu | Gly |     |
|     |     | 35  |     |     |     | 40  |     |     |     |     | 45  |     |     |     |     |     |
| ttc | aat | gcg | ata | agg | ctt | ccc | ttc | tgt | acc | cag | tca | gta | aaa | ccg | ggg | 192 |
| Phe | Asn | Ala | Ile | Arg | Leu | Pro | Phe | Cys | Thr | Gln | Ser | Val | Lys | Pro | Gly |     |
|     | 50  |     |     |     |     | 55  |     |     |     |     | 60  |     |     |     |     |     |
| acg | atg | cca | acg | gcg | att | gac | tac | gcc | aag | aac | cca | gac | ctc | cag | ggt | 240 |
| Thr | Met | Pro | Thr | Ala | Ile | Asp | Tyr | Ala | Lys | Asn | Pro | Asp | Leu | Gln | Gly |     |
| 65  |     |     |     | 70  |     |     |     |     | 75  |     |     |     |     | 80  |     |     |
| ctt | gac | agc | gtc | cag | ata | atg | gag | aaa | ata | atc | aag | aag | gct | gga | gac | 288 |
| Leu | Asp | Ser | Val | Gln | Ile | Met | Glu | Lys | Ile | Ile | Lys | Lys | Ala | Gly | Asp |     |
|     |     |     |     | 85  |     |     |     |     | 90  |     |     |     |     | 95  |     |     |
| ctg | ggc | ata | ttc | gtg | ctc | ctc | gac | tac | cac | aga | ata | gga | tgc | aac | ttc | 336 |
| Leu | Gly | Ile | Phe | Val | Leu | Leu | Asp | Tyr | His | Arg | Ile | Gly | Cys | Asn | Phe |     |
|     |     |     | 100 |     |     |     |     | 105 |     |     |     |     | 110 |     |     |     |
| ata | gaa | ccc | cta | tgg | tac | acc | gac | agc | ttc | tcg | gag | cag | gac | tac | ata | 384 |
| Ile | Glu | Pro | Leu | Trp | Tyr | Thr | Asp | Ser | Phe | Ser | Glu | Gln | Asp | Tyr | Ile |     |
|     |     | 115 |     |     |     |     | 120 |     |     |     |     | 125 |     |     |     |     |
| aac | acc | tgg | gtt | gaa | gtc | gcc | cag | agg | ttc | ggc | aag | tac | tgg | aac | gtt | 432 |
| Asn | Thr | Trp | Val | Glu | Val | Ala | Gln | Arg | Phe | Gly | Lys | Tyr | Trp | Asn | Val |     |
|     | 130 |     |     |     |     | 135 |     |     |     |     | 140 |     |     |     |     |     |
| atc | ggc | gcg | gac | ctg | aag | aac | gaa | ccc | cac | agc | tca | agc | ccc | gca | cct | 480 |
| Ile | Gly | Ala | Asp | Leu | Lys | Asn | Glu | Pro | His | Ser | Ser | Ser | Pro | Ala | Pro |     |
| 145 |     |     |     |     | 150 |     |     |     |     | 155 |     |     |     |     | 160 |     |
| gcc | gcc | tac | act | gac | gga | agt | ggg | gcc | acg | tgg | gga | atg | ggc | aac | aac | 528 |
| Ala | Ala | Tyr | Thr | Asp | Gly | Ser | Gly | Ala | Thr | Trp | Gly | Met | Gly | Asn | Asn |     |
|     |     |     |     | 165 |     |     |     |     | 170 |     |     |     |     | 175 |     |     |
| gcc | acc | gac | tgg | aac | ctg | gcg | gct | gag | agg | ata | gga | agg | gca | att | ctg | 576 |
| Ala | Thr | Asp | Trp | Asn | Leu | Ala | Ala | Glu | Arg | Ile | Gly | Arg | Ala | Ile | Leu |     |
|     |     |     | 180 |     |     |     |     | 185 |     |     |     |     | 190 |     |     |     |
| gag | gtt | gcc | cca | caa | tgg | gtt | ata | ttt | gtt | gag | gga | acc | cag | ttc | acc | 624 |
| Glu | Val | Ala | Pro | Gln | Trp | Val | Ile | Phe | Val | Glu | Gly | Thr | Gln | Phe | Thr |     |
|     |     | 195 |     |     |     |     | 200 |     |     |     |     | 205 |     |     |     |     |
| acc | ccc | gag | ata | gac | ggt | agg | tac | aag | tgg | ggc | cac | aac | gcc | tgg | tgg | 672 |
| Thr | Pro | Glu | Ile | Asp | Gly | Arg | Tyr | Lys | Trp | Gly | His | Asn | Ala | Trp | Trp |     |
|     | 210 |     |     |     |     | 215 |     |     |     |     | 220 |     |     |     |     |     |
| ggc | gga | aac | ctt | atg | ggt | gtt | agg | aag | tac | cca | gtt | aac | ctg | ccc | agg | 720 |
| Gly | Gly | Asn | Leu | Met | Gly | Val | Arg | Lys | Tyr | Pro | Val | Asn | Leu | Pro | Arg |     |
| 225 |     |     |     |     | 230 |     |     |     |     | 235 |     |     |     |     | 240 |     |
| gac | aag | ctt | gtt | tac | agc | ccc | caa | gtt | tac | ggt | cca | gac | gtt | tac | gac | 768 |
| Asp | Lys | Leu | Val | Tyr | Ser | Pro | Gln | Val | Tyr | Gly | Pro | Asp | Val | Tyr | Asp |     |
|     |     |     |     | 245 |     |     |     |     | 250 |     |     |     |     | 255 |     |     |
| cag | ccc | tac | ttt | gac | ccc | ggt | gag | ggg | ttc | ccc | gac | aac | ctc | ccc | gaa | 816 |
| Gln | Pro | Tyr | Phe | Asp | Pro | Gly | Glu | Gly | Phe | Pro | Asp | Asn | Leu | Pro | Glu |     |
|     |     |     | 260 |     |     |     |     | 265 |     |     |     |     | 270 |     |     |     |
| ata | tgg | tac | cac | cac | ttc | ggc | tac | gta | aag | ctt | gat | ctc | ggt | tac | cct | 864 |
| Ile | Trp | Tyr | His | His | Phe | Gly | Tyr | Val | Lys | Leu | Asp | Leu | Gly | Tyr | Pro |     |
|     |     | 275 |     |     |     |     | 280 |     |     |     |     | 285 |     |     |     |     |
| gtt | gtt | ata | ggt | gag | ttc | gga | ggc | aag | tac | ggc | cat | ggg | gga | gac | ccg | 912 |
| Val | Val | Ile | Gly | Glu | Phe | Gly | Gly | Lys | Tyr | Gly | His | Gly | Gly | Asp | Pro |     |
|     | 290 |     |     |     |     | 295 |     |     |     |     | 300 |     |     |     |     |     |
| agg | gat | gtc | act | tgg | cag | aac | aag | ata | ata | gac | tgg | atg | atc | cag | aac | 960 |
| Arg | Asp | Val | Thr | Trp | Gln | Asn | Lys | Ile | Ile | Asp | Trp | Met | Ile | Gln | Asn |     |
| 305 |     |     |     |     | 310 |     |     |     |     | 315 |     |     |     |     | 320 |     |
| aaa | ttc | tgt | gac | ttc | ttc | tac | tgg | agc | tgg | aac | cca | aac | agc | ggt | gac | 1008 |
| Lys | Phe | Cys | Asp | Phe | Phe | Tyr | Trp | Ser | Trp | Asn | Pro | Asn | Ser | Gly | Asp |     |
|     |     |     |     | 325 |     |     |     |     | 330 |     |     |     |     | 335 |     |     |
| acc | ggt | gga | att | ctg | aag | gat | gac | tgg | acg | aca | ata | tgg | gag | gac | aag | 1056 |
| Thr | Gly | Gly | Ile | Leu | Lys | Asp | Asp | Trp | Thr | Thr | Ile | Trp | Glu | Asp | Lys |     |

```
                     340                 345                 350
tac aac aac ctg aag agg ctc atg gac agc tgt tct gga aac gcc act    1104
Tyr Asn Asn Leu Lys Arg Leu Met Asp Ser Cys Ser Gly Asn Ala Thr
        355                 360                 365 gcc ccg tcc gtc ccc acg aca act aca aca agc aca ccg cca acg        1152
Ala Pro Ser Val Pro Thr Thr Thr Thr Thr Ser Thr Pro Pro Thr
370                 375                 380 acc aca acg act aca aca tcc act cca acg acc act acc cag acc ccg    1200
Thr Thr Thr Thr Thr Thr Ser Thr Pro Thr Thr Thr Thr Gln Thr Pro
385                 390                 395                 400 acc acc act act cca act acg aca acc acc acg acc aca act cct tca    1248
Thr Thr Thr Thr Pro Thr Thr Thr Thr Thr Thr Thr Thr Thr Pro Ser
                405                 410                 415 aat aac gtc cca ttt gaa att gtg aac gtt ctc ccg act agc tcc cag    1296
Asn Asn Val Pro Phe Glu Ile Val Asn Val Leu Pro Thr Ser Ser Gln
                420                 425                 430 tac gag gga acc agc gtg gag gtt gta tgt gat gga acc cag tgt gcc    1344
Tyr Glu Gly Thr Ser Val Glu Val Val Cys Asp Gly Thr Gln Cys Ala
                435                 440                 445 tcc agc gtt tgg gga gct ccg aac ctc tgg gga gtc gtt aaa atc gga    1392
Ser Ser Val Trp Gly Ala Pro Asn Leu Trp Gly Val Val Lys Ile Gly
450                 455                 460 aac gcc acc atg gac ccc aac gtt tgg ggc tgg gag gac gtt tac aag    1440
Asn Ala Thr Met Asp Pro Asn Val Trp Gly Trp Glu Asp Val Tyr Lys
465                 470                 475                 480 act gca ccc cag gac att gga acc ggc agc aca aag atg gag ata agg    1488
Thr Ala Pro Gln Asp Ile Gly Thr Gly Ser Thr Lys Met Glu Ile Arg
                485                 490                 495 aac ggg gtg ctc aag gtt aca aac ctc tgg aac atc aac atg cat ccg    1536
Asn Gly Val Leu Lys Val Thr Asn Leu Trp Asn Ile Asn Met His Pro
                500                 505                 510 aag tat aac aca atg gca tac ccg gag gtc ata tac ggc gcc aag cct    1584
Lys Tyr Asn Thr Met Ala Tyr Pro Glu Val Ile Tyr Gly Ala Lys Pro
                515                 520                 525 tgg ggc aac cag cca ata aac gct ccg aac ttc gtg ctc ccg ata aag    1632
Trp Gly Asn Gln Pro Ile Asn Ala Pro Asn Phe Val Leu Pro Ile Lys
530                 535                 540 gtc tcc cag ctt ccg agg ata ctc gtt gac aca aag tac acg ctc gaa    1680
Val Ser Gln Leu Pro Arg Ile Leu Val Asp Thr Lys Tyr Thr Leu Glu
545                 550                 555                 560 aag agc ttc ccg gga aac aac ttc gcc ttt gag gcc tgg ctc ttc aag    1728
Lys Ser Phe Pro Gly Asn Asn Phe Ala Phe Glu Ala Trp Leu Phe Lys
                565                 570                 575 gat gcc aac aac atg agg gca cca ggc cag ggg gac tac gag agg aat    1776
Asp Ala Asn Asn Met Arg Ala Pro Gly Gln Gly Asp Tyr Glu Arg Asn
                580                 585                 590 tcc gcc gat act gac ggg ctc cag gag tcg tcg cca cca atc ccc ata    1824
Ser Ala Asp Thr Asp Gly Leu Gln Glu Ser Ser Pro Pro Ile Pro Ile
                595                 600                 605 tgg aaa ccg tcg ata agc ttg cgg ccg cca ccg cgg tgg agc tcc agc    1872
Trp Lys Pro Ser Ile Ser Leu Arg Pro Pro Pro Arg Trp Ser Ser Ser
610                 615                 620 ttt tgt tcc ctt taa                                                1887
Phe Cys Ser Leu
625

<210> SEQ ID NO 30
<211> LENGTH: 628
<212> TYPE: PRT
<213> ORGANISM: Artificial Sequence
```

```
<220> FEATURE:
<223> OTHER INFORMATION: AEPII 1a (clone # 63GP4)

<400> SEQUENCE: 30

Met Ile Asn Val Ala Thr Gly Glu Glu Thr Pro Ile His Leu Phe Gly
 1               5                  10                  15

Val Asn Trp Phe Gly Phe Glu Thr Pro Asn Tyr Val Val His Gly Leu
             20                  25                  30

Trp Ser Arg Asn Trp Glu Asp Met Leu Leu Gln Ile Lys Ser Leu Gly
         35                  40                  45

Phe Asn Ala Ile Arg Leu Pro Phe Cys Thr Gln Ser Val Lys Pro Gly
 50                  55                  60

Thr Met Pro Thr Ala Ile Asp Tyr Ala Lys Asn Pro Asp Leu Gln Gly
65                  70                  75                  80

Leu Asp Ser Val Gln Ile Met Glu Lys Ile Ile Lys Lys Ala Gly Asp
                 85                  90                  95

Leu Gly Ile Phe Val Leu Leu Asp Tyr His Arg Ile Gly Cys Asn Phe
             100                 105                 110

Ile Glu Pro Leu Trp Tyr Thr Asp Ser Phe Ser Glu Gln Asp Tyr Ile
         115                 120                 125

Asn Thr Trp Val Glu Val Ala Gln Arg Phe Gly Lys Tyr Trp Asn Val
130                 135                 140

Ile Gly Ala Asp Leu Lys Asn Glu Pro His Ser Ser Pro Ala Pro
145                 150                 155                 160

Ala Ala Tyr Thr Asp Gly Ser Gly Ala Thr Trp Gly Met Gly Asn Asn
                 165                 170                 175

Ala Thr Asp Trp Asn Leu Ala Ala Glu Arg Ile Gly Arg Ala Ile Leu
             180                 185                 190

Glu Val Ala Pro Gln Trp Val Ile Phe Val Glu Gly Thr Gln Phe Thr
         195                 200                 205

Thr Pro Glu Ile Asp Gly Arg Tyr Lys Trp Gly His Asn Ala Trp Trp
210                 215                 220

Gly Gly Asn Leu Met Gly Val Arg Lys Tyr Pro Val Asn Leu Pro Arg
225                 230                 235                 240

Asp Lys Leu Val Tyr Ser Pro Gln Val Tyr Gly Pro Asp Val Tyr Asp
                 245                 250                 255

Gln Pro Tyr Phe Asp Pro Gly Glu Gly Phe Pro Asp Asn Leu Pro Glu
             260                 265                 270

Ile Trp Tyr His His Phe Gly Tyr Val Lys Leu Asp Leu Gly Tyr Pro
         275                 280                 285

Val Val Ile Gly Glu Phe Gly Gly Lys Tyr Gly His Gly Gly Asp Pro
290                 295                 300

Arg Asp Val Thr Trp Gln Asn Lys Ile Ile Asp Trp Met Ile Gln Asn
305                 310                 315                 320

Lys Phe Cys Asp Phe Phe Tyr Trp Ser Trp Asn Pro Asn Ser Gly Asp
                 325                 330                 335

Thr Gly Gly Ile Leu Lys Asp Asp Trp Thr Thr Ile Trp Glu Asp Lys
             340                 345                 350

Tyr Asn Asn Leu Lys Arg Leu Met Asp Ser Cys Ser Gly Asn Ala Thr
         355                 360                 365

Ala Pro Ser Val Pro Thr Thr Thr Thr Thr Ser Thr Pro Pro Thr
370                 375                 380

Thr Thr Thr Thr Thr Thr Ser Pro Thr Thr Thr Thr Gln Thr Pro
385                 390                 395                 400
```

```
Thr Thr Thr Thr Pro Thr Thr Thr Thr Thr Thr Thr Thr Pro Ser
                405                 410                 415

Asn Asn Val Pro Phe Glu Ile Val Asn Val Leu Pro Thr Ser Ser Gln
            420                 425                 430

Tyr Glu Gly Thr Ser Val Glu Val Val Cys Asp Gly Thr Gln Cys Ala
        435                 440                 445

Ser Ser Val Trp Gly Ala Pro Asn Leu Trp Gly Val Val Lys Ile Gly
    450                 455                 460

Asn Ala Thr Met Asp Pro Asn Val Trp Gly Trp Glu Asp Val Tyr Lys
465                 470                 475                 480

Thr Ala Pro Gln Asp Ile Gly Thr Gly Ser Thr Lys Met Glu Ile Arg
                485                 490                 495

Asn Gly Val Leu Lys Val Thr Asn Leu Trp Asn Ile Asn Met His Pro
            500                 505                 510

Lys Tyr Asn Thr Met Ala Tyr Pro Glu Val Ile Tyr Gly Ala Lys Pro
        515                 520                 525

Trp Gly Asn Gln Pro Ile Asn Ala Pro Asn Phe Val Leu Pro Ile Lys
    530                 535                 540

Val Ser Gln Leu Pro Arg Ile Leu Val Asp Thr Lys Tyr Thr Leu Glu
545                 550                 555                 560

Lys Ser Phe Pro Gly Asn Asn Phe Ala Phe Glu Ala Trp Leu Phe Lys
                565                 570                 575

Asp Ala Asn Asn Met Arg Ala Pro Gly Gln Gly Asp Tyr Glu Arg Asn
            580                 585                 590

Ser Ala Asp Thr Asp Gly Leu Gln Glu Ser Ser Pro Ile Pro Ile
        595                 600                 605

Trp Lys Pro Ser Ile Ser Leu Arg Pro Pro Arg Trp Ser Ser Ser
    610                 615                 620

Phe Cys Ser Leu
625

<210> SEQ ID NO 31
<211> LENGTH: 1443
<212> TYPE: DNA
<213> ORGANISM: Artificial Sequence
<220> FEATURE:
<223> OTHER INFORMATION: AEPII 1a (clone # 63GP4)
<220> FEATURE:
<221> NAME/KEY: CDS
<222> LOCATION: (1)...(1443)

<400> SEQUENCE: 31 gct gga gtg ggt gag caa cgg gat aac cta cca gat att ccc cga cag      48
Ala Gly Val Gly Glu Gln Arg Asp Asn Leu Pro Asp Ile Pro Arg Gln
 1               5                  10                  15 gtt caa caa cgg aaa cag gag caa cga tgc cct agc ttt gga cca cga      96
Val Gln Gln Arg Lys Gln Glu Gln Arg Cys Pro Ser Phe Gly Pro Arg
                20                  25                  30 cga gct aat tct gaa cca ggt caa tcc agg caa acc aat cct ctc caa     144
Arg Ala Asn Ser Glu Pro Gly Gln Ser Arg Gln Thr Asn Pro Leu Gln
            35                  40                  45 ctg gag cga ccc tat aac gcc cct cca ctg ctg cca cca gta ctt cgg     192
Leu Glu Arg Pro Tyr Asn Ala Pro Pro Leu Leu Pro Pro Val Leu Arg
        50                  55                  60 cgg cga cat aaa ggg aat aac gga gaa gct cga cta cct tca gag cct     240
Arg Arg His Lys Gly Asn Asn Gly Glu Ala Arg Leu Pro Ser Glu Pro
65                  70                  75                  80
```

```
agg tgt tac tat aat cta cct caa ccc gat ttt cct ctc ggg aag cgc    288
Arg Cys Tyr Tyr Asn Leu Pro Gln Pro Asp Phe Pro Leu Gly Lys Arg
                 85              90                  95 cca cgg cta cga cac cta cga cta cta ccg gct tga ccc caa gtt cgg    336
Pro Arg Leu Arg His Leu Arg Leu Leu Pro Ala  *  Pro Gln Val Arg
                100             105                 110 gac cga gga gga gct gag aga gtt cct cga tga ggc aca cag gcg ggg    384
Asp Arg Gly Gly Ala Glu Arg Val Pro Arg  *  Gly Thr Gln Ala Gly
                115             120                 125 aat gag ggt aat ttt cga ttt tgt gcc caa cca ctg cgg cat agg gaa    432
Asn Glu Gly Asn Phe Arg Phe Cys Ala Gln Pro Leu Arg His Arg Glu
                130             135                 140 tcc agc ctt cct aga agt ttg gaa gaa ggg caa cga aag ccc ata ctg    480
Ser Ser Leu Pro Arg Ser Leu Glu Glu Gly Gln Arg Lys Pro Ile Leu
                145             150                 155 gga ctg gtt ctt cgt caa gaa gtg gcc gtt caa gct cgg cga tgg gaa    528
Gly Leu Val Leu Arg Gln Glu Val Ala Val Gln Ala Arg Arg Trp Glu
        160             165                 170 cgc cta cgt cgg ctg gtg ggg ctt tgg gag cct tcc aaa gct caa cac    576
Arg Leu Arg Arg Leu Val Gly Leu Trp Glu Pro Ser Lys Ala Gln His
175             180                 185                 190 tgc caa ccc gga ggt cag gga ata cct gat agg agc ggc cct cca ctg    624
Cys Gln Pro Gly Gly Gln Gly Ile Pro Asp Arg Ser Gly Pro Pro Leu
                195             200                 205 gat aga gtt cgg ctt tga cgg cat cag ggt tga tgt gcc gaa cga agt    672
Asp Arg Val Arg Leu  *  Arg His Gln Gly  *  Cys Ala Glu Arg Ser
                210             215                 220 cct cga ccc ggg aac gtt ctt ccc gga gct gag aaa ggc agt caa gga    720
Pro Arg Pro Gly Asn Val Leu Pro Gly Ala Glu Lys Gly Ser Gln Gly
                225             230                 235 gaa aaa gcc gga cgc ata cct cgt cgg tga gat atg gac gct ctc ccc    768
Glu Lys Ala Gly Arg Ile Pro Arg Arg  *  Asp Met Asp Ala Leu Pro
                240             245                 250 tga gtg ggt gaa agg aga ccg ctt cga ctc cct cat gaa cta cgc cct    816
 *  Val Gly Glu Arg Arg Pro Leu Arg Leu Pro His Glu Leu Arg Pro
                255             260                 265 cgg gag gga cat cct cct gaa cta cgc gaa ggg cct gct cag tgg aga    864
Arg Glu Gly His Pro Pro Glu Leu Arg Glu Gly Pro Ala Gln Trp Arg
                270             275                 280 aag tgc aat gaa aat gat ggg acg tta cta tgc ttc cta cgg cga gaa    912
Lys Cys Asn Glu Asn Asp Gly Thr Leu Leu Cys Phe Leu Arg Arg Glu
                285             290                 295 cgt att gcg atg ggc ttc aac ctc gtt gat tcg cac gac act tcg agg    960
Arg Ile Ala Met Gly Phe Asn Leu Val Asp Ser His Asp Thr Ser Arg
300             305                 310 gtt ctc act gat ctc ggt ggg ggg agt ctc ggt gac aca ccg tca aac   1008
Val Leu Thr Asp Leu Gly Gly Gly Ser Leu Gly Asp Thr Pro Ser Asn
315             320                 325                 330 gag tca att cag aga ctc aag ctc ctc tca acg tcc tct atg ccc tgc   1056
Glu Ser Ile Gln Arg Leu Lys Leu Leu Ser Thr Ser Ser Met Pro Cys
                335             340                 345 ctg gaa ctc cgg tca cct tcc agg gga tga gag agg act gct cgg aga   1104
Leu Glu Leu Arg Ser Pro Ser Arg Gly  *  Glu Arg Thr Ala Arg Arg
                350             355                 360 caa ggg gca cta cga cga aca gcg cta ccc aat aca gtg gga tac tgt   1152
Gln Gly Ala Leu Arg Arg Thr Ala Leu Pro Asn Thr Val Gly Tyr Cys
                365             370                 375 gaa cga aga cgt cct gaa cca tta cag ggc att ggc gga gct cag aaa   1200
Glu Arg Arg Arg Pro Glu Pro Leu Gln Gly Ile Gly Gly Ala Gln Lys
                380             385                 390
```

-continued

| | | |
|---|---|---|
| aag agt tcc tgc att gag gag cag cgc aat aag gtt cta cac tgc caa<br>Lys Ser Ser Cys Ile Glu Glu Gln Arg Asn Lys Val Leu His Cys Gln<br>395                                400                              405 | 1248 |
| agg cgg cgt tat ggc ctt ctt cag ggg gca tca tga cga ggt tct tgt<br>Arg Arg Arg Tyr Gly Leu Leu Gln Gly Ala Ser * Arg Gly Ser Cys<br>410                                415                              420 | 1296 |
| cgt tgc caa cag ctg gaa gaa gcc agc cct act aaa gct tcc tga ggg<br>Arg Cys Gln Gln Leu Glu Glu Ala Ser Pro Thr Lys Ala Ser * Gly<br>425                                430                              435 | 1344 |
| aga gtg gaa agt aat ctg gcc tga gaa ttt cag ccc gga act gct tcg<br>Arg Val Glu Ser Asn Leu Ala * Glu Phe Gln Pro Gly Thr Ala Ser<br>440                                445                              450 | 1392 |
| cgg caa agt tga agt gcc agc cat agg gat aat cat cct tga gcg gag<br>Arg Gln Ser * Ser Ala Ser His Arg Asp Asn His Pro * Ala Glu<br>455                                460                              465 | 1440 |
| ttg<br>Leu | 1443 |

<210> SEQ ID NO 32
<211> LENGTH: 469
<212> TYPE: PRT
<213> ORGANISM: Artificial Sequence
<220> FEATURE:
<223> OTHER INFORMATION: AEPII 1a (clone # 63GP4)

<400> SEQUENCE: 32

```
Ala Gly Val Gly Glu Gln Arg Asp Asn Leu Pro Asp Ile Pro Arg Gln
  1               5                  10                  15

Val Gln Gln Arg Lys Gln Glu Gln Arg Cys Pro Ser Phe Gly Pro Arg
                 20                  25                  30

Arg Ala Asn Ser Glu Pro Gly Gln Ser Arg Gln Thr Asn Pro Leu Gln
             35                  40                  45

Leu Glu Arg Pro Tyr Asn Ala Pro Pro Leu Leu Pro Val Leu Arg
         50                  55                  60

Arg Arg His Lys Gly Asn Asn Gly Glu Ala Arg Leu Pro Ser Glu Pro
 65                  70                  75                  80

Arg Cys Tyr Tyr Asn Leu Pro Gln Pro Asp Phe Pro Leu Gly Lys Arg
                 85                  90                  95

Pro Arg Leu Arg His Leu Arg Leu Leu Pro Ala Pro Gln Val Arg Asp
            100                 105                 110

Arg Gly Gly Ala Glu Arg Val Pro Arg Gly Thr Gln Ala Gly Asn Glu
        115                 120                 125

Gly Asn Phe Arg Phe Cys Ala Gln Pro Leu Arg His Arg Glu Ser Ser
    130                 135                 140

Leu Pro Arg Ser Leu Glu Gly Gln Arg Lys Pro Ile Leu Gly Leu
145                 150                 155                 160

Val Leu Arg Gln Glu Val Ala Val Gln Ala Arg Arg Trp Glu Arg Leu
                165                 170                 175

Arg Arg Leu Val Gly Leu Trp Glu Pro Ser Lys Ala Gln His Cys Gln
            180                 185                 190

Pro Gly Gly Gln Gly Ile Pro Asp Arg Ser Gly Pro Pro Leu Asp Arg
        195                 200                 205

Val Arg Leu Arg His Gln Gly Cys Ala Glu Arg Ser Pro Arg Pro Gly
    210                 215                 220

Asn Val Leu Pro Gly Ala Glu Lys Gly Ser Gln Gly Glu Lys Ala Gly
225                 230                 235                 240
```

-continued

```
Arg Ile Pro Arg Arg Asp Met Asp Ala Leu Pro Val Gly Glu Arg Arg
                245                 250                 255

Pro Leu Arg Leu Pro His Glu Leu Arg Pro Arg Glu Gly His Pro Pro
            260                 265                 270

Glu Leu Arg Glu Gly Pro Ala Gln Trp Arg Lys Cys Asn Glu Asn Asp
        275                 280                 285

Gly Thr Leu Leu Cys Phe Leu Arg Arg Glu Arg Ile Ala Met Gly Phe
    290                 295                 300

Asn Leu Val Asp Ser His Asp Thr Ser Arg Val Leu Thr Asp Leu Gly
305                 310                 315                 320

Gly Gly Ser Leu Gly Asp Thr Pro Ser Asn Glu Ser Ile Gln Arg Leu
                325                 330                 335

Lys Leu Leu Ser Thr Ser Ser Met Pro Cys Leu Glu Leu Arg Ser Pro
            340                 345                 350

Ser Arg Gly Glu Arg Thr Ala Arg Arg Gln Gly Ala Leu Arg Arg Thr
        355                 360                 365

Ala Leu Pro Asn Thr Val Gly Tyr Cys Glu Arg Arg Pro Glu Pro
    370                 375                 380

Leu Gln Gly Ile Gly Gly Ala Gln Lys Ser Ser Cys Ile Glu Glu
385                 390                 395                 400

Gln Arg Asn Lys Val Leu His Cys Gln Arg Arg Tyr Gly Leu Leu
                405                 410                 415

Gln Gly Ala Ser Arg Gly Ser Cys Arg Cys Gln Gln Leu Glu Glu Ala
            420                 425                 430

Ser Pro Thr Lys Ala Ser Gly Arg Val Glu Ser Asn Leu Ala Glu Phe
        435                 440                 445

Gln Pro Gly Thr Ala Ser Arg Gln Ser Ser Ala Ser His Arg Asp Asn
    450                 455                 460

His Pro Ala Glu Leu
465

<210> SEQ ID NO 33
<211> LENGTH: 1032
<212> TYPE: DNA
<213> ORGANISM: Bacillus thermoloeovorans
<220> FEATURE:
<221> NAME/KEY: CDS
<222> LOCATION: (1)...(1032)
<223> OTHER INFORMATION: clone # 68GC1

<400> SEQUENCE: 33 atg act gaa tta tat ata aaa aat ccc ctg atc gaa cag cgg gca gat       48
Met Thr Glu Leu Tyr Ile Lys Asn Pro Leu Ile Glu Gln Arg Ala Asp
 1               5                  10                  15 ccc tgg atc tat aaa cat acc gat ggt tat tat tac ttt acc ggt tcc       96
Pro Trp Ile Tyr Lys His Thr Asp Gly Tyr Tyr Tyr Phe Thr Gly Ser
             20                  25                  30 gtg ccg gag tac gac cga att gag ctt aga cgc tcg caa acg att caa      144
Val Pro Glu Tyr Asp Arg Ile Glu Leu Arg Arg Ser Gln Thr Ile Gln
         35                  40                  45 ggg ctt gcg gat gcc gaa gga att acg atc tgg cgc aag cat gag tca      192
Gly Leu Ala Asp Ala Glu Gly Ile Thr Ile Trp Arg Lys His Glu Ser
     50                  55                  60 ggc ctg atg agt gcc aac ata tgg gca ccc gag att cat tat atg gat      240
Gly Leu Met Ser Ala Asn Ile Trp Ala Pro Glu Ile His Tyr Met Asp
 65                  70                  75                  80 ggc aaa tgg tat gtg tat tac gcc gct gcc cat act tca gaa acg agg      288
Gly Lys Trp Tyr Val Tyr Tyr Ala Ala Ala His Thr Ser Glu Thr Arg
```

|  |  |  |  |  |  |  |  |  |  |  |  |  |  |  |  |
|---|---|---|---|---|---|---|---|---|---|---|---|---|---|---|---|
|  |  |  |  | 85 |  |  |  |  | 90 |  |  |  |  | 95 |  |

```
gac gga ttg ttc gat cac cgc atg ttc gta ttg gag aac gct tcg gcg   336
Asp Gly Leu Phe Asp His Arg Met Phe Val Leu Glu Asn Ala Ser Ala
            100                 105                 110 aac ccg ctc gaa ggg gaa tgg gtg gag aag ggg caa gtg atc acg aag   384
Asn Pro Leu Glu Gly Glu Trp Val Glu Lys Gly Gln Val Ile Thr Lys
        115                 120                 125 tgg gaa tct ttc gcc ttg gac gca acg acg ttc gag cat aaa ggc aaa   432
Trp Glu Ser Phe Ala Leu Asp Ala Thr Thr Phe Glu His Lys Gly Lys
    130                 135                 140 cgg tac tat gta tgg gct cag aaa gat ccg ggc att cca ggc aat tcc   480
Arg Tyr Tyr Val Trp Ala Gln Lys Asp Pro Gly Ile Pro Gly Asn Ser
145                 150                 155                 160 aat ctg tat atc tca ttg atg gaa gac ccg tgg acc ctg aca ggg gaa   528
Asn Leu Tyr Ile Ser Leu Met Glu Asp Pro Trp Thr Leu Thr Gly Glu
                165                 170                 175 cag gta tgc ata tcg gtt ccc gag tac gat tgg gag aag atc ggg tat   576
Gln Val Cys Ile Ser Val Pro Glu Tyr Asp Trp Glu Lys Ile Gly Tyr
            180                 185                 190 ctt gtg aat gaa ggg gcc gcc gtt ctt aag cga aac ggg cga ata ttc   624
Leu Val Asn Glu Gly Ala Ala Val Leu Lys Arg Asn Gly Arg Ile Phe
        195                 200                 205 atg acc tat tcc gcg agc gcc acg gac cac aac tat gcg atg ggg ctg   672
Met Thr Tyr Ser Ala Ser Ala Thr Asp His Asn Tyr Ala Met Gly Leu
    210                 215                 220 ctg aca gcc gat gaa gac agt gat ttg ctg aat ccg agc tcc tgg gtc   720
Leu Thr Ala Asp Glu Asp Ser Asp Leu Leu Asn Pro Ser Ser Trp Val
225                 230                 235                 240 aag tcg cct gta cct gta ttt acg aca tct gaa gcc aat ggc caa tat   768
Lys Ser Pro Val Pro Val Phe Thr Thr Ser Glu Ala Asn Gly Gln Tyr
                245                 250                 255 ggt ccg ggg cac aac agc ttc acg att tcc gag gac ggc ttg cag gac   816
Gly Pro Gly His Asn Ser Phe Thr Ile Ser Glu Asp Gly Leu Gln Asp
            260                 265                 270 att ttg gta tac cat gca aga agt tac aag gag atc gtc ggg atc cac   864
Ile Leu Val Tyr His Ala Arg Ser Tyr Lys Glu Ile Val Gly Ile His
        275                 280                 285 tat atg atc cga acc gtc ata cgc gtg tac agg tca tcc gat gga acg   912
Tyr Met Ile Arg Thr Val Ile Arg Val Tyr Arg Ser Ser Asp Gly Thr
    290                 295                 300 aag acg gaa cgc cga att tcg ggg tgc caa gag cgg atc atg aac cgg   960
Lys Thr Glu Arg Arg Ile Ser Gly Cys Gln Glu Arg Ile Met Asn Arg
305                 310                 315                 320 tct cca agc cat gat gcc gac ttt gtc att ggg gtt gtg acc gga agg  1008
Ser Pro Ser His Asp Ala Asp Phe Val Ile Gly Val Val Thr Gly Arg
                325                 330                 335 att aac aaa cat cag acc gac tga                                  1032
Ile Asn Lys His Gln Thr Asp *
            340
```

<210> SEQ ID NO 34
<211> LENGTH: 343
<212> TYPE: PRT
<213> ORGANISM: Bacillus thermoloeovorans

<400> SEQUENCE: 34

```
Met Thr Glu Leu Tyr Ile Lys Asn Pro Leu Ile Glu Gln Arg Ala Asp
  1               5                  10                  15

Pro Trp Ile Tyr Lys His Thr Asp Gly Tyr Tyr Tyr Phe Thr Gly Ser
             20                  25                  30
```

```
Val Pro Glu Tyr Asp Arg Ile Glu Leu Arg Arg Ser Gln Thr Ile Gln
         35                  40                  45

Gly Leu Ala Asp Ala Glu Gly Ile Thr Ile Trp Arg Lys His Glu Ser
 50                  55                  60

Gly Leu Met Ser Ala Asn Ile Trp Ala Pro Glu Ile His Tyr Met Asp
 65                  70                  75                  80

Gly Lys Trp Tyr Val Tyr Ala Ala His Thr Ser Glu Thr Arg
                 85                  90                  95

Asp Gly Leu Phe Asp His Arg Met Phe Val Leu Glu Asn Ala Ser Ala
                100                 105                 110

Asn Pro Leu Glu Gly Glu Trp Val Glu Lys Gly Gln Val Ile Thr Lys
            115                 120                 125

Trp Glu Ser Phe Ala Leu Asp Ala Thr Thr Phe Glu His Lys Gly Lys
130                 135                 140

Arg Tyr Tyr Val Trp Ala Gln Lys Asp Pro Gly Ile Pro Gly Asn Ser
145                 150                 155                 160

Asn Leu Tyr Ile Ser Leu Met Glu Asp Pro Trp Thr Leu Thr Gly Glu
                165                 170                 175

Gln Val Cys Ile Ser Val Pro Glu Tyr Asp Trp Glu Lys Ile Gly Tyr
                180                 185                 190

Leu Val Asn Glu Gly Ala Ala Val Leu Lys Arg Asn Gly Arg Ile Phe
            195                 200                 205

Met Thr Tyr Ser Ala Ser Ala Thr Asp His Asn Tyr Ala Met Gly Leu
            210                 215                 220

Leu Thr Ala Asp Glu Asp Ser Asp Leu Leu Asn Pro Ser Ser Trp Val
225                 230                 235                 240

Lys Ser Pro Val Pro Val Phe Thr Thr Ser Glu Ala Asn Gly Gln Tyr
                245                 250                 255

Gly Pro Gly His Asn Ser Phe Thr Ile Ser Glu Asp Gly Leu Gln Asp
                260                 265                 270

Ile Leu Val Tyr His Ala Arg Ser Tyr Lys Glu Ile Val Gly Ile His
            275                 280                 285

Tyr Met Ile Arg Thr Val Ile Arg Val Tyr Arg Ser Ser Asp Gly Thr
            290                 295                 300

Lys Thr Glu Arg Arg Ile Ser Gly Cys Gln Glu Arg Ile Met Asn Arg
305                 310                 315                 320

Ser Pro Ser His Asp Ala Asp Phe Val Ile Gly Val Val Thr Gly Arg
                325                 330                 335

Ile Asn Lys His Gln Thr Asp
            340

<210> SEQ ID NO 35
<211> LENGTH: 990
<212> TYPE: DNA
<213> ORGANISM: Thermotoga maritima
<220> FEATURE:
<221> NAME/KEY: CDS
<222> LOCATION: (1)...(990)

<400> SEQUENCE: 35 ttg aat aac acc att cca aga tgg cgt ggt ttc aac ctt ctg gag gcc    48
Leu Asn Asn Thr Ile Pro Arg Trp Arg Gly Phe Asn Leu Leu Glu Ala
 1               5                  10                  15 ttt tcc att aaa agt aca gga aat ttt aaa gag gaa gat ttt ttg tgg    96
Phe Ser Ile Lys Ser Thr Gly Asn Phe Lys Glu Glu Asp Phe Leu Trp
             20                  25                  30
```

```
atg gct cag tgg gac ttt aat ttt gtt aga atc cct atg tgt cat ctt    144
Met Ala Gln Trp Asp Phe Asn Phe Val Arg Ile Pro Met Cys His Leu
         35                  40                  45 ctc tgg tca gac cgg ggc aac cca ttt att atc aga gaa gat ttt ttt    192
Leu Trp Ser Asp Arg Gly Asn Pro Phe Ile Ile Arg Glu Asp Phe Phe
 50                  55                  60 gag aaa atc gat cgt gta att ttc tgg gga gag aaa tat gga ata cat    240
Glu Lys Ile Asp Arg Val Ile Phe Trp Gly Glu Lys Tyr Gly Ile His
 65                  70                  75                  80 ata tgt att tct ctt cac agg gca cct ggc tat tct gtt aac aag gaa    288
Ile Cys Ile Ser Leu His Arg Ala Pro Gly Tyr Ser Val Asn Lys Glu
                 85                  90                  95 gta gaa gag aaa acc aat ctg tgg aaa gat gaa aca gct caa gaa gcg    336
Val Glu Glu Lys Thr Asn Leu Trp Lys Asp Glu Thr Ala Gln Glu Ala
            100                 105                 110 ttc att cat cac tgg tct ttt atc gca cgt cgt tac aaa gga att tct    384
Phe Ile His His Trp Ser Phe Ile Ala Arg Arg Tyr Lys Gly Ile Ser
        115                 120                 125 tcc aca cac ctg agt ttt aac tta ata aat gag cct cca ttt cct gat    432
Ser Thr His Leu Ser Phe Asn Leu Ile Asn Glu Pro Pro Phe Pro Asp
130                 135                 140 cca caa atc atg agt gtt gaa gat cac aac tct ctt atc aag aga act    480
Pro Gln Ile Met Ser Val Glu Asp His Asn Ser Leu Ile Lys Arg Thr
145                 150                 155                 160 att aca gaa att cga aaa ata gat ccc gaa aga tta att ata ata gat    528
Ile Thr Glu Ile Arg Lys Ile Asp Pro Glu Arg Leu Ile Ile Ile Asp
                165                 170                 175 gga tta ggc tat ggg aat att cca gtg gat gat tta aca att gag aat    576
Gly Leu Gly Tyr Gly Asn Ile Pro Val Asp Asp Leu Thr Ile Glu Asn
            180                 185                 190 aca gtg caa tca tgc aga ggg tac att ccc ttc agt gtt act cat tac    624
Thr Val Gln Ser Cys Arg Gly Tyr Ile Pro Phe Ser Val Thr His Tyr
        195                 200                 205 aaa gcg gaa tgg gtg gat agt aag gac ttt cct gtt cct gag tgg cca    672
Lys Ala Glu Trp Val Asp Ser Lys Asp Phe Pro Val Pro Glu Trp Pro
210                 215                 220 aat gga tgg cat ttt ggg gaa tac tgg aac aga gaa aag tta ttg gaa    720
Asn Gly Trp His Phe Gly Glu Tyr Trp Asn Arg Glu Lys Leu Leu Glu
225                 230                 235                 240 cat tat tta acg tgg ata aaa ctc aga caa aaa gga ata gaa gta ttc    768
His Tyr Leu Thr Trp Ile Lys Leu Arg Gln Lys Gly Ile Glu Val Phe
                245                 250                 255 tgt gga gaa atg gga gct tac aac aaa aca cct cac gat gtg gtt tta    816
Cys Gly Glu Met Gly Ala Tyr Asn Lys Thr Pro His Asp Val Val Leu
            260                 265                 270 aaa tgg ctt gaa gat ctt tta gaa att ttt aaa act ttg aac ata ggg    864
Lys Trp Leu Glu Asp Leu Leu Glu Ile Phe Lys Thr Leu Asn Ile Gly
        275                 280                 285 ttt gcc tta tgg aat ttt aga ggt cct ttt ggt att tta gat tcg gaa    912
Phe Ala Leu Trp Asn Phe Arg Gly Pro Phe Gly Ile Leu Asp Ser Glu
290                 295                 300 agg aaa gac gtt gaa tac gaa gaa tgg tat gga cat aaa ctg gat agg    960
Arg Lys Asp Val Glu Tyr Glu Glu Trp Tyr Gly His Lys Leu Asp Arg
305                 310                 315                 320 aaa atg ttg gaa cta ttg aga aaa tat tag                            990
Lys Met Leu Glu Leu Leu Arg Lys Tyr *
                325
```

<210> SEQ ID NO 36

<211> LENGTH: 329
<212> TYPE: PRT
<213> ORGANISM: Thermotoga maritima

<400> SEQUENCE: 36

```
Leu Asn Asn Thr Ile Pro Arg Trp Arg Gly Phe Asn Leu Leu Glu Ala
 1               5                  10                  15

Phe Ser Ile Lys Ser Thr Gly Asn Phe Lys Glu Glu Asp Phe Leu Trp
             20                  25                  30

Met Ala Gln Trp Asp Phe Asn Phe Val Arg Ile Pro Met Cys His Leu
         35                  40                  45

Leu Trp Ser Asp Arg Gly Asn Pro Phe Ile Ile Arg Glu Asp Phe Phe
     50                  55                  60

Glu Lys Ile Asp Arg Val Ile Phe Trp Gly Lys Tyr Gly Ile His
 65                  70                  75                  80

Ile Cys Ile Ser Leu His Arg Ala Pro Gly Tyr Ser Val Asn Lys Glu
                 85                  90                  95

Val Glu Glu Lys Thr Asn Leu Trp Lys Asp Glu Thr Ala Gln Glu Ala
            100                 105                 110

Phe Ile His His Trp Ser Phe Ile Ala Arg Arg Tyr Lys Gly Ile Ser
        115                 120                 125

Ser Thr His Leu Ser Phe Asn Leu Ile Asn Glu Pro Pro Phe Pro Asp
    130                 135                 140

Pro Gln Ile Met Ser Val Glu Asp His Asn Ser Leu Ile Lys Arg Thr
145                 150                 155                 160

Ile Thr Glu Ile Arg Lys Ile Asp Pro Glu Arg Leu Ile Ile Ile Asp
                165                 170                 175

Gly Leu Gly Tyr Gly Asn Ile Pro Val Asp Asp Leu Thr Ile Glu Asn
            180                 185                 190

Thr Val Gln Ser Cys Arg Gly Tyr Ile Pro Phe Ser Val Thr His Tyr
        195                 200                 205

Lys Ala Glu Trp Val Asp Ser Lys Asp Phe Pro Val Pro Glu Trp Pro
    210                 215                 220

Asn Gly Trp His Phe Gly Glu Tyr Trp Asn Arg Glu Lys Leu Leu Glu
225                 230                 235                 240

His Tyr Leu Thr Trp Ile Lys Leu Arg Gln Lys Gly Ile Glu Val Phe
                245                 250                 255

Cys Gly Glu Met Gly Ala Tyr Asn Lys Thr Pro His Asp Val Val Leu
            260                 265                 270

Lys Trp Leu Glu Asp Leu Leu Glu Ile Phe Lys Thr Leu Asn Ile Gly
        275                 280                 285

Phe Ala Leu Trp Asn Phe Arg Gly Pro Phe Gly Ile Leu Asp Ser Glu
    290                 295                 300

Arg Lys Asp Val Glu Tyr Glu Glu Trp Tyr Gly His Lys Leu Asp Arg
305                 310                 315                 320

Lys Met Leu Glu Leu Leu Arg Lys Tyr
                325
```

<210> SEQ ID NO 37
<211> LENGTH: 3012
<212> TYPE: DNA
<213> ORGANISM: Thermotoga maritima
<220> FEATURE:
<221> NAME/KEY: CDS
<222> LOCATION: (1)...(3012)
<223> OTHER INFORMATION: clone # 6GC17

<400> SEQUENCE: 37

```
atg ctc tca gag att gtt ccg tat act gtt ctg aga aga gaa aga ata     48
Met Leu Ser Glu Ile Val Pro Tyr Thr Val Leu Arg Arg Glu Arg Ile
 1               5                  10                  15 gaa agc tgg att ttc tcc gat gat gct gtt gag aga atc gtg gat cct     96
Glu Ser Trp Ile Phe Ser Asp Asp Ala Val Glu Arg Ile Val Asp Pro
             20                  25                  30 tcc ttc gaa tgg gac ttc agc tcc gct ccc gtc cgg ttc agg aaa gag    144
Ser Phe Glu Trp Asp Phe Ser Ser Ala Pro Val Arg Phe Arg Lys Glu
         35                  40                  45 cta gag cct ttc tcc gtc gct gga gag cag agg gcc tac ctg aaa ctc    192
Leu Glu Pro Phe Ser Val Ala Gly Glu Gln Arg Ala Tyr Leu Lys Leu
     50                  55                  60 tgg ttc ggt ggt gaa aca ctc gtt ctg ata gat ggg aag cct tac ggt    240
Trp Phe Gly Gly Glu Thr Leu Val Leu Ile Asp Gly Lys Pro Tyr Gly
 65                  70                  75                  80 gag atc aac gag tat cat agg atg ttg aac atc acc ccc ctt gct gat    288
Glu Ile Asn Glu Tyr His Arg Met Leu Asn Ile Thr Pro Leu Ala Asp
                 85                  90                  95 gga aaa cca cac acg ata gaa gct cag gtg atg cca agg ggt ctc ttt    336
Gly Lys Pro His Thr Ile Glu Ala Gln Val Met Pro Arg Gly Leu Phe
            100                 105                 110 gga aaa cca gaa aag ccg gtg ttc acg gaa gct ttc ttc atc gtc gtt    384
Gly Lys Pro Glu Lys Pro Val Phe Thr Glu Ala Phe Phe Ile Val Val
        115                 120                 125 gat gaa gca ctg atg aag gtg gtg aaa act ctc gaa ctc act ata aaa    432
Asp Glu Ala Leu Met Lys Val Val Lys Thr Leu Glu Leu Thr Ile Lys
    130                 135                 140 acg gca gaa gtg ata gaa gac gag tcg ctt tct aag aaa ctt ctg gac    480
Thr Ala Glu Val Ile Glu Asp Glu Ser Leu Ser Lys Lys Leu Leu Asp
145                 150                 155                 160 atc tcc gag gag ttt ctc tcg aaa gta tgg atc cca aga gac aca ggt    528
Ile Ser Glu Glu Phe Leu Ser Lys Val Trp Ile Pro Arg Asp Thr Gly
                165                 170                 175 acc tat ctg atg aca gca ctg gag gat ccg gga ata aaa gat gag atc    576
Thr Tyr Leu Met Thr Ala Leu Glu Asp Pro Gly Ile Lys Asp Glu Ile
            180                 185                 190 aaa aac acc tgg aac aca ccg gag ttc aaa gag ttc aca ggt gtg aag    624
Lys Asn Thr Trp Asn Thr Pro Glu Phe Lys Glu Phe Thr Gly Val Lys
        195                 200                 205 ctt cct gaa gag ttg aga aat cag att ctg gaa gag ttc gaa aaa ttc    672
Leu Pro Glu Glu Leu Arg Asn Gln Ile Leu Glu Glu Phe Glu Lys Phe
    210                 215                 220 aaa gaa aag ctg gat aga ata aga aaa aac cat ccg ggt ttt gga acg    720
Lys Glu Lys Leu Asp Arg Ile Arg Lys Asn His Pro Gly Phe Gly Thr
225                 230                 235                 240 att cac ctt gtg ggg cac gcg cac ata gac tac gcc tgg ctc tgg cca    768
Ile His Leu Val Gly His Ala His Ile Asp Tyr Ala Trp Leu Trp Pro
                245                 250                 255 gtt gag gag acg aag aga aag atc cta cgc act ttc gca aac tct gtg    816
Val Glu Glu Thr Lys Arg Lys Ile Leu Arg Thr Phe Ala Asn Ser Val
            260                 265                 270 ttg ctc tct aag ctt tat ccg gag ttc gtt tac act cag tct tct gct    864
Leu Leu Ser Lys Leu Tyr Pro Glu Phe Val Tyr Thr Gln Ser Ser Ala
        275                 280                 285 cag atg tac gag gat ctc aag caa aat tca cca gag ctt ttc gag gaa    912
Gln Met Tyr Glu Asp Leu Lys Gln Asn Ser Pro Glu Leu Phe Glu Glu
    290                 295                 300 gtg aga aag ctc gta gaa gag ggg aga tgg gag cca gtc ggt ggc atg    960
Val Arg Lys Leu Val Glu Glu Gly Arg Trp Glu Pro Val Gly Gly Met
```

```
Val Arg Lys Leu Val Glu Glu Gly Arg Trp Glu Pro Val Gly Gly Met
305                 310                 315                 320 tgg gtg gag tcg gac tgc aac gtt cca tcg ata gag tcg ctt gtg aga    1008
Trp Val Glu Ser Asp Cys Asn Val Pro Ser Ile Glu Ser Leu Val Arg
                    325                 330                 335 cag ttc tac tat ggg caa aaa ttc ttc gaa aga gaa ttc ggg aaa aag    1056
Gln Phe Tyr Tyr Gly Gln Lys Phe Phe Glu Arg Glu Phe Gly Lys Lys
                340                 345                 350 agc aag gtg tgc tgg ctt ccg gat gtg ttt ggg ttt tcc tgg gtg ctt    1104
Ser Lys Val Cys Trp Leu Pro Asp Val Phe Gly Phe Ser Trp Val Leu
            355                 360                 365 ccc caa att ctg aaa gaa gcc ggg ata aaa tac ttc gtc acc acg aaa    1152
Pro Gln Ile Leu Lys Glu Ala Gly Ile Lys Tyr Phe Val Thr Thr Lys
370                 375                 380 ctc aac tgg aac gac acg aac gag ttt ccg tac gat ctg tgc cgc tgg    1200
Leu Asn Trp Asn Asp Thr Asn Glu Phe Pro Tyr Asp Leu Cys Arg Trp
385                 390                 395                 400 agg gga ata gat gga tcc gaa gtg atc tat ttc agt ttc aaa aat ccc    1248
Arg Gly Ile Asp Gly Ser Glu Val Ile Tyr Phe Ser Phe Lys Asn Pro
                405                 410                 415 aac gag ggg tac aac gga aag ata gat ccc gat acg gtc tac aaa acc    1296
Asn Glu Gly Tyr Asn Gly Lys Ile Asp Pro Asp Thr Val Tyr Lys Thr
                420                 425                 430 tgg aag aac ttc agg cag aaa gat ctc aca aac aga gtt ctt ctt tcg    1344
Trp Lys Asn Phe Arg Gln Lys Asp Leu Thr Asn Arg Val Leu Leu Ser
            435                 440                 445 ttc gga cac ggt gat ggt ggc ggt cca acc gaa gag atg ctg gaa       1392
Phe Gly His Gly Asp Gly Gly Gly Pro Thr Glu Glu Met Leu Glu
        450                 455                 460 aat tac gag gtt ctg aag gat ttc cct gga cta ccg cac ctt gaa atg    1440
Asn Tyr Glu Val Leu Lys Asp Phe Pro Gly Leu Pro His Leu Glu Met
465                 470                 475                 480 gga act gtg gaa gaa ttt ttc aag aag gtg gag atc gac gaa gaa ctc    1488
Gly Thr Val Glu Glu Phe Phe Lys Lys Val Glu Ile Asp Glu Glu Leu
                485                 490                 495 cct gtg tgg gac gga gag ctt tac ctt gaa ctt cac agg gga acc tac    1536
Pro Val Trp Asp Gly Glu Leu Tyr Leu Glu Leu His Arg Gly Thr Tyr
                500                 505                 510 act tct cag ttc agg aca aag aaa ctt cac aaa gaa gcg gaa gac agt    1584
Thr Ser Gln Phe Arg Thr Lys Lys Leu His Lys Glu Ala Glu Asp Ser
            515                 520                 525 ctt tat ctt gca gag ttg atc tcg gct ttc acg gat aaa gat ttt tcg    1632
Leu Tyr Leu Ala Glu Leu Ile Ser Ala Phe Thr Asp Lys Asp Phe Ser
        530                 535                 540 gac gaa ata gac gaa ctc tgg aag att ctg ttg aga aac gaa ttt cac    1680
Asp Glu Ile Asp Glu Leu Trp Lys Ile Leu Leu Arg Asn Glu Phe His
545                 550                 555                 560 gat att cta cct gga tct tct ata aag gaa gtc tat gaa gat aca gaa    1728
Asp Ile Leu Pro Gly Ser Ser Ile Lys Glu Val Tyr Glu Asp Thr Glu
                565                 570                 575 aaa gag ctc aga cat gtg ata gaa aaa tca aaa gac atc gtt atc gaa    1776
Lys Glu Leu Arg His Val Ile Glu Lys Ser Lys Asp Ile Val Ile Glu
                580                 585                 590 tct ctc aaa gtt ctt tcc tct gag aac aaa gat gtt cta acc att ttg    1824
Ser Leu Lys Val Leu Ser Ser Glu Asn Lys Asp Val Leu Thr Ile Leu
            595                 600                 605 aac gct tca tcg ttt cca aag aag tgt ctt ttc ttc ctc aac gaa gat    1872
Asn Ala Ser Ser Phe Pro Lys Lys Cys Leu Phe Phe Leu Asn Glu Asp
        610                 615                 620
```

```
ctc gcg att tcc ttt gaa gga gaa gca ctc ttg aaa cag aaa act cac    1920
Leu Ala Ile Ser Phe Glu Gly Glu Ala Leu Leu Lys Gln Lys Thr His
625                 630                 635                 640 gat gga agg tat gtg tac ttc ata gac agg gag att cct ccg ttc acg    1968
Asp Gly Arg Tyr Val Tyr Phe Ile Asp Arg Glu Ile Pro Pro Phe Thr
            645                 650                 655 aaa gta gaa ctg aaa gtt cgc aaa gcc acg tct gag gaa act cca agt    2016
Lys Val Glu Leu Lys Val Arg Lys Ala Thr Ser Glu Glu Thr Pro Ser
        660                 665                 670 gag ttg aga gaa aca aac atc atg gag aac gaa ttt ctc agg gtg cac    2064
Glu Leu Arg Glu Thr Asn Ile Met Glu Asn Glu Phe Leu Arg Val His
    675                 680                 685 gtc aac gat gac gga aca att caa atc tac gac aaa gaa ctg gac agg    2112
Val Asn Asp Asp Gly Thr Ile Gln Ile Tyr Asp Lys Glu Leu Asp Arg
690                 695                 700 tac gtt ttc gaa gag aag gga aac atc ttg aaa ctt cat aaa aac atc    2160
Tyr Val Phe Glu Glu Lys Gly Asn Ile Leu Lys Leu His Lys Asn Ile
705                 710                 715                 720 cct gct tac tgg gac aac tgg gat atc gca gaa aac gtg gaa aag aca    2208
Pro Ala Tyr Trp Asp Asn Trp Asp Ile Ala Glu Asn Val Glu Lys Thr
            725                 730                 735 gga tat acc ctg agg gcg aaa aac ata gaa aaa ata gag tct ggc cct    2256
Gly Tyr Thr Leu Arg Ala Lys Asn Ile Glu Lys Ile Glu Ser Gly Pro
        740                 745                 750 gtt cga gaa gtg atc cgt gtt gaa cat gaa tca gaa gga agc agg atc    2304
Val Arg Glu Val Ile Arg Val Glu His Glu Ser Glu Gly Ser Arg Ile
    755                 760                 765 acg cag cat tac atc ctt tac aga aag agt aga agg ctc gat ata gaa    2352
Thr Gln His Tyr Ile Leu Tyr Arg Lys Ser Arg Arg Leu Asp Ile Glu
770                 775                 780 acg aag gta gac tgg cac aca agg cgt gcg ctt ctc aga gcc tac ttc    2400
Thr Lys Val Asp Trp His Thr Arg Arg Ala Leu Leu Arg Ala Tyr Phe
785                 790                 795                 800 cca aca act gtt ctg tcg aga aag gct agg ttc gat atc tcc ggt ggt    2448
Pro Thr Thr Val Leu Ser Arg Lys Ala Arg Phe Asp Ile Ser Gly Gly
            805                 810                 815 ttc atc gaa agg ccc aca cac aga aac acc agt ttc gaa cag gcg cgt    2496
Phe Ile Glu Arg Pro Thr His Arg Asn Thr Ser Phe Glu Gln Ala Arg
        820                 825                 830 ttc gag gtg ccg ttt cac agg tgg atg gat ctt tcc cag aca gac ttc    2544
Phe Glu Val Pro Phe His Arg Trp Met Asp Leu Ser Gln Thr Asp Phe
    835                 840                 845 ggc gtg tcc att ctg aac gac gga aaa tac ggt ggc agt gtt cat cag    2592
Gly Val Ser Ile Leu Asn Asp Gly Lys Tyr Gly Gly Ser Val His Gln
850                 855                 860 ggt atc atg gcg ctt tca ctg ata aaa gcg ggt att ttc ccc gat ttt    2640
Gly Ile Met Ala Leu Ser Leu Ile Lys Ala Gly Ile Phe Pro Asp Phe
865                 870                 875                 880 ctc tgt gac gaa ggc gaa cac act ttc acc tat tct gtc tac gta cac    2688
Leu Cys Asp Glu Gly Glu His Thr Phe Thr Tyr Ser Val Tyr Val His
            885                 890                 895 cct gga gac agc ttg aga gat gtt gta aaa gga tca gaa gat ctc aac    2736
Pro Gly Asp Ser Leu Arg Asp Val Val Lys Gly Ser Glu Asp Leu Asn
        900                 905                 910 aga tct ttc atc gtt cat cgc ggg gtg ttg aac ctc ccc tct cct tta    2784
Arg Ser Phe Ile Val His Arg Gly Val Leu Asn Leu Pro Ser Pro Leu
    915                 920                 925 ctg gag atc tct cct caa aac ttc cgt ctc acc tca ctg aga agg gtg    2832
Leu Glu Ile Ser Pro Gln Asn Phe Arg Leu Thr Ser Leu Arg Arg Val
930                 935                 940
```

-continued

```
aag gac aaa att gtt ttg agg ctt gtt gag att ttc gga aca tca ggg    2880
Lys Asp Lys Ile Val Leu Arg Leu Val Glu Ile Phe Gly Thr Ser Gly
945                 950                 955                 960 aaa ctt tcc att aaa ctc cca tgg cat ggt gaa atc tat cag acg aac    2928
Lys Leu Ser Ile Lys Leu Pro Trp His Gly Glu Ile Tyr Gln Thr Asn
            965                 970                 975 gtt ctg gaa gag aaa aaa cag aaa gtc acc ttc cca gtg gtt tac cat    2976
Val Leu Glu Glu Lys Lys Gln Lys Val Thr Phe Pro Val Val Tyr His
        980                 985                 990 ccg ttc aag atc tac act ttt gtt gta gaa ggt tga                    3012
Pro Phe Lys Ile Tyr Thr Phe Val Val Glu Gly *
    995                 1000
```

<210> SEQ ID NO 38
<211> LENGTH: 1003
<212> TYPE: PRT
<213> ORGANISM: Thermotoga maritima

<400> SEQUENCE: 38

```
Met Leu Ser Glu Ile Val Pro Tyr Thr Val Leu Arg Arg Glu Arg Ile
1               5                   10                  15

Glu Ser Trp Ile Phe Ser Asp Asp Ala Val Glu Arg Ile Val Asp Pro
            20                  25                  30

Ser Phe Glu Trp Asp Phe Ser Ser Ala Pro Val Arg Phe Arg Lys Glu
        35                  40                  45

Leu Glu Pro Phe Ser Val Ala Gly Glu Gln Arg Ala Tyr Leu Lys Leu
    50                  55                  60

Trp Phe Gly Gly Glu Thr Leu Val Leu Ile Asp Gly Lys Pro Tyr Gly
65                  70                  75                  80

Glu Ile Asn Glu Tyr His Arg Met Leu Asn Ile Thr Pro Leu Ala Asp
                85                  90                  95

Gly Lys Pro His Thr Ile Glu Ala Gln Val Met Pro Arg Gly Leu Phe
            100                 105                 110

Gly Lys Pro Glu Lys Pro Val Phe Thr Glu Ala Phe Phe Ile Val Val
        115                 120                 125

Asp Glu Ala Leu Met Lys Val Val Lys Thr Leu Glu Leu Thr Ile Lys
    130                 135                 140

Thr Ala Glu Val Ile Glu Asp Glu Ser Leu Ser Lys Lys Leu Leu Asp
145                 150                 155                 160

Ile Ser Glu Glu Phe Leu Ser Lys Val Trp Ile Pro Arg Asp Thr Gly
                165                 170                 175

Thr Tyr Leu Met Thr Ala Leu Glu Asp Pro Gly Ile Lys Asp Glu Ile
            180                 185                 190

Lys Asn Thr Trp Asn Thr Pro Glu Phe Lys Glu Phe Thr Gly Val Lys
        195                 200                 205

Leu Pro Glu Glu Leu Arg Asn Gln Ile Leu Glu Phe Glu Lys Phe
    210                 215                 220

Lys Glu Lys Leu Asp Arg Ile Arg Lys Asn His Pro Gly Phe Gly Thr
225                 230                 235                 240

Ile His Leu Val Gly His Ala His Ile Asp Tyr Ala Trp Leu Trp Pro
                245                 250                 255

Val Glu Glu Thr Lys Arg Lys Ile Leu Arg Thr Phe Ala Asn Ser Val
            260                 265                 270

Leu Leu Ser Lys Leu Tyr Pro Glu Phe Val Tyr Thr Gln Ser Ser Ala
        275                 280                 285
```

-continued

```
Gln Met Tyr Glu Asp Leu Lys Gln Asn Ser Pro Glu Leu Phe Glu Glu
    290                 295                 300

Val Arg Lys Leu Val Glu Glu Gly Arg Trp Glu Pro Val Gly Gly Met
305                 310                 315                 320

Trp Val Glu Ser Asp Cys Asn Val Pro Ser Ile Glu Ser Leu Val Arg
                325                 330                 335

Gln Phe Tyr Tyr Gly Gln Lys Phe Phe Glu Arg Glu Phe Gly Lys Lys
            340                 345                 350

Ser Lys Val Cys Trp Leu Pro Asp Val Phe Gly Phe Ser Trp Val Leu
        355                 360                 365

Pro Gln Ile Leu Lys Glu Ala Gly Ile Lys Tyr Phe Val Thr Thr Lys
    370                 375                 380

Leu Asn Trp Asn Asp Thr Asn Glu Phe Pro Tyr Asp Leu Cys Arg Trp
385                 390                 395                 400

Arg Gly Ile Asp Gly Ser Glu Val Ile Tyr Phe Ser Phe Lys Asn Pro
                405                 410                 415

Asn Glu Gly Tyr Asn Gly Lys Ile Asp Pro Asp Thr Val Tyr Lys Thr
            420                 425                 430

Trp Lys Asn Phe Arg Gln Lys Asp Leu Thr Asn Arg Val Leu Leu Ser
        435                 440                 445

Phe Gly His Gly Asp Gly Gly Gly Pro Thr Glu Glu Met Leu Glu
    450                 455                 460

Asn Tyr Glu Val Leu Lys Asp Phe Pro Gly Leu Pro His Leu Glu Met
465                 470                 475                 480

Gly Thr Val Glu Glu Phe Phe Lys Lys Val Glu Ile Asp Glu Glu Leu
                485                 490                 495

Pro Val Trp Asp Gly Glu Leu Tyr Leu Glu Leu His Arg Gly Thr Tyr
            500                 505                 510

Thr Ser Gln Phe Arg Thr Lys Lys Leu His Lys Glu Ala Glu Asp Ser
        515                 520                 525

Leu Tyr Leu Ala Glu Leu Ile Ser Ala Phe Thr Asp Lys Asp Phe Ser
    530                 535                 540

Asp Glu Ile Asp Glu Leu Trp Lys Ile Leu Leu Arg Asn Glu Phe His
545                 550                 555                 560

Asp Ile Leu Pro Gly Ser Ser Ile Lys Glu Val Tyr Glu Asp Thr Glu
                565                 570                 575

Lys Glu Leu Arg His Val Ile Glu Lys Ser Lys Asp Ile Val Ile Glu
            580                 585                 590

Ser Leu Lys Val Leu Ser Ser Glu Asn Lys Asp Val Leu Thr Ile Leu
        595                 600                 605

Asn Ala Ser Ser Phe Pro Lys Lys Cys Leu Phe Phe Leu Asn Glu Asp
    610                 615                 620

Leu Ala Ile Ser Phe Glu Gly Glu Ala Leu Leu Lys Gln Lys Thr His
625                 630                 635                 640

Asp Gly Arg Tyr Val Tyr Phe Ile Asp Arg Glu Ile Pro Pro Phe Thr
                645                 650                 655

Lys Val Glu Leu Lys Val Arg Lys Ala Thr Ser Glu Glu Thr Pro Ser
            660                 665                 670

Glu Leu Arg Glu Thr Asn Ile Met Glu Asn Glu Phe Leu Arg Val His
        675                 680                 685

Val Asn Asp Asp Gly Thr Ile Gln Ile Tyr Asp Lys Glu Leu Asp Arg
    690                 695                 700

Tyr Val Phe Glu Glu Lys Gly Asn Ile Leu Lys Leu His Lys Asn Ile
```

```
                         705                 710                 715                 720
Pro Ala Tyr Trp Asp Asn Trp Asp Ile Ala Glu Asn Val Glu Lys Thr
                    725                 730                 735
Gly Tyr Thr Leu Arg Ala Lys Asn Ile Glu Lys Ile Glu Ser Gly Pro
                740                 745                 750
Val Arg Glu Val Ile Arg Val Glu His Glu Ser Glu Gly Ser Arg Ile
            755                 760                 765
Thr Gln His Tyr Ile Leu Tyr Arg Lys Ser Arg Arg Leu Asp Ile Glu
        770                 775                 780
Thr Lys Val Asp Trp His Thr Arg Arg Ala Leu Leu Arg Ala Tyr Phe
785                 790                 795                 800
Pro Thr Thr Val Leu Ser Arg Lys Ala Arg Phe Asp Ile Ser Gly Gly
                805                 810                 815
Phe Ile Glu Arg Pro Thr His Arg Asn Thr Ser Phe Glu Gln Ala Arg
            820                 825                 830
Phe Glu Val Pro Phe His Arg Trp Met Asp Leu Ser Gln Thr Asp Phe
        835                 840                 845
Gly Val Ser Ile Leu Asn Asp Gly Lys Tyr Gly Gly Ser Val His Gln
850                 855                 860
Gly Ile Met Ala Leu Ser Leu Ile Lys Ala Gly Ile Phe Pro Asp Phe
865                 870                 875                 880
Leu Cys Asp Glu Gly Glu His Thr Phe Thr Tyr Ser Val Tyr Val His
                885                 890                 895
Pro Gly Asp Ser Leu Arg Asp Val Val Lys Gly Ser Glu Asp Leu Asn
            900                 905                 910
Arg Ser Phe Ile Val His Arg Gly Val Leu Asn Leu Pro Ser Pro Leu
        915                 920                 925
Leu Glu Ile Ser Pro Gln Asn Phe Arg Leu Thr Ser Leu Arg Arg Val
    930                 935                 940
Lys Asp Lys Ile Val Leu Arg Leu Val Glu Ile Phe Gly Thr Ser Gly
945                 950                 955                 960
Lys Leu Ser Ile Lys Leu Pro Trp His Gly Glu Ile Tyr Gln Thr Asn
                965                 970                 975
Val Leu Glu Glu Lys Lys Gln Lys Val Thr Phe Pro Val Val Tyr His
            980                 985                 990
Pro Phe Lys Ile Tyr Thr Phe Val Val Glu Gly
        995                 1000

<210> SEQ ID NO 39
<211> LENGTH: 2337
<212> TYPE: DNA
<213> ORGANISM: Thermotoga maritima
<220> FEATURE:
<221> NAME/KEY: CDS
<222> LOCATION: (1)...(2337)
<223> OTHER INFORMATION: clone # 6GC18

<400> SEQUENCE: 39 atg gaa ctg tac agg gat cct tcg caa ccc atc gaa gtg aga gtg aga          48
Met Glu Leu Tyr Arg Asp Pro Ser Gln Pro Ile Glu Val Arg Val Arg
  1               5                  10                  15 gat ctt ctt tcc aga atg acg ctg gaa gag aaa gtg gcc cag ctt ggg          96
Asp Leu Leu Ser Arg Met Thr Leu Glu Glu Lys Val Ala Gln Leu Gly
             20                  25                  30 tct gtc tgg ggt tac gaa ctg ata gac gag agg gga aag ttc agt aga         144
Ser Val Trp Gly Tyr Glu Leu Ile Asp Glu Arg Gly Lys Phe Ser Arg
         35                  40                  45
```

-continued

| | |
|---|---|
| gaa aaa gca aaa gaa ctc ctc aaa aat ggt ata ggc cag atc aca agg<br>Glu Lys Ala Lys Glu Leu Leu Lys Asn Gly Ile Gly Gln Ile Thr Arg<br>50                            55                        60 | 192 |
| cct ggt gga tca acg aac ctt gaa cct caa gaa gcc gcg gaa ctt gtg<br>Pro Gly Gly Ser Thr Asn Leu Glu Pro Gln Glu Ala Ala Glu Leu Val<br>65                            70                        75                        80 | 240 |
| aac gaa ata cag aga ttt ctt gtg gaa gaa aca cgc ctt gga att cct<br>Asn Glu Ile Gln Arg Phe Leu Val Glu Glu Thr Arg Leu Gly Ile Pro<br>                        85                        90                        95 | 288 |
| gcg atg ata cac gaa gaa tgt ctc acc ggt tac atg gga ctt gga gga<br>Ala Met Ile His Glu Glu Cys Leu Thr Gly Tyr Met Gly Leu Gly Gly<br>                      100                     105                     110 | 336 |
| acc aac ttc cct cag gcg ata gca atg gcg agt aca tgg gat cca gat<br>Thr Asn Phe Pro Gln Ala Ile Ala Met Ala Ser Thr Trp Asp Pro Asp<br>               115                     120                     125 | 384 |
| ctc ata gaa aaa atg acc acc gcc gtc aga gag gat atg aga aag ata<br>Leu Ile Glu Lys Met Thr Thr Ala Val Arg Glu Asp Met Arg Lys Ile<br>130                            135                     140 | 432 |
| ggg gca cat cag ggt ctc gca cct gtt ctg gat gtc gca aga gat cca<br>Gly Ala His Gln Gly Leu Ala Pro Val Leu Asp Val Ala Arg Asp Pro<br>145                            150                     155                     160 | 480 |
| agg tgg gga aga aca gaa gag acg ttc gga gaa tct ccc tat ctg gtg<br>Arg Trp Gly Arg Thr Glu Glu Thr Phe Gly Glu Ser Pro Tyr Leu Val<br>                      165                     170                     175 | 528 |
| gcg agg atg gga gtc tct tac gtg aaa ggc ctc cag ggg gaa gat atc<br>Ala Arg Met Gly Val Ser Tyr Val Lys Gly Leu Gln Gly Glu Asp Ile<br>                        180                     185                     190 | 576 |
| aaa aaa ggt gtc gtt gcc aca gtg aaa cac ttc gcc gga tac agc gct<br>Lys Lys Gly Val Val Ala Thr Val Lys His Phe Ala Gly Tyr Ser Ala<br>               195                     200                     205 | 624 |
| tct gaa ggt gga aag aac tgg gca cca acg aac att ccg gag agg gaa<br>Ser Glu Gly Gly Lys Asn Trp Ala Pro Thr Asn Ile Pro Glu Arg Glu<br>210                            215                     220 | 672 |
| ttc aaa gag gtc ttt ctc ttt ccg ttc gaa gcg gcc gtt aaa gaa gcg<br>Phe Lys Glu Val Phe Leu Phe Pro Phe Glu Ala Ala Val Lys Glu Ala<br>225                            230                     235                     240 | 720 |
| aat gtg ctt tct gtg atg aac tcc tac agc gaa ata gac ggt gtc cca<br>Asn Val Leu Ser Val Met Asn Ser Tyr Ser Glu Ile Asp Gly Val Pro<br>                        245                     250                     255 | 768 |
| tgt gca gcg aac agg aaa ctc ctc aca gac att ctc aga aaa gac tgg<br>Cys Ala Ala Asn Arg Lys Leu Leu Thr Asp Ile Leu Arg Lys Asp Trp<br>                      260                     265                     270 | 816 |
| gga ttc gaa gga atc gtc gtt tct gac tat ttt gct gtg aaa gtt ctg<br>Gly Phe Glu Gly Ile Val Val Ser Asp Tyr Phe Ala Val Lys Val Leu<br>               275                     280                     285 | 864 |
| gaa gat tat cac aga ata gca agg gat aag tca gaa gcc gca aga ctc<br>Glu Asp Tyr His Arg Ile Ala Arg Asp Lys Ser Glu Ala Ala Arg Leu<br>290                            295                     300 | 912 |
| gca ctt gaa gcg ggg ata gat gtt gaa ctt ccg aag aca gaa tgt tat<br>Ala Leu Glu Ala Gly Ile Asp Val Glu Leu Pro Lys Thr Glu Cys Tyr<br>305                            310                     315                     320 | 960 |
| caa tat ttg aaa gac ctt gtt gaa aaa ggc atc atc tcc gaa gct ttg<br>Gln Tyr Leu Lys Asp Leu Val Glu Lys Gly Ile Ile Ser Glu Ala Leu<br>                        325                     330                     335 | 1008 |
| atc gac gag gca gtc acc agg gtg ctg agg ctg aag ttc atg ctc ggg<br>Ile Asp Glu Ala Val Thr Arg Val Leu Arg Leu Lys Phe Met Leu Gly<br>                      340                     345                     350 | 1056 |
| ctc ttc gaa aat ccc tac gtt gag gtg gaa aaa gca aag ata gaa agt<br>Leu Phe Glu Asn Pro Tyr Val Glu Val Glu Lys Ala Lys Ile Glu Ser | 1104 |

-continued

```
            355                 360                 365
cac aga gac atc gca ctc gag ata gca agg aaa tcc att atc ctt ctc    1152
His Arg Asp Ile Ala Leu Glu Ile Ala Arg Lys Ser Ile Ile Leu Leu
    370                 375                 380 aag aat gat gga att ctg cct ctt cag aaa aac aaa aaa gtt gcc ctg    1200
Lys Asn Asp Gly Ile Leu Pro Leu Gln Lys Asn Lys Lys Val Ala Leu
385                 390                 395                 400 atc gga ccg aac gcg ggt gag gtg aga aat ctc ctc gga gat tac atg    1248
Ile Gly Pro Asn Ala Gly Glu Val Arg Asn Leu Leu Gly Asp Tyr Met
            405                 410                 415 tac ctt gca cac ata agg gct ctc ctc gac aac ata gac gac gtc ttt    1296
Tyr Leu Ala His Ile Arg Ala Leu Leu Asp Asn Ile Asp Asp Val Phe
                420                 425                 430 gga aat cct cag atc ccg aga gaa aac tac gaa aga ctg aag aag agc    1344
Gly Asn Pro Gln Ile Pro Arg Glu Asn Tyr Glu Arg Leu Lys Lys Ser
            435                 440                 445 ata gaa gaa cat atg aag agc att ccg agt gtt ctc gat gcc ttc aaa    1392
Ile Glu Glu His Met Lys Ser Ile Pro Ser Val Leu Asp Ala Phe Lys
450                 455                 460 gaa gaa ggg atc gaa ttc gaa tat gca aaa ggc tgt gaa gtg aca ggg    1440
Glu Glu Gly Ile Glu Phe Glu Tyr Ala Lys Gly Cys Glu Val Thr Gly
465                 470                 475                 480 gaa gac aga agc ggt ttc gaa gag gcg ata gaa att gca aag aaa tcc    1488
Glu Asp Arg Ser Gly Phe Glu Glu Ala Ile Glu Ile Ala Lys Lys Ser
            485                 490                 495 gac gtt gcc atc gtt gtc gta ggg gac aaa tct gga ctc acc ctt gac    1536
Asp Val Ala Ile Val Val Val Gly Asp Lys Ser Gly Leu Thr Leu Asp
                500                 505                 510 tgc aca acc ggt gag tcc aga gac atg gca aac ctc aag ctt cca gga    1584
Cys Thr Thr Gly Glu Ser Arg Asp Met Ala Asn Leu Lys Leu Pro Gly
            515                 520                 525 gtc cag gaa gaa ctc gtc ctc gaa gtt gca aag aca gga aaa ccc gtc    1632
Val Gln Glu Glu Leu Val Leu Glu Val Ala Lys Thr Gly Lys Pro Val
        530                 535                 540 gtt ctt gtc ctc atc acg gga aga ccc tat tca ctc aaa aac gtc gtc    1680
Val Leu Val Leu Ile Thr Gly Arg Pro Tyr Ser Leu Lys Asn Val Val
545                 550                 555                 560 gac aag gtg aac gcg atc ctt cag gtg tgg ctt cct gga gaa gcg gga    1728
Asp Lys Val Asn Ala Ile Leu Gln Val Trp Leu Pro Gly Glu Ala Gly
            565                 570                 575 gga aga gcg atc gtt gac atc atc tat gga aag gtg aat ccc tct gga    1776
Gly Arg Ala Ile Val Asp Ile Ile Tyr Gly Lys Val Asn Pro Ser Gly
                580                 585                 590 aaa ctc ccg atc agc ttt cca aga agc gct ggt cag att cct gtc ttc    1824
Lys Leu Pro Ile Ser Phe Pro Arg Ser Ala Gly Gln Ile Pro Val Phe
            595                 600                 605 cac tac gtc aaa cca tcc ggg gga agg tct cac tgg cac gga gac tac    1872
His Tyr Val Lys Pro Ser Gly Gly Arg Ser His Trp His Gly Asp Tyr
        610                 615                 620 gtg gat gag agc aca aag cct ctc ttc ccg ttt ggg cac ggt ttg tct    1920
Val Asp Glu Ser Thr Lys Pro Leu Phe Pro Phe Gly His Gly Leu Ser
625                 630                 635                 640 tac acg aag ttc gag tac agc aac ctc aga atc gag ccg aag gaa gtg    1968
Tyr Thr Lys Phe Glu Tyr Ser Asn Leu Arg Ile Glu Pro Lys Glu Val
            645                 650                 655 cca ccg gcc ggc gaa gtg gta ata aag gtg gac gtg gaa aac atc gga    2016
Pro Pro Ala Gly Glu Val Val Ile Lys Val Asp Val Glu Asn Ile Gly
                660                 665                 670 gac aga gac gga gac gag gtg gtt caa ctt tac atc ggt cgt gag ttt    2064
Asp Arg Asp Gly Asp Glu Val Val Gln Leu Tyr Ile Gly Arg Glu Phe
```

```
Asp Arg Asp Gly Asp Glu Val Val Gln Leu Tyr Ile Gly Arg Glu Phe
            675                 680                 685 gca agc gtc aca agg cct gtg aaa gag ctg aag ggc ttc aag agg gtt      2112
Ala Ser Val Thr Arg Pro Val Lys Glu Leu Lys Gly Phe Lys Arg Val
            690                 695                 700 tct ttg aag gcg aaa gag aag aag act gtt gtg ttc agg ctt cac atg      2160
Ser Leu Lys Ala Lys Glu Lys Lys Thr Val Val Phe Arg Leu His Met
705                 710                 715                 720 gac gtg ctc gcc tac tac aac aga gac atg aaa ctc gtg gtt gaa ccc      2208
Asp Val Leu Ala Tyr Tyr Asn Arg Asp Met Lys Leu Val Val Glu Pro
            725                 730                 735 ggt gag ttc aaa gtg atg gtg gga agc tct tct gaa gac atc aga ctc      2256
Gly Glu Phe Lys Val Met Val Gly Ser Ser Ser Glu Asp Ile Arg Leu
            740                 745                 750 aca ggt tct ttc tcc gtc gtc ggt gaa aaa aga gaa gtg gtg gga atg      2304
Thr Gly Ser Phe Ser Val Val Gly Glu Lys Arg Glu Val Val Gly Met
            755                 760                 765 agg aaa ttc ttc acg gaa gcc tgc gag gag tga                          2337
Arg Lys Phe Phe Thr Glu Ala Cys Glu Glu *
            770                 775

<210> SEQ ID NO 40
<211> LENGTH: 778
<212> TYPE: PRT
<213> ORGANISM: Thermotoga maritima

<400> SEQUENCE: 40

Met Glu Leu Tyr Arg Asp Pro Ser Gln Pro Ile Glu Val Arg Val Arg
  1               5                  10                  15

Asp Leu Leu Ser Arg Met Thr Leu Glu Glu Lys Val Ala Gln Leu Gly
                 20                  25                  30

Ser Val Trp Gly Tyr Glu Leu Ile Asp Glu Arg Gly Lys Phe Ser Arg
             35                  40                  45

Glu Lys Ala Lys Glu Leu Leu Lys Asn Gly Ile Gly Gln Ile Thr Arg
         50                  55                  60

Pro Gly Gly Ser Thr Asn Leu Glu Pro Gln Glu Ala Ala Glu Leu Val
 65                  70                  75                  80

Asn Glu Ile Gln Arg Phe Leu Val Glu Thr Arg Leu Gly Ile Pro
                 85                  90                  95

Ala Met Ile His Glu Glu Cys Leu Thr Gly Tyr Met Gly Leu Gly Gly
            100                 105                 110

Thr Asn Phe Pro Gln Ala Ile Ala Met Ala Ser Thr Trp Asp Pro Asp
            115                 120                 125

Leu Ile Glu Lys Met Thr Thr Ala Val Arg Glu Asp Met Arg Lys Ile
        130                 135                 140

Gly Ala His Gln Gly Leu Ala Pro Val Leu Asp Val Ala Arg Asp Pro
145                 150                 155                 160

Arg Trp Gly Arg Thr Glu Thr Phe Gly Glu Ser Pro Tyr Leu Val
            165                 170                 175

Ala Arg Met Gly Val Ser Tyr Val Lys Gly Leu Gln Gly Glu Asp Ile
            180                 185                 190

Lys Lys Gly Val Val Ala Thr Val Lys His Phe Ala Gly Tyr Ser Ala
        195                 200                 205

Ser Glu Gly Gly Lys Asn Trp Ala Pro Thr Asn Ile Pro Glu Arg Glu
    210                 215                 220

Phe Lys Glu Val Phe Leu Phe Pro Phe Glu Ala Ala Val Lys Glu Ala
225                 230                 235                 240
```

-continued

```
Asn Val Leu Ser Val Met Asn Ser Tyr Ser Glu Ile Asp Gly Val Pro
                245                 250                 255
Cys Ala Ala Asn Arg Lys Leu Leu Thr Asp Ile Leu Arg Lys Asp Trp
            260                 265                 270
Gly Phe Glu Gly Ile Val Val Ser Asp Tyr Phe Ala Val Lys Val Leu
        275                 280                 285
Glu Asp Tyr His Arg Ile Ala Arg Asp Lys Ser Glu Ala Ala Arg Leu
    290                 295                 300
Ala Leu Glu Ala Gly Ile Asp Val Glu Leu Pro Lys Thr Glu Cys Tyr
305                 310                 315                 320
Gln Tyr Leu Lys Asp Leu Val Glu Lys Gly Ile Ile Ser Glu Ala Leu
                325                 330                 335
Ile Asp Glu Ala Val Thr Arg Val Leu Arg Leu Lys Phe Met Leu Gly
            340                 345                 350
Leu Phe Glu Asn Pro Tyr Val Glu Val Glu Lys Ala Lys Ile Glu Ser
        355                 360                 365
His Arg Asp Ile Ala Leu Glu Ile Ala Arg Lys Ser Ile Ile Leu Leu
    370                 375                 380
Lys Asn Asp Gly Ile Leu Pro Leu Gln Lys Asn Lys Lys Val Ala Leu
385                 390                 395                 400
Ile Gly Pro Asn Ala Gly Glu Val Arg Asn Leu Leu Gly Asp Tyr Met
                405                 410                 415
Tyr Leu Ala His Ile Arg Ala Leu Leu Asp Asn Ile Asp Asp Val Phe
            420                 425                 430
Gly Asn Pro Gln Ile Pro Arg Glu Asn Tyr Glu Arg Leu Lys Lys Ser
        435                 440                 445
Ile Glu Glu His Met Lys Ser Ile Pro Ser Val Leu Asp Ala Phe Lys
    450                 455                 460
Glu Glu Gly Ile Glu Phe Glu Tyr Ala Lys Gly Cys Glu Val Thr Gly
465                 470                 475                 480
Glu Asp Arg Ser Gly Phe Glu Glu Ala Ile Glu Ile Ala Lys Lys Ser
                485                 490                 495
Asp Val Ala Ile Val Val Val Gly Asp Lys Ser Gly Leu Thr Leu Asp
            500                 505                 510
Cys Thr Thr Gly Glu Ser Arg Asp Met Ala Asn Leu Lys Leu Pro Gly
        515                 520                 525
Val Gln Glu Glu Leu Val Leu Glu Val Ala Lys Thr Gly Lys Pro Val
    530                 535                 540
Val Leu Val Leu Ile Thr Gly Arg Pro Tyr Ser Leu Lys Asn Val Val
545                 550                 555                 560
Asp Lys Val Asn Ala Ile Leu Gln Val Trp Leu Pro Gly Glu Ala Gly
                565                 570                 575
Gly Arg Ala Ile Val Asp Ile Ile Tyr Gly Lys Val Asn Pro Ser Gly
            580                 585                 590
Lys Leu Pro Ile Ser Phe Pro Arg Ser Ala Gly Gln Ile Pro Val Phe
        595                 600                 605
His Tyr Val Lys Pro Ser Gly Gly Arg Ser His Trp His Gly Asp Tyr
    610                 615                 620
Val Asp Glu Ser Thr Lys Pro Leu Phe Pro Phe Gly His Gly Leu Ser
625                 630                 635                 640
Tyr Thr Lys Phe Glu Tyr Ser Asn Leu Arg Ile Glu Pro Lys Glu Val
                645                 650                 655
```

-continued

```
Pro Pro Ala Gly Glu Val Val Ile Lys Val Asp Val Glu Asn Ile Gly
        660                 665                 670

Asp Arg Asp Gly Asp Glu Val Val Gln Leu Tyr Ile Gly Arg Glu Phe
    675                 680                 685

Ala Ser Val Thr Arg Pro Val Lys Glu Leu Lys Gly Phe Lys Arg Val
    690                 695                 700

Ser Leu Lys Ala Lys Glu Lys Lys Thr Val Val Phe Arg Leu His Met
705                 710                 715                 720

Asp Val Leu Ala Tyr Tyr Asn Arg Asp Met Lys Leu Val Val Glu Pro
            725                 730                 735

Gly Glu Phe Lys Val Met Val Gly Ser Ser Glu Asp Ile Arg Leu
        740                 745                 750

Thr Gly Ser Phe Ser Val Val Gly Glu Lys Arg Glu Val Val Gly Met
            755                 760                 765

Arg Lys Phe Phe Thr Glu Ala Cys Glu Glu
    770                 775

<210> SEQ ID NO 41
<211> LENGTH: 2043
<212> TYPE: DNA
<213> ORGANISM: Thermotoga maritima
<220> FEATURE:
<221> NAME/KEY: CDS
<222> LOCATION: (1)...(2043)
<223> OTHER INFORMATION: clone # 6GP2

<400> SEQUENCE: 41 atg ggg att ggt ggc gac gac tcc tgg agc ccg tca gta tcg gcg gaa       48
Met Gly Ile Gly Gly Asp Asp Ser Trp Ser Pro Ser Val Ser Ala Glu
  1               5                  10                  15 ttc ctt tta ttg atc gtt gag ctc tct ttc gtt ctc ttt gca agt gac       96
Phe Leu Leu Leu Ile Val Glu Leu Ser Phe Val Leu Phe Ala Ser Asp
             20                  25                  30 gag ttc gtg aaa gtg gaa aac gga aaa ttc gct ctg aac gga aaa gaa      144
Glu Phe Val Lys Val Glu Asn Gly Lys Phe Ala Leu Asn Gly Lys Glu
         35                  40                  45 ttc aga ttc att gga agc aac aac tac tac atg cac tac aag agc aac      192
Phe Arg Phe Ile Gly Ser Asn Asn Tyr Tyr Met His Tyr Lys Ser Asn
     50                  55                  60 gga atg ata gac agt gtt ctg gag agt gcc aga gac atg ggt ata aag      240
Gly Met Ile Asp Ser Val Leu Glu Ser Ala Arg Asp Met Gly Ile Lys
 65                  70                  75                  80 gtc ctc aga atc tgg ggt ttc ctc gac ggg gag agt tac tgc aga gac      288
Val Leu Arg Ile Trp Gly Phe Leu Asp Gly Glu Ser Tyr Cys Arg Asp
                 85                  90                  95 aag aac acc tac atg cat cct gag ccc ggt gtt ttc ggg gtg cca gaa      336
Lys Asn Thr Tyr Met His Pro Glu Pro Gly Val Phe Gly Val Pro Glu
            100                 105                 110 gga ata tcg aac gcc cag agc ggt ttc gaa aga ctc gac tac aca gtt      384
Gly Ile Ser Asn Ala Gln Ser Gly Phe Glu Arg Leu Asp Tyr Thr Val
        115                 120                 125 gcg aaa gcg aaa gaa ctc ggt ata aaa ctt gtc att gtt ctt gtg aac      432
Ala Lys Ala Lys Glu Leu Gly Ile Lys Leu Val Ile Val Leu Val Asn
    130                 135                 140 aac tgg gac gac ttc ggt gga atg aac cag tac gtg agg tgg ttt gga      480
Asn Trp Asp Asp Phe Gly Gly Met Asn Gln Tyr Val Arg Trp Phe Gly
145                 150                 155                 160 gga acc cat cac gac gat ttc tac aga gat gag aag atc aaa gaa gag      528
Gly Thr His His Asp Asp Phe Tyr Arg Asp Glu Lys Ile Lys Glu Glu
                165                 170                 175
```

```
tac aaa aag tac gtc tcc ttt ctc gta aac cat gtc aat acc tac acg      576
Tyr Lys Lys Tyr Val Ser Phe Leu Val Asn His Val Asn Thr Tyr Thr
            180                 185                 190 gga gtt cct tac agg gaa gag ccc acc atc atg gcc tgg gag ctt gca      624
Gly Val Pro Tyr Arg Glu Glu Pro Thr Ile Met Ala Trp Glu Leu Ala
            195                 200                 205 aac gaa ccg cgc tgt gag acg gac aaa tcg ggg aac acg ctc gtt gag      672
Asn Glu Pro Arg Cys Glu Thr Asp Lys Ser Gly Asn Thr Leu Val Glu
210                 215                 220 tgg gtg aag gag atg agc tcc tac ata aag agt ctg gat ccc aac cac      720
Trp Val Lys Glu Met Ser Ser Tyr Ile Lys Ser Leu Asp Pro Asn His
225                 230                 235                 240 ctc gtg gct gtg ggg gac gaa gga ttc ttc agc aac tac gaa gga ttc      768
Leu Val Ala Val Gly Asp Glu Gly Phe Phe Ser Asn Tyr Glu Gly Phe
            245                 250                 255 aaa cct tac ggt gga gaa gcc gag tgg gcc tac aac ggc tgg tcc ggt      816
Lys Pro Tyr Gly Gly Glu Ala Glu Trp Ala Tyr Asn Gly Trp Ser Gly
            260                 265                 270 gtt gac tgg aag aag ctc ctt tcg ata gag acg gtg gac ttc ggc acg      864
Val Asp Trp Lys Lys Leu Leu Ser Ile Glu Thr Val Asp Phe Gly Thr
            275                 280                 285 ttc cac ctc tat ccg tcc cac tgg ggt gtc agt cca gag aac tat gcc      912
Phe His Leu Tyr Pro Ser His Trp Gly Val Ser Pro Glu Asn Tyr Ala
            290                 295                 300 cag tgg gga gcg aag tgg ata gaa gac cac ata aag atc gca aaa gag      960
Gln Trp Gly Ala Lys Trp Ile Glu Asp His Ile Lys Ile Ala Lys Glu
305                 310                 315                 320 atc gga aaa ccc gtt gtt ctg gaa gaa tat gga att cca aag agt gcg     1008
Ile Gly Lys Pro Val Val Leu Glu Glu Tyr Gly Ile Pro Lys Ser Ala
            325                 330                 335 cca gtt aac aga acg gcc atc tac aga ctc tgg aac gat ctg gtc tac     1056
Pro Val Asn Arg Thr Ala Ile Tyr Arg Leu Trp Asn Asp Leu Val Tyr
            340                 345                 350 gat ctc ggt gga gat gga gcg atg ttc tgg atg ctc gcg gga atc ggg     1104
Asp Leu Gly Gly Asp Gly Ala Met Phe Trp Met Leu Ala Gly Ile Gly
            355                 360                 365 gaa ggt tcg gac aga gac gag aga ggg tac tat ccg gac tac gac ggt     1152
Glu Gly Ser Asp Arg Asp Glu Arg Gly Tyr Tyr Pro Asp Tyr Asp Gly
            370                 375                 380 ttc aga ata gtg aac gac gac agt cca gaa gcg gaa ctg ata aga gaa     1200
Phe Arg Ile Val Asn Asp Asp Ser Pro Glu Ala Glu Leu Ile Arg Glu
385                 390                 395                 400 tac gcg aag ctg ttc aac aca ggt gaa gac ata aga gaa gac acc tgc     1248
Tyr Ala Lys Leu Phe Asn Thr Gly Glu Asp Ile Arg Glu Asp Thr Cys
            405                 410                 415 tct ttc atc ctt cca aaa gac ggc atg gag atc aaa aag acc gtg gaa     1296
Ser Phe Ile Leu Pro Lys Asp Gly Met Glu Ile Lys Lys Thr Val Glu
            420                 425                 430 gtg agg gct ggt gtt ttc gac tac agc aac acg ttt gaa aag ttg tct     1344
Val Arg Ala Gly Val Phe Asp Tyr Ser Asn Thr Phe Glu Lys Leu Ser
            435                 440                 445 gtc aaa gtc gaa gat ctg gtt ttt gaa aat gag ata gag cat ctc gga     1392
Val Lys Val Glu Asp Leu Val Phe Glu Asn Glu Ile Glu His Leu Gly
450                 455                 460 tac gga att tac ggc ttt gat ctc gac aca acc cgg atc ccg gat gga     1440
Tyr Gly Ile Tyr Gly Phe Asp Leu Asp Thr Thr Arg Ile Pro Asp Gly
465                 470                 475                 480 gaa cat gaa atg ttc ctt gaa ggc cac ttt cag gga aaa acg gtg aaa     1488
Glu His Glu Met Phe Leu Glu Gly His Phe Gln Gly Lys Thr Val Lys
```

```
                     485                 490                 495
gac tct atc aaa gcg aaa gtg gtg aac gaa gca cgg tac gtg ctc gca     1536
Asp Ser Ile Lys Ala Lys Val Val Asn Glu Ala Arg Tyr Val Leu Ala
            500                 505                 510 gag gaa gtt gat ttt tcc tct cca gaa gag gtg aaa aac tgg tgg aac     1584
Glu Glu Val Asp Phe Ser Ser Pro Glu Glu Val Lys Asn Trp Trp Asn
        515                 520                 525 agc gga acc tgg cag gca gag ttc ggg tca cct gac att gaa tgg aac     1632
Ser Gly Thr Trp Gln Ala Glu Phe Gly Ser Pro Asp Ile Glu Trp Asn
    530                 535                 540 ggt gag gtg gga aat gga gca ctg cag ctg aac gtg aaa ctg ccc gga     1680
Gly Glu Val Gly Asn Gly Ala Leu Gln Leu Asn Val Lys Leu Pro Gly
545                 550                 555                 560 aag agc gac tgg gaa gaa gtg aga gta gca agg aag ttc gaa aga ctc     1728
Lys Ser Asp Trp Glu Glu Val Arg Val Ala Arg Lys Phe Glu Arg Leu
                565                 570                 575 tca gaa tgt gag atc ctc gag tac gac atc tac att cca aac gtc gag     1776
Ser Glu Cys Glu Ile Leu Glu Tyr Asp Ile Tyr Ile Pro Asn Val Glu
            580                 585                 590 gga ctc aag gga agg ttg agg ccg tac gcg gtt ctg aac ccc ggc tgg     1824
Gly Leu Lys Gly Arg Leu Arg Pro Tyr Ala Val Leu Asn Pro Gly Trp
        595                 600                 605 gtg aag ata ggc ctc gac atg aac aac gcg aac gtg gaa agt gcg gag     1872
Val Lys Ile Gly Leu Asp Met Asn Asn Ala Asn Val Glu Ser Ala Glu
    610                 615                 620 atc atc act ttc ggc gga aaa gag tac aga aga ttc cat gta aga att     1920
Ile Ile Thr Phe Gly Gly Lys Glu Tyr Arg Arg Phe His Val Arg Ile
625                 630                 635                 640 gag ttc gac aga aca gcg ggg gtg aaa gaa ctt cac ata gga gtt gtc     1968
Glu Phe Asp Arg Thr Ala Gly Val Lys Glu Leu His Ile Gly Val Val
                645                 650                 655 ggt gat cat ctg agg tac gat gga ccg att ttc atc gat aat gtg aga     2016
Gly Asp His Leu Arg Tyr Asp Gly Pro Ile Phe Ile Asp Asn Val Arg
            660                 665                 670 ctt tat aaa aga aca gga ggt atg tga                                 2043
Leu Tyr Lys Arg Thr Gly Gly Met *
        675                 680

<210> SEQ ID NO 42
<211> LENGTH: 680
<212> TYPE: PRT
<213> ORGANISM: Thermotoga maritima

<400> SEQUENCE: 42

Met Gly Ile Gly Gly Asp Asp Ser Trp Ser Pro Ser Val Ser Ala Glu
 1               5                  10                  15

Phe Leu Leu Leu Ile Val Glu Leu Ser Phe Val Leu Phe Ala Ser Asp
                20                  25                  30

Glu Phe Val Lys Val Glu Asn Gly Lys Phe Ala Leu Asn Gly Lys Glu
            35                  40                  45

Phe Arg Phe Ile Gly Ser Asn Asn Tyr Tyr Met His Tyr Lys Ser Asn
        50                  55                  60

Gly Met Ile Asp Ser Val Leu Glu Ser Ala Arg Asp Met Gly Ile Lys
65                  70                  75                  80

Val Leu Arg Ile Trp Gly Phe Leu Asp Gly Glu Ser Tyr Cys Arg Asp
                85                  90                  95

Lys Asn Thr Tyr Met His Pro Glu Pro Gly Val Phe Gly Val Pro Glu
            100                 105                 110
```

-continued

```
Gly Ile Ser Asn Ala Gln Ser Gly Phe Glu Arg Leu Asp Tyr Thr Val
            115                 120                 125
Ala Lys Ala Lys Glu Leu Gly Ile Lys Leu Val Ile Val Leu Val Asn
        130                 135                 140
Asn Trp Asp Asp Phe Gly Gly Met Asn Gln Tyr Val Arg Trp Phe Gly
145                 150                 155                 160
Gly Thr His His Asp Asp Phe Tyr Arg Asp Glu Lys Ile Lys Glu Glu
                165                 170                 175
Tyr Lys Lys Tyr Val Ser Phe Leu Val Asn His Val Asn Thr Tyr Thr
            180                 185                 190
Gly Val Pro Tyr Arg Glu Glu Pro Thr Ile Met Ala Trp Glu Leu Ala
        195                 200                 205
Asn Glu Pro Arg Cys Glu Thr Asp Lys Ser Gly Asn Thr Leu Val Glu
    210                 215                 220
Trp Val Lys Glu Met Ser Ser Tyr Ile Lys Ser Leu Asp Pro Asn His
225                 230                 235                 240
Leu Val Ala Val Gly Asp Glu Gly Phe Phe Ser Asn Tyr Glu Gly Phe
                245                 250                 255
Lys Pro Tyr Gly Gly Glu Ala Glu Trp Ala Tyr Asn Gly Trp Ser Gly
            260                 265                 270
Val Asp Trp Lys Lys Leu Leu Ser Ile Glu Thr Val Asp Phe Gly Thr
        275                 280                 285
Phe His Leu Tyr Pro Ser His Trp Gly Val Ser Pro Glu Asn Tyr Ala
    290                 295                 300
Gln Trp Gly Ala Lys Trp Ile Glu Asp His Ile Lys Ile Ala Lys Glu
305                 310                 315                 320
Ile Gly Lys Pro Val Val Leu Glu Glu Tyr Gly Ile Pro Lys Ser Ala
                325                 330                 335
Pro Val Asn Arg Thr Ala Ile Tyr Arg Leu Trp Asn Asp Leu Val Tyr
            340                 345                 350
Asp Leu Gly Gly Asp Gly Ala Met Phe Trp Met Leu Ala Gly Ile Gly
        355                 360                 365
Glu Gly Ser Asp Arg Asp Glu Arg Gly Tyr Tyr Pro Asp Tyr Asp Gly
    370                 375                 380
Phe Arg Ile Val Asn Asp Asp Ser Pro Glu Ala Glu Leu Ile Arg Glu
385                 390                 395                 400
Tyr Ala Lys Leu Phe Asn Thr Gly Glu Asp Ile Arg Glu Asp Thr Cys
                405                 410                 415
Ser Phe Ile Leu Pro Lys Asp Gly Met Glu Ile Lys Lys Thr Val Glu
            420                 425                 430
Val Arg Ala Gly Val Phe Asp Tyr Ser Asn Thr Phe Glu Lys Leu Ser
        435                 440                 445
Val Lys Val Glu Asp Leu Val Phe Glu Asn Glu Ile Glu His Leu Gly
    450                 455                 460
Tyr Gly Ile Tyr Gly Phe Asp Leu Asp Thr Thr Arg Ile Pro Asp Gly
465                 470                 475                 480
Glu His Glu Met Phe Leu Glu Gly His Phe Gln Gly Lys Thr Val Lys
                485                 490                 495
Asp Ser Ile Lys Ala Lys Val Val Asn Glu Ala Arg Tyr Val Leu Ala
            500                 505                 510
Glu Glu Val Asp Phe Ser Ser Pro Glu Glu Val Lys Asn Trp Trp Asn
        515                 520                 525
Ser Gly Thr Trp Gln Ala Glu Phe Gly Ser Pro Asp Ile Glu Trp Asn
```

-continued

```
                530                 535                 540
Gly Glu Val Gly Asn Gly Ala Leu Gln Leu Asn Val Lys Leu Pro Gly
545                 550                 555                 560

Lys Ser Asp Trp Glu Glu Val Arg Val Ala Arg Lys Phe Glu Arg Leu
                565                 570                 575

Ser Glu Cys Glu Ile Leu Glu Tyr Asp Ile Tyr Ile Pro Asn Val Glu
                580                 585                 590

Gly Leu Lys Gly Arg Leu Arg Pro Tyr Ala Val Leu Asn Pro Gly Trp
                595                 600                 605

Val Lys Ile Gly Leu Asp Met Asn Asn Ala Asn Val Glu Ser Ala Glu
                610                 615                 620

Ile Ile Thr Phe Gly Lys Glu Tyr Arg Arg Phe His Val Arg Ile
625                 630                 635                 640

Glu Phe Asp Arg Thr Ala Gly Val Lys Glu Leu His Ile Gly Val Val
                645                 650                 655

Gly Asp His Leu Arg Tyr Asp Gly Pro Ile Phe Ile Asp Asn Val Arg
                660                 665                 670

Leu Tyr Lys Arg Thr Gly Gly Met
            675                 680

<210> SEQ ID NO 43
<211> LENGTH: 2712
<212> TYPE: DNA
<213> ORGANISM: Polyangium brachysporum
<220> FEATURE:
<221> NAME/KEY: CDS
<222> LOCATION: (1)...(2712)
<223> OTHER INFORMATION: clone # 78GA1

<400> SEQUENCE: 43 atg ttc ctg cat ccg agg ggt cgc atg acc cgc cta gcg ctc ggc tgt    48
Met Phe Leu His Pro Arg Gly Arg Met Thr Arg Leu Ala Leu Gly Cys
1               5                   10                  15 gcc gtg ctg tgt ctg gcc gtc gca ggc tgc ggt ggt ggt gat gac gac    96
Ala Val Leu Cys Leu Ala Val Ala Gly Cys Gly Gly Gly Asp Asp Asp
                20                  25                  30 ggc gac gac aac ggc acc gcc ccc cag ccc gca cct ggt caa ccc gag   144
Gly Asp Asp Asn Gly Thr Ala Pro Gln Pro Ala Pro Gly Gln Pro Glu
            35                  40                  45 ccc ccg act gac acc gtg ctg aaa gac tgg cct cgc atc aac agc agc   192
Pro Pro Thr Asp Thr Val Leu Lys Asp Trp Pro Arg Ile Asn Ser Ser
        50                  55                  60 atc acc gcc gac gca gcg atc gaa agc cgc gtc aac tca ctc gtc gcg   240
Ile Thr Ala Asp Ala Ala Ile Glu Ser Arg Val Asn Ser Leu Val Ala
65                  70                  75                  80 gcg atg acg ctg gaa gaa aaa gtc ggc cag atg acg cag gtc gaa atc   288
Ala Met Thr Leu Glu Glu Lys Val Gly Gln Met Thr Gln Val Glu Ile
                85                  90                  95 cag gag gtg acg ccg gag gag atc cgg cag tac cac atc ggc tcc gtg   336
Gln Glu Val Thr Pro Glu Glu Ile Arg Gln Tyr His Ile Gly Ser Val
                100                 105                 110 ctc aac ggc ggt ggt tcg ttc ccg aag cag gac aag ggc gcg gcg gtg   384
Leu Asn Gly Gly Gly Ser Phe Pro Lys Gln Asp Lys Gly Ala Ala Val
            115                 120                 125 acc gac tgg ctg gcg gtg gcc gac gcc ttg tgg gcc gcg tcg atg gat   432
Thr Asp Trp Leu Ala Val Ala Asp Ala Leu Trp Ala Ala Ser Met Asp
        130                 135                 140 ccc gcc aag ccg cgg cgc atc ccg ctc atc tgg ggc acc gac gcc gtc   480
Pro Ala Lys Pro Arg Arg Ile Pro Leu Ile Trp Gly Thr Asp Ala Val
```

```
                      -continued
145                 150                 155                 160 cac ggc cac aac aac gtc aag ggc gcg acc atc ttc ccg cac aac atc     528
His Gly His Asn Asn Val Lys Gly Ala Thr Ile Phe Pro His Asn Ile
                165                 170                 175 ggc ctg ggc gcc gcg cgc gac ccc gac ttg gtc gcc cgc atc ggc gcc     576
Gly Leu Gly Ala Ala Arg Asp Pro Asp Leu Val Ala Arg Ile Gly Ala
            180                 185                 190 gcc acg gcg ctg gaa gtg gca cgc acc ggc atc gac tgg gtg ttc gcg     624
Ala Thr Ala Leu Glu Val Ala Arg Thr Gly Ile Asp Trp Val Phe Ala
        195                 200                 205 cca acg ctg gcg gtc gtg cgc gac gac cgc tgg ggc cgc agc tac gaa     672
Pro Thr Leu Ala Val Val Arg Asp Asp Arg Trp Gly Arg Ser Tyr Glu
    210                 215                 220 ggc tat tcg gaa gac ccc gaa atc gtc gtc tcc tat gcc ggc aag atg     720
Gly Tyr Ser Glu Asp Pro Glu Ile Val Val Ser Tyr Ala Gly Lys Met
225                 230                 235                 240 gtc gaa ggc ctg cag ggc cga ttg gcg cag gac gcg aag gcc aac gag     768
Val Glu Gly Leu Gln Gly Arg Leu Ala Gln Asp Ala Lys Ala Asn Glu
                245                 250                 255 aag gtg gtg gcc acc gcc aag cat ttc gtc ggc gac ggc ggc acc gac     816
Lys Val Val Ala Thr Ala Lys His Phe Val Gly Asp Gly Gly Thr Asp
            260                 265                 270 cag ggc aag gac cag ggg gtc acc cgg gtc acc gag cgc gac ctg ttg     864
Gln Gly Lys Asp Gln Gly Val Thr Arg Val Thr Glu Arg Asp Leu Leu
        275                 280                 285 aac gtc cat gcg cgc ggc tac atc ccc gcg ctc gag gcg ggc gcg caa     912
Asn Val His Ala Arg Gly Tyr Ile Pro Ala Leu Glu Ala Gly Ala Gln
    290                 295                 300 acc gtg atg gcc tcc ttc aac agc tgg cag gac ccg tcg cag ggc gag     960
Thr Val Met Ala Ser Phe Asn Ser Trp Gln Asp Pro Ser Gln Gly Glu
305                 310                 315                 320 ggc gcc aag gcc ttc aag atg cat ggc agc cgc tac ctg ctc acc gag    1008
Gly Ala Lys Ala Phe Lys Met His Gly Ser Arg Tyr Leu Leu Thr Glu
                325                 330                 335 gcc ctc aag cag aag atg ggc ttc gac ggt ttc gtg gtg tcc gac tgg    1056
Ala Leu Lys Gln Lys Met Gly Phe Asp Gly Phe Val Val Ser Asp Trp
            340                 345                 350 aac ggc atc ggc cag gtc acc acc gag aac agc aac gcg acg cgc aac    1104
Asn Gly Ile Gly Gln Val Thr Thr Glu Asn Ser Asn Ala Thr Arg Asn
        355                 360                 365 tgc agc aac agc gac tgc ccc gag gcc atc aac gct ggc atc gac atg    1152
Cys Ser Asn Ser Asp Cys Pro Glu Ala Ile Asn Ala Gly Ile Asp Met
    370                 375                 380 gtg atg gtg ccg tac cgg gcc gac tgg aag gcc ttc atc acc aac aca    1200
Val Met Val Pro Tyr Arg Ala Asp Trp Lys Ala Phe Ile Thr Asn Thr
385                 390                 395                 400 att gca att gtc cgc aaa ggc gag atc gcg cag gag cgc atc gac aac    1248
Ile Ala Ile Val Arg Lys Gly Glu Ile Ala Gln Glu Arg Ile Asp Asn
                405                 410                 415 gcg gtg cgg cgc atc ctg cgc gtc aag ttg cgc gcc ggt ctg ttc gac    1296
Ala Val Arg Arg Ile Leu Arg Val Lys Leu Arg Ala Gly Leu Phe Asp
            420                 425                 430 aag ccc aca ccc tcc gcc cgt ctg gcc tcg cgc gag gtc ggc agc gcc    1344
Lys Pro Thr Pro Ser Ala Arg Leu Ala Ser Arg Glu Val Gly Ser Ala
        435                 440                 445 gaa cac cgg gcg ctc gcg cgt gaa gcg gtg cgc aag tcg ttg gtg ctg    1392
Glu His Arg Ala Leu Ala Arg Glu Ala Val Arg Lys Ser Leu Val Leu
    450                 455                 460 ttg aag aac aac ggc cgg gtg ctg ccg ctg gca cgc aat gcc aag gtc    1440
```

```
          Leu Lys Asn Asn Gly Arg Val Leu Pro Leu Ala Arg Asn Ala Lys Val
          465                 470                 475                 480 ctg gtg gcc ggc aag agc gcc aac agc ctc gag aac cag acc ggc ggc       1488
Leu Val Ala Gly Lys Ser Ala Asn Ser Leu Glu Asn Gln Thr Gly Gly
                    485                 490                 495 tgg tcg ctc agc tgg caa ggc acc ggc aac gcc aac gcc gat ttc ggc       1536
Trp Ser Leu Ser Trp Gln Gly Thr Gly Asn Ala Asn Ala Asp Phe Gly
            500                 505                 510 ggc ggc acg acc gtg tgg cag gcg atc cag aag atc gcc ccg aat gcc       1584
Gly Gly Thr Thr Val Trp Gln Ala Ile Gln Lys Ile Ala Pro Asn Ala
        515                 520                 525 gaa ctc gac acc agc gcc gac ggc gcc aag ggc agc gat gcc tac gac       1632
Glu Leu Asp Thr Ser Ala Asp Gly Ala Lys Gly Ser Asp Ala Tyr Asp
    530                 535                 540 gcc gcg atc gtc gtg atc ggt gaa aca ccg tac gcc gaa ggt gtc gga       1680
Ala Ala Ile Val Val Ile Gly Glu Thr Pro Tyr Ala Glu Gly Val Gly
545                 550                 555                 560 gac atc ggc cgc agc aag acg ctg gaa ctc acc aag ctg cgt cca gaa       1728
Asp Ile Gly Arg Ser Lys Thr Leu Glu Leu Thr Lys Leu Arg Pro Glu
                565                 570                 575 gac ctc gcc gtg atc gaa ggc ctg cgc gcc aag ggc gtg aag aaa atc       1776
Asp Leu Ala Val Ile Glu Gly Leu Arg Ala Lys Gly Val Lys Lys Ile
            580                 585                 590 gtc acg ctg ctg gtc tcc ggc cgc ccg ctc tac gtc aac aag gag ctg       1824
Val Thr Leu Leu Val Ser Gly Arg Pro Leu Tyr Val Asn Lys Glu Leu
        595                 600                 605 aac cgc tcg gac gcc ttc gtg gcg gcg tgg ctg ccc ggc acc gaa ggc       1872
Asn Arg Ser Asp Ala Phe Val Ala Ala Trp Leu Pro Gly Thr Glu Gly
    610                 615                 620 gac ggc gtc gcc gac gtg ctg ttc cgt gcg gcc gac ggc agc gtc gcg       1920
Asp Gly Val Ala Asp Val Leu Phe Arg Ala Ala Asp Gly Ser Val Ala
625                 630                 635                 640 cat ggc ttc agc ggc aag ctg tcg ttc tcg tgg ccg aag tcg gcc tgc       1968
His Gly Phe Ser Gly Lys Leu Ser Phe Ser Trp Pro Lys Ser Ala Cys
                645                 650                 655 cag acg ccg ctc aac cgt ggc gac gcc acc tac gac ccg ctc tac gct       2016
Gln Thr Pro Leu Asn Arg Gly Asp Ala Thr Tyr Asp Pro Leu Tyr Ala
            660                 665                 670 tat ggc tac ggc ctt caa tac ggc gag gag acc gat cag agc gcg tac       2064
Tyr Gly Tyr Gly Leu Gln Tyr Gly Glu Glu Thr Asp Gln Ser Ala Tyr
        675                 680                 685 gac gaa agc agt gcc acg gtc ggc tgc ggc atc cag gac ggc ggc ggc       2112
Asp Glu Ser Ser Ala Thr Val Gly Cys Gly Ile Gln Asp Gly Gly Gly
    690                 695                 700 acc acg gcc gag ccg ctg gcg gtg ttc gaa ggc gga gcc aac cag ggc       2160
Thr Thr Ala Glu Pro Leu Ala Val Phe Glu Gly Gly Ala Asn Gln Gly
705                 710                 715                 720 aac tgg aag ctg cgc atc ggc gcc gag tcg agc tgg agc aac gat gtg       2208
Asn Trp Lys Leu Arg Ile Gly Ala Glu Ser Ser Trp Ser Asn Asp Val
                725                 730                 735 acg ctg gcc agc agc gcg gtg acg tcg acg ccg tcc aac gaa ctg cag       2256
Thr Leu Ala Ser Ser Ala Val Thr Ser Thr Pro Ser Asn Glu Leu Gln
            740                 745                 750 gcc gtg ccg gtg gac gac aag gcc ggg cgg caa tgg gcg gcg gtg aag       2304
Ala Val Pro Val Asp Asp Lys Ala Gly Arg Gln Trp Ala Ala Val Lys
        755                 760                 765 gcg acc tgg aac gac aag ccc ggc cag ctc tac atg caa agc gcc aac       2352
Ala Thr Trp Asn Asp Lys Pro Gly Gln Leu Tyr Met Gln Ser Ala Asn
    770                 775                 780
```

-continued

```
ccc ggc gac ctg gtg gac ctg atg gcc tat cag aac tcc ggt ggc gcg    2400
Pro

-continued

```
Pro Thr Leu Ala Val Val Arg Asp Asp Arg Trp Gly Arg Ser Tyr Glu
    210                 215                 220
Gly Tyr Ser Glu Asp Pro Glu Ile Val Val Ser Tyr Ala Gly Lys Met
225                 230                 235                 240
Val Glu Gly Leu Gln Gly Arg Leu Ala Gln Asp Ala Lys Ala Asn Glu
                245                 250                 255
Lys Val Val Ala Thr Ala Lys His Phe Val Gly Asp Gly Gly Thr Asp
            260                 265                 270
Gln Gly Lys Asp Gln Gly Val Thr Arg Val Thr Glu Arg Asp Leu Leu
        275                 280                 285
Asn Val His Ala Arg Gly Tyr Ile Pro Ala Leu Glu Ala Gly Ala Gln
    290                 295                 300
Thr Val Met Ala Ser Phe Asn Ser Trp Gln Asp Pro Ser Gln Gly Glu
305                 310                 315                 320
Gly Ala Lys Ala Phe Lys Met His Gly Ser Arg Tyr Leu Leu Thr Glu
                325                 330                 335
Ala Leu Lys Gln Lys Met Gly Phe Asp Gly Phe Val Val Ser Asp Trp
            340                 345                 350
Asn Gly Ile Gly Gln Val Thr Thr Glu Asn Ser Asn Ala Thr Arg Asn
        355                 360                 365
Cys Ser Asn Ser Asp Cys Pro Glu Ala Ile Asn Ala Gly Ile Asp Met
    370                 375                 380
Val Met Val Pro Tyr Arg Ala Asp Trp Lys Ala Phe Ile Thr Asn Thr
385                 390                 395                 400
Ile Ala Ile Val Arg Lys Gly Glu Ile Ala Gln Glu Arg Ile Asp Asn
                405                 410                 415
Ala Val Arg Arg Ile Leu Arg Val Lys Leu Arg Ala Gly Leu Phe Asp
            420                 425                 430
Lys Pro Thr Pro Ser Ala Arg Leu Ala Ser Arg Glu Val Gly Ser Ala
        435                 440                 445
Glu His Arg Ala Leu Ala Arg Glu Ala Val Arg Lys Ser Leu Val Leu
    450                 455                 460
Leu Lys Asn Asn Gly Arg Val Leu Pro Leu Ala Arg Asn Ala Lys Val
465                 470                 475                 480
Leu Val Ala Gly Lys Ser Ala Asn Ser Leu Glu Asn Gln Thr Gly Gly
                485                 490                 495
Trp Ser Leu Ser Trp Gln Gly Thr Gly Asn Ala Asn Ala Asp Phe Gly
            500                 505                 510
Gly Gly Thr Thr Val Trp Gln Ala Ile Gln Lys Ile Ala Pro Asn Ala
        515                 520                 525
Glu Leu Asp Thr Ser Ala Asp Gly Ala Lys Gly Ser Asp Ala Tyr Asp
    530                 535                 540
Ala Ala Ile Val Val Ile Gly Glu Thr Pro Tyr Ala Glu Gly Val Gly
545                 550                 555                 560
Asp Ile Gly Arg Ser Lys Thr Leu Glu Leu Thr Lys Leu Arg Pro Glu
                565                 570                 575
Asp Leu Ala Val Ile Glu Gly Leu Arg Ala Lys Gly Val Lys Lys Ile
            580                 585                 590
Val Thr Leu Leu Val Ser Gly Arg Pro Leu Tyr Val Asn Lys Glu Leu
        595                 600                 605
Asn Arg Ser Asp Ala Phe Val Ala Ala Trp Leu Pro Gly Thr Glu Gly
    610                 615                 620
Asp Gly Val Ala Asp Val Leu Phe Arg Ala Ala Asp Gly Ser Val Ala
```

```
                      625                 630                 635                 640

His Gly Phe Ser Gly Lys Leu Ser Phe Ser Trp Pro Lys Ser Ala Cys
                    645                 650                 655

Gln Thr Pro Leu Asn Arg Gly Asp Ala Thr Tyr Asp Pro Leu Tyr Ala
                    660                 665                 670

Tyr Gly Tyr Gly Leu Gln Tyr Gly Glu Glu Thr Asp Gln Ser Ala Tyr
                    675                 680                 685

Asp Glu Ser Ser Ala Thr Val Gly Cys Gly Ile Gln Asp Gly Gly Gly
                    690                 695                 700

Thr Thr Ala Glu Pro Leu Ala Val Phe Glu Gly Gly Ala Asn Gln Gly
705                 710                 715                 720

Asn Trp Lys Leu Arg Ile Gly Ala Glu Ser Ser Trp Ser Asn Asp Val
                    725                 730                 735

Thr Leu Ala Ser Ser Ala Val Thr Ser Thr Pro Ser Asn Glu Leu Gln
                    740                 745                 750

Ala Val Pro Val Asp Asp Lys Ala Gly Arg Gln Trp Ala Ala Val Lys
                    755                 760                 765

Ala Thr Trp Asn Asp Lys Pro Gly Gln Leu Tyr Met Gln Ser Ala Asn
                    770                 775                 780

Pro Gly Asp Leu Val Asp Leu Met Ala Tyr Gln Asn Ser Gly Gly Ala
785                 790                 795                 800

Leu Val Phe Asp Leu Arg Val Val Ser Ala Pro Thr Asp Pro Val Lys
                    805                 810                 815

Leu Arg Val Asp Cys Gly Trp Pro Cys Leu Gly Glu Ile Asp Val Thr
                    820                 825                 830

Ser Ala Val Lys Ala Gln Pro Val Asn Ala Trp Lys Glu Val Ala Val
                    835                 840                 845

Ser Leu Gln Cys Phe Ala Asp Ala Gly Thr Asp Leu Ala Ile Val Asn
                    850                 855                 860

Thr Pro Phe Leu Met Tyr Thr Ser Gly Arg Phe Glu Ala Ala Val Ala
865                 870                 875                 880

Asn Ile Arg Trp Glu Pro Lys Arg Thr Pro Asn Val Gly Cys Asn Gly
                    885                 890                 895

Ala Pro Ile Ala Ala Ala Pro
                    900

<210> SEQ ID NO 45
<211> LENGTH: 960
<212> TYPE: DNA
<213> ORGANISM: Pyrococcus furiosus
<220> FEATURE:
<221> NAME/KEY: CDS
<222> LOCATION: (1)...(960)
<223> OTHER INFORMATION: clone # 7EG1

<400> SEQUENCE: 45 atg agc aag aaa aag ttc gtc atc gta tct atc tta aca atc ctt tta      48
Met Ser Lys Lys Lys Phe Val Ile Val Ser Ile Leu Thr Ile Leu Leu
1               5                   10                  15 gta cag gca ata tat ttt gta gaa aag tat cat acc tct gag gac aag      96
Val Gln Ala Ile Tyr Phe Val Glu Lys Tyr His Thr Ser Glu Asp Lys
            20                  25                  30 tca act tca aat acc tca tct aca cca ccc caa aca aca ctt tcc act     144
Ser Thr Ser Asn Thr Ser Ser Thr Pro Pro Gln Thr Thr Leu Ser Thr
        35                  40                  45 acc aag gtt ctc aag att aga tac cct gat gac ggt gag tgg cca gga     192
Thr Lys Val Leu Lys Ile Arg Tyr Pro Asp Asp Gly Glu Trp Pro Gly
    50                  55                  60
```

```
              50                  55                  60
gct cct att gat aag gat ggt gat ggg aac cca gaa ttc tac att gaa     240
Ala Pro Ile Asp Lys Asp Gly Asp Gly Asn Pro Glu Phe Tyr Ile Glu
 65              70                  75                  80 ata aac cta tgg aac att ctt aat gct act gga ttt gct gag atg acg     288
Ile Asn Leu Trp Asn Ile Leu Asn Ala Thr Gly Phe Ala Glu Met Thr
                 85                  90                  95 tac aat tta acc agc ggc gtc ctt cac tac gtc caa caa ctt gac aac     336
Tyr Asn Leu Thr Ser Gly Val Leu His Tyr Val Gln Gln Leu Asp Asn
            100                 105                 110 att gtc ttg agg gat aga agt aat tgg gtg cat gga tac ccc gaa ata     384
Ile Val Leu Arg Asp Arg Ser Asn Trp Val His Gly Tyr Pro Glu Ile
        115                 120                 125 ttc tat gga aac aag cca tgg aat gca aac tac gca act gat ggc cca     432
Phe Tyr Gly Asn Lys Pro Trp Asn Ala Asn Tyr Ala Thr Asp Gly Pro
    130                 135                 140 ata cca tta ccc agt aaa gtt tca aac cta aca gac ttc tat cta aca     480
Ile Pro Leu Pro Ser Lys Val Ser Asn Leu Thr Asp Phe Tyr Leu Thr
145                 150                 155                 160 atc tcc tat aaa ctt gag ccc aag aac ggc ctg cca att aac ttc gca     528
Ile Ser Tyr Lys Leu Glu Pro Lys Asn Gly Leu Pro Ile Asn Phe Ala
                165                 170                 175 ata gaa tcc tgg tta acg aga gaa gct tgg aga aca aca gga att aac     576
Ile Glu Ser Trp Leu Thr Arg Glu Ala Trp Arg Thr Thr Gly Ile Asn
            180                 185                 190 agc gat gag caa gaa gta atg ata tgg att tac tat gac gga tta caa     624
Ser Asp Glu Gln Glu Val Met Ile Trp Ile Tyr Tyr Asp Gly Leu Gln
        195                 200                 205 ccg gct ggc tcc aaa gtt aag gag att gta gtc cca ata ata gtt aac     672
Pro Ala Gly Ser Lys Val Lys Glu Ile Val Val Pro Ile Ile Val Asn
    210                 215                 220 gga aca cca gta aat gct aca ttt gaa gta tgg aag gca aac att ggt     720
Gly Thr Pro Val Asn Ala Thr Phe Glu Val Trp Lys Ala Asn Ile Gly
225                 230                 235                 240 tgg gag tat gtt gca ttt aga ata aag acc cca atc aaa gag gga aca     768
Trp Glu Tyr Val Ala Phe Arg Ile Lys Thr Pro Ile Lys Glu Gly Thr
                245                 250                 255 gtg aca att cca tac gga gca ttt ata agt gtt gca gcc aac att tca     816
Val Thr Ile Pro Tyr Gly Ala Phe Ile Ser Val Ala Ala Asn Ile Ser
            260                 265                 270 agc tta cca aat tac aca gaa ctt tac tta gag gac gtg gag att gga     864
Ser Leu Pro Asn Tyr Thr Glu Leu Tyr Leu Glu Asp Val Glu Ile Gly
        275                 280                 285 act gag ttt gga acg cca agc act acc tcc gcc cac cta gag tgg tgg     912
Thr Glu Phe Gly Thr Pro Ser Thr Thr Ser Ala His Leu Glu Trp Trp
    290                 295                 300 atc aca aac ata aca cta act cct cta gat aga cct ctt att tcc taa     960
Ile Thr Asn Ile Thr Leu Thr Pro Leu Asp Arg Pro Leu Ile Ser  *
305                 310                 315
```

<210> SEQ ID NO 46
<211> LENGTH: 319
<212> TYPE: PRT
<213> ORGANISM: Pyrococcus furiosus

<400> SEQUENCE: 46

```
Met Ser Lys Lys Phe Val Ile Val Ser Ile Leu Thr Ile Leu Leu
 1               5                  10                  15

Val Gln Ala Ile Tyr Phe Val Glu Lys Tyr His Thr Ser Glu Asp Lys
            20                  25                  30
```

```
Ser Thr Ser Asn Thr Ser Ser Thr Pro Pro Gln Thr Thr Leu Ser Thr
         35                  40                  45

Thr Lys Val Leu Lys Ile Arg Tyr Pro Asp Asp Gly Glu Trp Pro Gly
 50                  55                  60

Ala Pro Ile Asp Lys Asp Gly Asp Gly Asn Pro Glu Phe Tyr Ile Glu
 65                  70                  75                  80

Ile Asn Leu Trp Asn Ile Leu Asn Ala Thr Gly Phe Ala Glu Met Thr
                 85                  90                  95

Tyr Asn Leu Thr Ser Gly Val Leu His Tyr Val Gln Gln Leu Asp Asn
                100                 105                 110

Ile Val Leu Arg Asp Arg Ser Asn Trp Val His Gly Tyr Pro Glu Ile
            115                 120                 125

Phe Tyr Gly Asn Lys Pro Trp Asn Ala Asn Tyr Ala Thr Asp Gly Pro
130                 135                 140

Ile Pro Leu Pro Ser Lys Val Ser Asn Leu Thr Asp Phe Tyr Leu Thr
145                 150                 155                 160

Ile Ser Tyr Lys Leu Glu Pro Lys Asn Gly Leu Pro Ile Asn Phe Ala
                165                 170                 175

Ile Glu Ser Trp Leu Thr Arg Glu Ala Trp Arg Thr Thr Gly Ile Asn
                180                 185                 190

Ser Asp Glu Gln Glu Val Met Ile Trp Ile Tyr Tyr Asp Gly Leu Gln
            195                 200                 205

Pro Ala Gly Ser Lys Val Lys Glu Ile Val Pro Ile Ile Val Asn
210                 215                 220

Gly Thr Pro Val Asn Ala Thr Phe Glu Val Trp Lys Ala Asn Ile Gly
225                 230                 235                 240

Trp Glu Tyr Val Ala Phe Arg Ile Lys Thr Pro Ile Lys Glu Gly Thr
                245                 250                 255

Val Thr Ile Pro Tyr Gly Ala Phe Ile Ser Val Ala Ala Asn Ile Ser
            260                 265                 270

Ser Leu Pro Asn Tyr Thr Glu Leu Tyr Leu Glu Asp Val Glu Ile Gly
275                 280                 285

Thr Glu Phe Gly Thr Pro Ser Thr Thr Ser Ala His Leu Glu Trp Trp
290                 295                 300

Ile Thr Asn Ile Thr Leu Thr Pro Leu Asp Arg Pro Leu Ile Ser
305                 310                 315

<210> SEQ ID NO 47
<211> LENGTH: 1515
<212> TYPE: DNA
<213> ORGANISM: Vibrio harveyi
<220> FEATURE:
<221> NAME/KEY: CDS
<222> LOCATION: (1)...(1515)
<223> OTHER INFORMATION: clone # 91GP2

<400> SEQUENCE: 47 atg aga ggt aac acg atg aag caa aaa gcg cta tat cga gca gta gca        48
Met Arg Gly Asn Thr Met Lys Gln Lys Ala Leu Tyr Arg Ala Val Ala
 1               5                  10                  15 atg ggt ttg agt ggt ctt gcg aac gtc gca tcc gct aat gag atg gta        96
Met Gly Leu Ser Gly Leu Ala Asn Val Ala Ser Ala Asn Glu Met Val
                 20                  25                  30 aat cct gat ggt ggt gtc gta gtg ggt tac tgg cat aac tgg tgc gat       144
Asn Pro Asp Gly Gly Val Val Val Gly Tyr Trp His Asn Trp Cys Asp
         35                  40                  45
```

```
ggc gct ggt tac aag gga ggt aat gca ccg tgt gta aca ttg gat gaa      192
Gly Ala Gly Tyr Lys Gly Gly Asn Ala Pro Cys Val Thr Leu Asp Glu
        50                  55                  60 gtt gat cct atg tac aat gtg gtt aac gtc tcc ttt atg aag gta ttc      240
Val Asp Pro Met Tyr Asn Val Val Asn Val Ser Phe Met Lys Val Phe
 65                  70                  75                  80 aat acc agt gaa ggt cgt att cca acc ttt aag ctc gat cca aat atc      288
Asn Thr Ser Glu Gly Arg Ile Pro Thr Phe Lys Leu Asp Pro Asn Ile
                 85                  90                  95 ggc ctt tca gaa caa caa ttt ttt gac caa att gaa gct cta aac caa      336
Gly Leu Ser Glu Gln Gln Phe Phe Asp Gln Ile Glu Ala Leu Asn Gln
            100                 105                 110 caa gga cgt gcc gtt ctc atc gct ctt ggt ggc gca gat gct cac gtt      384
Gln Gly Arg Ala Val Leu Ile Ala Leu Gly Gly Ala Asp Ala His Val
        115                 120                 125 gaa ctt aga act ggt gac gaa caa gcg ttc gca caa gag att att cgt      432
Glu Leu Arg Thr Gly Asp Glu Gln Ala Phe Ala Gln Glu Ile Ile Arg
130                 135                 140 tta acg gat aag ttc ggt ttt gat ggt cta gat atc gat tta gag cag      480
Leu Thr Asp Lys Phe Gly Phe Asp Gly Leu Asp Ile Asp Leu Glu Gln
145                 150                 155                 160 tca gca gta acg gca gag aac aac caa acc gta att cca gct gca ctt      528
Ser Ala Val Thr Ala Glu Asn Asn Gln Thr Val Ile Pro Ala Ala Leu
                165                 170                 175 cgc ctt gta aaa gag cat tat caa caa caa ggt aag aac ttc cta att      576
Arg Leu Val Lys Glu His Tyr Gln Gln Gln Gly Lys Asn Phe Leu Ile
            180                 185                 190 acg atg gcg cct gaa ttc cct tat cta aca gaa ggt ggc aag tat gtt      624
Thr Met Ala Pro Glu Phe Pro Tyr Leu Thr Glu Gly Gly Lys Tyr Val
        195                 200                 205 cct tac att act ggt tta gaa ggg tac tac gat tgg atc aac cct cag      672
Pro Tyr Ile Thr Gly Leu Glu Gly Tyr Tyr Asp Trp Ile Asn Pro Gln
    210                 215                 220 ttt tac aat caa ggt ggt gac ggt att tgg gtt gat ggc gtg ggt tgg      720
Phe Tyr Asn Gln Gly Gly Asp Gly Ile Trp Val Asp Gly Val Gly Trp
225                 230                 235                 240 ata gcg caa aac aat gat gag tta aaa caa gag ttt att tac tac att      768
Ile Ala Gln Asn Asn Asp Glu Leu Lys Gln Glu Phe Ile Tyr Tyr Ile
                245                 250                 255 tcg gac gct cta tcg aac ggt aca cgc ggt ttc cac aaa atc ccg cat      816
Ser Asp Ala Leu Ser Asn Gly Thr Arg Gly Phe His Lys Ile Pro His
            260                 265                 270 gac aaa ctg gtg ttt ggt atc cca tct aac att gat gct gct gca acg      864
Asp Lys Leu Val Phe Gly Ile Pro Ser Asn Ile Asp Ala Ala Ala Thr
        275                 280                 285 ggc ttt gtt caa aac cct caa gac ctt tac gac gcg ttt gat caa ctt      912
Gly Phe Val Gln Asn Pro Gln Asp Leu Tyr Asp Ala Phe Asp Gln Leu
    290                 295                 300 aaa gcg caa ggg cag gca ctt cgt ggc gta atg aca tgg tcg gtg aac      960
Lys Ala Gln Gly Gln Ala Leu Arg Gly Val Met Thr Trp Ser Val Asn
305                 310                 315                 320 tgg gat atg ggc acc gat aaa aat ggc caa gcg tac ggt gaa aaa ttc     1008
Trp Asp Met Gly Thr Asp Lys Asn Gly Gln Ala Tyr Gly Glu Lys Phe
                325                 330                 335 gtg aag gat tac ggt ccg ttt atc cac ggg cag act cca cca cca agt     1056
Val Lys Asp Tyr Gly Pro Phe Ile His Gly Gln Thr Pro Pro Pro Ser
            340                 345                 350 gaa ggt gaa cca gtt ttt agt ggc ctc aac gat gtt cgt gtg cat cac     1104
Glu Gly Glu Pro Val Phe Ser Gly Leu Asn Asp Val Arg Val His His
        355                 360                 365
```

-continued

```
ggt agt tca ttt gac ccg tat gca ggt gtt act gcg tct gat aaa gaa    1152
Gly Ser Ser Phe Asp Pro Tyr Ala Gly Val Thr Ala Ser Asp Lys Glu
    370                 375                 380 gat gga gac cta acc aac agc atc act gtc gaa ggt tca gtt gat gtg    1200
Asp Gly Asp Leu Thr Asn Ser Ile Thr Val Glu Gly Ser Val Asp Val
385                 390                 395                 400 aac acg gta ggc aca tat gtt ttg gtt tac agt gta aaa gac agc gac    1248
Asn Thr Val Gly Thr Tyr Val Leu Val Tyr Ser Val Lys Asp Ser Asp
                405                 410                 415 aac aat gaa acc aag caa agt aga acg gtt gtt gtt tac agc cta gtg    1296
Asn Asn Glu Thr Lys Gln Ser Arg Thr Val Val Val Tyr Ser Leu Val
            420                 425                 430 cct gag ttt gaa ggt gtc gca gat acg acc atc cag ctt ggt gac gct    1344
Pro Glu Phe Glu Gly Val Ala Asp Thr Thr Ile Gln Leu Gly Asp Ala
        435                 440                 445 ttt gac cca atg gca ggc gta aaa gcg acg gat gca gaa gac ggt gat    1392
Phe Asp Pro Met Ala Gly Val Lys Ala Thr Asp Ala Glu Asp Gly Asp
    450                 455                 460 ttg act gat cgg tat cta cgc cgc cta agg tca ctt ctg cgg tgc gat    1440
Leu Thr Asp Arg Tyr Leu Arg Arg Leu Arg Ser Leu Leu Arg Cys Asp
465                 470                 475                 480 agc ctt ctg tgc cat ttg gtg caa ccg ccc agt ttt cca gac gct caa    1488
Ser Leu Leu Cys His Leu Val Gln Pro Pro Ser Phe Pro Asp Ala Gln
                485                 490                 495 cga tgg ttg cca tct ctt tct ggt tga                                1515
Arg Trp Leu Pro Ser Leu Ser Gly  *
            500

<210> SEQ ID NO 48
<211> LENGTH: 504
<212> TYPE: PRT
<213> ORGANISM: Vibrio harveyi

<400> SEQUENCE: 48

Met Arg Gly Asn Thr Met Lys Gln Lys Ala Leu Tyr Arg Ala Val Ala
  1               5                  10                  15

Met Gly Leu Ser Gly Leu Ala Asn Val Ala Ser Ala Asn Glu Met Val
             20                  25                  30

Asn Pro Asp Gly Gly Val Val Gly Tyr Trp His Asn Trp Cys Asp
         35                  40                  45

Gly Ala Gly Tyr Lys Gly Gly Asn Ala Pro Cys Val Thr Leu Asp Glu
     50                  55                  60

Val Asp Pro Met Tyr Asn Val Val Asn Val Ser Phe Met Lys Val Phe
 65                  70                  75                  80

Asn Thr Ser Glu Gly Arg Ile Pro Thr Phe Lys Leu Asp Pro Asn Ile
                 85                  90                  95

Gly Leu Ser Glu Gln Gln Phe Phe Asp Gln Ile Glu Ala Leu Asn Gln
            100                 105                 110

Gln Gly Arg Ala Val Leu Ile Ala Leu Gly Gly Ala Asp Ala His Val
        115                 120                 125

Glu Leu Arg Thr Gly Asp Glu Gln Ala Phe Ala Glu Ile Ile Arg
    130                 135                 140

Leu Thr Asp Lys Phe Gly Phe Asp Gly Leu Asp Ile Asp Leu Glu Gln
145                 150                 155                 160

Ser Ala Val Thr Ala Glu Asn Asn Gln Thr Val Ile Pro Ala Ala Leu
                165                 170                 175

Arg Leu Val Lys Glu His Tyr Gln Gln Gln Gly Lys Asn Phe Leu Ile
```

```
                    180                 185                 190
Thr Met Ala Pro Glu Phe Pro Tyr Leu Thr Glu Gly Gly Lys Tyr Val
            195                 200                 205
Pro Tyr Ile Thr Gly Leu Glu Gly Tyr Tyr Asp Trp Ile Asn Pro Gln
210                 215                 220
Phe Tyr Asn Gln Gly Asp Gly Ile Trp Val Asp Gly Val Gly Trp
225                 230                 235                 240
Ile Ala Gln Asn Asn Asp Glu Leu Lys Gln Glu Phe Ile Tyr Tyr Ile
                245                 250                 255
Ser Asp Ala Leu Ser Asn Gly Thr Arg Gly Phe His Lys Ile Pro His
            260                 265                 270
Asp Lys Leu Val Phe Gly Ile Pro Ser Asn Ile Asp Ala Ala Ala Thr
        275                 280                 285
Gly Phe Val Gln Asn Pro Gln Asp Leu Tyr Asp Ala Phe Asp Gln Leu
    290                 295                 300
Lys Ala Gln Gly Gln Ala Leu Arg Gly Val Met Thr Trp Ser Val Asn
305                 310                 315                 320
Trp Asp Met Gly Thr Asp Lys Asn Gly Gln Ala Tyr Gly Glu Lys Phe
                325                 330                 335
Val Lys Asp Tyr Gly Pro Phe Ile His Gly Gln Thr Pro Pro Ser
            340                 345                 350
Glu Gly Glu Pro Val Phe Ser Gly Leu Asn Asp Val Arg Val His His
        355                 360                 365
Gly Ser Ser Phe Asp Pro Tyr Ala Gly Val Thr Ala Ser Asp Lys Glu
    370                 375                 380
Asp Gly Asp Leu Thr Asn Ser Ile Thr Val Glu Gly Ser Val Asp Val
385                 390                 395                 400
Asn Thr Val Gly Thr Tyr Val Leu Val Tyr Ser Val Lys Asp Ser Asp
                405                 410                 415
Asn Asn Glu Thr Lys Gln Ser Arg Thr Val Val Tyr Ser Leu Val
            420                 425                 430
Pro Glu Phe Glu Gly Val Ala Asp Thr Thr Ile Gln Leu Gly Asp Ala
        435                 440                 445
Phe Asp Pro Met Ala Gly Val Lys Ala Thr Asp Ala Glu Asp Gly Asp
    450                 455                 460
Leu Thr Asp Arg Tyr Leu Arg Arg Leu Arg Ser Leu Leu Arg Cys Asp
465                 470                 475                 480
Ser Leu Leu Cys His Leu Val Gln Pro Pro Ser Phe Pro Asp Ala Gln
                485                 490                 495
Arg Trp Leu Pro Ser Leu Ser Gly
            500
```

<210> SEQ ID NO 49
<211> LENGTH: 46
<212> TYPE: DNA
<213> ORGANISM: Artificial Sequence
<220> FEATURE:
<223> OTHER INFORMATION: primer for PCR

<400> SEQUENCE: 49
aatagcggcc gcaagcttat cgacggtttc catatgggga ttggtg        46

<210> SEQ ID NO 50
<211> LENGTH: 42
<212> TYPE: DNA
<213> ORGANISM: Artificial Sequence

```
<220> FEATURE:
<223> OTHER INFORMATION: primer for PCR

<400> SEQUENCE: 50
aatagcggcc gcggatccag accaactggt aatggtagcg ac                    42

<210> SEQ ID NO 51
<211> LENGTH: 60
<212> TYPE: DNA
<213> ORGANISM: Artificial Sequence
<220> FEATURE:
<223> OTHER INFORMATION: primer for PCR

<400> SEQUENCE: 51
tttattcaat tgattaaaga ggagaaatta actatgataa acgttgcaac gggagaggag   60

<210> SEQ ID NO 52
<211> LENGTH: 35
<212> TYPE: DNA
<213> ORGANISM: Artificial Sequence
<220> FEATURE:
<223> OTHER INFORMATION: primer for PCR

<400> SEQUENCE: 52
tttattggat cctactttgt gtcaacgaag tatcc                             35
```